(12) United States Patent
Shluzas

(10) Patent No.: US 7,645,232 B2
(45) Date of Patent: Jan. 12, 2010

(54) ACCESS DEVICE FOR MINIMALLY INVASIVE SURGERY

(75) Inventor: Alan E. Shluzas, West Roxbury, MA (US)

(73) Assignee: Zimmer Spine, Inc., Minneapolis, MN (US)

(*) Notice: Subject to any disclaimer, the term of this patent is extended or adjusted under 35 U.S.C. 154(b) by 719 days.

(21) Appl. No.: 10/845,389

(22) Filed: May 13, 2004

(65) Prior Publication Data

US 2004/0230100 A1 Nov. 18, 2004

Related U.S. Application Data

(60) Provisional application No. 60/471,431, filed on May 16, 2003, provisional application No. 60/513,796, filed on Oct. 22, 2003.

(51) Int. Cl.
*A61B 1/32* (2006.01)

(52) U.S. Cl. .................................................. 600/219

(58) Field of Classification Search ................ 600/190, 600/196, 201, 204, 208, 210, 215, 225, 219–222; 606/108, 61; 604/104, 106
See application file for complete search history.

(56) References Cited

U.S. PATENT DOCUMENTS

| | | | |
|---|---|---|---|
| 151,228 A | 5/1874 | Knaffl | |
| 530,728 A | 12/1894 | Sherbrook | |
| 2,083,573 A | 6/1937 | Morgan | |
| 2,313,164 A | 3/1943 | Nelson | |
| 2,594,086 A | 4/1952 | Smith | |
| 2,623,517 A | 12/1952 | Barlow et al. | |
| 3,044,461 A | 7/1962 | Murdock | |
| 3,070,088 A | 12/1962 | Brahos | |
| 3,509,873 A | 5/1970 | Karlin et al. | |
| 3,749,088 A | 7/1973 | Kohlmann | |

(Continued)

FOREIGN PATENT DOCUMENTS

DE 103 27 972 A1 5/2004

(Continued)

OTHER PUBLICATIONS

International Search Report, Jan. 17, 2005.

(Continued)

*Primary Examiner*—Cris L Rodriguez
*Assistant Examiner*—Hao D Mai
(74) *Attorney, Agent, or Firm*—Crompton, Seager & Tufte, LLC.

(57) ABSTRACT

A retractor has a proximal portion comprising a first side portion having a first longitudinal edge and a second side portion having a second longitudinal edge. The first and second portions being movable relative to each other such that the first and second longitudinal edges can be positioned in close proximity to each other or spaced apart by a selected distance. A distal portion is coupled with the proximal portion. The distal portion has an outer surface and an inner surface partially defining a passage. The distal portion is capable of having a configuration when inserted within the patient wherein the cross-sectional area of the passage at a first location is greater than the cross-sectional area of the passage at a second location, wherein the first location is distal to the second location.

20 Claims, 75 Drawing Sheets

U.S. PATENT DOCUMENTS

| | | |
|---|---|---|
| 3,789,852 A | 2/1974 | Kim et al. |
| 3,841,317 A | 10/1974 | Awais |
| 3,965,890 A | 6/1976 | Gauthier |
| 3,998,217 A | 12/1976 | Trumbull et al. |
| 4,010,741 A | 3/1977 | Gauthier |
| 4,130,113 A | 12/1978 | Graham |
| 4,155,355 A | 5/1979 | Yamamoto |
| 4,254,763 A | 3/1981 | McCready et al. |
| 4,421,107 A | 12/1983 | Estes et al. |
| 4,545,374 A | 10/1985 | Jacobson |
| 4,601,713 A | 7/1986 | Fuqua |
| 4,716,901 A | 1/1988 | Jackson et al. |
| 4,819,620 A | 4/1989 | Okutsu |
| 4,863,133 A | 9/1989 | Bonnell |
| 4,921,478 A | 5/1990 | Solano et al. |
| 4,984,564 A | 1/1991 | Yuen |
| 5,020,519 A | 6/1991 | Hayes et al. |
| 5,025,778 A | 6/1991 | Silverstein et al. |
| 5,131,382 A | 7/1992 | Meyer |
| 5,139,499 A | 8/1992 | Small et al. |
| 5,163,949 A | 11/1992 | Bonutti |
| 5,171,279 A | 12/1992 | Mathews |
| 5,190,561 A | 3/1993 | Graber |
| 5,195,541 A | 3/1993 | Obenchain |
| 5,197,971 A | 3/1993 | Bonutti |
| 5,224,680 A | 7/1993 | Greenstein et al. |
| 5,231,974 A | 8/1993 | Giglio et al. |
| 5,287,845 A | 2/1994 | Faul et al. |
| 5,295,994 A | 3/1994 | Bonutti |
| 5,312,417 A | 5/1994 | Wilk |
| 5,345,927 A | 9/1994 | Bonutti |
| 5,354,302 A | 10/1994 | Ko |
| 5,370,647 A | 12/1994 | Graber et al. |
| 5,395,317 A | 3/1995 | Kambin |
| 5,400,774 A | 3/1995 | Villalta et al. |
| 5,439,464 A | 8/1995 | Shapiro |
| 5,454,365 A | 10/1995 | Bonutti |
| 5,472,426 A | 12/1995 | Bonati et al. |
| 5,484,437 A | 1/1996 | Michelson |
| 5,489,307 A | 2/1996 | Kuslich et al. |
| 5,505,690 A | 4/1996 | Patton et al. |
| 5,520,607 A | 5/1996 | Frassica et al. |
| 5,571,072 A | 11/1996 | Kronner |
| 5,575,754 A | 11/1996 | Konomura |
| 5,601,590 A | 2/1997 | Bonutti et al. |
| 5,667,481 A | 9/1997 | Villalta et al. |
| 5,667,520 A | 9/1997 | Bonutti et al. |
| 5,681,265 A | 10/1997 | Maeda et al. |
| 5,688,223 A | 11/1997 | Rosendahl |
| 5,707,359 A | 1/1998 | Bufalini |
| 5,720,751 A | 2/1998 | Jackson |
| 5,728,046 A | 3/1998 | Mayer et al. |
| 5,782,831 A | 7/1998 | Sherman et al. |
| 5,792,044 A | 8/1998 | Foley et al. |
| 5,795,289 A | 8/1998 | Wyttenbach |
| 5,795,291 A | 8/1998 | Koros et al. |
| 5,813,978 A | 9/1998 | Jako |
| 5,827,319 A | 10/1998 | Carlson et al. |
| 5,868,668 A | 2/1999 | Weiss |
| 5,902,231 A | 5/1999 | Foley et al. |
| 5,910,141 A | 6/1999 | Morrison et al. |
| 5,944,658 A | 8/1999 | Koros et al. |
| 5,954,635 A | 9/1999 | Foley et al. |
| 5,961,499 A | 10/1999 | Bonutti |
| 5,997,508 A | 12/1999 | Lunn et al. |
| 6,024,697 A | 2/2000 | Pisarik |
| 6,036,638 A | 3/2000 | Nwawka |
| 6,083,154 A | 7/2000 | Liu et al. |
| 6,096,046 A | 8/2000 | Weiss |
| 6,120,437 A | 9/2000 | Yoon et al. |
| 6,139,493 A | 10/2000 | Koros et al. |
| 6,162,236 A | 12/2000 | Osada |
| 6,171,299 B1 | 1/2001 | Bonutti |
| 6,187,000 B1 | 2/2001 | Davison et al. |
| 6,193,715 B1 | 2/2001 | Wrublewski et al. |
| 6,206,826 B1 | 3/2001 | Mathews et al. |
| 6,224,545 B1 | 5/2001 | Cocchia et al. |
| 6,251,111 B1 | 6/2001 | Barker et al. |
| 6,306,170 B2 | 10/2001 | Ray |
| 6,312,443 B1 | 11/2001 | Stone |
| 6,338,730 B1 | 1/2002 | Bonutti et al. |
| 6,354,995 B1 | 3/2002 | Hoftman et al. |
| 6,358,266 B1 | 3/2002 | Bonutti |
| 6,361,488 B1 | 3/2002 | Davison et al. |
| 6,364,832 B1 | 4/2002 | Propp |
| 6,371,968 B1 | 4/2002 | Kogasaka et al. |
| 6,383,195 B1 | 5/2002 | Richard |
| 6,432,048 B1 | 8/2002 | Francois |
| 6,464,634 B1 | 10/2002 | Fraser |
| 6,494,893 B2 | 12/2002 | Dubrul et al. |
| 6,497,654 B1 | 12/2002 | Leonard et al. |
| 6,524,320 B2 | 2/2003 | DiPoto |
| 6,530,880 B2 | 3/2003 | Pagliuca |
| 6,530,926 B1 | 3/2003 | Davison |
| 6,564,078 B1 | 5/2003 | Marino et al. |
| 6,616,605 B2 | 9/2003 | Wright et al. |
| 6,648,888 B1 | 11/2003 | Shluzas |
| 6,652,553 B2 | 11/2003 | Davison et al. |
| 6,712,795 B1 | 3/2004 | Cohen |
| 6,800,084 B2 | 10/2004 | Davison et al. |
| 6,837,889 B2 | 1/2005 | Shluzas |
| 6,849,064 B2 * | 2/2005 | Hamada .................. 604/164.01 |
| 6,945,933 B2 | 9/2005 | Branch et al. |
| 7,014,608 B2 | 3/2006 | Larson et al. |
| 7,056,321 B2 | 6/2006 | Pagliuca et al. |
| 7,066,937 B2 | 6/2006 | Shluzas |
| 7,226,451 B2 | 6/2007 | Shluzas et al. |
| 2001/0011170 A1 | 8/2001 | Davison et al. |
| 2001/0049498 A1 | 12/2001 | Davison et al. |
| 2002/0002360 A1 | 1/2002 | Orth et al. |
| 2003/0009130 A1 | 1/2003 | Stecker et al. |
| 2003/0014068 A1 | 1/2003 | Bonutti et al. |
| 2003/0040656 A1 | 2/2003 | Pagliuca et al. |
| 2003/0073998 A1 | 4/2003 | Pagliuca et al. |
| 2003/0097045 A1 | 5/2003 | Kashyap |
| 2003/0139648 A1 | 7/2003 | Foley et al. |
| 2003/0153927 A1 | 8/2003 | DiPoto et al. |
| 2003/0191371 A1 | 10/2003 | Smith et al. |
| 2003/0195405 A1 | 10/2003 | Marino et al. |
| 2003/0195493 A1 | 10/2003 | Davison et al. |
| 2003/0195549 A1 | 10/2003 | Davison et al. |
| 2003/0195550 A1 | 10/2003 | Davison et al. |
| 2003/0195551 A1 | 10/2003 | Davison et al. |
| 2003/0199871 A1 | 10/2003 | Foley et al. |
| 2003/0199885 A1 | 10/2003 | Davison et al. |
| 2004/0002629 A1 | 1/2004 | Branch et al. |
| 2004/0059339 A1 | 3/2004 | Roehm, III et al. |
| 2004/0078051 A1 | 4/2004 | Davison et al. |
| 2004/0087833 A1 | 5/2004 | Bauer et al. |
| 2004/0093001 A1 | 5/2004 | Hamada |
| 2004/0093002 A1 | 5/2004 | Davison et al. |
| 2004/0098012 A1 | 5/2004 | Davison et al. |
| 2004/0176665 A1 | 9/2004 | Branch et al. |
| 2004/0181231 A1 | 9/2004 | Emstad et al. |
| 2005/0090822 A1 | 4/2005 | DiPoto |
| 2005/0090833 A1 | 4/2005 | DiPoto |
| 2005/0090899 A1 | 4/2005 | DiPoto |
| 2005/0137461 A1 | 6/2005 | Marchek et al. |
| 2005/0159650 A1 | 7/2005 | Raymond et al. |
| 2005/0159651 A1 | 7/2005 | Raymond et al. |
| 2005/0245942 A1 | 11/2005 | DiPoto |
| 2005/0251192 A1 | 11/2005 | Shluzas et al. |
| 2005/0273131 A1 | 12/2005 | Shluzas et al. |
| 2005/0273132 A1 | 12/2005 | Shluzas et al. |

| | | | |
|---|---|---|---|
| 2005/0273133 A1 | 12/2005 | Shluzas et al. | |
| 2006/0004401 A1 | 1/2006 | Abernathie et al. | |
| 2006/0069404 A1 | 3/2006 | Shluzas et al. | |
| 2006/0106416 A1 | 5/2006 | Raymond et al. | |

FOREIGN PATENT DOCUMENTS

| | | |
|---|---|---|
| EP | 0807415 A2 | 11/1987 |
| EP | 0528562 A2 | 2/1993 |
| EP | 0807415 A3 | 8/1998 |
| EP | 0 980 677 | 2/2000 |
| EP | 1305077 A1 | 5/2003 |
| FR | 2701379 | 8/1994 |
| JP | 2000083960 A2 | 3/2000 |
| JP | 2001149376 A2 | 6/2001 |
| WO | WO 92/21292 A2 | 12/1992 |
| WO | WO 93/14801 | 8/1993 |
| WO | WO 94/03114 | 2/1994 |
| WO | WO 95/10218 A1 | 4/1995 |
| WO | WO 95/32663 | 12/1995 |
| WO | WO 01/54560 A2 | 8/2001 |
| WO | WO 01/54560 A3 | 8/2001 |
| WO | WO 02/09801 A1 | 2/2002 |
| WO | WO 02/078767 | 10/2002 |
| WO | WO03/007783 A2 | 1/2003 |
| WO | 03068083 | 8/2003 |
| WO | 2004021899 | 3/2004 |
| WO | 2004022108 | 3/2004 |
| WO | 2004103188 | 12/2004 |
| WO | 2005018466 | 3/2005 |
| WO | 2005046492 | 5/2005 |
| WO | 2005096968 | 10/2005 |

OTHER PUBLICATIONS

Wolfhard Caspar, M.D., et al., *Neurosurgery*, vol. 28, No. 1, Jan. 1991, pp. 78-87 "The Caspar Microsurgical Discectomy and Comparison with a Conventional Standard Lumbar Disc Procedure".

V. Mueller, *Balfour Retractors and Blades Catalog*, c. 1997, pp. 140, 175, 233.

* cited by examiner

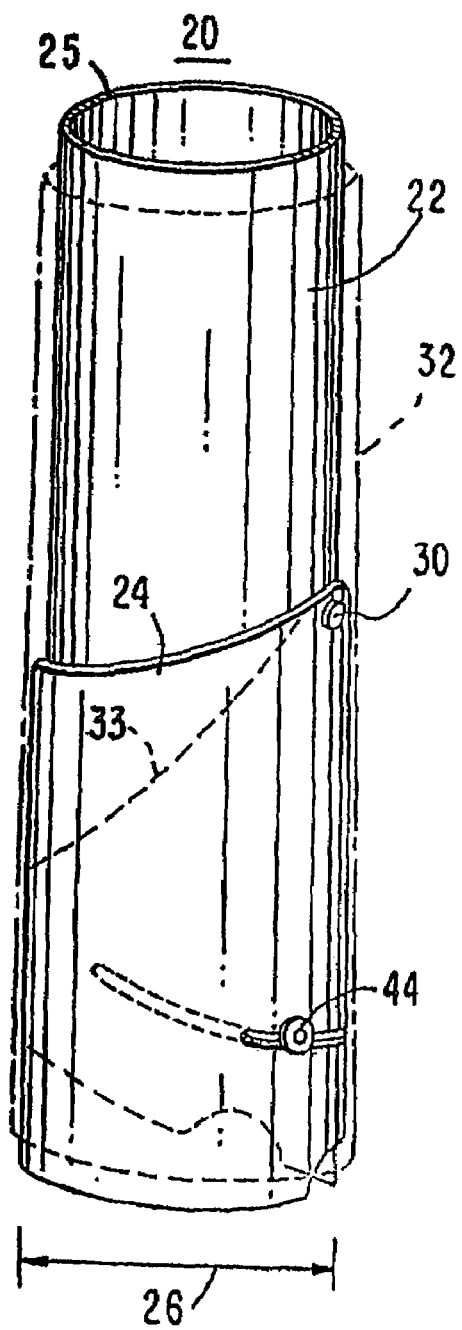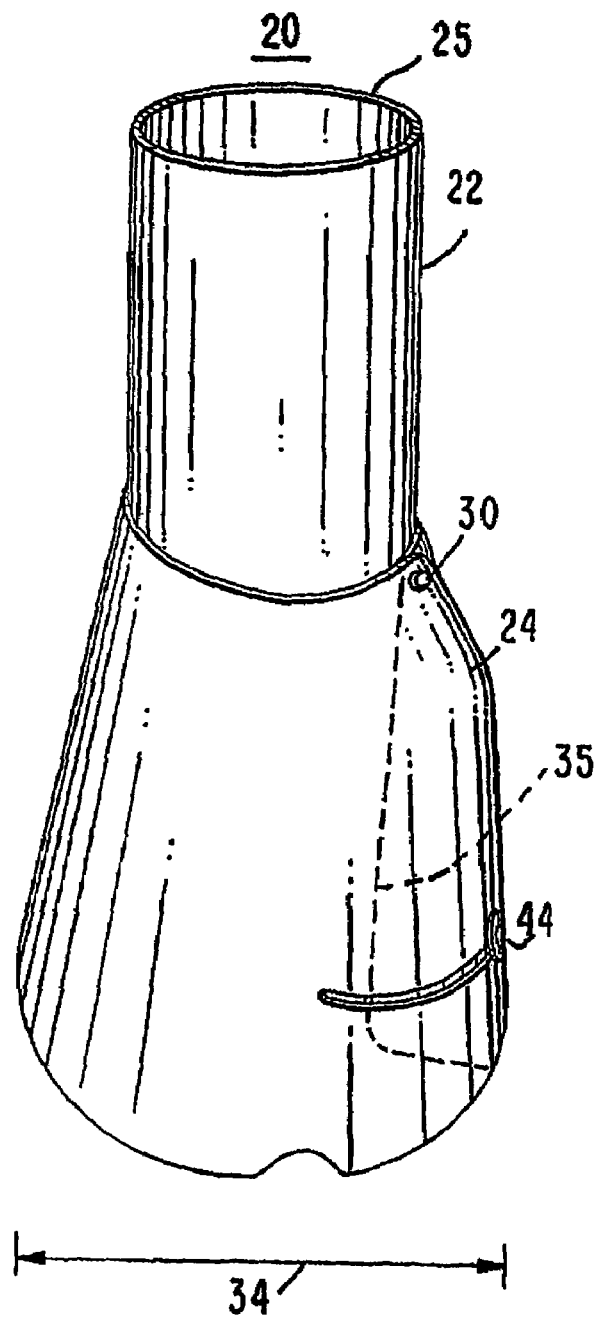

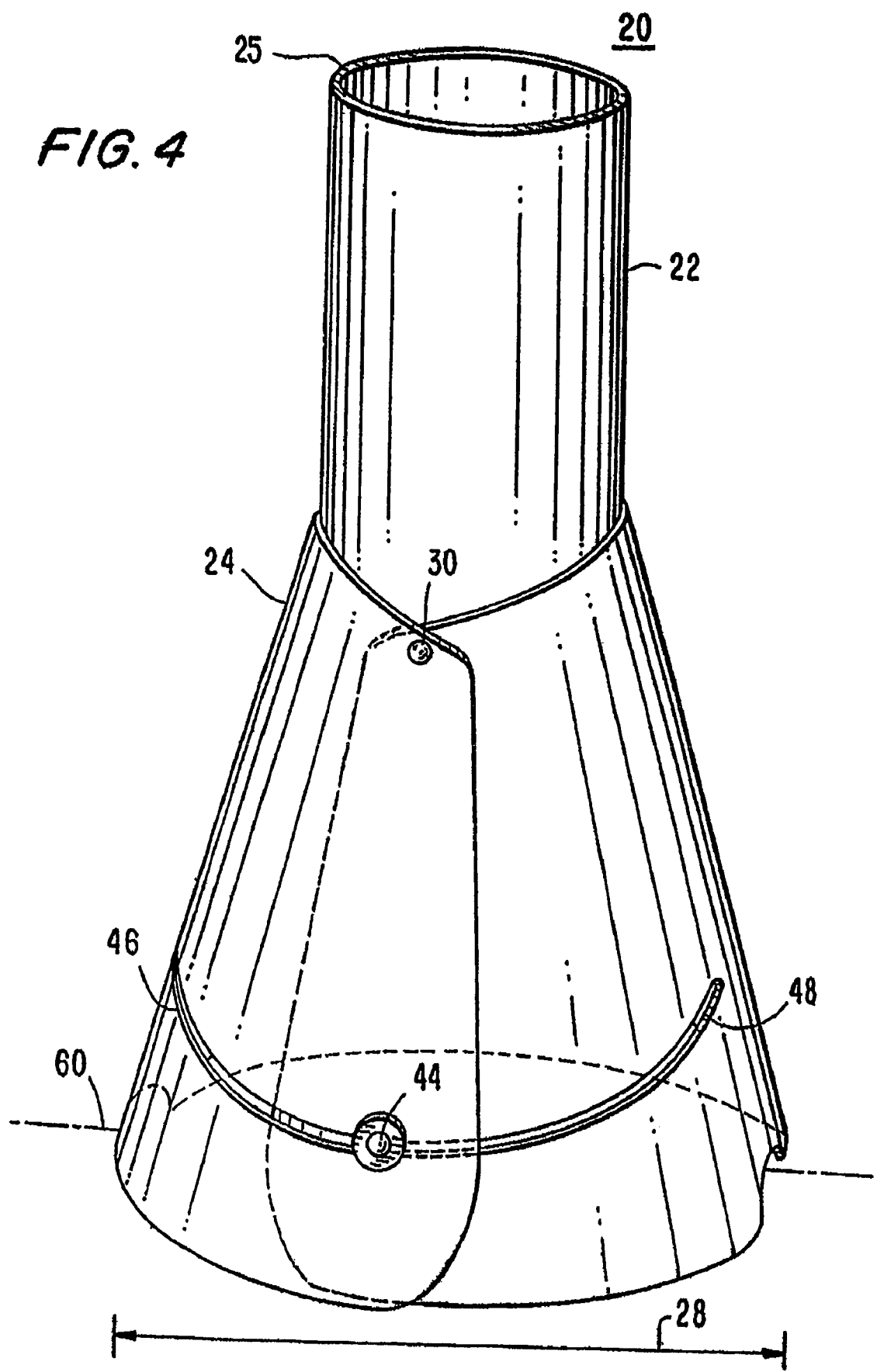

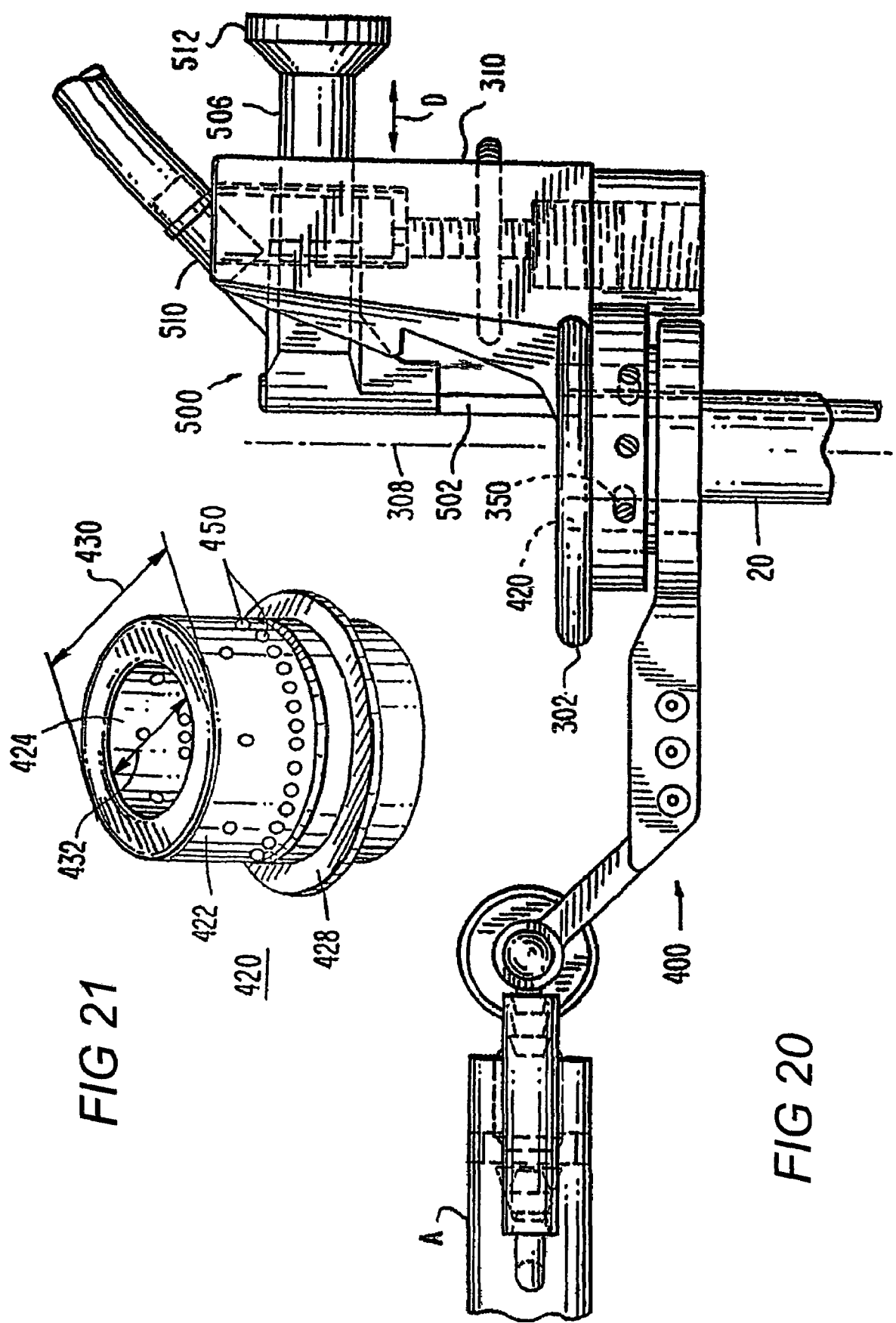

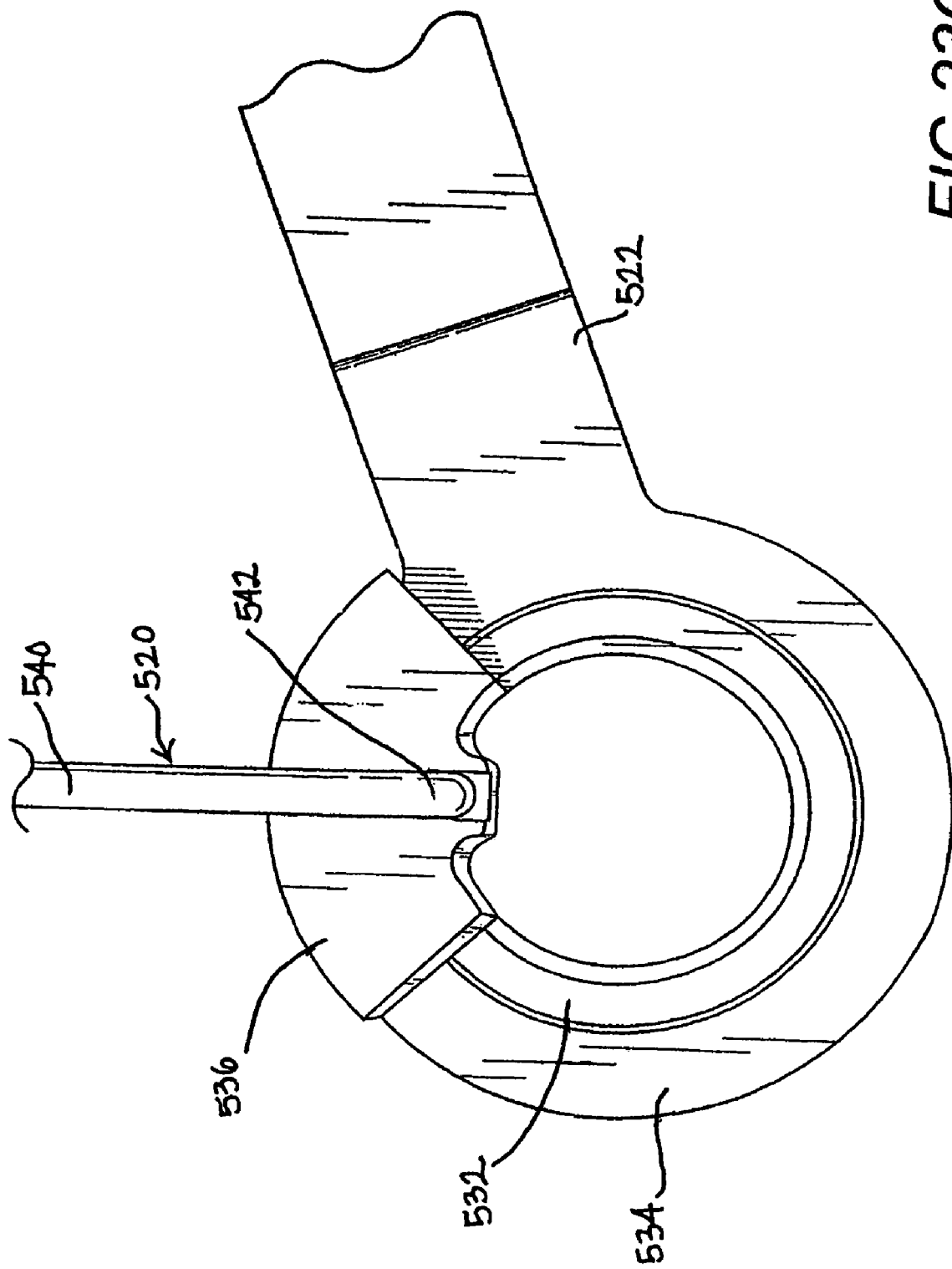

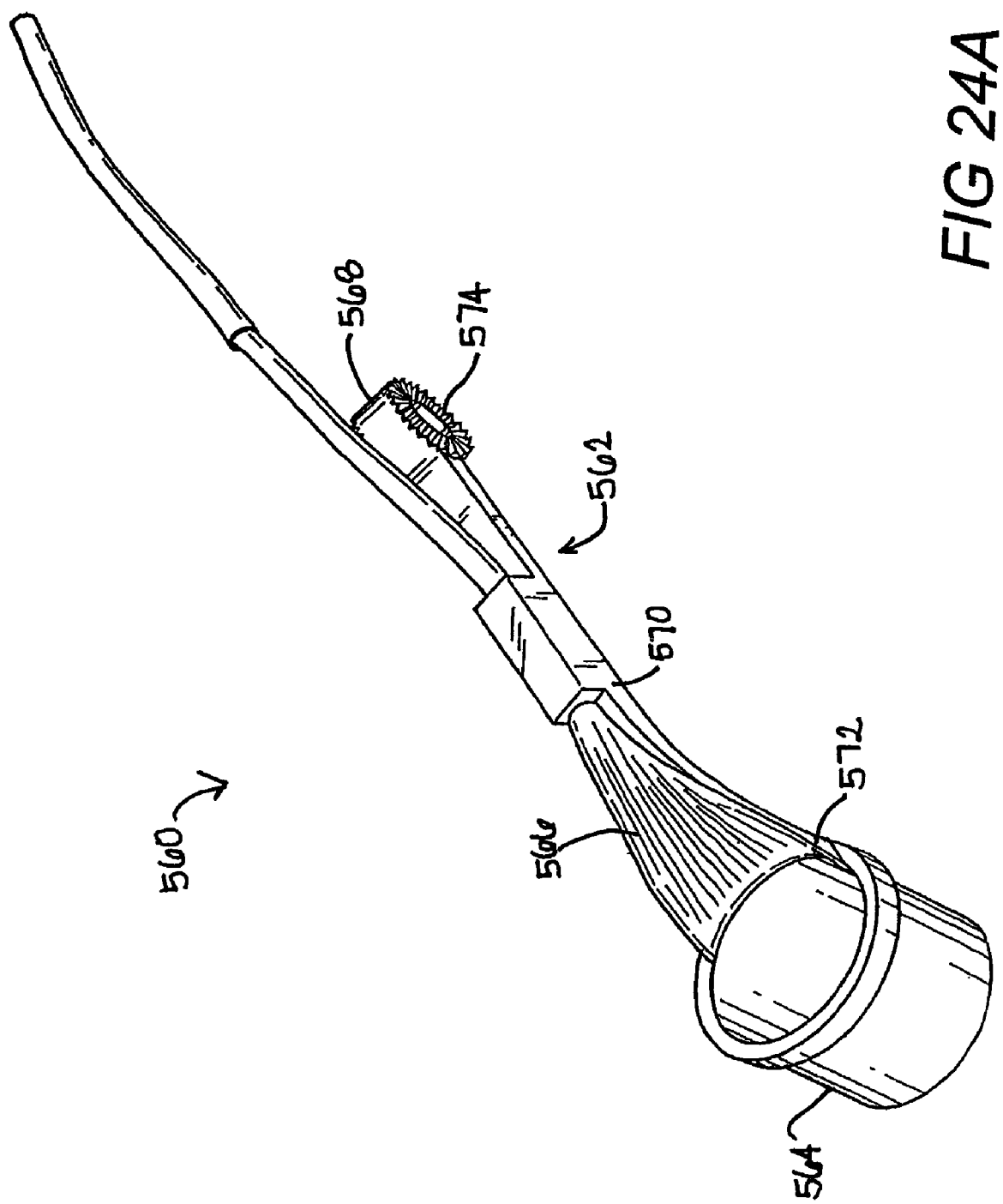

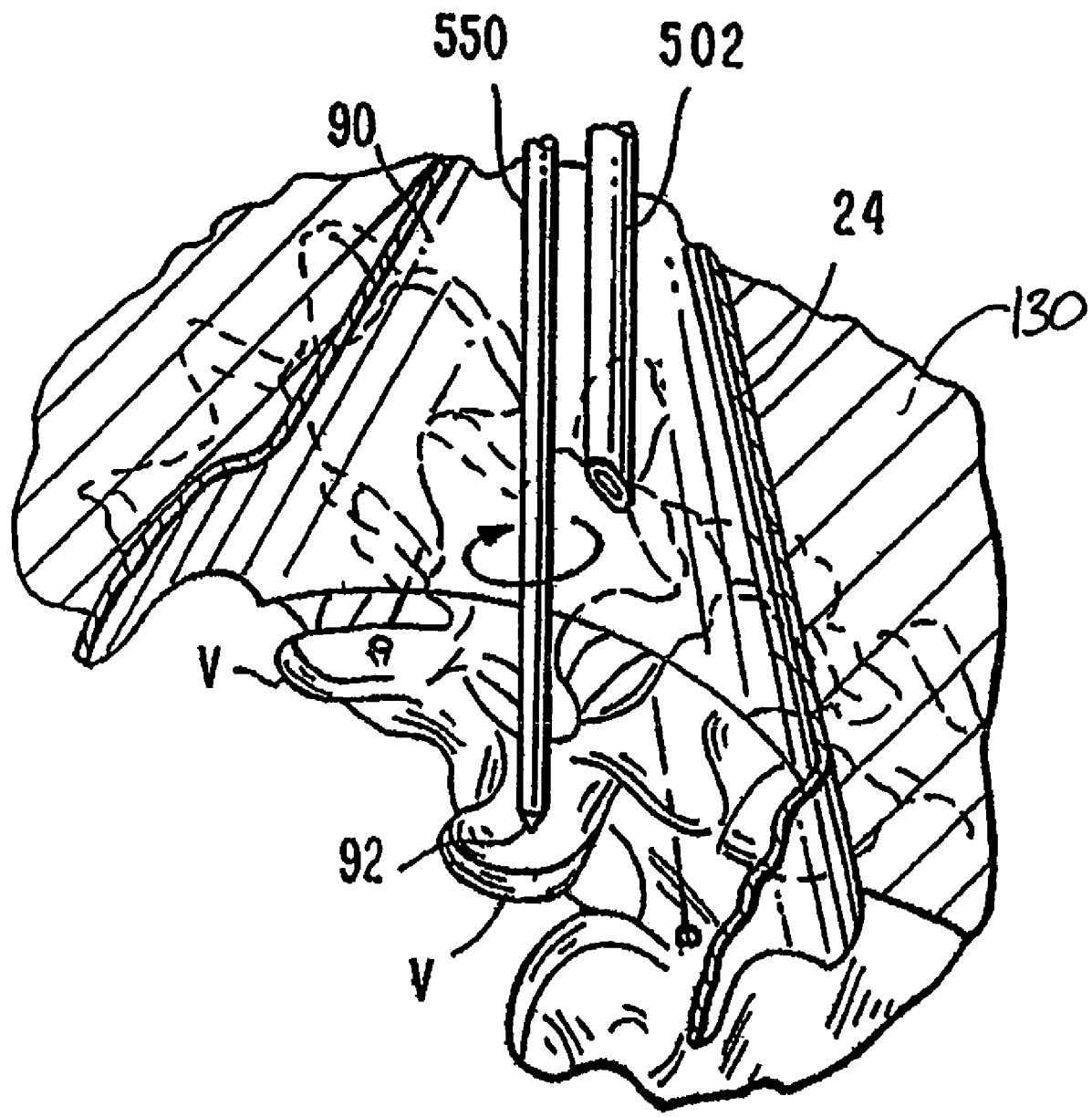

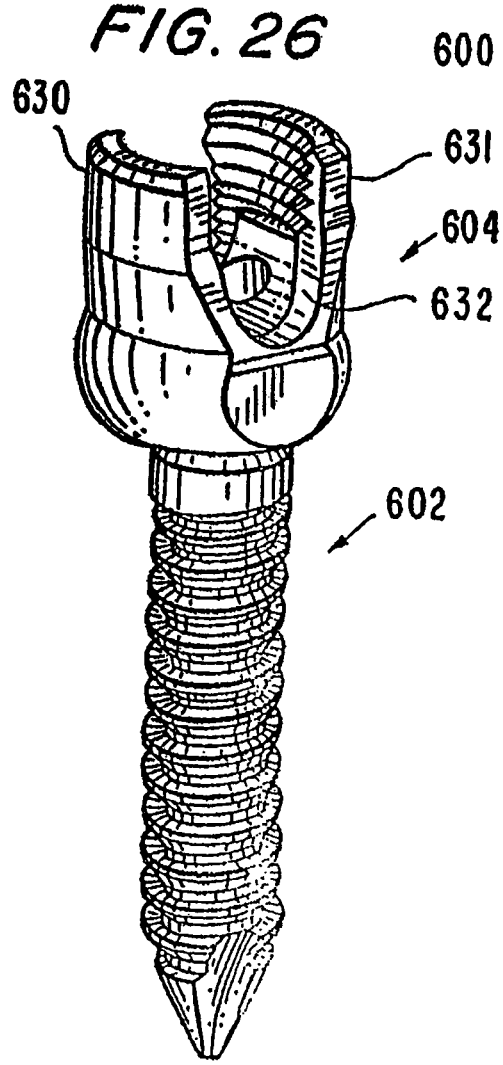
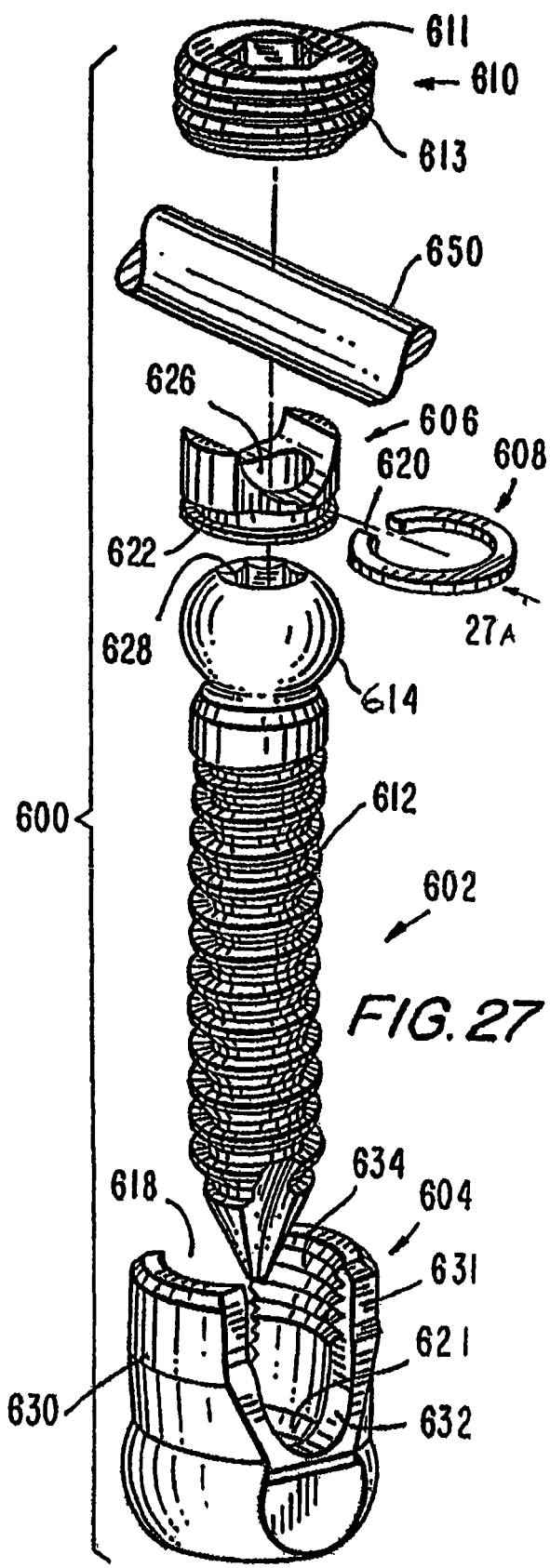

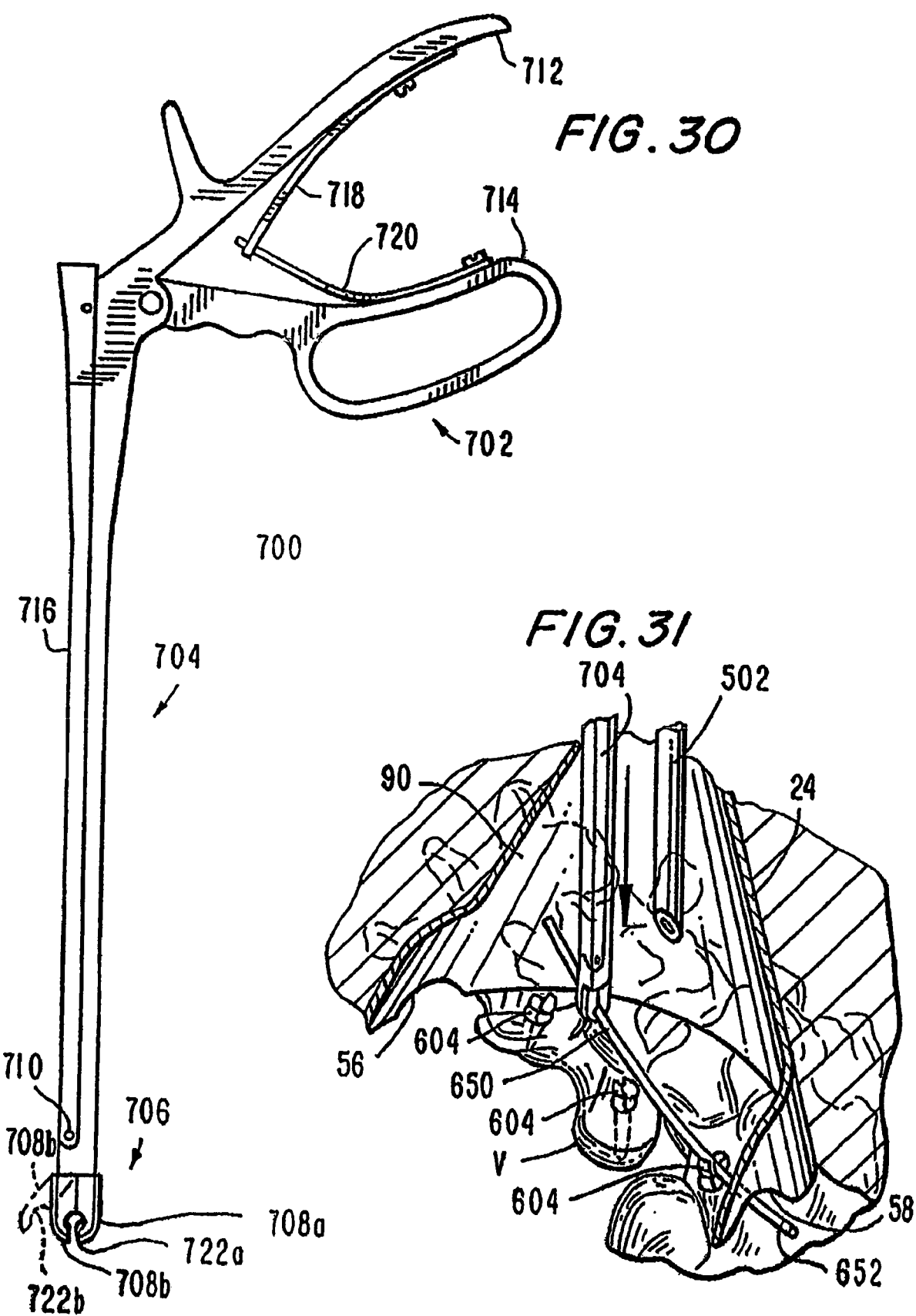

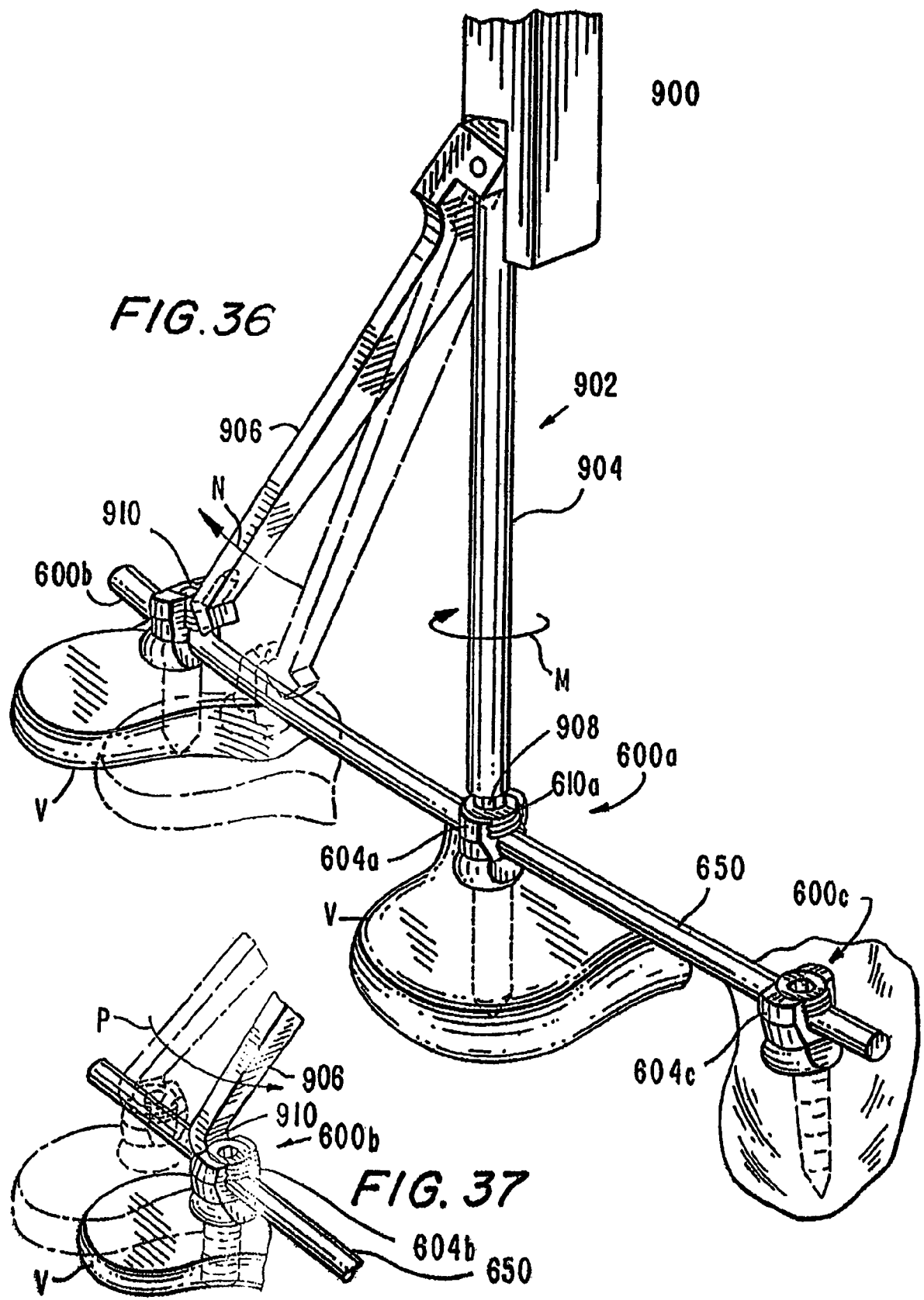

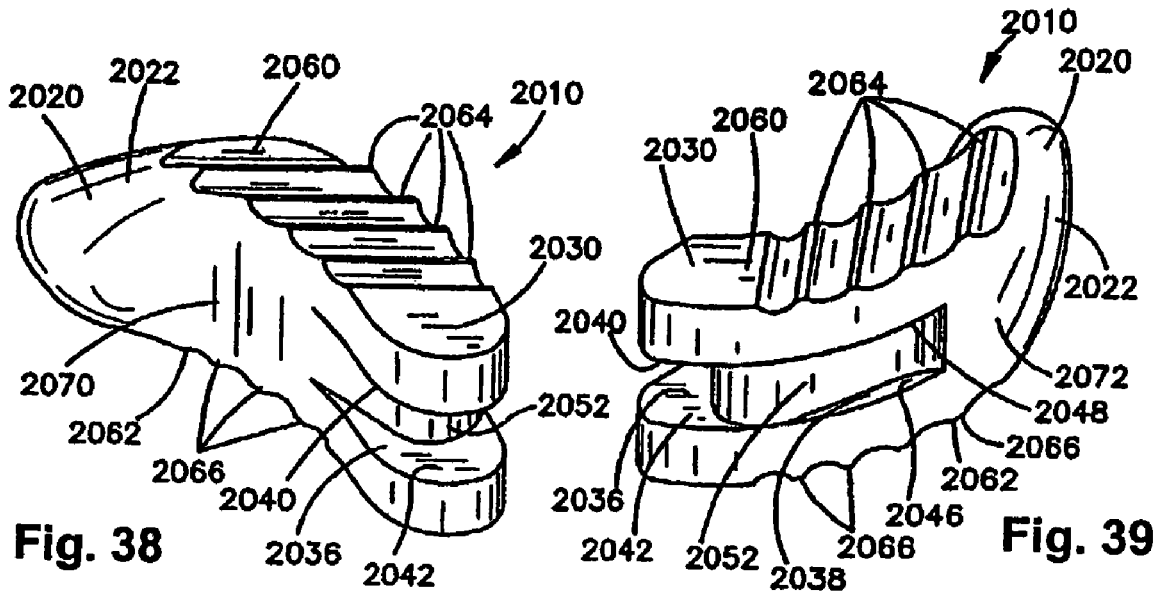
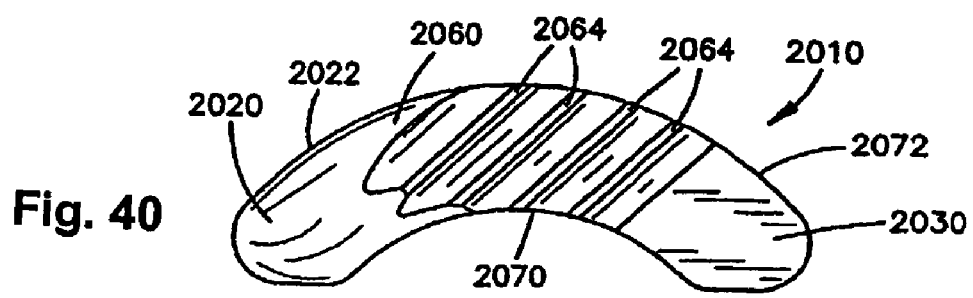
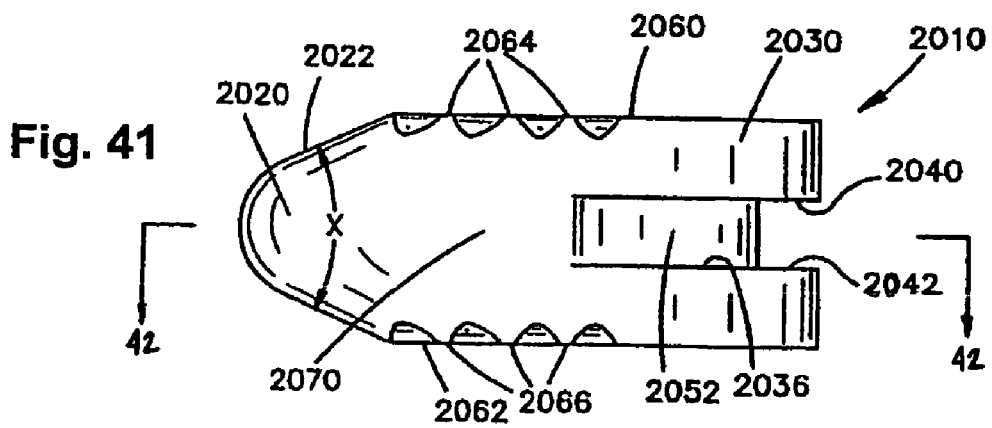
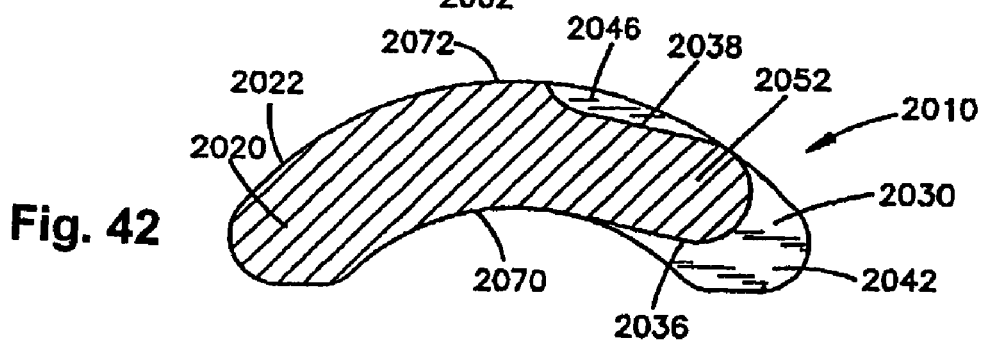

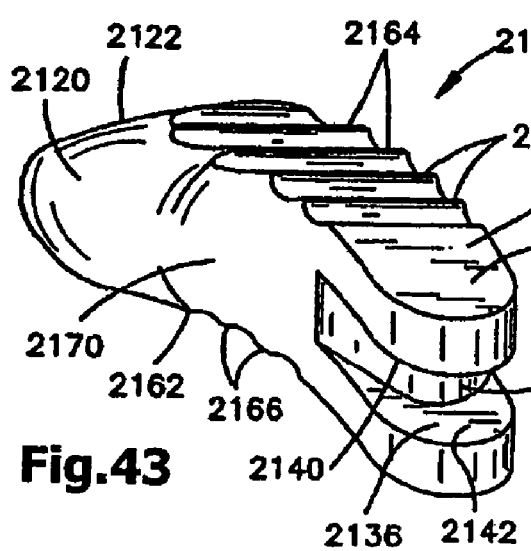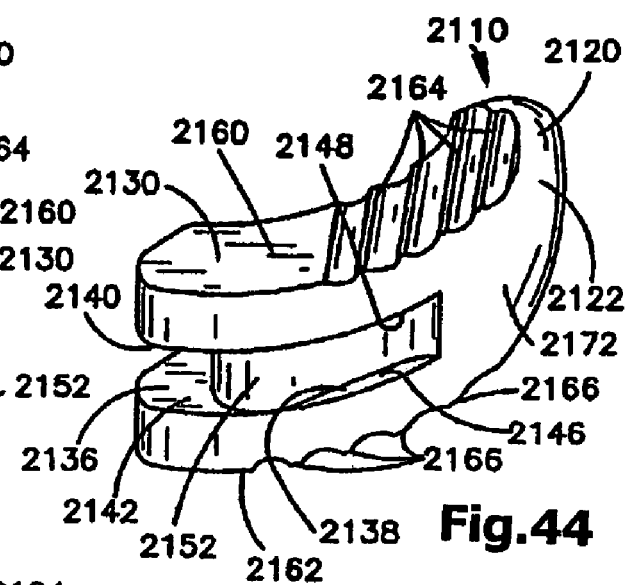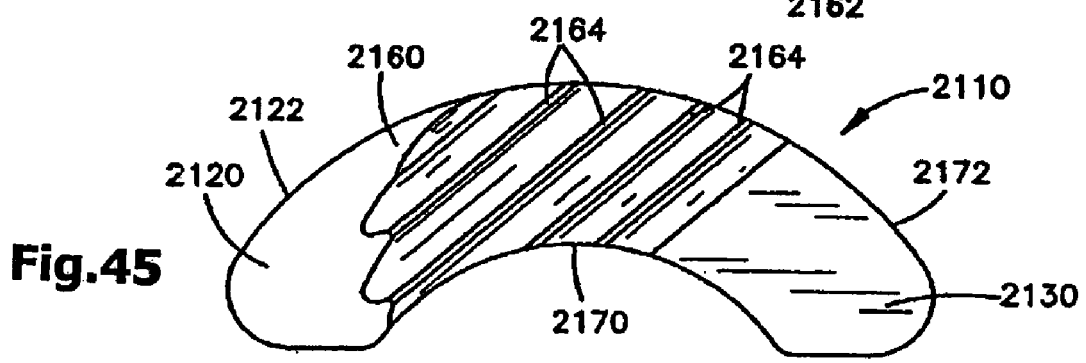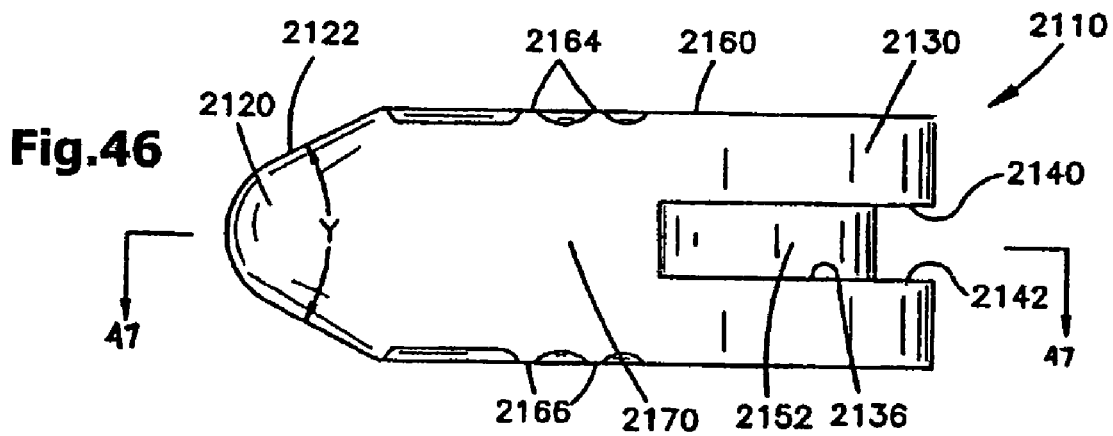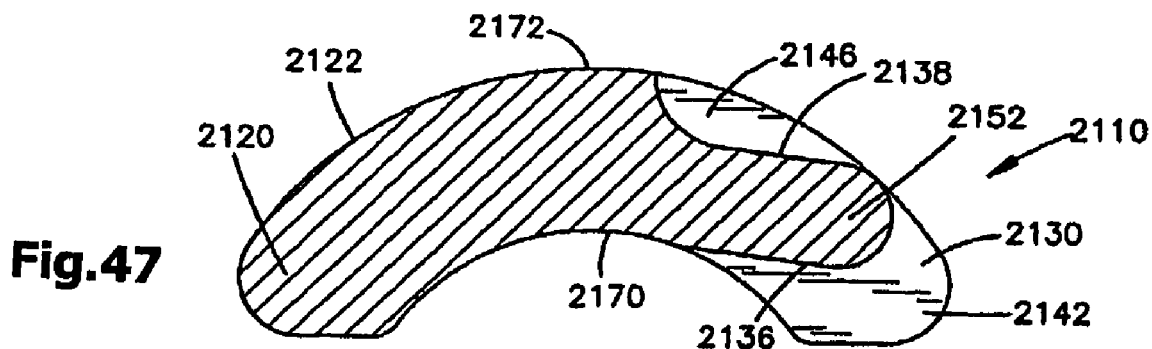

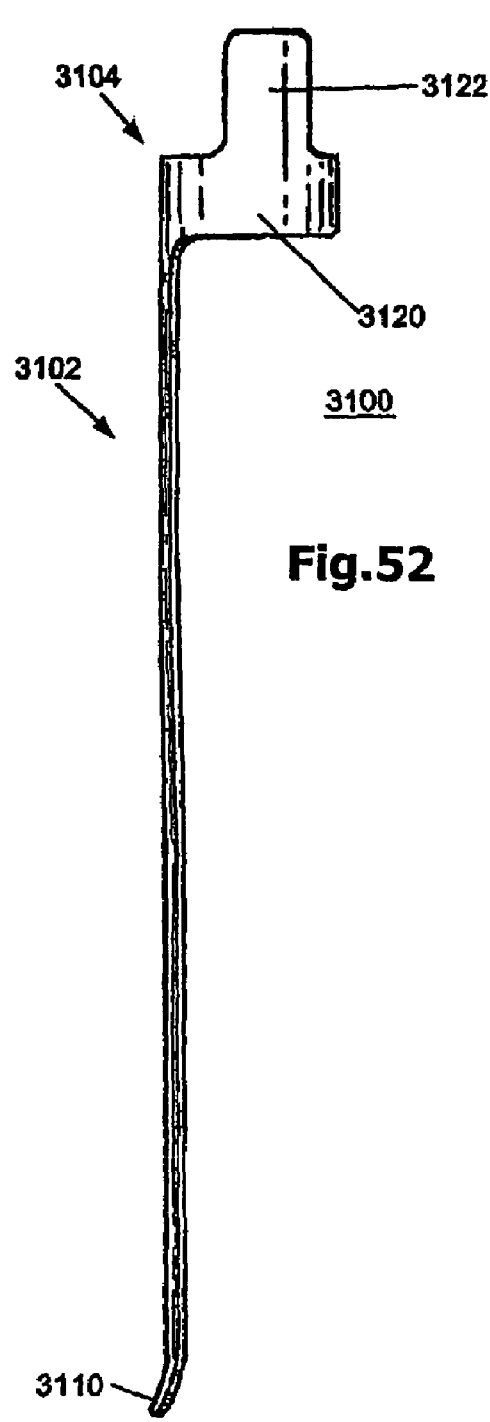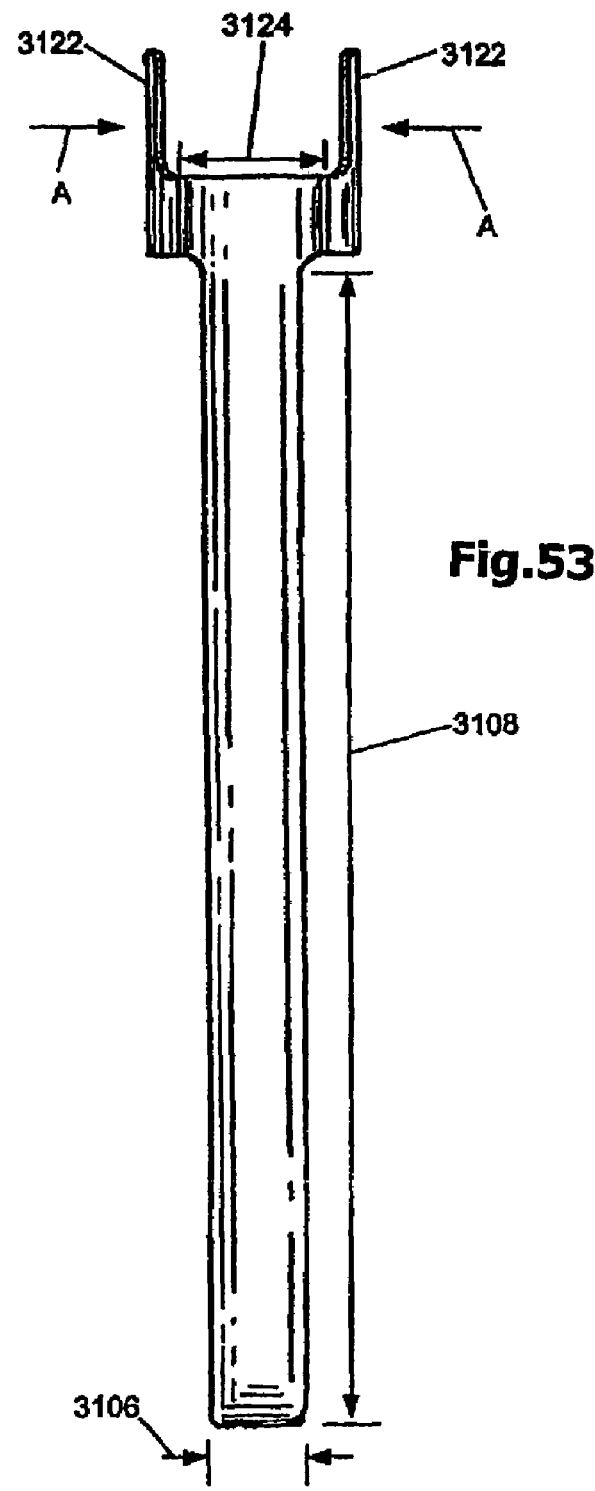
Fig.52
Fig.53

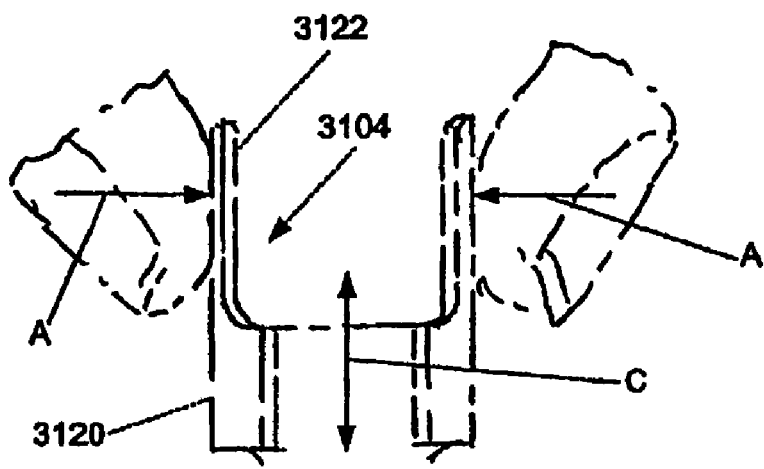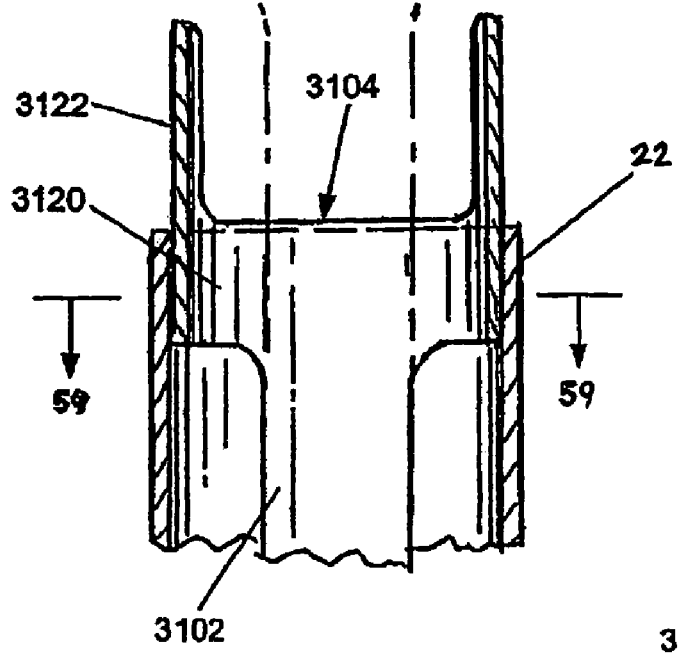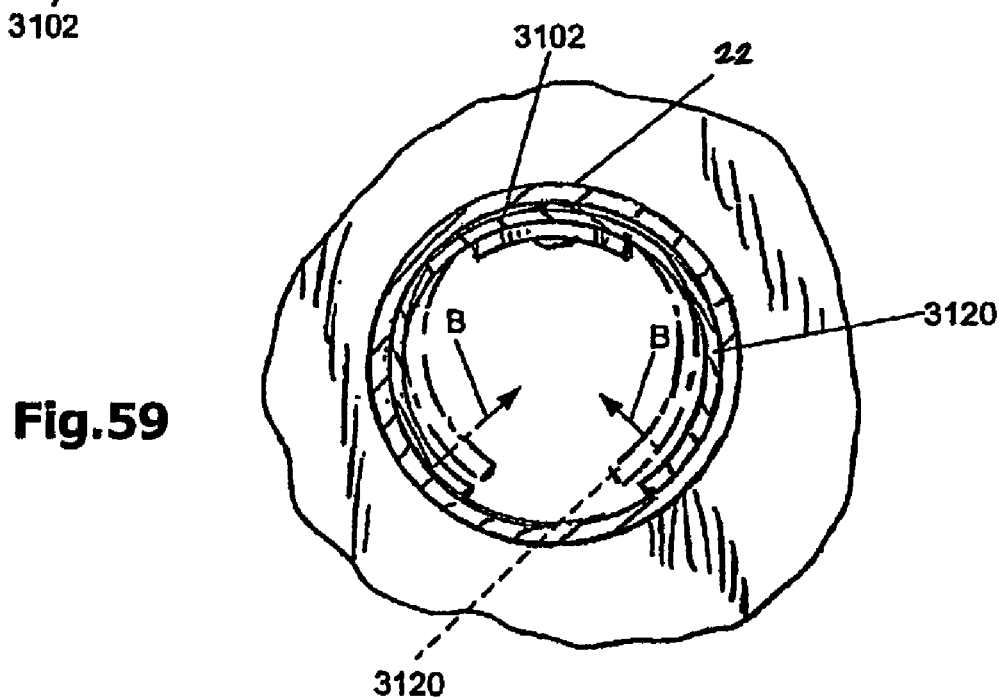
Fig.58
Fig.59

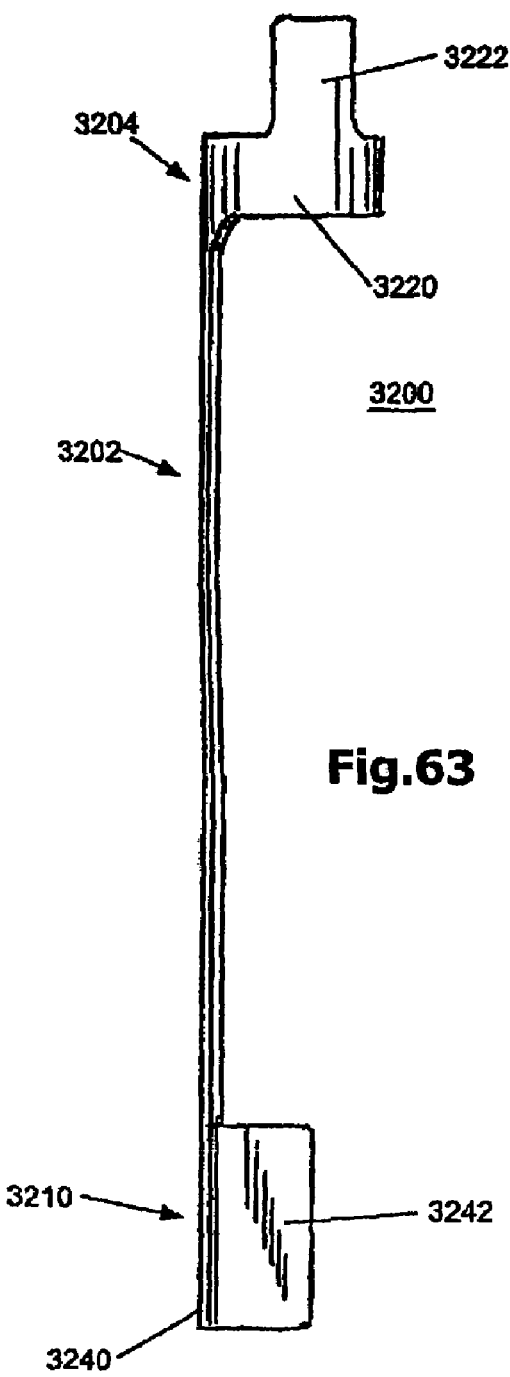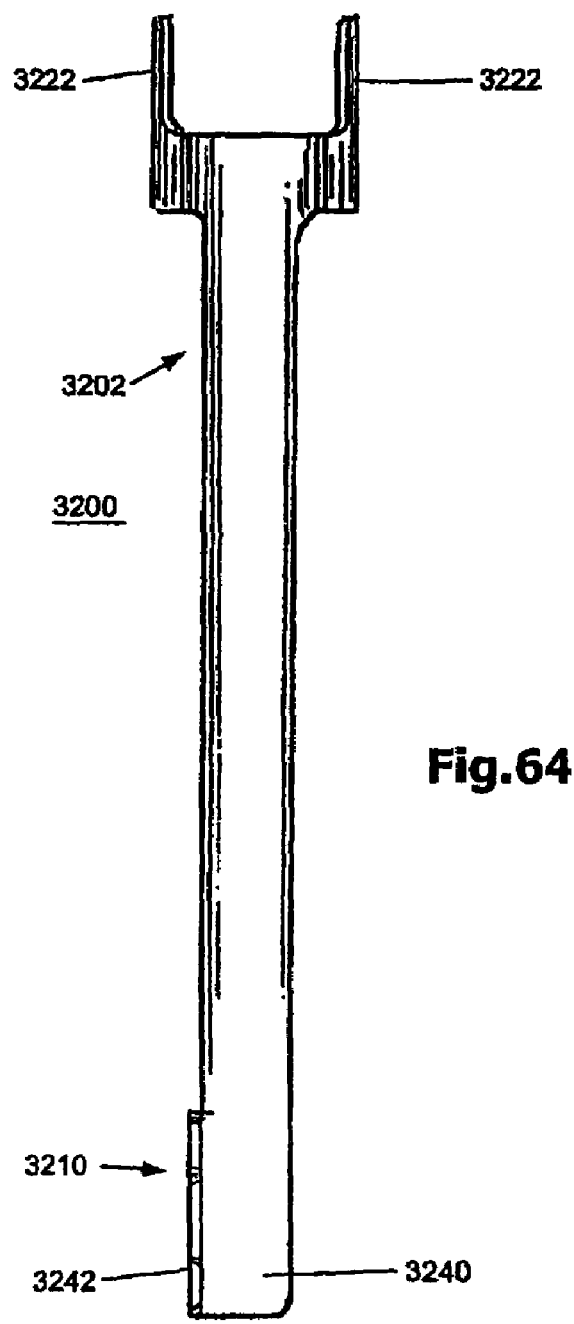
Fig.63
Fig.64

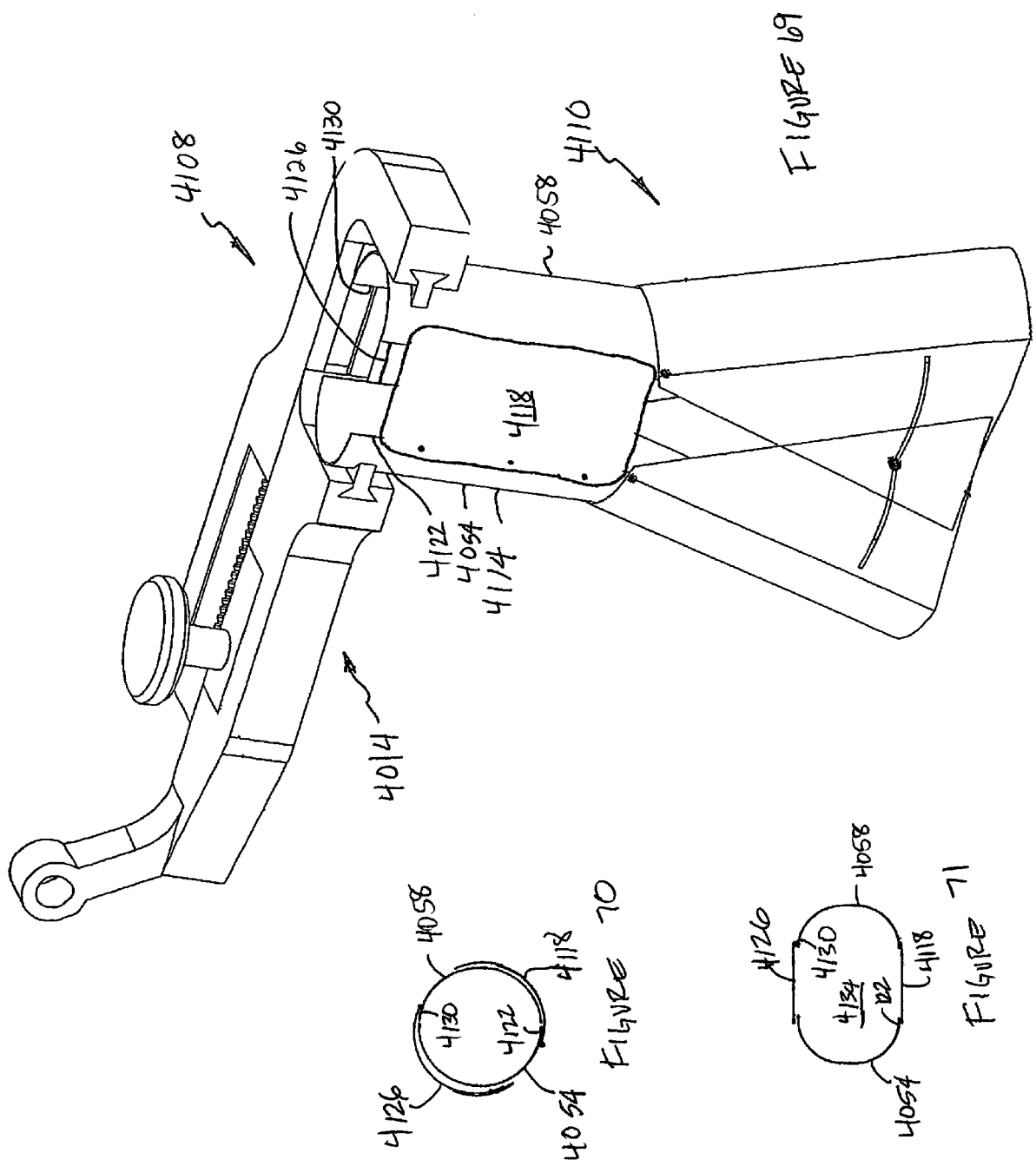

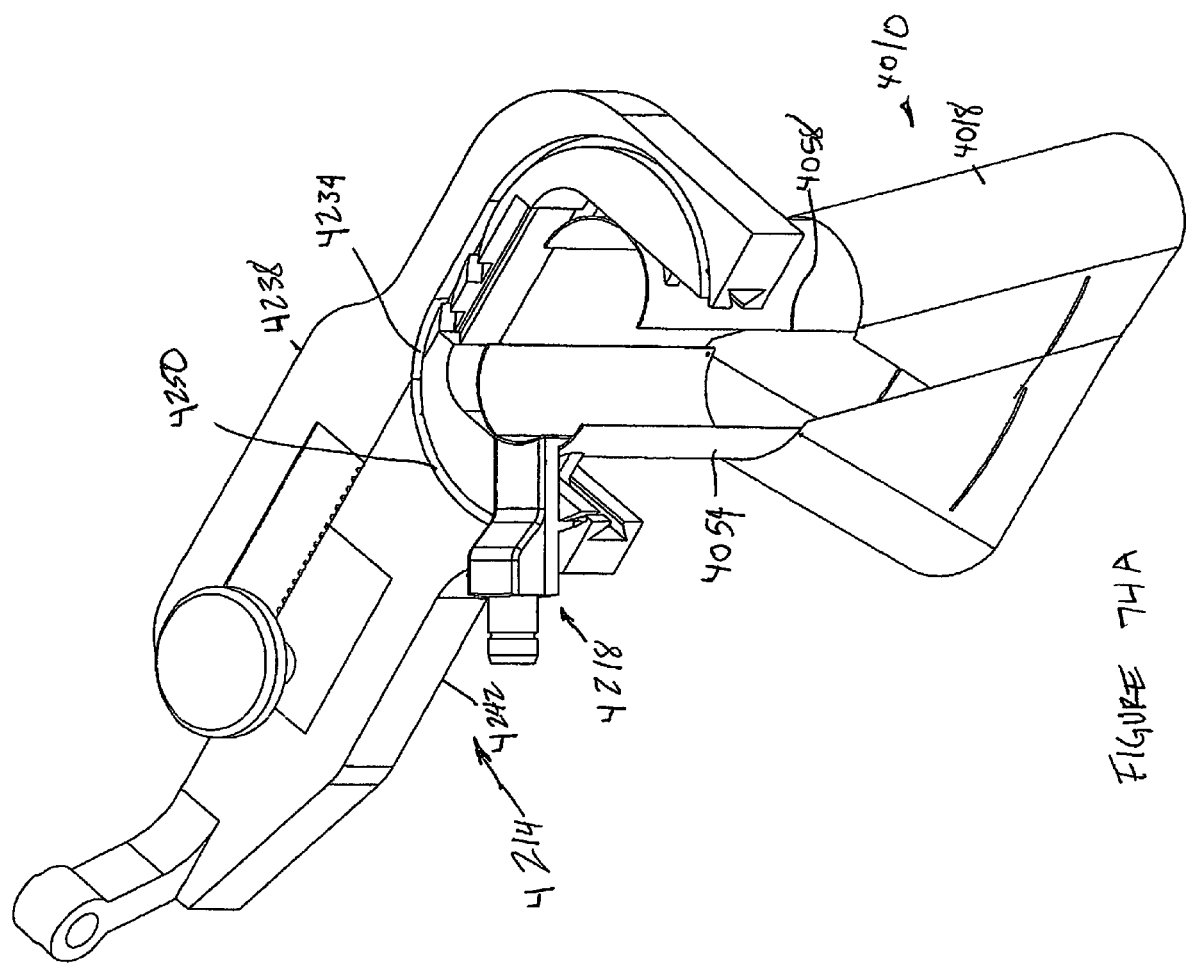

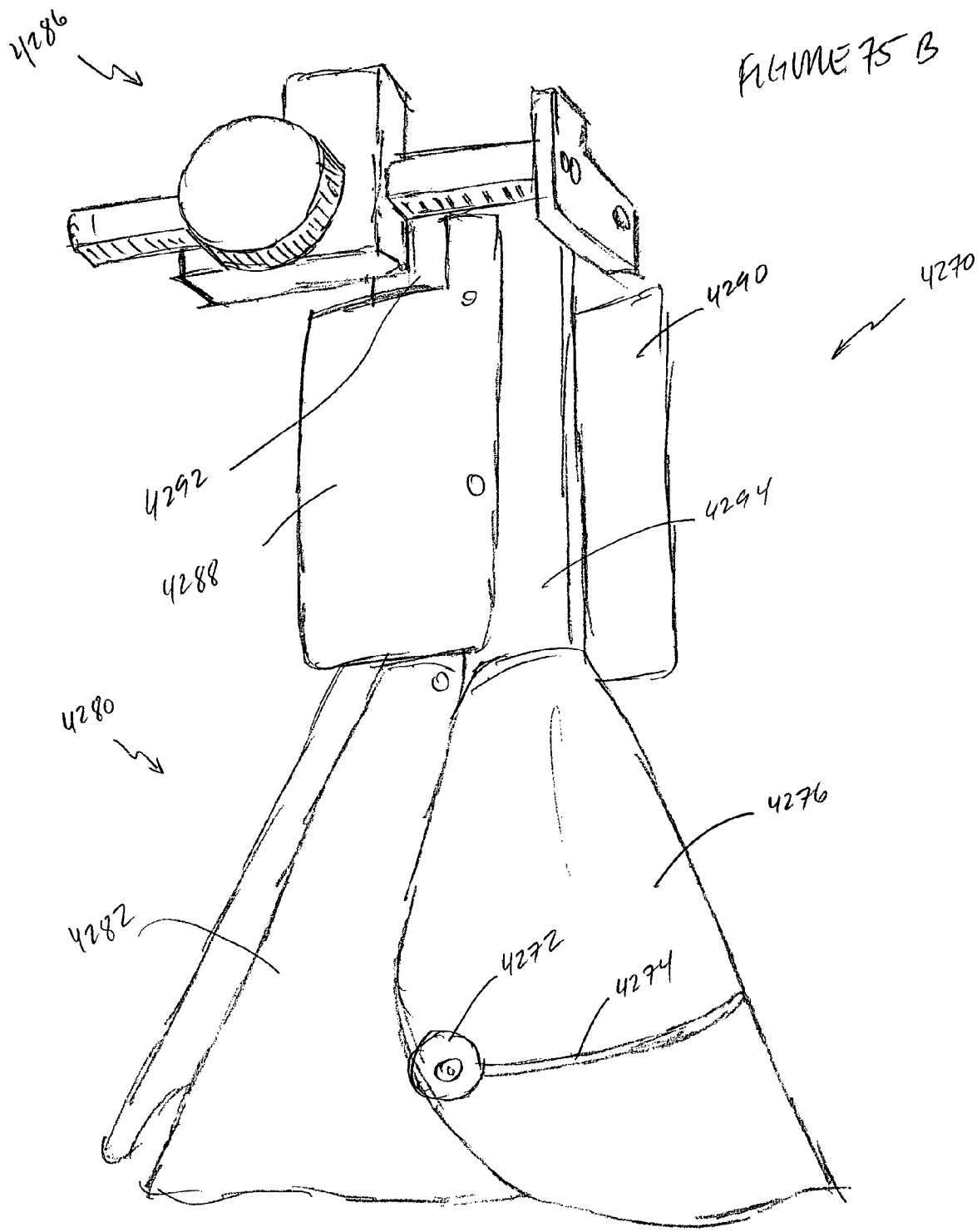

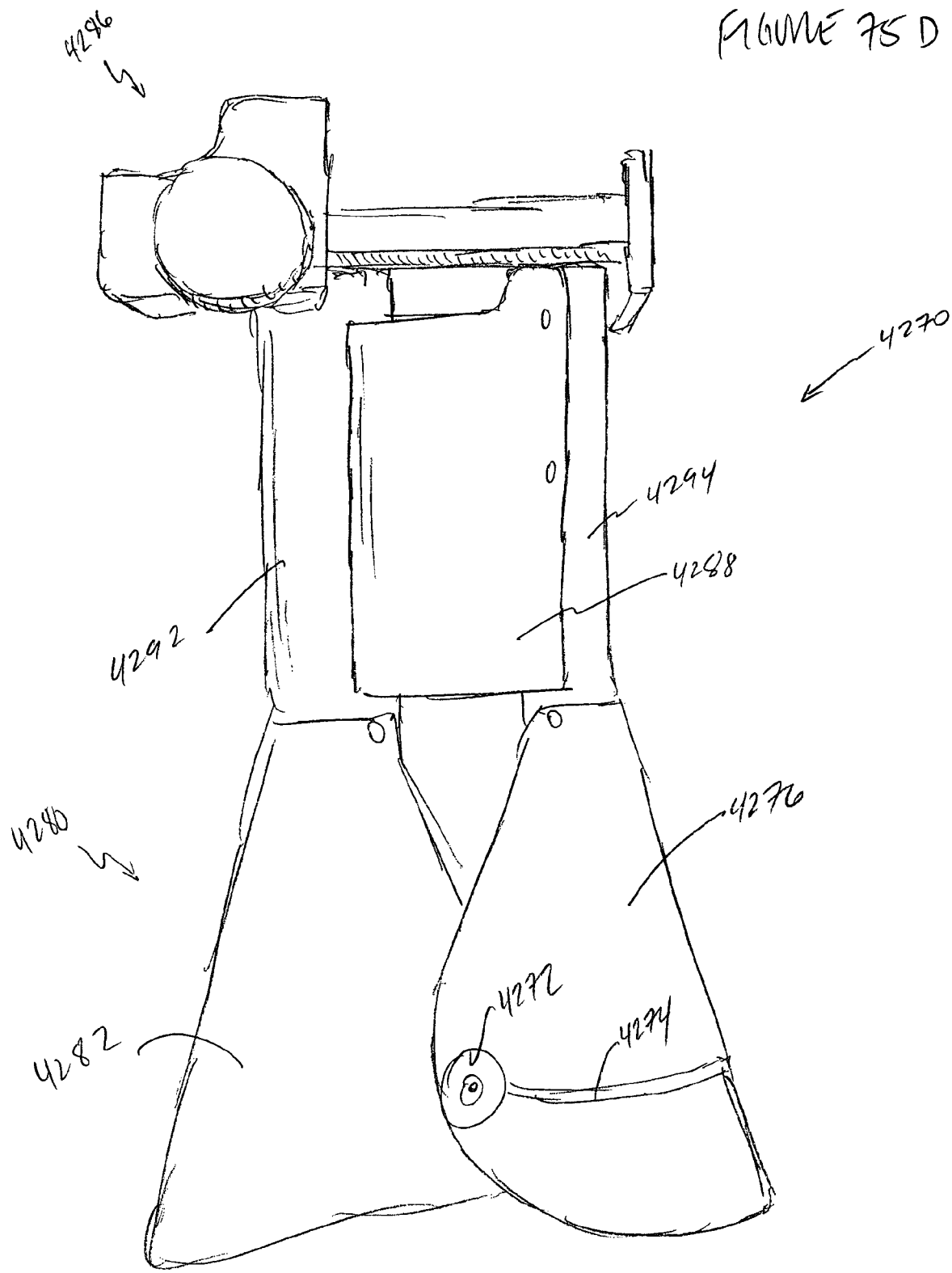

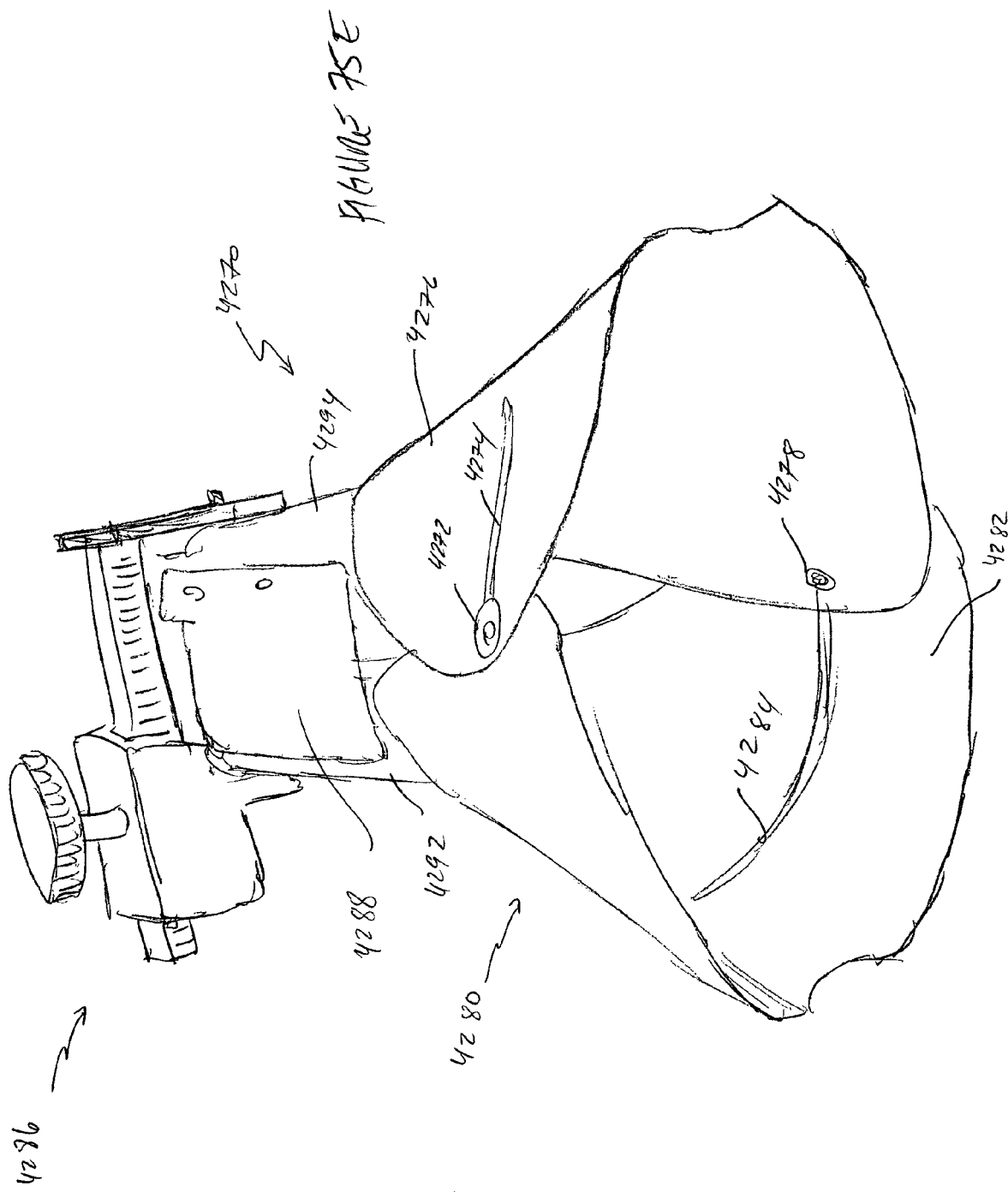

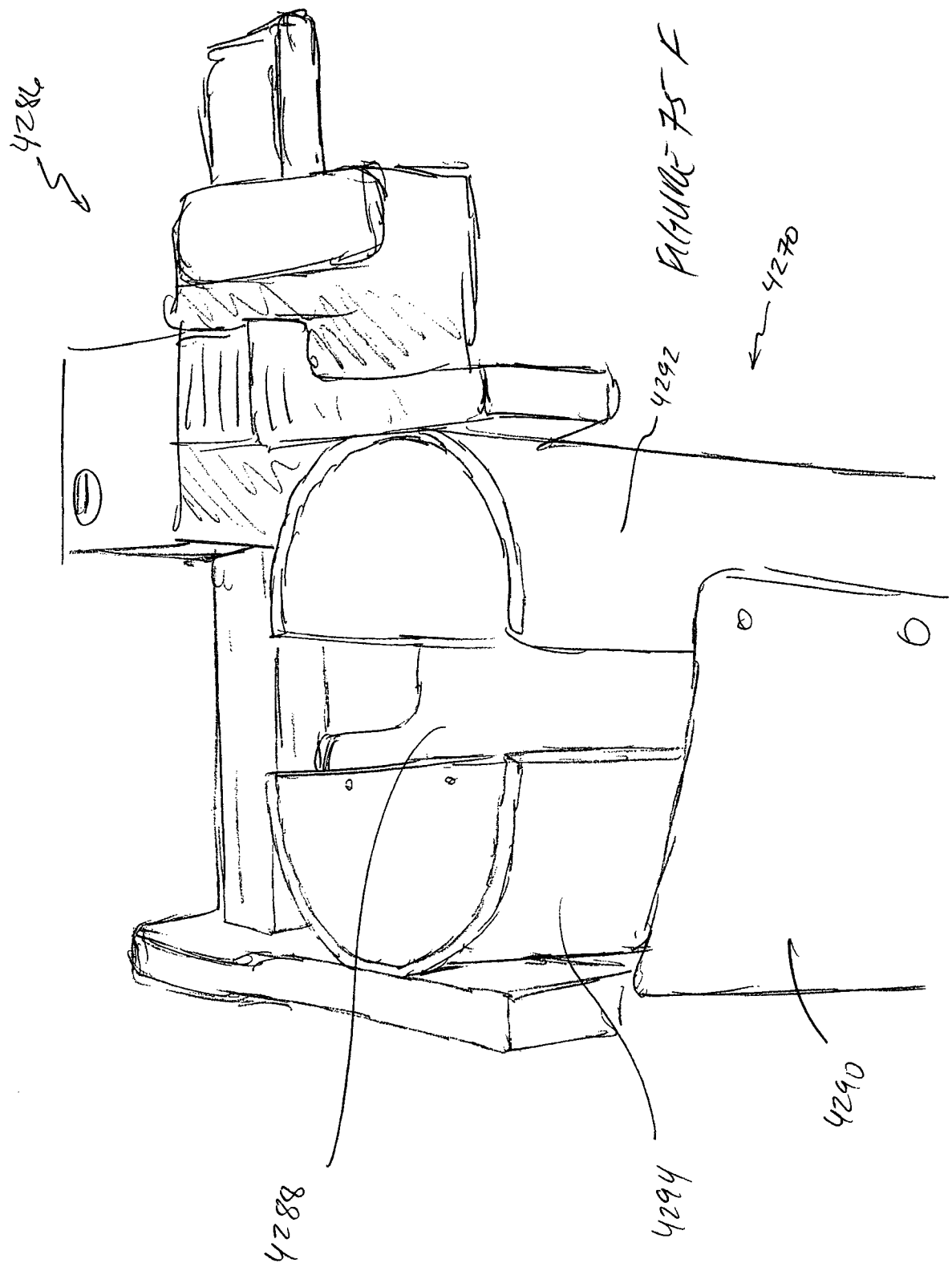

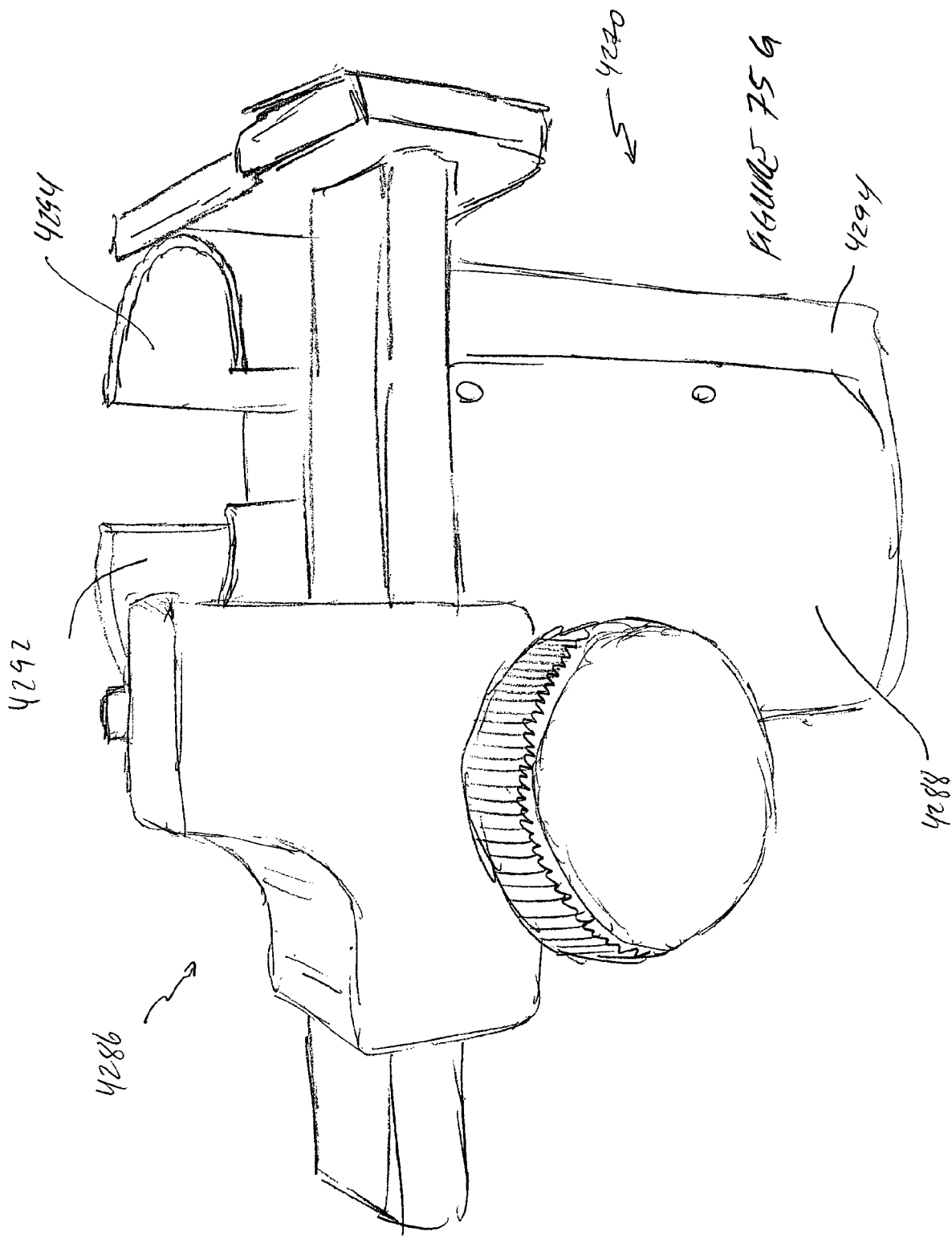

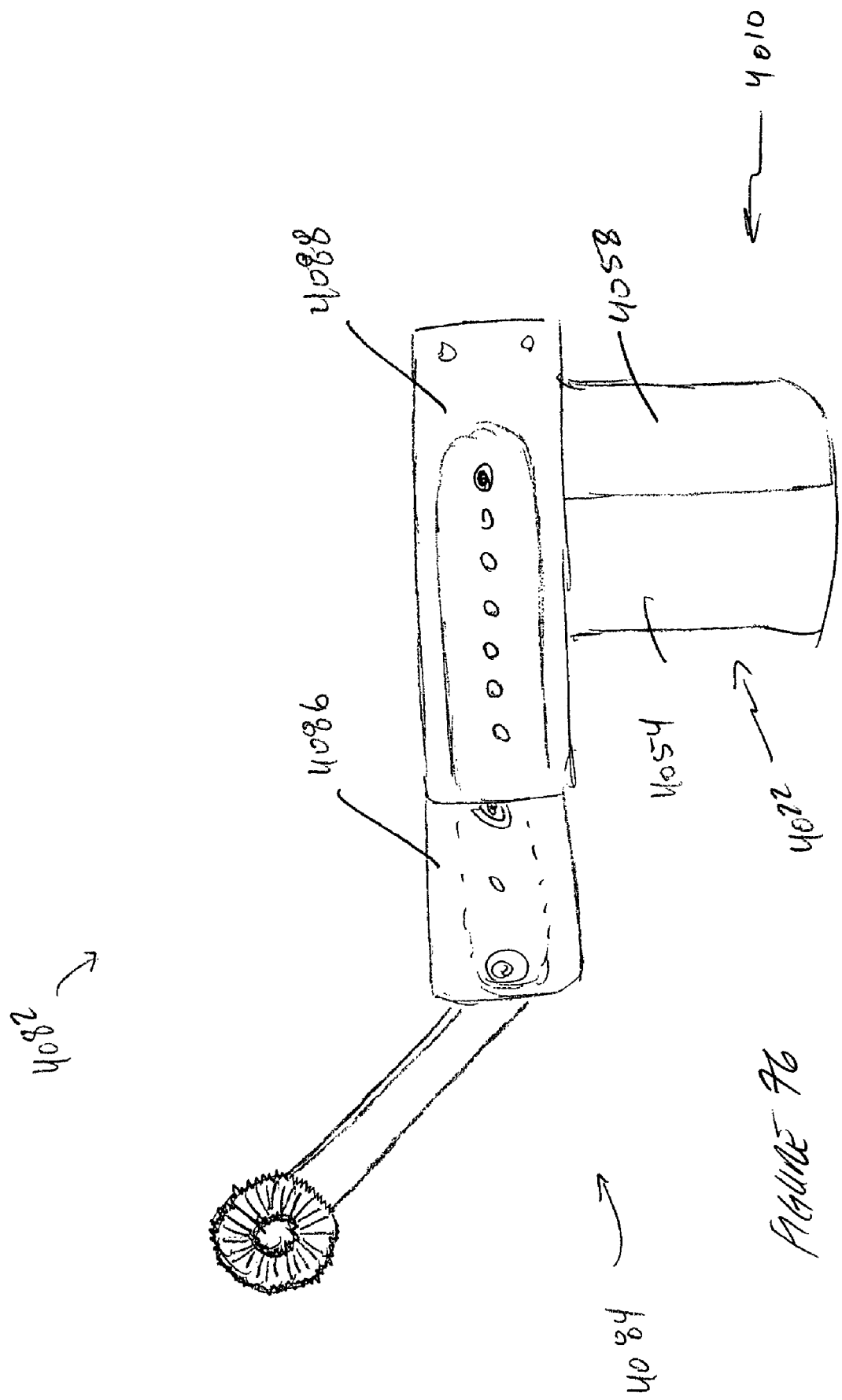

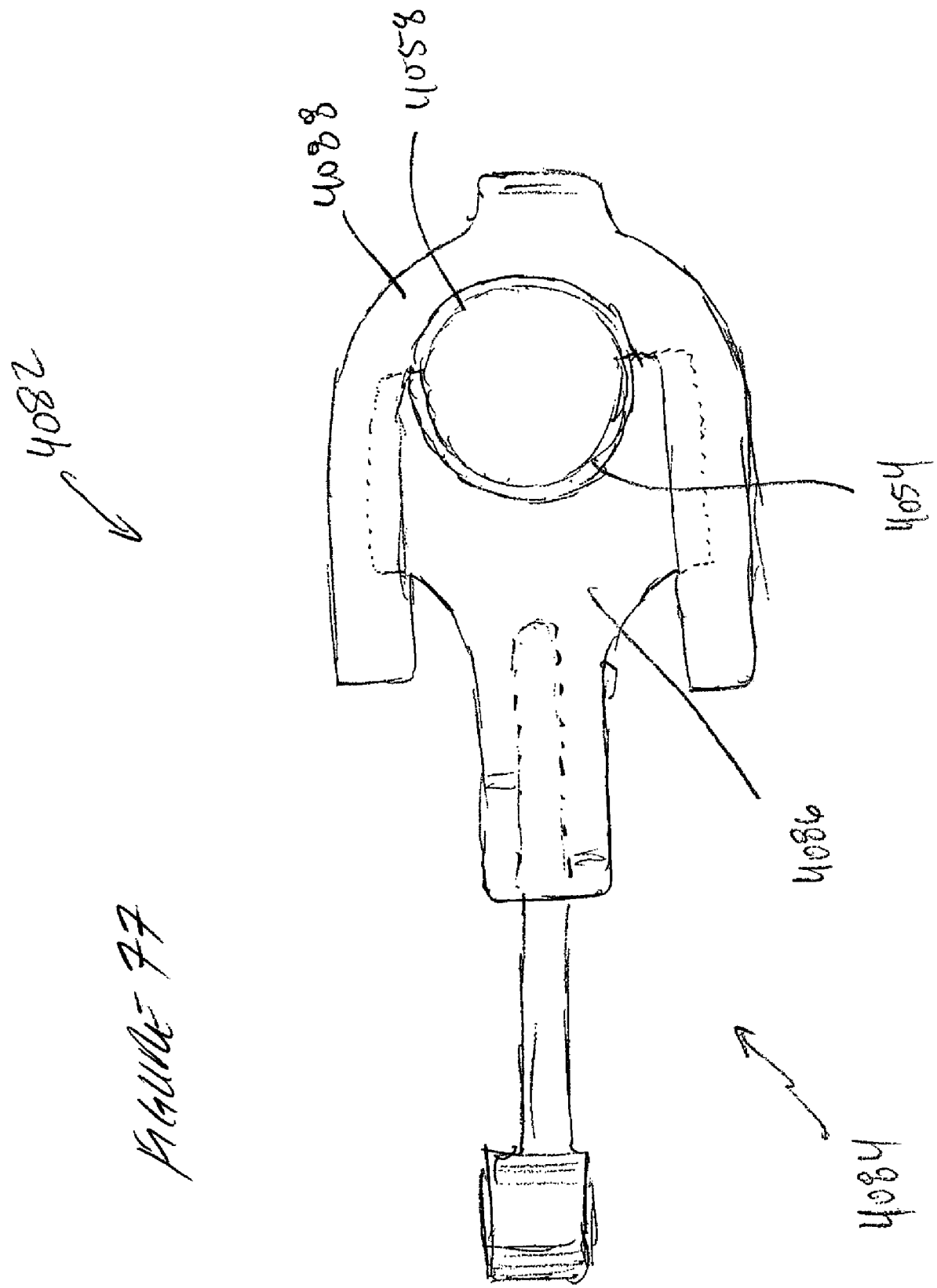

US 7,645,232 B2

ACCESS DEVICE FOR MINIMALLY INVASIVE SURGERY

PRIORITY INFORMATION

This application is based on and claims priority to U.S. Provisional Patent Applications No. 60/471,431 (filed May 16, 2003) and 60/513,796 (filed Oct. 22, 2003), the entire contents of both of which are hereby expressly incorporated by reference.

BACKGROUND OF THE INVENTION

1. Field of the Invention

This application relates to surgical systems and assemblies that include an access device for minimally invasive surgery, and in particular relates to systems and devices that provide access to a surgical location, e.g. adjacent a spine, for one or more instruments to perform a procedure at the surgical location.

2. Description of the Related Art

Spine surgery presents significant difficulties to the physician attempting to reduce chronic back pain or correct spinal deformities without introducing additional trauma due to the spine surgery itself. In order to access the vertebrae to perform spinal procedures, the physician typically makes large incisions and cuts or strips muscle tissue surrounding the spine. In addition, care must be taken not to injure nerve tissue in the area. Consequently, traditional spine surgery carries high risks of scarring, pain, significant blood loss, and extended recovery times.

Apparatuses for performing minimally invasive techniques have been proposed to reduce the trauma of spine surgery by reducing the size of the incision and the degree of muscle stripping in order to access the vertebrae. One such apparatus provides a constant diameter cannula that is made narrow in order to provide a small entry profile. As a result, the cannula provides minimal space for the physician to observe the anatomy and manipulate surgical instruments in order to perform the required procedures. For example, a narrow cannula is typically insufficient to perform one level spinal fixation procedures, which sometimes involves visualization of two vertebrae and introduction of screws, rods, and other large spinal fixation devices.

SUMMARY OF THE INVENTION

Accordingly, there is a need in the art for systems and methods for treating the spine that provide minimally invasive access to the spine such that a variety of procedures, and preferably the entire procedure or at least a substantial portion thereof, can be performed via a single access device.

In one embodiment, a device is provided for accessing a surgical location within a patient. The device comprises an elongate body having an outer surface and an inner surface, the inner surface defining a passage extending through the elongate body and through which multiple surgical instruments can be inserted simultaneously to the surgical location. The elongate body is capable of having a configuration when inserted within the patient wherein the cross-sectional area of the passage at a first location is greater than the cross-sectional area of the passage at a second location, wherein the first location is distal to the second location. In one embodiment, the first location is at the distal end of the elongate body, and the second location is at an intermediate location between the proximal and distal ends of the elongate body. The intermediate location separates the elongate body into proximal and distal portions.

The distal portion may comprise first and second overlapping sections which are expandable at both the proximal and distal ends thereof. The overlapping sections may be connected by one or more sliding rivets which extend through corresponding arcuate slots in each of the overlapping sections. The proximal portion may be pivotally mounted at a distal end thereof to the proximal ends of the overlapping sections. The proximal portion may also be expandable, and in one embodiment, the proximal portion expands such that the cross-sectional area of the passage in the proximal portion increases while remaining constant along the length of the proximal portion. In one embodiment, the proximal portion comprises half-tubes that are separable from each other in a direction perpendicular to a longitudinal axis of the elongate body. Once separated, the proximal portion in one embodiment defines a generally oval cross-sectional area or profile.

In one embodiment, the proximal portion of the device may be coupled with, e.g., supported by, a mount outside the body. The mount may include a fixed arm attached to one section of the proximal portion, e.g., one of the half-tubes, and an articulating arm attached to a second section of the proximal portion, e.g., the other of the half-tubes. A suitable mechanism, such as a rack and pinion mechanism, may be used to move the articulating arm relative to the fixed arm to expand the proximal portion.

Advantageously, the device as described herein allows for improved access to a surgical location, such as for performing a procedure on a spinal location. Preferably the expandable proximal portion of the device provides the operator with an enlarged passage at the proximal end of the access device to improve the field of vision to a working space near the distal end of the device. Moreover, the enlarged passage allows for multiple instruments to be placed in the passage, with the ability to articulate the instruments at desired angles to reach desired locations in the working space near the distal end of the device.

In another embodiment, a retractor comprises a proximal portion comprising a first side portion having a first longitudinal edge and a second side portion having a second longitudinal edge. The first and second portions being movable relative to each other such that the first and second longitudinal edges can be positioned in close proximity to each other or spaced apart by a selected distance. A distal portion is coupled with the proximal portion. The distal portion has an outer surface and an inner surface partially defining a passage. The distal portion is capable of having a configuration when inserted within the patient wherein the cross-sectional area of the passage at a first location is greater than the cross-sectional area of the passage at a second location, wherein the first location is distal to the second location.

In another embodiment, a surgical assembly is configured to facilitate surgical procedures. The surgical assembly comprises a fixture having a first arm, a second arm, a side surface, and an upper surface. The surgical assembly includes a retractor that has a low-profile configuration and an enlarged configuration. The retractor is coupled with the side surface of the fixture. The retractor comprises a first elongate body coupled with the first arm and a second elongate body coupled with the second arm. Each of the first elongate body and the second elongate body partially define a passage through which surgical instruments can be inserted to the surgical location. A viewing element is coupled with the upper surface of the fixture and extends adjacent the passage to assist in visualization of a surgical site.

In another embodiment, a system provides access to a surgical location adjacent the spine. The system comprises a fixture that has a first arm and a second arm capable of moving relative to the first arm. A retractor comprises a first elongate body coupled with the first arm. The first elongate body partially defines a passage through which surgical instruments can be inserted to the surgical location adjacent the spine. A second elongate body is coupled with the second arm. The second elongate body partially defines the passage. A shroud is coupled with an outside surface of one of the first elongate body and the second elongate body. The system is capable of having a low-profile configuration for insertion into the patient wherein the first elongate body is adjacent the second elongate body. The system is capable of having an enlarged profile configuration wherein a gap is provided between the first elongate body and the second elongate body. The shroud covers at least a portion of the gap.

In another embodiment, a method for accessing a surgical location within a patient comprises providing a retractor for insertion into the patient. The retractor has a first elongate body, a second elongate body, and a shroud. The first and second elongate bodies partially define a passage through which surgical instruments can be inserted to the surgical location. The shroud is coupled with an outside surface of one of the first elongate body and the second elongate body. The retractor is positioned in a low-profile configuration for insertion into the patient. In the low-profile configuration, the first elongate body is adjacent the second elongate body. The retractor is positioned in an enlarged profile configuration. In the enlarged profile configuration, a gap is provided between the first elongate body and the second elongate body. The shroud covers at least a portion of the gap.

In another embodiment, a method for accessing a surgical location within a patient, comprises providing a retractor for insertion into the patient. The retractor has a proximal portion and a distal portion. The proximal portion has a first longitudinal edge on a first side portion and a second longitudinal edge on a second side portion. The distal portion is coupled with the proximal portion and has an outer surface and an inner surface partially defining a passage. The retractor is inserted into the patient to the surgical location with the first and second longitudinal edges of the proximal portion positioned in close proximity to each other. The retractor is configured such that the first and second longitudinal edges are spaced apart by a selected distance. The retractor is configured such that the cross-sectional area of the passage at a first location is greater than the cross-sectional area of said passage at a second location the first distal the second.

In another embodiment, a method for facilitating access to a surgical location within a patient is provided. A surgical assembly having a fixture, a retractor and a viewing element is provided. The fixture has a first arm, a second arm, a side surface, and an upper surface. The retractor has a first elongate body and a second elongate body. The retractor has a low-profile configuration and an enlarged configuration. The first elongate body of the retractor is coupled with the first arm and the second elongate body is coupled with the second arm. The fixture is articulated such that the retractor is in a low profile configuration. The retractor is inserted into the patient. The fixture is articulated such that the retractor is in an enlarged configuration. The viewing element is coupled with the upper surface of the fixture to direct the viewing element toward the surgical site to provide enhanced viewing of the surgical site.

BRIEF DESCRIPTION OF THE DRAWINGS

Further objects, features and advantages of the invention will become apparent from the following detailed description taken in conjunction with the accompanying figures showing illustrative embodiments of the invention, in which:

FIG. 2 is a perspective view of one embodiment of an access device in a reduced profile configuration.

FIG. 3 is a perspective view of the access device of FIG. 2 in a first enlarged configuration.

FIG. 4 is a perspective view of the access device of FIG. 2 in a second enlarged configuration.

FIG. 20 is a side view of the endoscope mount platform of FIG. 18 illustrated with one embodiment of an indexing arm and one embodiment of an endoscope.

FIG. 21 is a perspective view of one embodiment of an indexing collar of the endoscope mount platform FIG. 18.

FIG. 23C is a top view of the access system of FIG. 23A.

FIG. 24A is a perspective view of one embodiment of a lighting element.

FIG. 25 is a partial sectional view of one stage of one application of a method for treating the spine of a patient.

FIG. 26 is a perspective view of one embodiment of a fastener.

FIG. 27 is an exploded perspective view of the fastener of FIG. 26.

FIG. 27A is an enlarged side view of one embodiment of a biasing member illustrated in FIG. 27 taken from the perspective of the arrow 27A.

FIG. 30 is side view of one embodiment of another surgical instrument.

FIG. 31 is a partial sectional view of one stage of one application for treating the spine of a patient.

FIG. 36 is an enlarged view in partial section illustrating one stage of one application for treating the spine of a patient.

FIG. 37 is a partial view of illustrating one stage of one application for treating the spine of a patient.

FIG. 38 is a perspective view of a spinal implant or fusion device constructed according to another embodiment showing a first side surface of the spinal implant.

FIG. 39 is a perspective view of the spinal implant of FIG. 38 showing a second side surface of the spinal implant.

FIG. 40 is a plan view of the spinal implant of FIG. 38 showing an upper surface of the spinal implant.

FIG. 41 is a side view of the spinal implant of FIG. 38 showing the first side surface.

FIG. 42 is a cross-sectional view of the spinal implant taken along the line 42-42 in FIG. 41.

FIG. 43 is a perspective view of another embodiment of a spinal implant constructed according to another embodiment showing a first side surface of the spinal implant.

FIG. 44 is a perspective view of the spinal implant of FIG. 43 showing a second side surface of the spinal implant.

FIG. 45 is a plan view of the spinal implant of FIG. 43 showing an upper surface of the spinal implant.

FIG. 46 is a side view of the spinal implant of FIG. 43 showing the first side surface.

FIG. 47 is a cross-sectional view of the spinal implant taken along the line 47-47 in FIG. 46.

FIG. 52 is a side view of an apparatus according to another embodiment.

FIG. 53 is a front view of the apparatus of FIG. 52.

FIG. 58 is a longitudinal sectional view of the apparatus of FIG. 57 taken from line 58-58 of FIG. 57.

FIG. 59 is a transverse sectional view of the apparatus of FIG. 58 taken from line 59-59 of FIG. 58.

FIG. 63 is a side view, similar to FIG. 52, of another apparatus.

FIG. 64 is a front view, similar to FIG. 55, of the embodiment of FIG. 63.

FIG. 69 is a perspective view of another embodiment of an access device coupled with a mount for supporting the access device.

FIG. 70 is a schematic top view of a proximal end of a proximal portion of the access device of FIG. 69, wherein the access device is in a wrapped configuration.

FIG. 71 is a schematic top view of the proximal end of the proximal portion of the access device of FIG. 69, wherein the access device is in an unwrapped configuration.

FIG. 74A-74B illustrate the operation of the multi-leaved track of FIG. 72 when the access device is in the second position.

FIG. 75B is a side view of the access device of FIG. 75A.

FIG. 75D is a side view of the access device of FIG. 75C.

FIGS. 75E-75G are perspective views of the access device of FIG. 75C.

FIG. 76 is a font view of an access assembly that includes a mount fixture and an access device, shown in a contracted configuration.

FIG. 77 is a top view of the access assembly of FIG. 76, shown in the contracted configuration.

Figure 1:
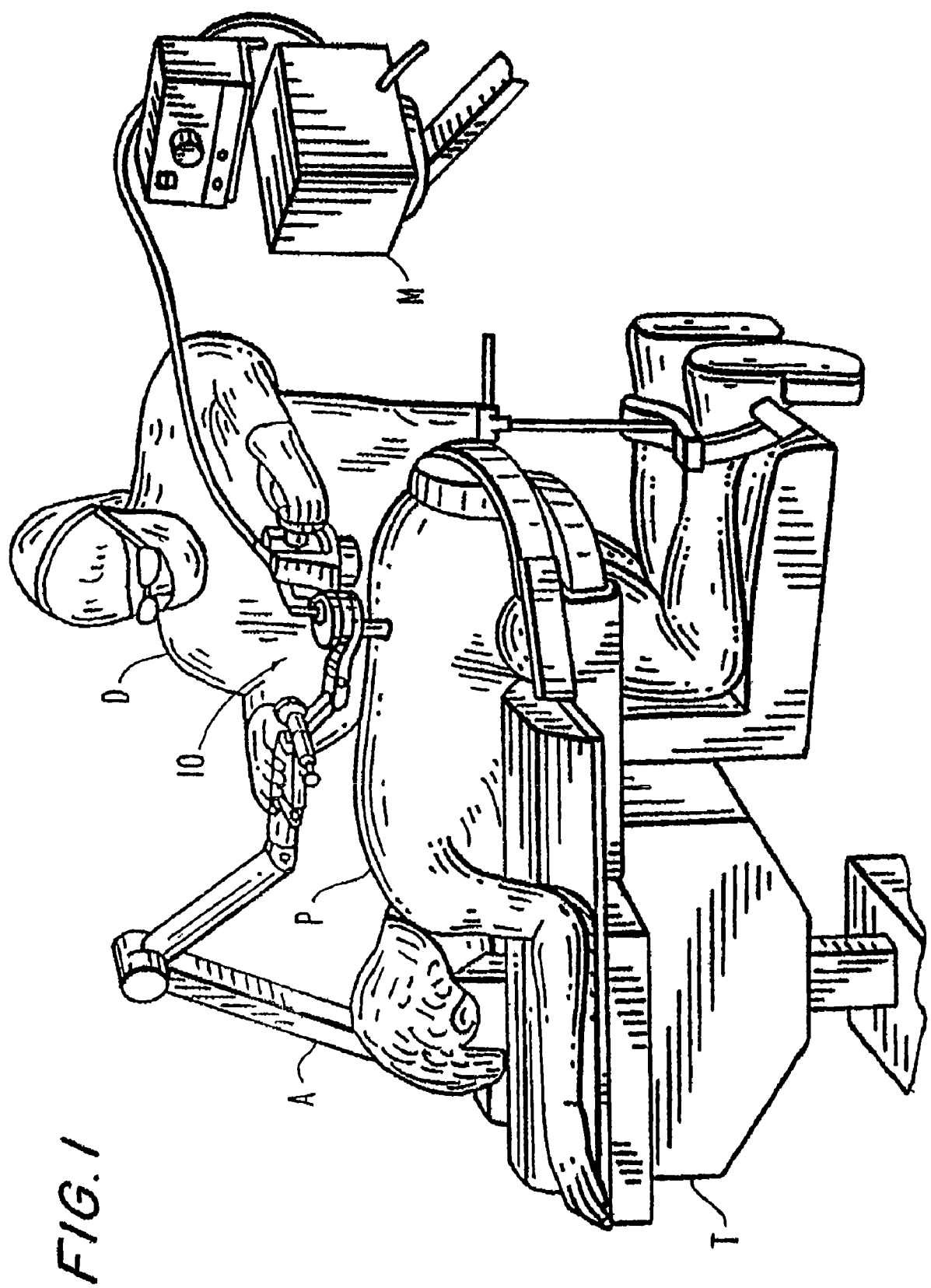
FIG. 1 is a perspective view of one embodiment of a surgical system and one application for treating the spine of a patient.
Figure 6:
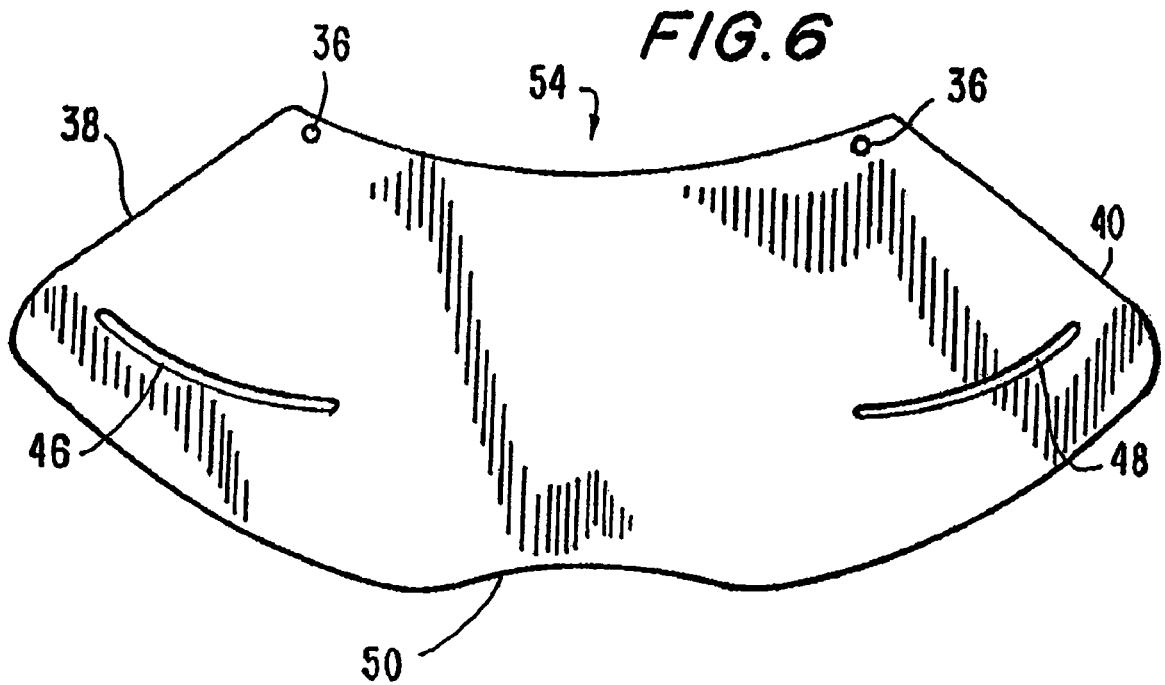
FIG. 6 is a view of another embodiment of a skirt portion of an access device.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention.

DETAILED DESCRIPTION OF THE PREFERRED EMBODIMENT

As should be understood in view of the following detailed description, this application is primarily directed to apparatuses and methods providing access to and for treating the spine of a patient. The apparatuses described below provide access to surgical locations at or near the spine and provide a variety of tools useful treating the spine. In particular, some embodiments described hereinbelow include access devices that are particularly well adapted for multistage expansion. In some embodiments, an access device is provided with an expandable proximal portion that is configured to expand to increase the size of a passage defined by the access device. The apparatuses described herein enable a surgeon to perform a wide variety of methods of treatment as described herein.

I. Systems for Performing Procedures at a Surgical Location

Various embodiments of apparatuses and procedures described herein will be discussed in terms of minimally invasive procedures and apparatuses, e.g., of endoscopic apparatuses and procedures. However, various embodiments may find use in conventional, open, and mini-open procedures. As used herein, the term "proximal," as is traditional, refers to the end portion of an apparatus that is closest to the operator, while the term "distal" refers to the end portion that is farthest from the operator.

FIG. 1 shows one embodiment of a surgical system 10 that can be used to perform a variety of methods or procedures. In one embodiment, as discussed more fully below, the patient P is placed in the prone position on operating table T, taking care that the abdomen is not compressed and physiological lordosis is preserved. The physician D is able to access the surgical site and perform the surgical procedure with the components of the system 10, which will be described in greater detail herein. The system 10 may be supported, in part, by a mechanical support arm A, such as the type generally disclosed in U.S. Pat. No. 4,863,133, which is hereby incorporated by reference herein in its entirety. One mechanical arm of this type is manufactured by Leonard Medical, Inc., 1464 Holcomb Road, Huntington Valley, Pa., 19006. The mechanical support arm A is sometimes referred to as a "flex arm." As discussed in greater detail below, the mechanical support arm A is coupled with at least one of an access device and a viewing element.

The term "access device" is used in its ordinary sense to mean a device that can provide access and is a broad term and it includes structures having an elongated dimension and defining a passage, e.g., a cannula or a conduit. The access device is configured to be inserted through the skin of the patient to provide access during a surgical procedure to a surgical location within a patient, e.g., a spinal location. The term "surgical location" is used in its ordinary sense (i.e. a location where a surgical procedure is performed) and is a broad term and it includes locations subject to or affected by a surgery. The term "spinal location" is used in its ordinary sense (i.e. a location at or near a spine) and is a broad term and it includes locations adjacent to or associated with a spine that may be sites for surgical spinal procedures. The access device also can retract tissue to provide greater access to the surgical location. The term "retractor" is used in its ordinary sense to mean a device that can displace tissue and is a broad term and it includes structures having an elongated dimension and defining a passage, e.g., a cannula or a conduit, to retract tissue.

Visualization of the surgical site may be achieved in any suitable manner, e.g., by direct visualization, or by use of a viewing element, such as an endoscope, a camera, loupes, a microscope, or any other suitable viewing element, or a combination of the foregoing. The term "viewing element" is used in its ordinary sense to mean a device useful for viewing and is a broad term and it also includes elements that enhance viewing, such as, for example, a light source or lighting element. In one embodiment, the viewing element provides a video signal representing images, such as images of the surgical site, to a monitor M. The viewing element may be an endoscope and camera that captures images to be displayed on the monitor M whereby the physician D is able to view the surgical site as the procedure is being performed. The endoscope and camera will be described in greater detail herein.

The systems are described herein in connection with minimally invasive postero-lateral spinal surgery. One such procedure is a two level postero-lateral fixation and fusion of the spine involving the L4, L5, and S1 vertebrae. In the drawings, the vertebrae will generally be denoted by reference letter V. The usefulness of the apparatuses and procedures is neither restricted to the postero-lateral approach nor to the L4, L5, and S1 vertebrae. The apparatuses and procedures may be used in other anatomical approaches and with other vertebra (e) within the cervical, thoracic, and lumbar regions of the spine. The procedures may be directed toward surgery involving one or more vertebral levels. Some embodiments are useful for anterior and/or lateral procedures. A retroperitoneal approach can also be used with some embodiments. In one retroperitoneal approach, an initial transverse incision is made just left of the midline, just above the pubis, about 3 centimeters in length. The incision can be carried down through the subcutaneous tissues to the anterior rectus sheath, which is incised transversely and the rectus is retracted medially. At this level, the posterior sheath, where present, can be incised. With blunt finger dissection, the retroperitoneal space can be entered. The space can be enlarged with blunt dissection or with a retroperitoneal balloon dissector. The peritoneal sack can be retracted, e.g., by one of the access devices described herein.

It is believed that embodiments of the invention are also particularly useful where any body structures must be accessed beneath the skin and muscle tissue of the patient, and/or where it is desirable to provide sufficient space and visibility in order to manipulate surgical instruments and treat the underlying body structures. For example, certain features or instrumentation described herein are particularly useful for minimally invasive procedures, e.g., arthroscopic procedures. As discussed more fully below, one embodiment of an apparatus described herein provides an access device that is expandable, e.g., including an expandable distal portion. In addition to providing greater access to a surgical site than would be provided with a device having a constant cross-section from proximal to distal, the expandable distal portion prevents or substantially prevents the access device, or instruments extended therethrough to the surgical site, from dislodging or popping out of the operative site.

A. Systems and Devices for Establishing Access

In one embodiment, the system 10 includes an access device that provides an internal passage for surgical instruments to be inserted through the skin and muscle tissue of the patient P to the surgical site. The access device preferably has a wall portion defining a reduced profile, or low-profile, configuration for initial percutaneous insertion into the patient. This wall portion may have any suitable arrangement. In one embodiment, discussed in more detail below, the wall portion has a generally tubular configuration that may be passed over a dilator that has been inserted into the patient to atraumatically enlarge an opening sufficiently large to receive the access device therein.

The wall portion of the access device preferably can be subsequently expanded to an enlarged configuration, by moving against the surrounding muscle tissue to at least partially define an enlarged surgical space in which the surgical procedures will be performed. In a sense, it acts as its own dilator. The access device may also be thought of as a retractor, and may be referred to herein as such. Both the distal and proximal portion may be expanded, as discussed further below. However, the distal portion preferably expands to a greater extent than the proximal portion, because the surgical procedures are to be performed at the surgical site, which is adjacent the distal portion when the access device is inserted into the patient.

While in the reduced profile configuration, the access device preferably defines a first unexpanded configuration. Thereafter, the access device can enlarge the surgical space defined thereby by engaging the tissue surrounding the access device and displacing the tissue outwardly as the access device expands. The access device preferably is sufficiently rigid to displace such tissue during the expansion thereof. The access device may be resiliently biased to expand from the reduced profile configuration to the enlarged configuration. In addition, the access device may also be manually expanded by an expander device with or without one or more surgical instruments inserted therein, as will be described below. The surgical site preferably is at least partially defined by the expanded access device itself. During expansion, the access device can move from a first overlapping configuration to a second overlapping configuration in some embodiments.

In some embodiments, the proximal and distal portions are separate components that may be coupled together in a suitable fashion. For example, the distal end portion of the access device may be configured for relative movement with respect to the proximal end portion in order to allow the physician to position the distal end portion at a desired location. This relative movement also provides the advantage that the proximal portion of the access device nearest the physician D may remain substantially stable during such distal movement. In one embodiment, the distal portion is a separate component that is pivotally or movably coupled to the proximal portion. In another embodiment, the distal portion is flexible or resilient in order to permit such relative movement.

1. Access Devices

One embodiment of an access device is illustrated in FIGS. 2-6 and designated by reference number 20. In one embodiment, the access device 20 includes a proximal wall portion 22 that has a tubular configuration, and a distal wall portion that has an expandable skirt portion 24. The skirt portion 24 preferably is enlargeable from a reduced profile configuration having an initial dimension 26 (illustrated in FIG. 2) and corresponding cross-sectional area, to an enlarged configuration having a second dimension 28 (illustrated in FIG. 4) and corresponding cross-sectional area. In one embodiment, the skirt portion 24 is coupled to the proximal wall portion 22 with a rivet 30, pin, or similar connecting device to permit movement of the skirt portion 24 relative to the proximal wall portion 22.

In the illustrated embodiment, the skirt portion 24 is manufactured from a resilient material, such as stainless steel. The skirt portion 24 preferably is manufactured so that it normally assumes an expanded configuration as illustrated in FIG. 4. With reference to FIG. 3, the skirt portion 24 may assume an intermediate dimension 34 and corresponding cross-sectional area, which is greater than the initial dimension 26 of the reduced profile configuration of FIG. 2, and smaller than the dimension 28 of the enlarged configuration of FIG. 4. The skirt portion 24 may assume the intermediate configuration of FIG. 3 when deployed in the patient in response to the force of the tissue acting on the skirt portion 24. The intermediate dimension 34 can depend upon several factors, such as the rigidity of the skirt portion 24, the surrounding tissue, and whether such surrounding tissue has relaxed or tightened during the course of the procedure. An outer sleeve 32 (illustrated in dashed line in FIG. 2) may be provided. Preferably, the outer sleeve surrounds the access device 20 and maintains the skirt portion 24 in the reduced profile configuration prior to insertion into the patient. The outer sleeve 32 may be made of plastic. Where provided, the outer sleeve 32 preferably is configured to be easily deployed. For example, a release device may be provided that releases or removes the outer sleeve 32 upon being operated by the user. In one embodiment, a braided polyester suture is embedded within the sleeve 32, aligned substantially along the longitudinal axis thereof. In use, when the suture is withdrawn, the outer sleeve 32 is torn, allowing the access device 20 to resiliently expand from the reduced profile configuration of FIG. 2 to the expanded configurations of FIGS. 3-4. While in the reduced profile configuration of FIG. 2, the skirt portion 24 defines a first overlapping configuration 33, as illustrated by the dashed line. As the skirt portion 24 resiliently expands, the skirt portion 24 assumes the expanded configuration, as illustrated in FIGS. 3-4.

The skirt portion 24 preferably is sufficiently rigid that it is capable of displacing the tissue surrounding the skirt portion 24 as it expands. Depending upon the resistance exerted by surrounding tissue, the skirt portion 24 preferably is sufficiently rigid to provide some resistance against the tissue to remain in the configurations of FIGS. 3-4. Moreover, the expanded configuration of the skirt portion 24 is at least partially supported by the body tissue of the patient. The rigidity of the skirt portion 24 and the greater expansion at the distal portion preferably creates a stable configuration that is at least temporarily stationary in the patient. This arrangement preferably frees the physician from the need to actively support the access device 20, e.g., prior to adding an endoscope mount platform 300 and a support arm 400 (see FIGS. 21-22).

Figure 5:
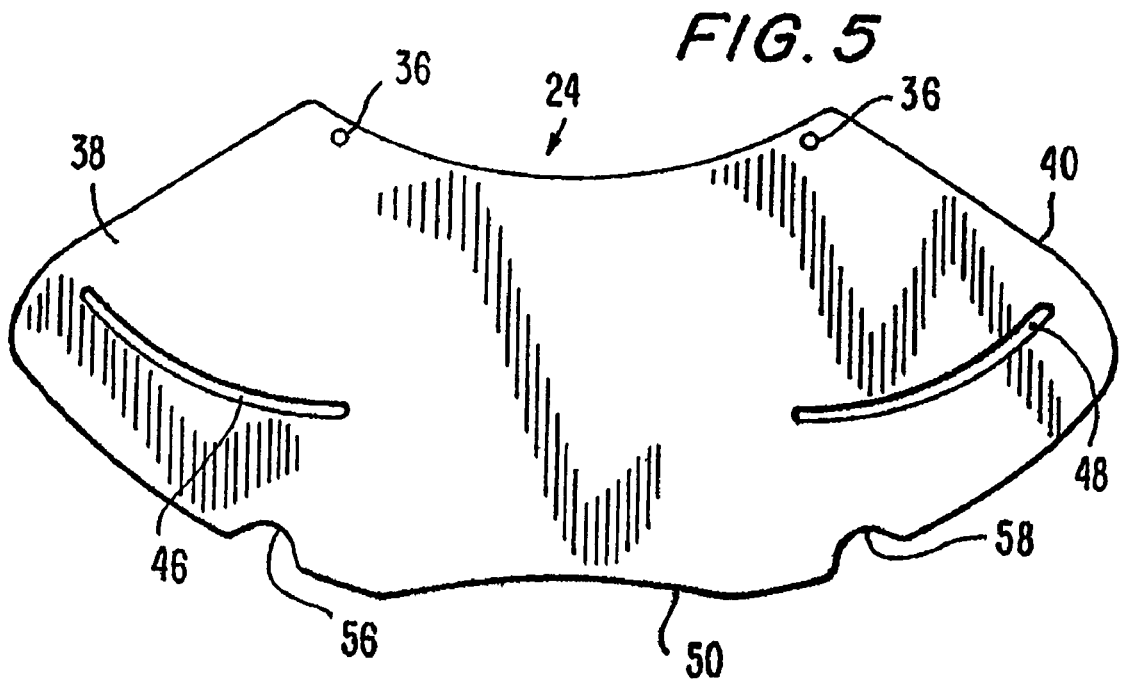
FIG. 5 is a view of one embodiment of a skirt portion of an access device.
Figure 7:
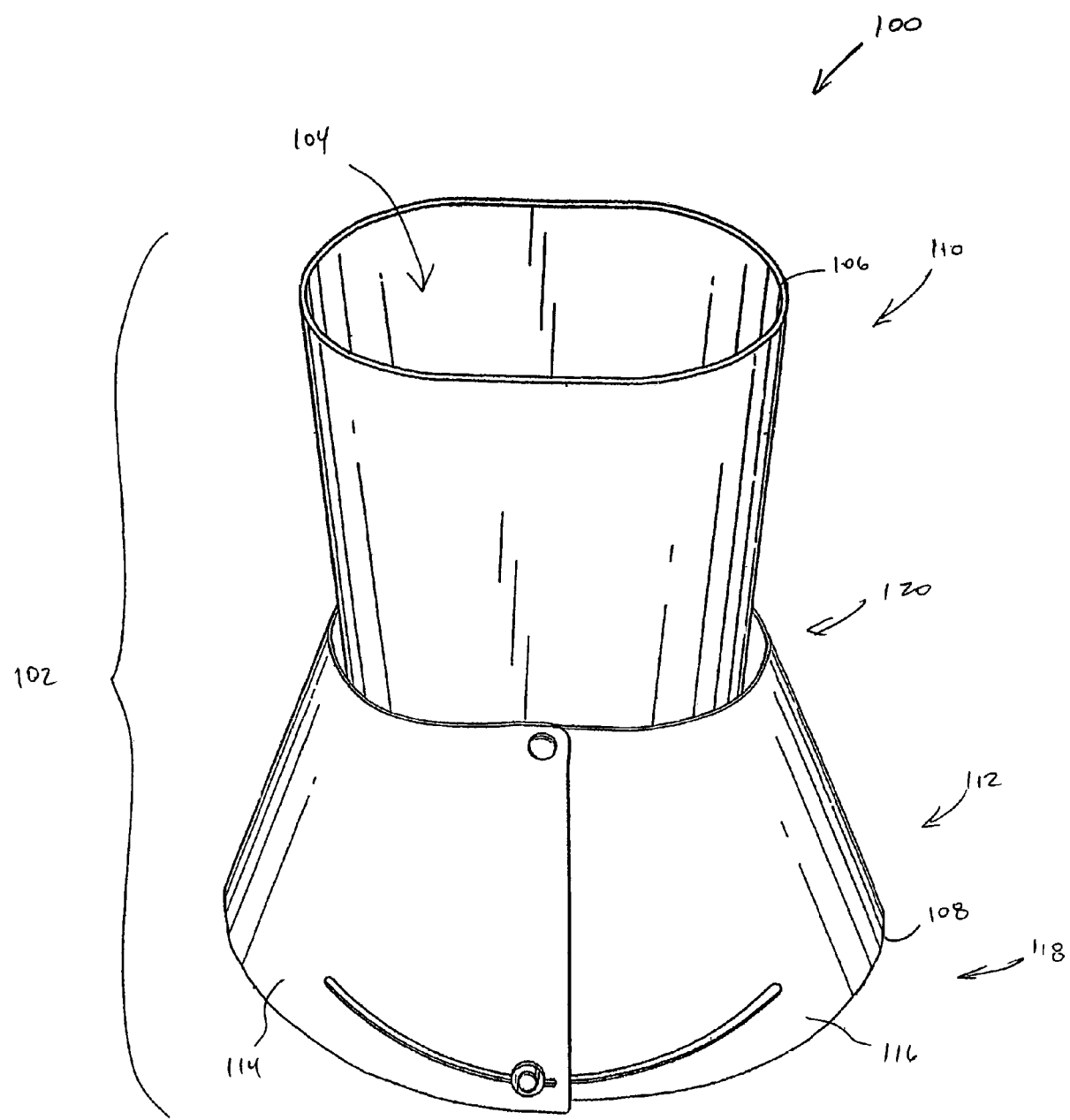
FIG. 7 is a perspective view of another embodiment of an access device.
Figure 8:
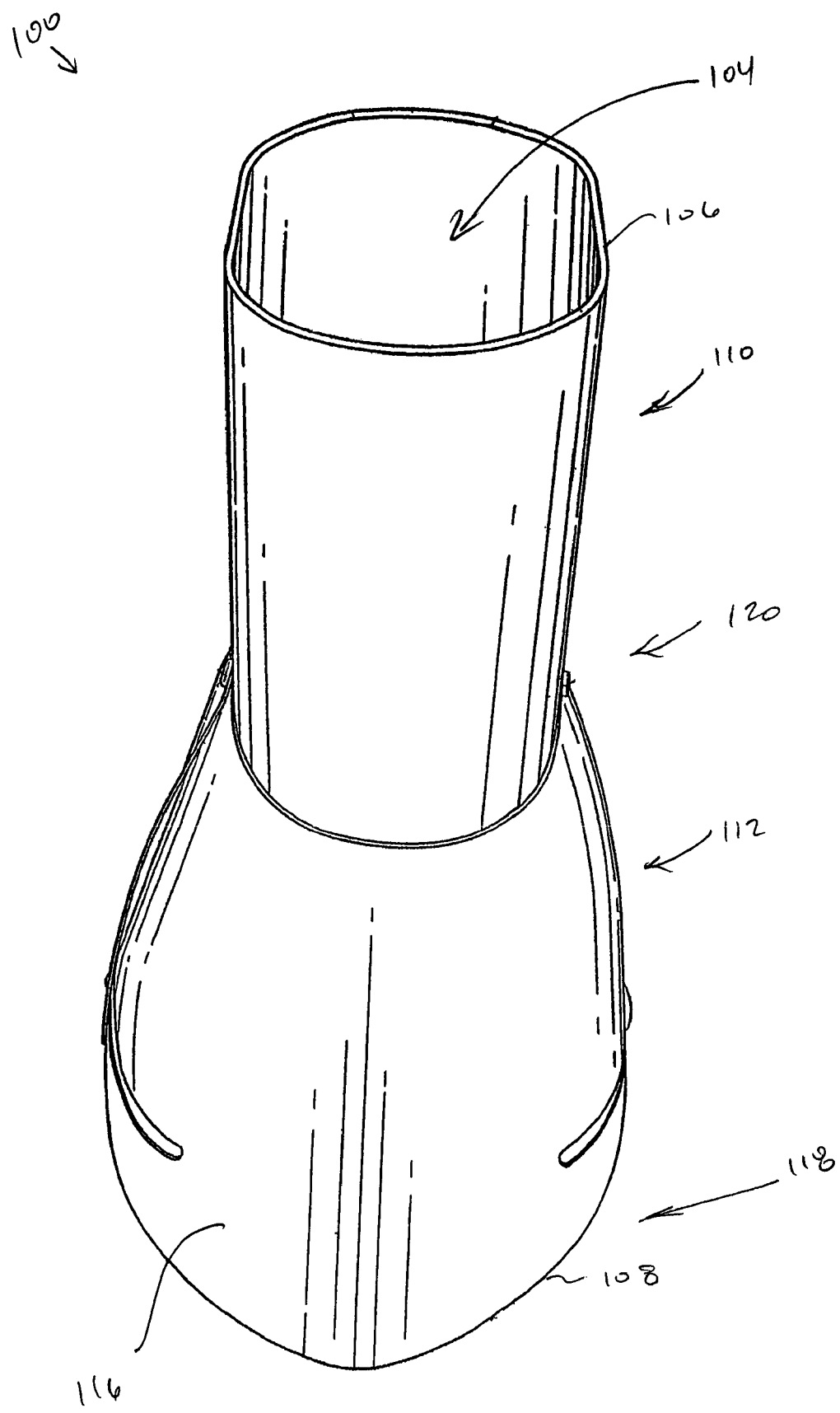
FIG. 8 is a side view of the access device of FIG. 7.
Figure 9:
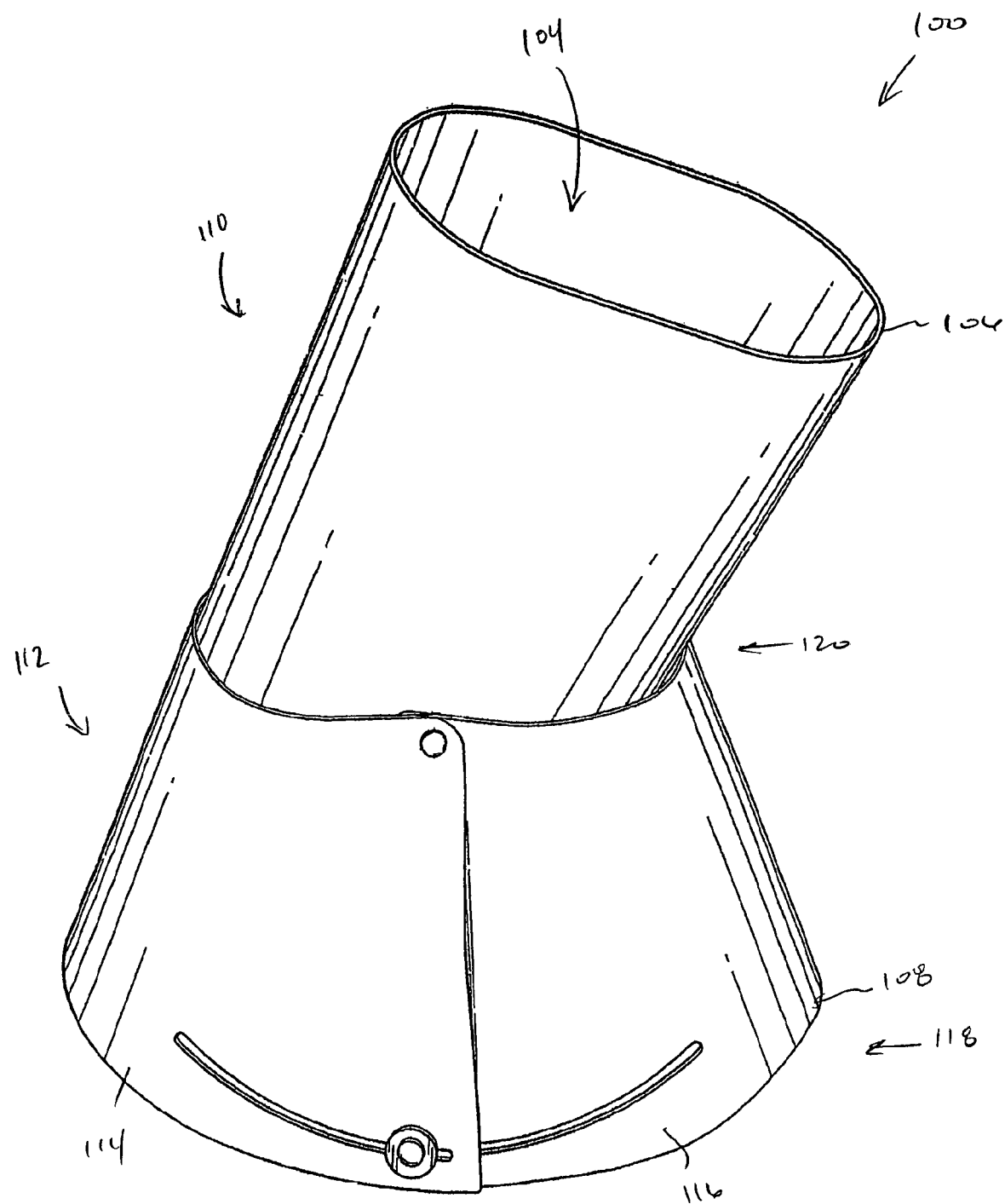
FIG. 9 is a front view of the access device of FIG. 7.
Figure 10:
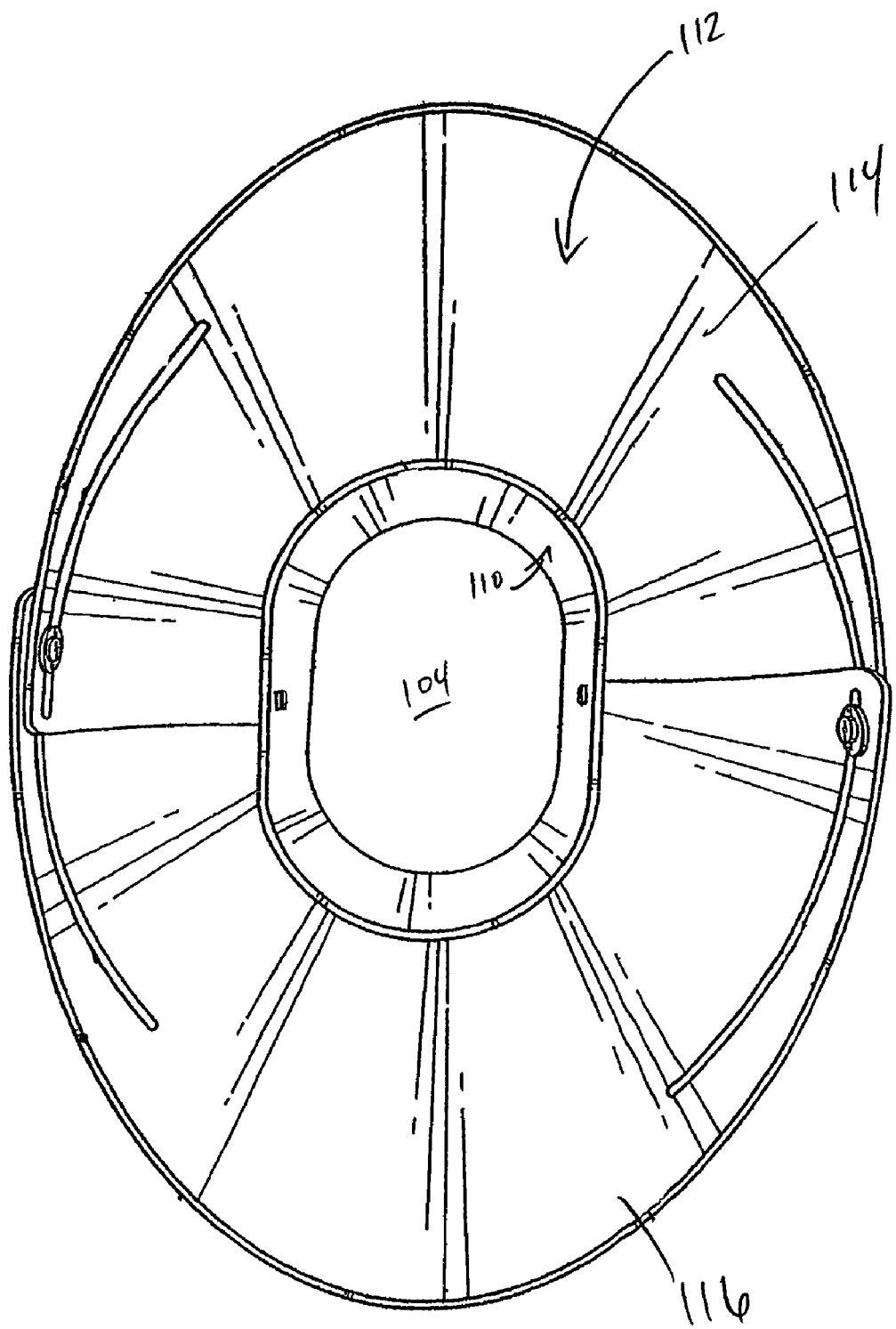
FIG. 10 is a bottom view of the access device of FIG. 7.
Figure 11:
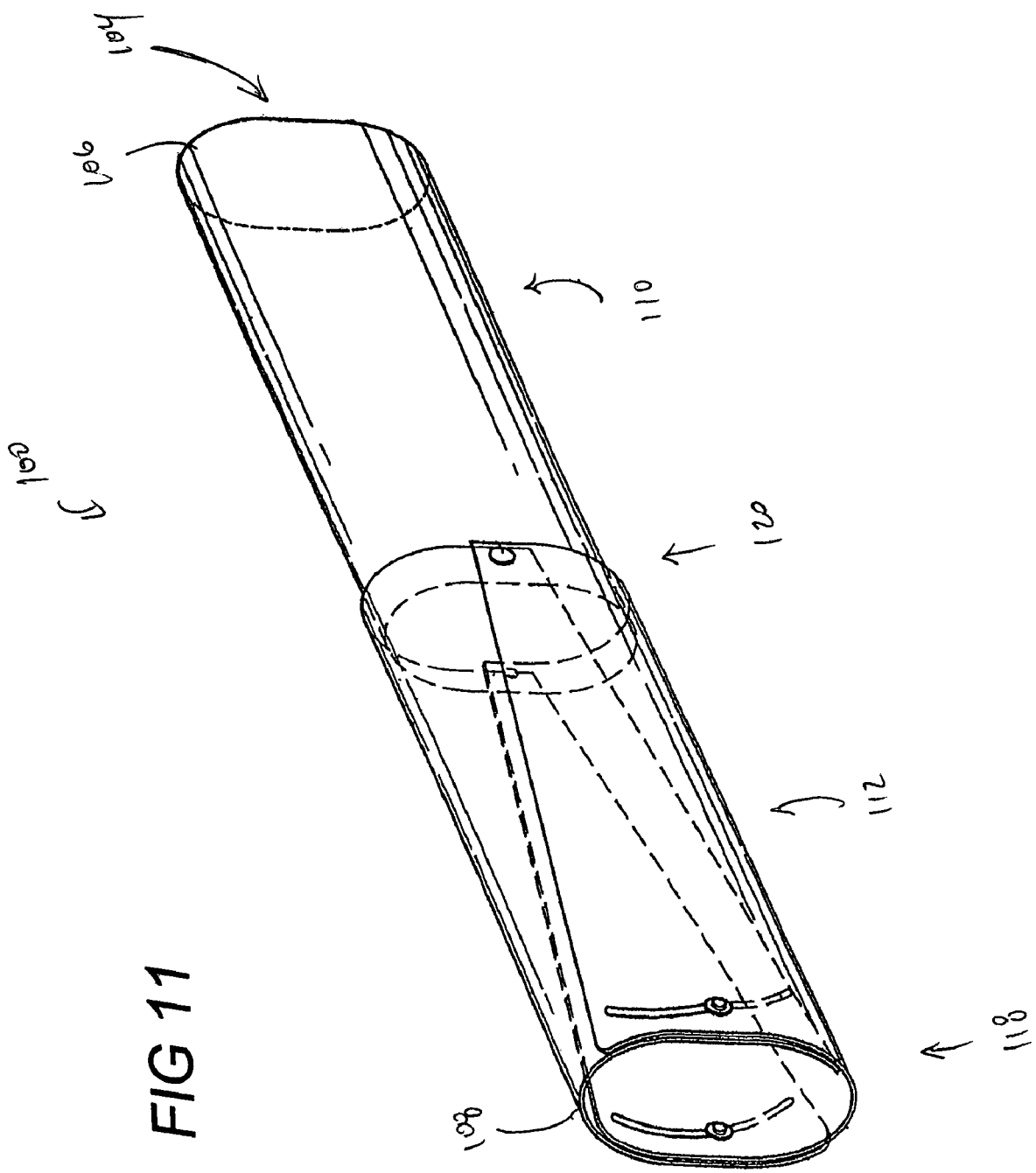
FIG. 11 is a perspective view of the access device of FIG. 7 in a first configuration.
Figure 12:
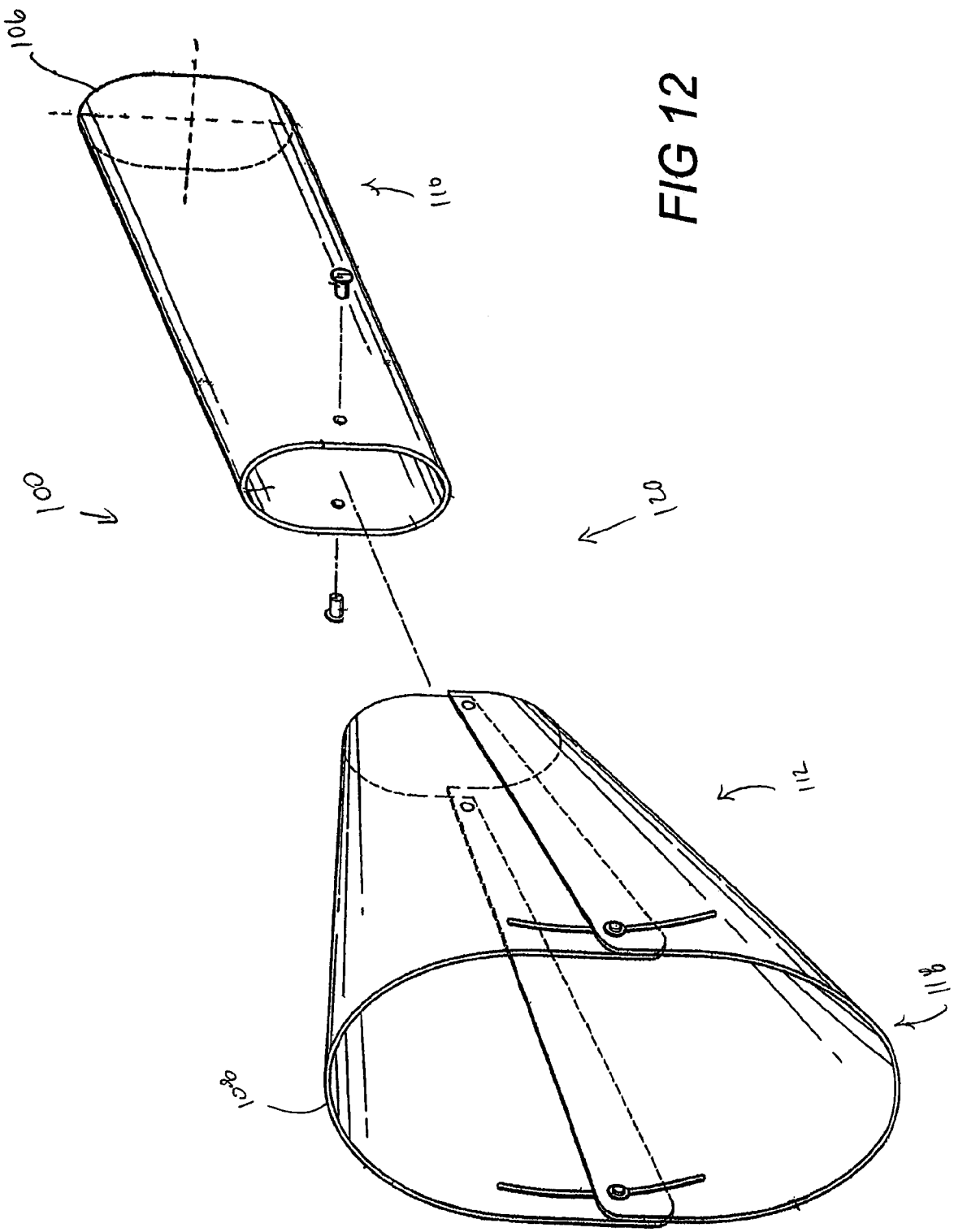
FIG. 12 is an exploded perspective view of the access device of FIG. 7 in a second configuration.

One embodiment of the skirt portion 24 of the access device 20 is illustrated in an initial flattened configuration in FIG. 5. The skirt portion 24 may be manufactured from a sheet of stainless steel having a thickness of about 0.007 inches. In various embodiments, the dimension 28 of the skirt portion 24 is about equal to or greater than 50 mm, is about equal to or greater than 60 mm, is about equal to or greater than 70 mm, is about equal to or greater than 80 mm, or is any other suitable size, when the skirt portion 24 is in the enlarged configuration. In one embodiment, the dimension 28 is about 63 mm, when the skirt portion 24 is in the enlarged configuration. The unrestricted shape of the skirt portion 24 is a circular shape in one embodiment and is an oblong shape in another embodiment. In another embodiment, the skirt portion 24 has an oval shape, wherein the dimension 28 defines a longer dimension of the skirt portion 24 and would be about 85 mm. In another embodiment, the skirt portion 24 has an oval shape and the dimension 28 defines a longer dimension of the skirt portion 24 of about 63 mm. An increased thickness, e.g., about 0.010 inches, may be used in connection with skirt portions having a larger diameter, such as about 65 mm. Other materials, such as nitinol or plastics having similar properties, may also be useful.

As discussed above, the skirt portion 24 preferably is coupled to the proximal wall portion 22 with a pivotal connection, such as rivet 30. A pair of rivet holes 36 can be provided in the skirt portion 24 to receive the rivet 30. The skirt portion 24 also has two free ends 38 and 40 in one embodiment that are secured by a slidable connection, such as a second rivet 44 (not shown in FIG. 5, illustrated in FIGS. 2-4). A pair of complementary slots 46 and 48 preferably are defined in the skirt portion 24 adjacent the free ends 38 and 40. The rivet 44 is permitted to move freely within the slots 46 and 48. This slot and rivet configuration allows the skirt portion 24 to move between the reduced profile configuration of FIG. 2 and the enlarged or expanded configurations of FIGS. 3-4. The use of a pair of slots 46 and 48 reduces the risk of the "button-holing" of the rivet 44, e.g., a situation in which the opening of the slot becomes distorted and enlarged such that the rivet may slide out of the slot, and cause failure of the device. The likelihood of such occurrence is reduced in skirt portion 24 because each of the slots 46 and 48 in the double slot configuration has a relatively shorter length than a single slot configuration. Being shorter, the slots 46, 48 are less likely to be distorted to the extent that a rivet may slide out of position. In addition, the configuration of rivet 44 and slots 46 and 48 permits a smoother operation of enlarging and reducing the skirt portion 24, and allows the skirt portion 24 to expand to span three or more vertebrae, e.g., L4, L5, and S1. This arrangement enables multi-level procedures, such as multilevel fixation procedures alone or in combination with a variety of other procedures, as discussed below. Other embodiments include a single slot rather than the slots 46, 48, or more than two slots.

An additional feature of the skirt portion 24 is the provision of a shallow concave profile 50 defined along the distal edge of the skirt portion 24, which allows for improved placement of the skirt portion 24 with respect to the body structures and the surgical instruments defined herein. In one embodiment, a pair of small scalloped or notched portions 56 and 58, are provided, as illustrated in FIG. 5. When the skirt portion 24 is assembled, the notched portions 56 and 58 are generally across from each other. When the skirt portion 24 is applied to a patient, the notched portions 56, 58 are oriented in the cephcaudal direction (indicated by a dashed line 60 in FIG. 4). In this arrangement, instruments and implants, such as an elongated member 650 used in a fixation procedure (described in detail below), may extend beyond the area enclosed by the skirt portion 24 without moving or raising the skirt portion 24, e.g., by allowing the elongated member 650 (or other implant or instrument) to pass under the skirt portion 24. The notched portions 56, 58 also enable the elongated member 650 (or other implant or instrument) to extend beyond the portion of the surgical space defined within the outline of the distal end of the skirt portion 24. The notched portions 56, 58 are optional, as illustrated in connection with another embodiment of an access device 54, illustrated in FIG. 6, and may be eliminated if, for example, the physician deems the notches to be unnecessary for the procedures to be performed. For example, in some fixation procedures such extended access is not needed, as discussed more fully below. As illustrated in FIG. 4, the skirt portion 24 may be expanded to a substantially conical configuration having a substantially circular or elliptical profile.

Furthermore, it is contemplated that the skirt portion 24 of the access device 20 can include a stop that retains the skirt portion in an expanded configuration, as shown in U.S. patent application Ser. No. 10/361,887, filed Feb. 10, 2003, now U.S. Application Patent Publication No. US2003/153927 A1, which is hereby incorporated by reference in its entirety herein.

With reference to FIGS. 7-12, another embodiment of an access device 100 comprises an elongate body 102 defining a passage 104 and having a proximal end 106 and a distal end 108. The elongate body 102 has a proximal portion 110 and a distal portion 112. The proximal portion 110 has an oblong or generally oval shaped cross section in one embodiment. The term "oblong" is used in its ordinary sense (i.e., having an elongated form) and is a broad term and it includes a structure having a dimension, especially one of two perpendicular dimensions, such as, for example, width or length, that is greater than another and includes shapes such as rectangles, ovals, ellipses, triangles, diamonds, trapezoids, parabolas, and other elongated shapes having straight or curved sides. The term "oval" is used in its ordinary sense (i.e., egg like or elliptical) and is a broad term and includes oblong shapes having curved portions.

The proximal portion 110 comprises an oblong, generally oval shaped cross section over the elongated portion. It will be apparent to those of skill in the art that the cross section can be of any suitable oblong shape. The proximal portion 110 can be any desired size. The proximal portion 110 can have a cross-sectional area that varies from one end of the proximal portion to another end. For example, the cross-sectional area of the proximal portion can increase or decrease along the length of the proximal portion 110. Preferably, the proximal portion 110 is sized to provide sufficient space for inserting multiple surgical instruments through the elongate body 102 to the surgical location. The distal portion 112 preferably is expandable and comprises first and second overlapping skirt members 114, 116. The degree of expansion of the distal portion 112 is determined by an amount of overlap between the first skirt member 114 and the second skirt member 116 in one embodiment.

The elongate body 102 of the access device 100 has a first location 118 distal of a second location 120. The elongate body 102 preferably is capable of having a configuration when inserted within the patient wherein the cross-sectional area of the passage 104 at the first location 118 is greater than the cross-sectional area of the passage 104 at the second location 120. The passage 104 preferably is capable of having an oblong shaped cross section between the second location 120 and the proximal end 106. In some embodiments the passage 104 preferably is capable of having a generally elliptical cross section between the second location 120 and the proximal end 106. Additionally, the passage 104 preferably is capable of having a non-circular cross section between the second location 120 and the proximal end 106. Additionally, in some embodiments, the cross section of the passage 104 can be symmetrical about a first axis and a second axis, the first axis being generally normal to the second axis. Other embodiments that can have an oblong cross-section are discussed below in connection with FIGS. 67-95.

In another embodiment, an access device comprises an elongate body defining a passage and having a proximal end and a distal end. The elongate body can be a unitary structure and can have a generally uniform cross section from the proximal end to the distal end. In one embodiment, the elongate body preferably has an oblong or generally oval shaped cross section along the entire length of the elongate body. The passage can have a generally elliptical cross section between the proximal end and the distal end. The elongate body preferably has a relatively fixed cross-sectional area along its entire length. In one embodiment, the elongate body is capable of having a configuration when inserted within the patient wherein the cross-sectional area of the passage at a first location is equal to the cross-sectional area of the passage at a second location. The passage preferably is capable of having an oblong shaped cross section between the first and second locations. The cross section of the passage can be of any suitable oblong shape and the elongate body can be any desired size. Preferably, the elongate body is sized to provide sufficient space for inserting multiple surgical instruments sequentially or simultaneously through the elongate body to the surgical location.

In one embodiment, the access device has a uniform, generally oblong shaped cross section and is sized or configured to approach, dock on, or provide access to, anatomical structures. The access device preferably is configured to approach the spine from a posterior position or from a postero-lateral position. A distal portion of the access device can be configured to dock on, or provide access to, posterior portions of the spine for performing spinal procedures, such as, for example, fixation, fusion, or any other procedure described herein. In one embodiment, the distal portion of the access device has a uniform, generally oblong shaped cross section and is configured to dock on, or provide access to, generally posterior spinal structures. Generally posterior spinal structures can include, for example, one or more of the transverse process, the superior articular process, the inferior articular process, and the spinous process. In some embodiments, the access device can have a contoured distal end to facilitate docking on one or more of the posterior spinal structures. Accordingly, in one embodiment, the access device has a uniform, generally oblong shaped cross section with a distal end sized, configured, or contoured to approach, dock on, or provide access to, spinal structures from a posterior or postero-lateral position.

Further details and features pertaining to access devices and systems are described in U.S. patent application Ser. No. 09/772,605, filed Jan. 30, 2001, application Ser. No. 09/906, 463, filed Jul. 16, 2001, application Ser. No. 10/361,887, filed Feb. 10, 2003, application Ser. No. 10/280,489, filed Oct. 25, 2002, and application Ser. No. 10/678,744 filed Oct. 2, 2003, which are incorporated by reference in their entireties herein.

2. Dilators and Expander Devices

According to one application or procedure, an early stage involves determining a point in the skin of the patient at which to insert the access device 20. The access point preferably corresponds to a posterior-lateral aspect of the spine. Manual palpation and Anterior-Posterior (AP) fluoroscopy may be used to determine preferred or optimal locations for forming an incision in the skin of the patient. In one application, the access device 20 preferably is placed midway (in the cephcaudal direction) between the L4 through S1 vertebrae, centrally about 4-7 cm from the midline of the spine.

After the above-described location is determined, an incision is made at the location. A guide wire (not shown) is introduced under fluoroscopic guidance through the skin, fascia, and muscle to the approximate surgical site. A series of dilators is used to sequentially expand the incision to the desired width, about 23 mm in one procedure, preferably minimizing damage to the structure of surrounding tissue and muscles. A first dilator can be placed over the guide wire to expand the opening. The guide wire may then be removed. A second dilator, slightly larger than the first dilator, is placed over the first dilator to expand the opening further. Once the second dilator is in place, the first dilator may be removed. This process of (1) introducing a next-larger-sized dilator coaxially over the previous dilator and (2) optionally removing the previous dilator(s) when the next-larger-sized dilator is in place continues until an opening of the desired size is created in the skin, muscle, and subcutaneous tissue. According to one application, the desired opening size is about 23 mm. (Other dimensions of the opening, e.g., about 20 mm, about 27 mm, about 30 mm, etc., are also useful with this apparatus in connection with spinal surgery, and still other dimensions are contemplated.)

Figure 13:
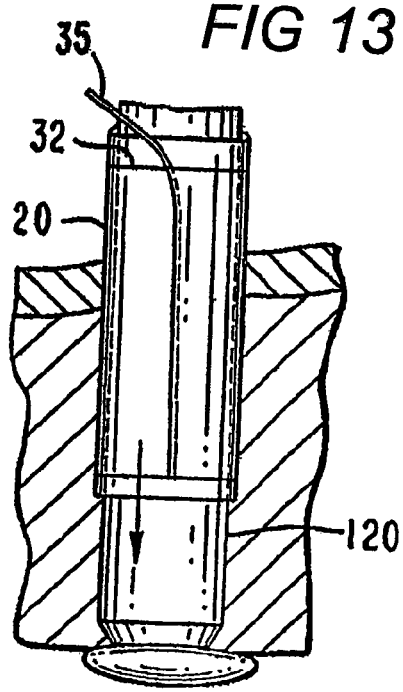
FIG. 13 is a sectional view illustrating one stage of one application for treating the spine of a patient.

FIG. 13 shows that following placement of a dilator 120, which is the largest dilator in the above-described dilation process, the access device 20 is introduced in its reduced profile configuration and positioned over the dilator 120. The dilator 120 is subsequently removed from the patient, and the access device 20 remains in position.

Once positioned in the patient, the access device 20 may be enlarged to provide a passage for the insertion of various surgical instruments and to provide an enlarged space for performing the procedures described herein. As described above, the access device may achieve the enlargement in several ways. In one embodiment, a distal portion of the access device may be enlarged, and a proximal portion may maintain a constant diameter. The relative lengths of the proximal portion 22 and the skirt portion 24 may be adjusted to vary the overall expansion of the access device 20. Alternatively, such expansion may extend along the entire length of the access device 20. In one application, the access device 20 may be expanded by removing a suture 35 and tearing the outer sleeve 32 surrounding the access device 20, and subsequently allowing the skirt portion 24 to resiliently expand towards its fully expanded configuration as (illustrated in FIG. 4) to create an enlarged surgical space from the L4 to the S1 vertebrae. The resisting force exerted on the skirt portion 24 may result in the skirt portion 24 assuming the intermediate configuration illustrated in FIG. 3. Under many circumstances, the space created by the skirt portion 24 in the intermediate configuration is a sufficiently large working space to perform the procedure described herein. Once the skirt portion 24 has expanded, the rigidity and resilient characteristics of the skirt portion 24 preferably allow the access device 20 to resist closing to the reduced profile configuration of FIG. 2 and to at least temporarily resist being expelled from the incision. These characteristics create a stable configuration for the access device 20 to remain in position in the body, supported by the surrounding tissue. It is understood that additional support may be needed, especially if an endoscope is added.

According to one embodiment of a procedure, the access device 20 may be further enlarged at the skirt portion 24 using an expander apparatus to create a surgical access space. An expander apparatus useful for enlarging the access device has a reduced profile configuration and an enlarged configuration. The expander apparatus is inserted into the access device in the reduced profile configuration, and subsequently expanded to the enlarged configuration. The expansion of the expander apparatus also causes the access device to be expanded to the enlarged configuration. In some embodiments, the expander apparatus may increase the diameter of the access device along substantially its entire length in a generally conical configuration. In other embodiments, the expander apparatus expands only a distal portion of the access device, allowing a proximal portion to maintain a relatively constant diameter.

In addition to expanding the access device, in some embodiments the expander apparatus may also be used to position the distal portion of the access device at the desired location for the surgical procedure. The expander can engage an interior wall of the access device to move the access device to the desired location. For embodiments in which the distal portion of the access device is relatively movable with respect to the proximal portion, the expander apparatus is useful to position the distal portion without substantially disturbing the proximal portion.

Figure 15:
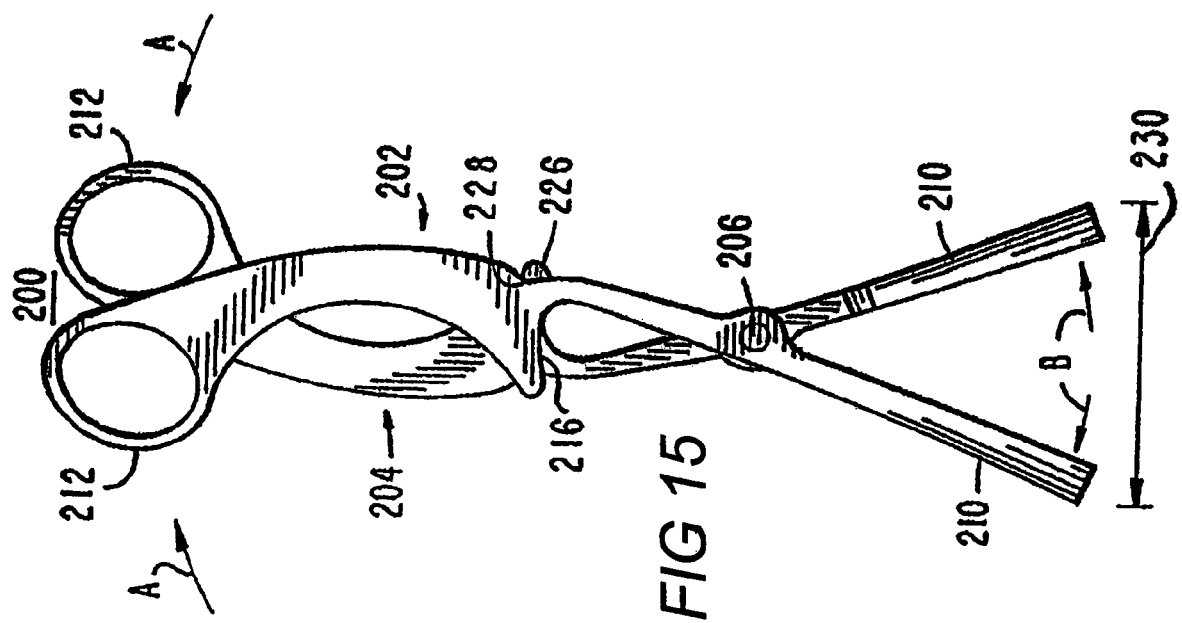
FIG. 15 is a side view of the expander apparatus of FIG. 14 in an expanded configuration.
Figure 14:
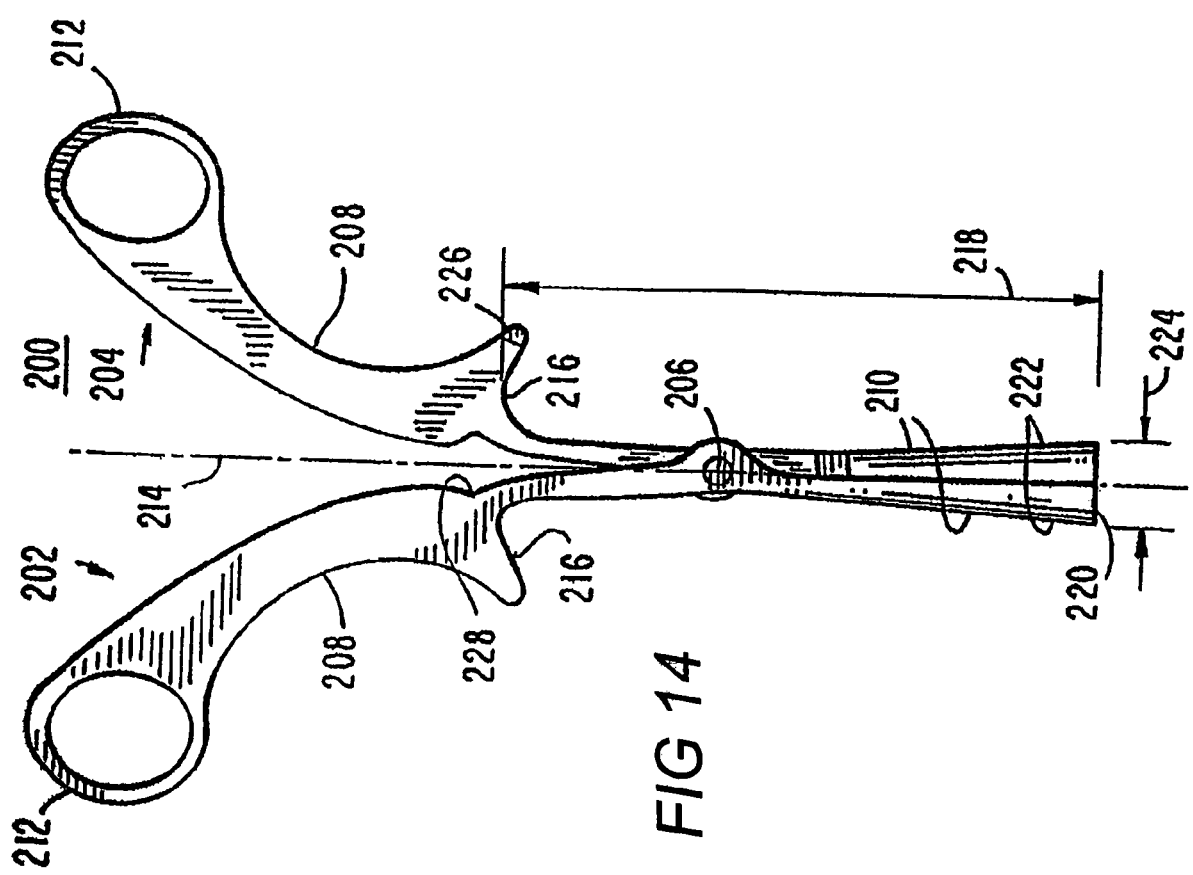
FIG. 14 is a side view of one embodiment of an expander apparatus in a reduced profile configuration.
Figure 18:
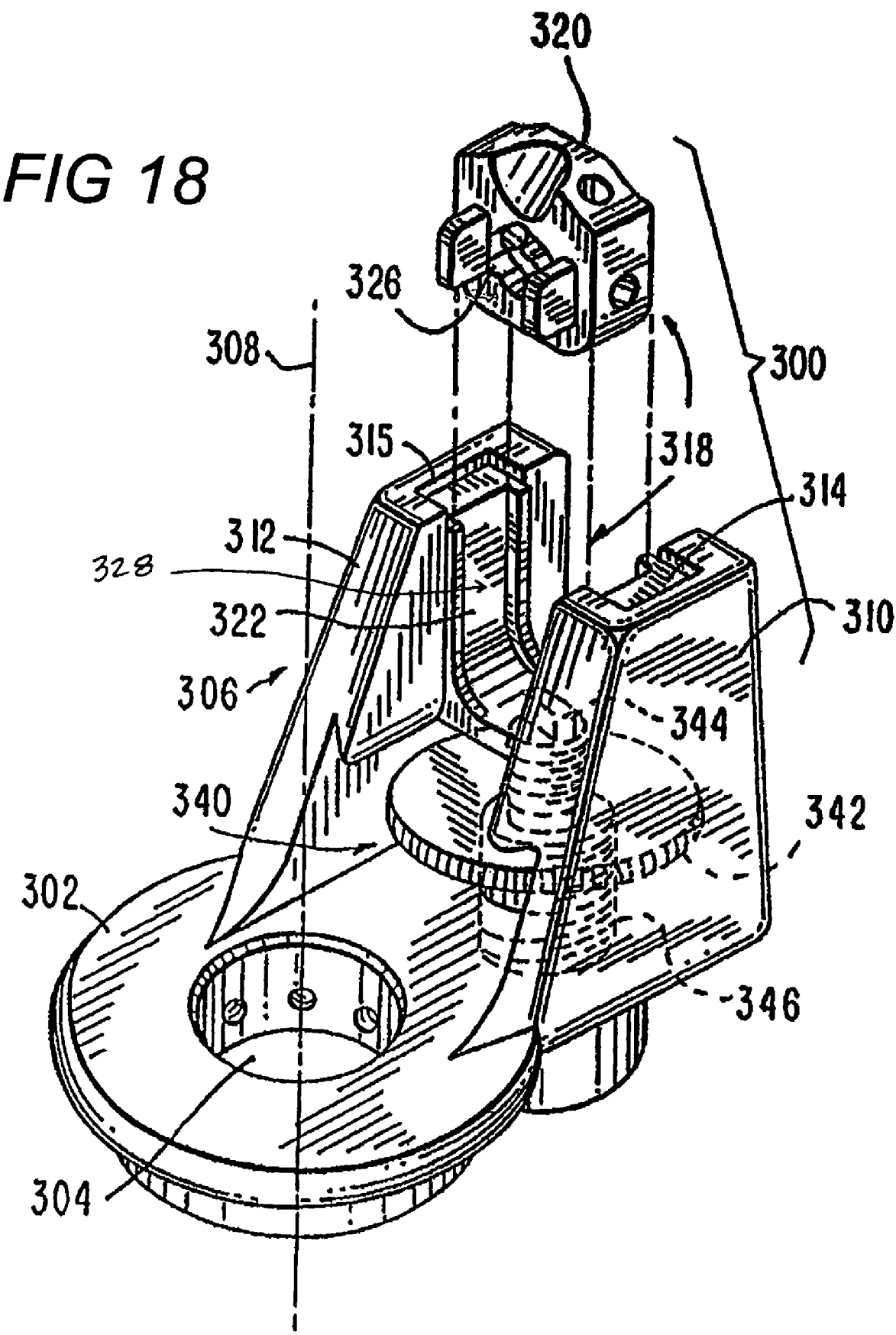
FIG. 18 is an exploded perspective view of one embodiment of an endoscope mount platform.

In some procedures, an expander apparatus is used to further expand the skirt portion 24 towards the enlarged configuration (illustrated in FIG. 4). The expander apparatus is inserted into the access device, and typically has two or more members that are movable to engage the interior wall of the skirt portion 24 and apply a force sufficient to further expand the skirt portion 24. FIGS. 14 and 15 show one embodiment of an expander apparatus 200 that has a first component 202 and a second component 204. The first component 202 and the second component 204 of the expander apparatus 200 are arranged in a tongs-like configuration and are pivotable about a pin 206. The first and second components 202 and 204 can be constructed of steel having a thickness of about 9.7 mm. Each of the first and second components 202 and 204 has a proximal handle portion 208 and a distal expander portion 210. Each proximal handle portion 208 has a finger grip 212 that may extend transversely from an axis, e.g., a longitudinal axis 214, of the apparatus 200. The proximal handle portion 208 may further include a stop element, such as flange 216, that extends transversely from the longitudinal axis 214. The flange 216 preferably is dimensioned to engage the proximal end 25 of the access device 20 when the apparatus 200 is inserted a predetermined depth. This arrangement provides a visual and tactile indication of the proper depth for inserting the expander apparatus 200. In one embodiment, a dimension 218 from the flange 216 to the distal tip 220 is about 106 mm. The dimension 218 is determined by the length of the access device 20, which in turn is a function of the depth of the body structures beneath the skin surface at which the surgical procedure is to be performed. The distal portions 210 are each provided with an outer surface 222 for engaging the inside wall of the skirt portion 24. The outer surface 222 is a frusto-conical surface in one embodiment. The expander apparatus 200 has an unexpanded distal width 224 at the distal tip 220 that is about 18.5 mm in one embodiment.

In use, the finger grips 212 are approximated towards one another, as indicated by arrows A in FIG. 15, which causes the distal portions 210 to move to the enlarged configuration, as indicated by arrows B. The components 202 and 204 are also provided with a cooperating tab 226 and shoulder portion 228 which are configured for mutual engagement when the distal portions 210 are in the expanded configuration. In the illustrated embodiment, the expander apparatus 200 has an expanded distal width 230 that extends between the distal portions 210. The expanded distal width 230 can be about 65 mm or less, about as large as 83 mm or less, or any other suitable width. The tab 226 and shoulder portion 228 together limit the expansion of the expander apparatus 200 to prevent expansion of the skirt portion 24 of the access device 20 beyond its designed dimension, and to minimize trauma to the underlying tissue. Further features related to the expander apparatus are described in U.S. Pat. No. 6,652,553, issued Nov. 25, 2003, which is incorporated by reference in its entirety herein.

When the access device 20 is inserted into the patient and the outer sleeve 32 is removed, the skirt portion 24 expands to a point where the outward resilient expansion of the skirt portion 24 is balanced by the force of the surrounding tissue. The surgical space defined by the access device 20 may be sufficient to perform any of a number of surgical procedures or combination of surgical procedures described herein. However, if it is desired to expand the access device 20 further, the expander apparatus 200, or a similar device, may be inserted into the access device 20 in the reduced profile configuration until the shoulder portions 216 are in approximation with the proximal end 25 of the skirt portion 24 of the access device 20, as shown in FIG. 16.

Figure 16:
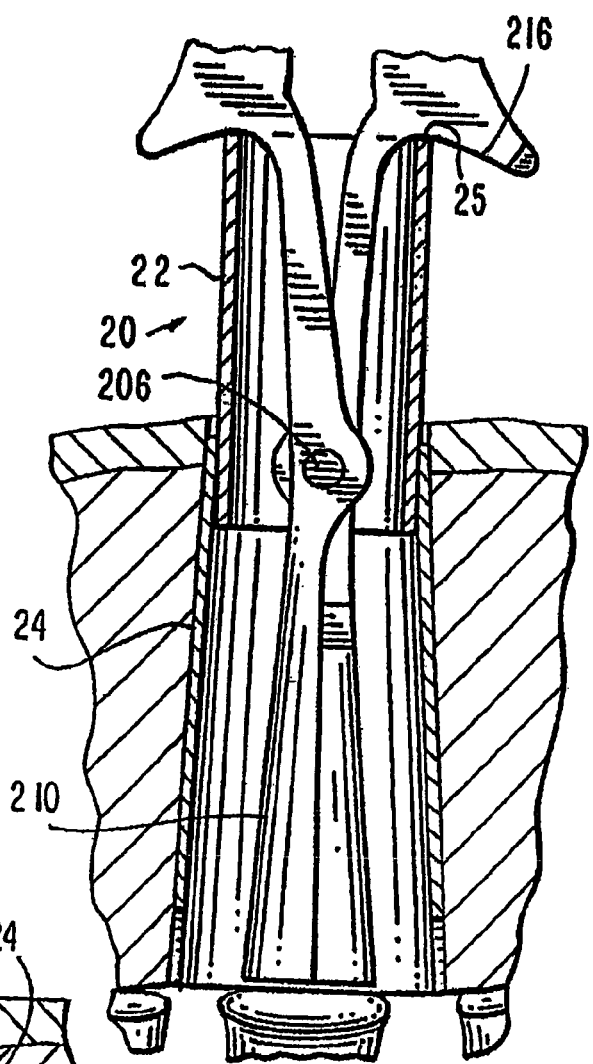
FIG. 16 is a sectional view of the expander apparatus of FIGS. 14-15 inserted into the access device of FIG. 2, which has been inserted into a patient.
Figure 17:
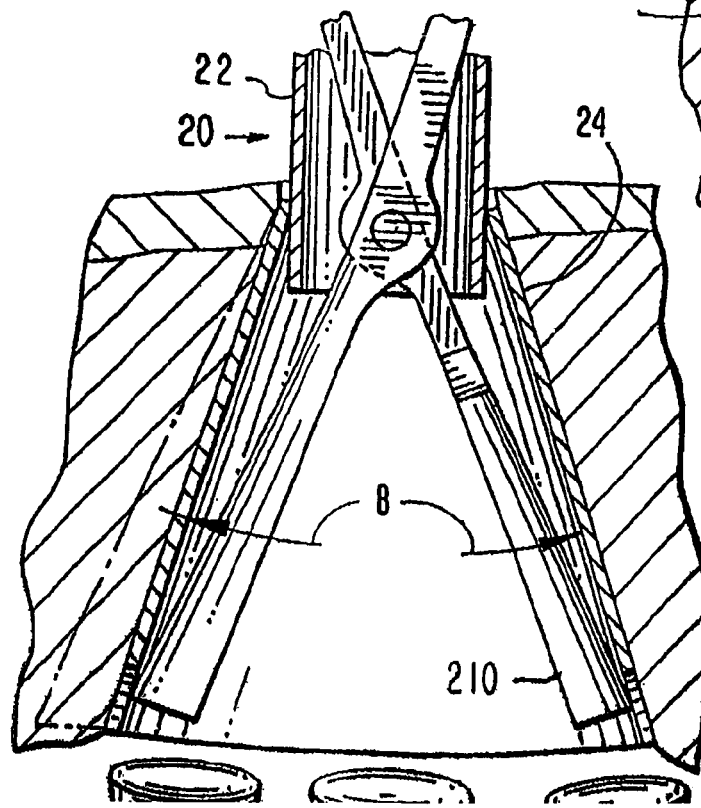
FIG. 17 is a sectional view of the expander apparatus of FIGS. 14-15 inserted into the access device of FIG. 2 and expanded to the expanded configuration to retract tissue.

FIG. 16 shows the expander apparatus 200 inserted in the access device 20 in the reduced profiled configuration. Expansion of the expander apparatus 200 is achieved by approximating the handle portions 212 (not shown in FIG. 16), which causes the distal portions 210 of the expander apparatus 200 to move to a spaced apart configuration. As the distal portions 210 move apart and contact the inner wall of the skirt portion 24, the rivet 44 is allowed to slide within the slots 46 and 48 of the skirt portion 24, thus permitting the skirt portion 24 to expand. When the distal portions 210 reach the maximum expansion of the skirt portion 24 (illustrated by a dashed line in FIG. 17), the tab 226 and shoulder portion 228 of the expander apparatus 200 come into engagement to prevent further expansion of the tongs-like portions (as illustrated in FIG. 15). Alternatively, the access device 20 may be expanded with another device that can selectively have a reduced profile configuration and an expanded configuration, e.g., a balloon or similar device.

An optional step in the procedure is to adjust the location of the distal portion of the access device 20 relative to the body structures to be operated on. For example, the expander apparatus 200 may also be used to engage the inner wall of the skirt portion 24 of the access device 20 in order to move the skirt portion 24 of the access device 20 to the desired location. For an embodiment in which the skirt portion 24 of the access device 20 is relatively movable relative to the proximal portion, e.g. by use of the rivet 30, the expander apparatus 200 is useful to position the skirt portion 24 without substantially disturbing the proximal portion 22 or the tissues closer to the skin surface of the patient. As will be described below, the ability to move the distal end portion, e.g., the skirt portion 24, without disturbing the proximal portion is especially beneficial when an additional apparatus is mounted relative to the proximal portion of the access device, as described below.

B. Systems and Devices for Stabilization and Visualization

Some procedures can be conducted through the access device 20 without any additional peripheral components being connected thereto. In other procedures it may be beneficial to provide at least one of a support device and a viewing element. As discussed more fully below, support devices can be advantageously employed to provide support to peripheral equipment and to surgical tools of various types. Various embodiments of support devices and viewing elements are discussed herein below.

1. Support Devices

One type of support device that can be coupled with the access device 20 is a device that supports a viewing element. In one embodiment, an endoscope mount platform 300 and indexing arm 400 support an endoscope 500 on the proximal end 25 of the access device 20 for remotely viewing the surgical procedure, as illustrated in FIGS. 18-21. The endoscope mount platform 300 may also provide several other functions during the surgical procedure. The endoscope mount platform 300 preferably includes a base 302 that extends laterally from a central opening 304 in a generally ring-shaped configuration. In one application, the physician views the procedure primarily by observing a monitor, when inserting surgical instruments into the central opening 304. The base 302 advantageously enables the physician by providing a visual indicator (in that it may be observable in the physician's peripheral vision) as well as tactile feedback as instruments are lowered towards the central opening 304 and into the access device 20.

The endoscope mount platform 300 preferably has a guide portion 306 at a location off-set from the central opening 304 that extends substantially parallel to a longitudinal axis 308. The base 302 can be molded as one piece with the guide portion 306. The base 302 and guide portion 306 may be constructed with a suitable polymer, such as, for example, polyetheretherketone (PEEK).

The guide portion 306 includes a first upright member 310 that extends upward from the base 302 and a second upright member 312 that extends upward from the base 302. In one embodiment, the upright members 310, 312 each have a respective vertical grooves 314 and 315 that can slidably receive an endoscopic mount assembly 318.

The endoscope 500 (not shown in FIG. 18) can be movably mounted to the endoscope mount platform 300 with the endoscope mount assembly 318 in one embodiment. The endoscope mount assembly 318 includes an endoscope mount 320 and a saddle unit 322. The saddle unit 322 is slidably mounted within the grooves 314 and 315 in the upright members 310 and 312. The endoscope mount 320 receives the endoscope 500 through a bore 326 which passes through the endoscope mount 320. Part of the endoscope 500 may extend through the access device 20 substantially parallel to longitudinal axis 308 into the patient's body 130, as shown in FIG. 25.

The endoscope mount 320 is removably positioned in a recess 328 defined in the substantially "U"-shaped saddle unit 322. In one embodiment, the saddle unit 322 is selectively movable in a direction parallel to the longitudinal axis 308 in order to position the endoscope 500 at the desired height within the access device 20. The movement of the endoscope 500 by way of the saddle unit 322 also advantageously enables the physician to increase visualization of a particular portion of the surgical space defined by the access device, e.g., by way of a zoom feature, as required for a given procedure or a step of a procedure.

In one embodiment, an elevation adjustment mechanism 340, which may be a screw mechanism, is positioned on the base 302 between the upright members 310 and 312. The elevation adjustment mechanism 340 can be used to selectively move a viewing element, e.g., the endoscope 500 by way of the saddle unit 322. In one embodiment, the elevation adjustment mechanism 340 comprises a thumb wheel 342 and a spindle 344. The thumb wheel 343 is rotatably mounted in a bore in the base 302. The thumb wheel 342 has an external thread 346 received in a cooperating thread in the base 302. The spindle 344 is mounted for movement substantially parallel to the central axis 308. The spindle 344 preferably has a first end received in a rectangular opening in the saddle unit 322, which inhibits rotational movement of the spindle 344. The second end of the spindle 344 has an external thread that cooperates with an internal thread formed in a bore within the thumb wheel 342. Rotation of the thumb wheel 342 relative to the spindle 344, causes relative axial movement of the spindle unit 344 along with the saddle unit 322. Further details and features related to endoscope mount platforms are described in U.S. Pat. No. 6,361,488, issued Mar. 26, 2002; U.S. Pat. No. 6,530,880, issued Mar. 11, 2003, and U.S. patent application Ser. No. 09/940,402, filed Aug. 27, 2001, published as Publication No. 2003/0040656 on Feb. 27, 2003, which are incorporated by reference in their entireties herein.

Figure 19:
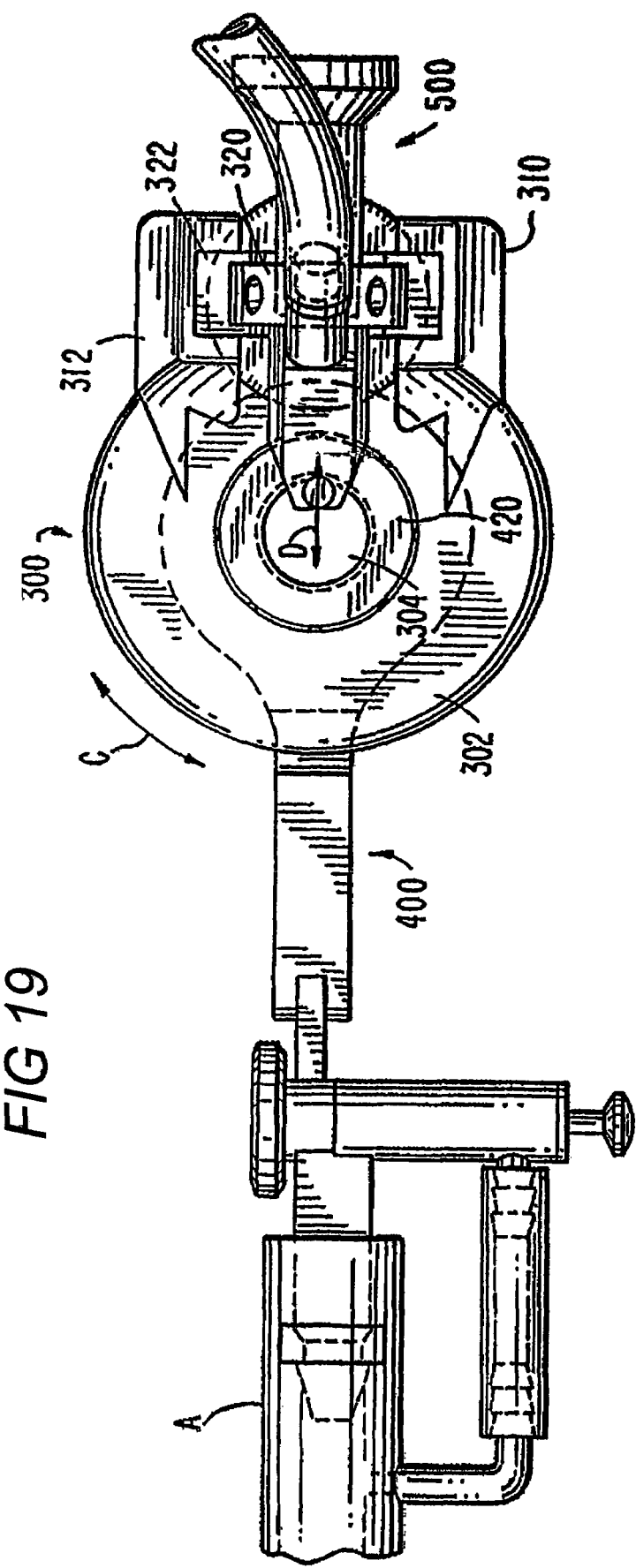
FIG. 19 is a top view of the endoscope mount platform of FIG. 18 coupled with one embodiment of an indexing arm and one embodiment of an endoscope.

FIGS. 19-21 show that the endoscope mount platform 300 is mountable to the support arm 400 in one embodiment. The support arm 400, in turn, preferably is mountable to a mechanical support, such as mechanical support arm A, discussed above in connection with FIG. 1. The support arm 400 preferably rests on, or is otherwise coupled to, the proximal end 25 of the access device 20. In one embodiment, the support arm 400 is coupled with an indexing collar 420, which is configured to be received in the central opening 304 of the base 302 of endoscope mount platform 300. The indexing collar 420 is substantially toroidal in section and has an outer peripheral wall surface 422, an inner wall surface 424, and a wall thickness 426 that is the distance between the wall surfaces 422, 424. The indexing collar 420 further includes a flange 428, which supports the indexing collar 420 on the support arm 400.

In one embodiment, a plurality of collars 420 may be provided to make the surgical system 10 modular in that different access devices 20 may be used with a single endoscope mount platform 300. For example, access devices 20 of different dimensions may be supported by providing indexing collars 420 to accommodate each access device size while using a single endoscope mount platform 300. The central opening 304 of the endoscope mount platform 300 can have a constant dimension, e.g., a diameter of about 32.6 mm. An appropriate indexing collar 420 is selected, e.g., one that is appropriately sized to support a selected access device 20. Thus, the outer wall 422 and the outer diameter 430 are unchanged between different indexing collars 420, although the inner wall 424 and the inner diameter 432 vary to accommodate differently sized access devices 20.

The indexing collar 420 can be mounted to the proximal portion of the access device 20 to allow angular movement of the endoscope mount platform 300 with respect thereto about the longitudinal axis 308 (as indicated by an arrow C in FIG. 19). The outer wall 422 of the index collar 420 includes a plurality of hemispherical recesses 450 that can receive one or more ball plungers 350 on the endoscope mount platform 300 (indicated in dashed line). This arrangement permits the endoscope mount platform 300, along with the endoscope 500, to be fixed in a plurality of discrete angular positions.

Further details and features related to support arms and indexing collars are described in U.S. Pat. No. 6,361,488, issued Mar. 26, 2002, U.S. Pat. No. 6,530,880 issued Mar. 11, 2003, and application Ser. No. 09/940,402 filed Aug. 27, 2001, published as Publication No. 2003/0040656 on Feb. 27, 2003, which are incorporated by reference in their entireties herein.

2. Viewing Elements

As discussed above, a variety of viewing elements and visualization techniques are embodied in variations of the surgical system 10. One viewing element that is provided in one embodiment is an endoscope.

Figure 22:
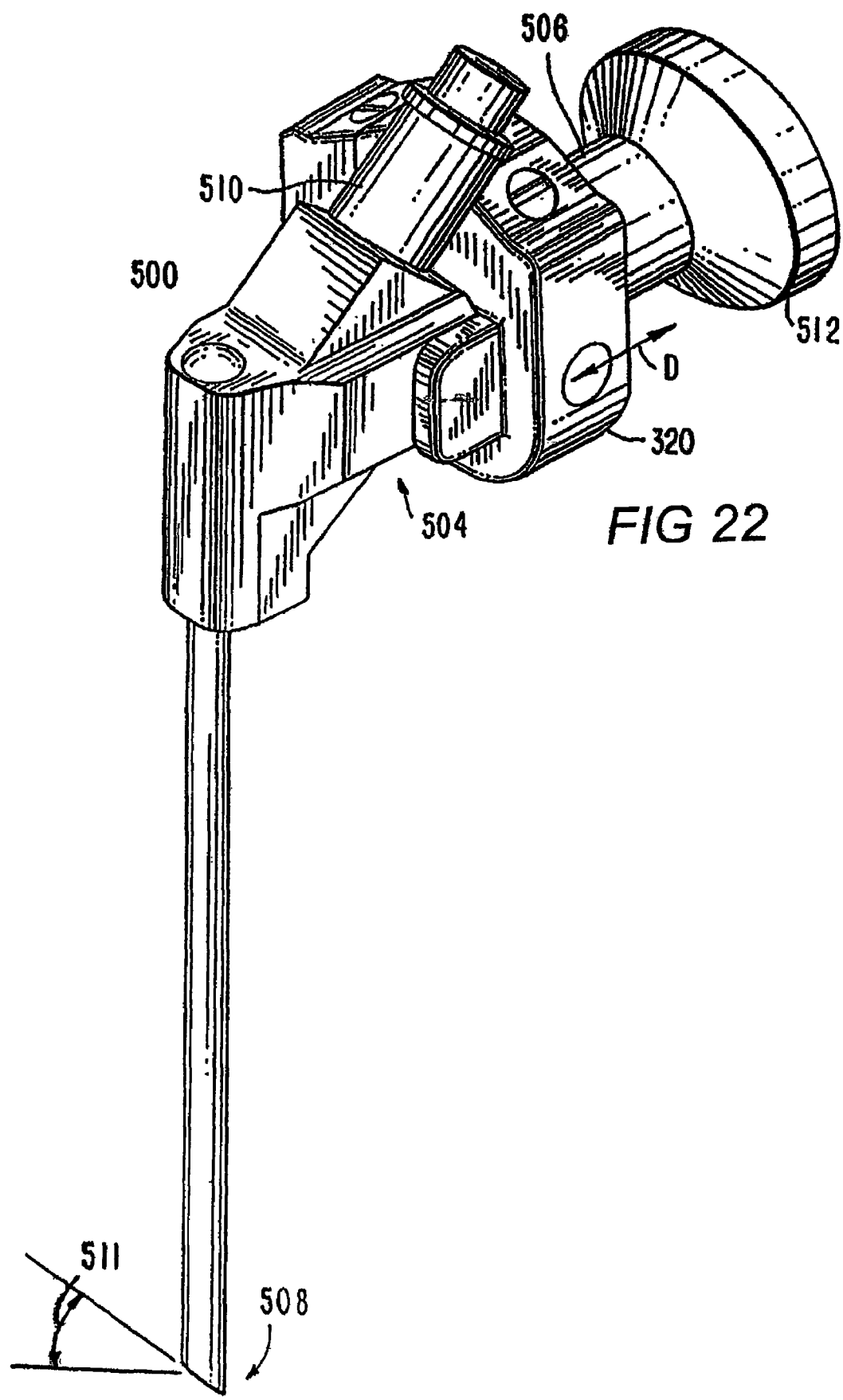
FIG. 22 is a perspective view of one embodiment of an endoscope.

FIG. 22 shows one embodiment of the endoscope 500 that has an elongated configuration that extends into the access device 20 in order to enable viewing of the surgical site. In particular, the endoscope 500 has an elongated rod portion 502 and a body portion 504. The rod portion 502 extends generally perpendicularly from the body portion 504. In one embodiment, the rod portion 502 of endoscope 500 has a diameter of about 4 mm and a length of about 106 mm. Body portion 504 may define a tubular portion 506 configured to be slidably received in the bore 326 of endoscope mount 320 as indicated by an arrow D. The slidable mounting of the endoscope 500 on the endoscope mount platform 300 permits the endoscope 500 to adjust to access device configurations that have different diameters. Additional mobility of the endoscope 500 in viewing the surgical site may be provided by rotating the endoscope mount platform 300 about the central axis 308 (as indicated by arrow C in FIG. 19).

The rod portion 502 supports an optical portion (not shown) at a distal end 508 thereof. In one embodiment, the rod portion 502 defines a field of view of about 105 degrees and a direction of view 511 of about 25-30 degrees. An eyepiece 512 preferably is positioned at an end portion of the body portion 504. A suitable camera (not shown) preferably is attached to the endoscope 500 adjacent the eyepiece 512 with a standard coupler unit. A light post 510 can supply illumination to the surgical site at the distal end portion 508. A preferred camera for use in the system and procedures described herein is a three chip unit that provides greater resolution to the viewed image than a single chip device.

Figure 23A:
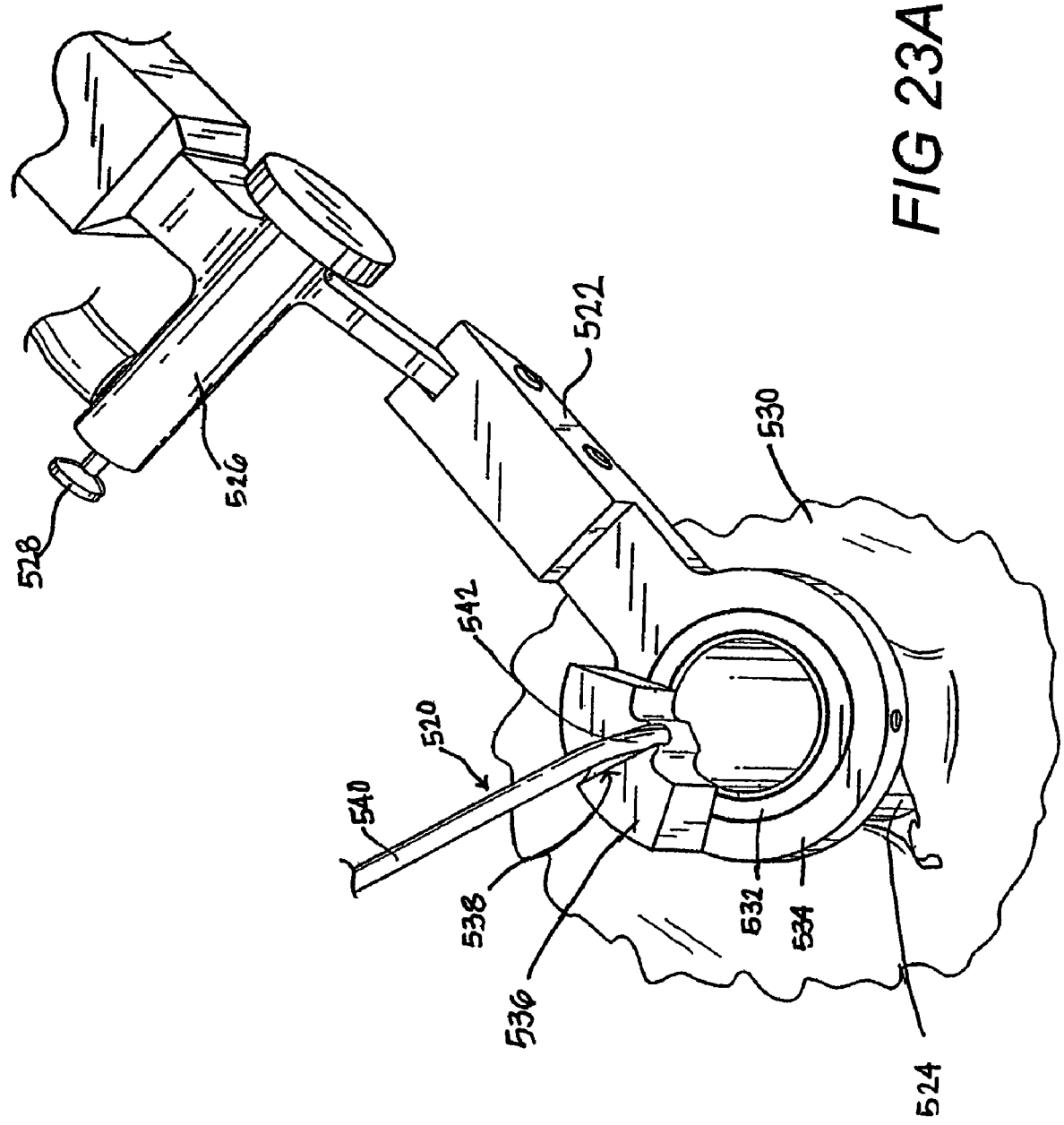
FIG. 23A is a top perspective view of one embodiment of an access system.
Figure 23B:
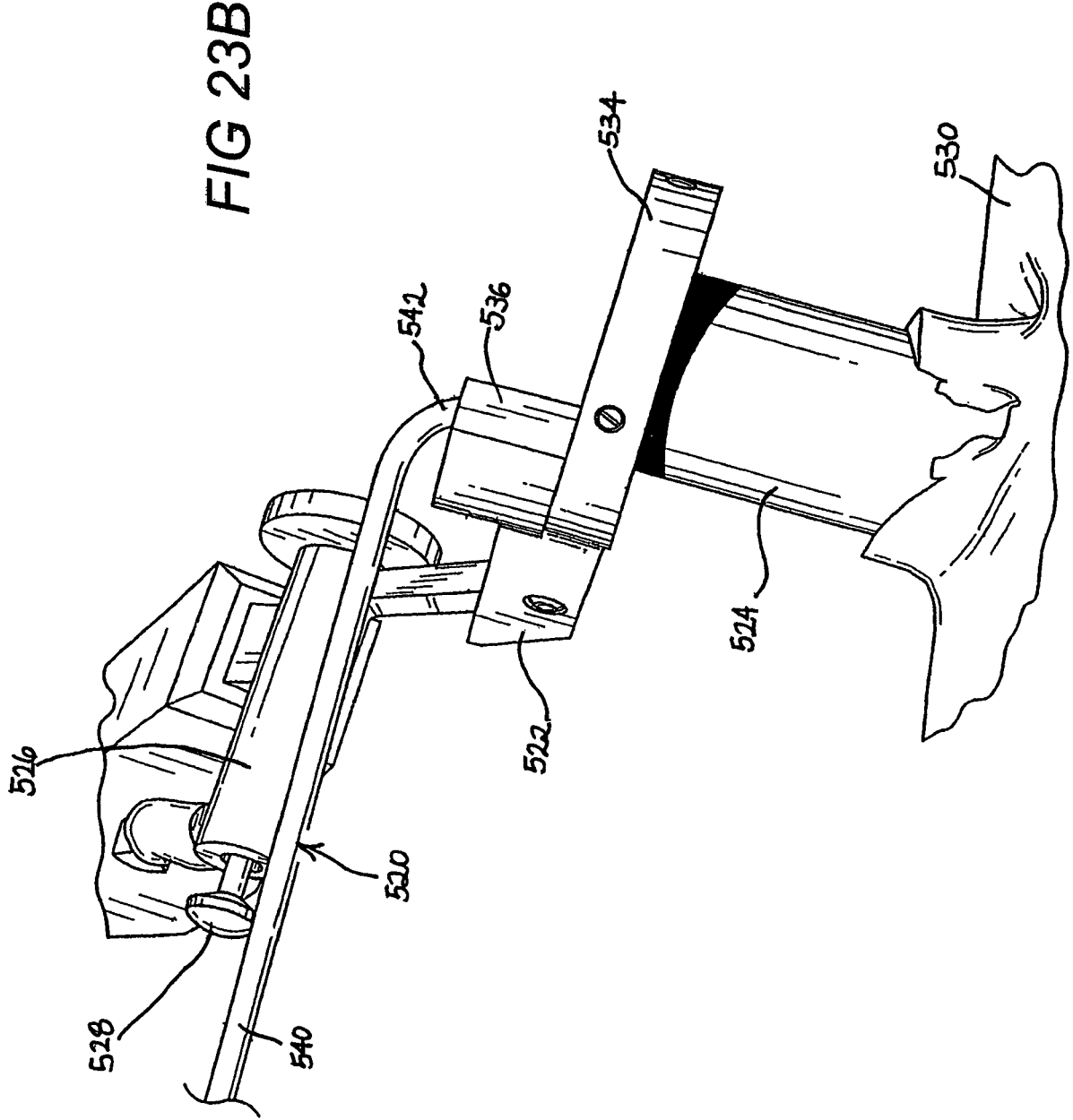
FIG. 23B is a side perspective view of the access system of FIG. 23A.

FIGS. 23A, 23B, 23C, 24A, 24B, and 24C illustrate other embodiments of support devices and viewing elements. FIGS. 23A, 23B, and 23C illustrate one embodiment of a lighting element 520 coupled with a support arm 522 compatible with an access device 524 having a proximal portion with a generally circular cross section. In other embodiments, support arms can be configured to be coupled with access devices having proximal portions with generally oblong or oval cross sections.

The support arm 522 preferably is coupled with the access device 524 to provide support for the access device 524 during a procedure. As shown in FIGS. 23A, 23B, and 23C, the support arm 522 comprises a pneumatic element 526 for maintaining the support arm 522 in a desired position. Depressing a button 528 coupled with a valve of the pneumatic element 526 releases pressure and allows the support arm 522 and access device 524 to be moved relative the patient 530. Releasing the button 528 of the pneumatic element 526 increases pressure and maintains the access device 524 and support arm 522 in the desired position. The support arm 522, as shown, is configured for use with a mechanical arm using a suction, or a vacuum to maintain the access device in a desired location. One of skill in the art will recognize that various other support arms and mechanical arms can be used. For example, commercially available mechanical arms having clamping mechanisms can be used as well as suction or pressure based arms.

The support arm 522 can comprise an inner ring portion 532 and an outer ring portion 534 for surrounding the access device 524 at its proximal end. In the illustrated embodiment, the inner and outer ring portions 532, 534 are fixed relative each other. In other embodiments the inner and outer ring portions 532, 534 can move relative each other. The support arm 522 preferably comprises a lighting element support portion 536. In the illustrated embodiment, the lighting element support portion 536 extends above upper surfaces of the inner and outer ring portions 532, 534. The lighting element support portion 536 can extend from the inner ring portion 532, the outer ring portion 534, or both. The lighting element support portion 536 can have a notch or groove 538 for receiving and supporting the lighting element 520. Additionally, the lighting element support portion 536 can have one or more prongs extending at least partially over the lighting element 520 to hold it in place.

In the illustrated embodiment, the lighting element 520 has an elongated proximal portion 540 and a curved distal portion 542. The proximal portion 540 of the lighting element 520 preferably is coupled with a light source (not shown). The curved distal portion of the lighting element 520 in one embodiment extends only a short distance into the access device and is configured to direct light from the light source down into the access device 524. In another embodiment, the lighting element 520 can be provided such that it does not extend into the access device. In such an embodiment, the right portions 532 and 534 only partially surround the proximal end of the access device 524. Providing a lighting element 520 for use with the access device 524 preferably allows a user to see down into the access device 524 to view a surgical location. Accordingly, use of a lighting element 520 in some cases, enables the user to perform a procedure, in whole or in part, without the use of an endoscope. In one embodiment, the lighting element 520 enables a surgeon to perform the procedure with the use of microscopes or loupes.

Figure 24C:
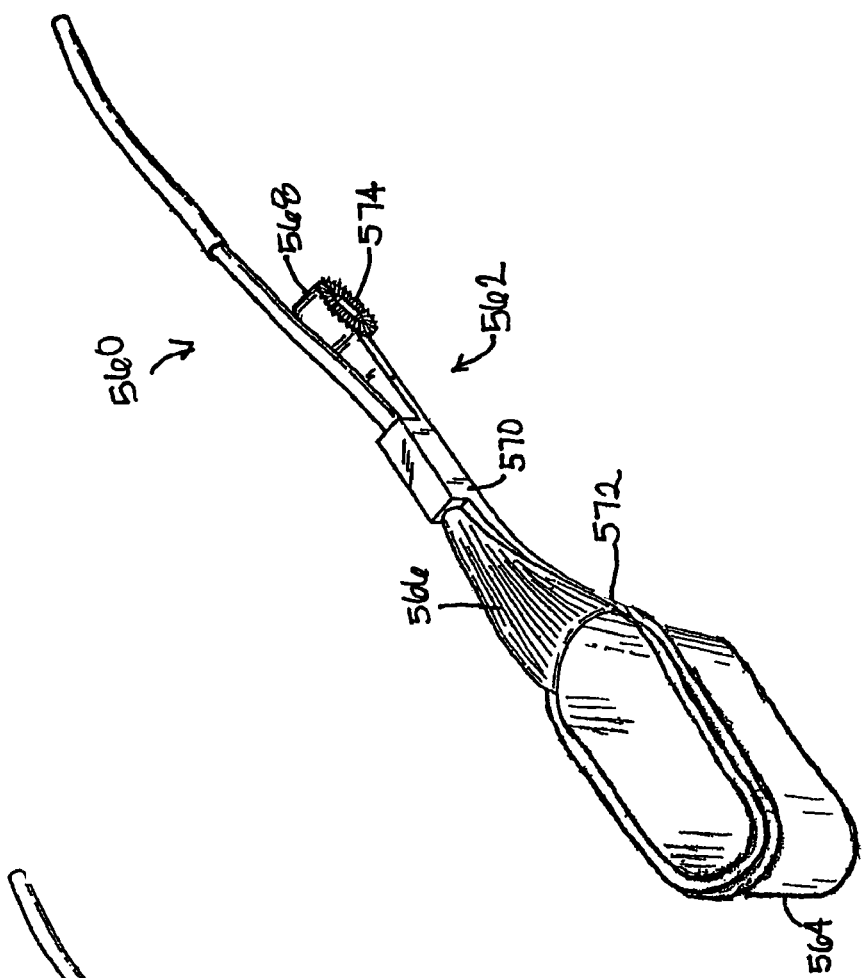
FIG. 24C is a perspective view of another embodiment of a lighting element.
Figure 24B:
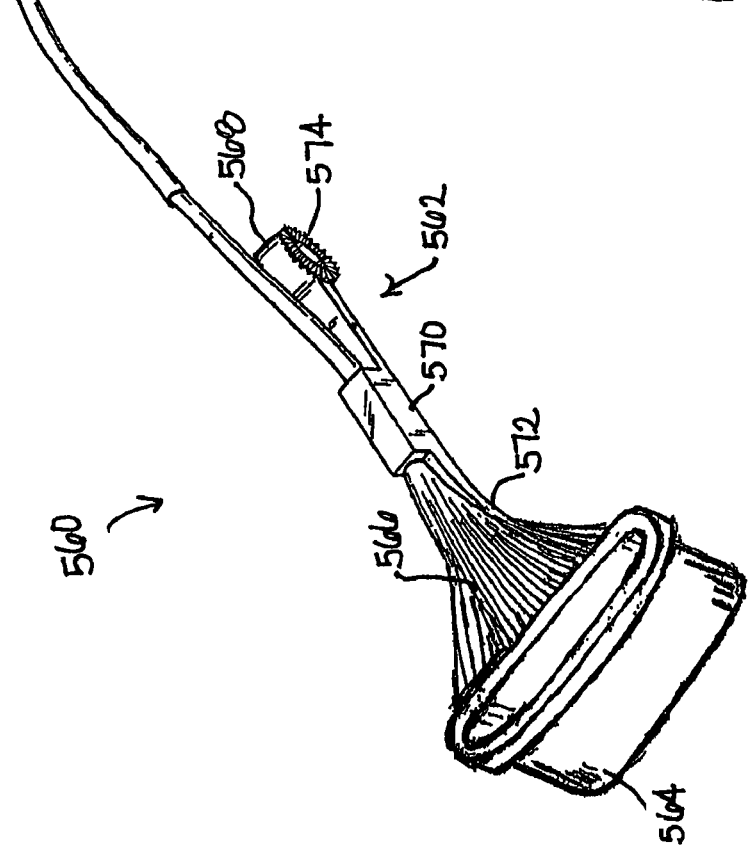
FIG. 24B is a perspective view of another embodiment of a lighting element.

FIGS. 24A, 24B, and 24C illustrate other embodiments of visualization elements. As shown in FIG. 24A, a lighting element 560 comprises a support member 562, an access device insert 564, and fiber optic elements 566. The support member 562 has a proximal end 568, a central portion 570, and a distal end 572. The proximal end 568 preferably has a coupling portion 574 for coupling the support member 562 to a support arm or other support system (not shown). The central portion 570 preferably is coupled with the fiber optic elements 566 to provide support there to. The distal end 572 preferably is coupled with the access device insert 564.

In the illustrated embodiment, the access device insert 564 is configured to be inserted in an access device having a proximal portion with a generally circular cross section. The access device insert 564 is coupled with the fiber optic elements 566. The fiber optic elements 566 extend down into the access device insert 564 so that the ends of the fiber optic elements 566 can direct light down inside an access device along side portions there of.

FIGS. 24B and 24C illustrate other embodiments of visualization elements similar to the embodiment described with reference to FIG. 24A. In the illustrated embodiments, the access device inserts 564 are configured to be inserted into access devices having proximal portions with generally oblong, or oval, cross sections. As shown in FIG. 24B, the access device insert 564 has a generally oblong or oval shaped cross section. The access device insert 564 is coupled with the fiber optic elements 566 along a longer side surface of the access device insert 564. As shown in FIG. 24C, the access device insert 564 has a generally oblong or oval shaped cross section. The access device insert 564 is coupled with the fiber optic elements 566 along a shorter side surface of the access device insert 564. Use of an illumination element with an expandable access device having an oblong shaped proximal section, in some cases, allows a doctor to perform procedures that would be difficult to perform using an endoscope. Increased visualization of the surgical location through the access device can simplify some procedures. For example, decompression of the contra-lateral side can be achieved more easily in some cases without the use of an endoscope.

C. Apparatuses and Methods for Performing Spinal Procedures

The surgical assembly 10 described above can be deployed to perform a wide variety of surgical procedures on the spine. In many cases, the procedures are facilitated by inserting the access device and configuring it to provide greater access to a surgical location, as discussed above and by mounting the support arm 400 and the endoscope mount platform 300 on the proximal portion, e.g., on the proximal end 25, of the access device 20 (FIGS. 1 and 22). As discussed above, visualization of the surgical location is enhanced by mounting a viewing element, such as the endoscope 500, on the endoscope mount platform 300. Having established increased access to and visualization of the surgical location, a number of procedures may be effectively performed.

Generally, the procedures involve inserting one or more surgical instruments into the access device 20 to manipulate or act on the body structures that are located at least partially within the operative space defined by the expanded portion of the access device 20. FIG. 25 shows that in one method, the skirt portion 24 of access device 20 at least partially defines a surgical site or operative space 90 in which the surgical procedures described herein may be performed. Depending upon the overlap of the skirt portion, the skirt portion may define a surface which is continuous about the perimeter or which is discontinuous, having one or more gaps where the material of the skirt portion does not overlap.

One procedure performable through the access device 20, described in greater detail below, is a two-level spinal fusion and fixation. Surgical instruments inserted into the access device may be used for debridement and decortication. In particular, the soft tissue, such as fat and muscle, covering the vertebrae may be removed in order to allow the physician to visually identify the various "landmarks," or vertebral structures, which enable the physician to determine the location for attaching a fastener, such a fastener 600, discussed below, or other procedures, as will be described herein. Enabling visual identification of the vertebral structures enables the physician to perform the procedure while viewing the surgical area through the endoscope, microscope, loupes, or other viewing element, or in a conventional, open manner.

Tissue debridement and decortication of bone are completed using one or more of a debrider blades, a bipolar sheath, a high speed burr, and any other conventional manual instrument. The debrider blades are used to excise, remove and aspirate the soft tissue. The bipolar sheath is used to achieve hemostasis through spot and bulk tissue coagulation. Additional features of debrider blades and bipolar sheaths are described in U.S. Pat. No. 6,193,715, assigned to Medical Scientific, Inc., which is incorporated by reference in its entirety herein. The high speed burr and conventional manual instruments are also used to continue to expose the structure of the vertebrae.

1. Fixation Systems and Devices

Having increased visualization of the pertinent anatomical structure, various procedures may be carried out on the structures. In one procedure, one or more fasteners are attached to adjacent vertebrae V. As discussed in more detail below, the fasteners can be used to provide temporary or permanent fixation and to provide dynamic stabilization of the vertebrae V. These procedures may combined with other procedures, such as procedures employing other types of implant, e.g., procedures employing fusion devices, prosthetic disc components, or other suitable implants. In some procedures, fasteners are attached to the vertebrae before or after fusion devices are inserted between the vertebrae V. Fusion systems and devices are discussed further below.

In one application, the desired location and orientation of the fastener is determined before the fastener is applied to the vertebra. The desired location and orientation of the fastener may be determined in any suitable manner. For example, the pedicle entry point of the L5 vertebrae may be located by identifying visual landmarks alone or in combination with lateral and A/P fluoroscopy, as is known in the art. With continued reference to FIG. 25, an entry point 92 into the vertebra V is prepared. In procedure, the entry point 92 may be prepared with an awl 550. The entry point 92 corresponds to the pedicle in one procedure. The entry point 92 may be prepared in any suitable manner, e.g., employing a bone probe, a tap, and a sounder to create and verify the integrity of the prepared vertebra. The sounder, as is known in the art, determines whether the hole that is made is surrounded by bone on all sides, and can be used to confirm that there has been no perforation of the pedicle wall.

After the hole in the pedicle beneath the entry point 92 is prepared, a fastener may be advanced into the hole. Prior to advancing the fastener, or at any other point during the procedure, it may be desirable to adjust the location of the distal portion of the access device 20. The distal portion of the access device 20 may be adjusted by inserting the expander apparatus 200 into the access device 20, expanding the distal portions 210, and contacting the inner wall of the skirt portion 24 to move the skirt portion 24 to the desired location. This step may be performed while the endoscope 500 is positioned within the access device 20, and without substantially disturbing the location of the proximal portion of the access device 20 to which the endoscope mount platform 300 may be attached.

FIGS. 26-27 illustrate one embodiment of a fastener 600 that is particularly applicable in procedures involving fixation. The fastener 600 preferably includes a screw portion 602, a housing 604, a spacer member 606, a biasing member 608, and a clamping member, such as a cap screw 610. The screw portion 602 has a distal threaded portion 612 and a proximal, substantially spherical joint portion 614. The threaded portion 612 is inserted into the hole that extends away from the entry point 92 into the vertebrae, as will be described below. The substantially spherical joint portion 614 is received in a substantially annular, partly spherical recess 616 in the housing 604 in a ball and socket joint relationship (see also FIG. 29).

As illustrated in FIG. 27, the fastener 600 is assembled by inserting the screw portion 602 into a bore in a passage 618 in the housing 604 until the joint portion 614 engages the annular recess 616. The screw portion 602 is retained in the housing 604 by the spacer member 606 and by the biasing member 608. The biasing member 608 provides a biasing force to drive the spacer member 606 into frictional engagement with the joint portion 614 of the screw member 602 and the annular recess 616 of the housing 604. The biasing provided by the biasing member 602 frictionally maintains the relative positions of the housing 604 with respect to the screw portion 602. The biasing member 608 preferably is selected such that biasing force prevents unrestricted movement of the housing 604 relative to the screw portion 602. However, in some embodiments the biasing force is insufficient to resist the application of force by a physician to move the housing 604 relative to the screw portion 602. In other words, this biasing force is strong enough maintain the housing 604 stationary relative to the screw portion 602, but this force may be overcome by the physician to reorient the housing 604 with respect to the screw member 602, as will be described below.

In the illustrated embodiment, the biasing member 608 is a resilient ring having a gap 620, which permits the biasing member 608 to radially contract and expand. FIG. 27A illustrates that the biasing member 608 may have an arched shape, when viewed end-on. The arched shape of the spring member 608 provides the biasing force, as will be described below. The spacer member 606 and the biasing member 608 are inserted into the housing 604 by radially compressing the biasing member into an annular groove 622 in the spacer member 606. The spacer member 606 and the biasing member 608 are slid into the passage 618 until the distal surface of the spacer member 606 engages the joint portion 614 of the screw portion 602, and the biasing member 608 expands radially into the annular groove 622 in the housing 604. The annular groove 622 in the housing 604 has a dimension 623 that is smaller than the uncompressed height of the arched shape of the biasing member 608. When the biasing member 608 is inserted in the annular groove 620, the biasing member 608 is flattened against its normal bias, thereby exerting the biasing force to the spacer member 606. It is understood that similar biasing members, such as coiled springs, belleville washers, or the like may be used to supply the biasing force described herein.

The spacer member 606 is provided with a longitudinal bore 626, which provides access to a hexagonal recess 628 in the proximal end of the joint portion 614 of the screw member 602. The proximal portion of the housing 604 includes a pair of upright members 630 and 631 that are separated by substantially "U"-shaped grooves 632. A recess for receiving elongated member 650 is defined by the pair of grooves 632 between upright members 630 and 631. Elongated member 650 preferably is configured to be placed distally into the housing 604 in an orientation substantially transverse to the longitudinal axis of the housing 604, as will be described below. The inner walls of he upright members 630 and 631 are provided with threads 634 for attachment of the cap screw 610 by threads 613 therein.

Additional features of the fastener 600 are also described in U.S. patent application Ser. No. 10/075,668, filed Feb. 13, 2002, published as U.S. Application Publication No. 2003/0153911A1 on Aug. 14, 2003, and application Ser. No. 10/087,489, filed Mar. 1, 2002, published as U.S. Application Publication No. 2003/0167058A1 on Sep. 4, 2003, which are incorporated by reference in their entireties herein.

Figure 28:
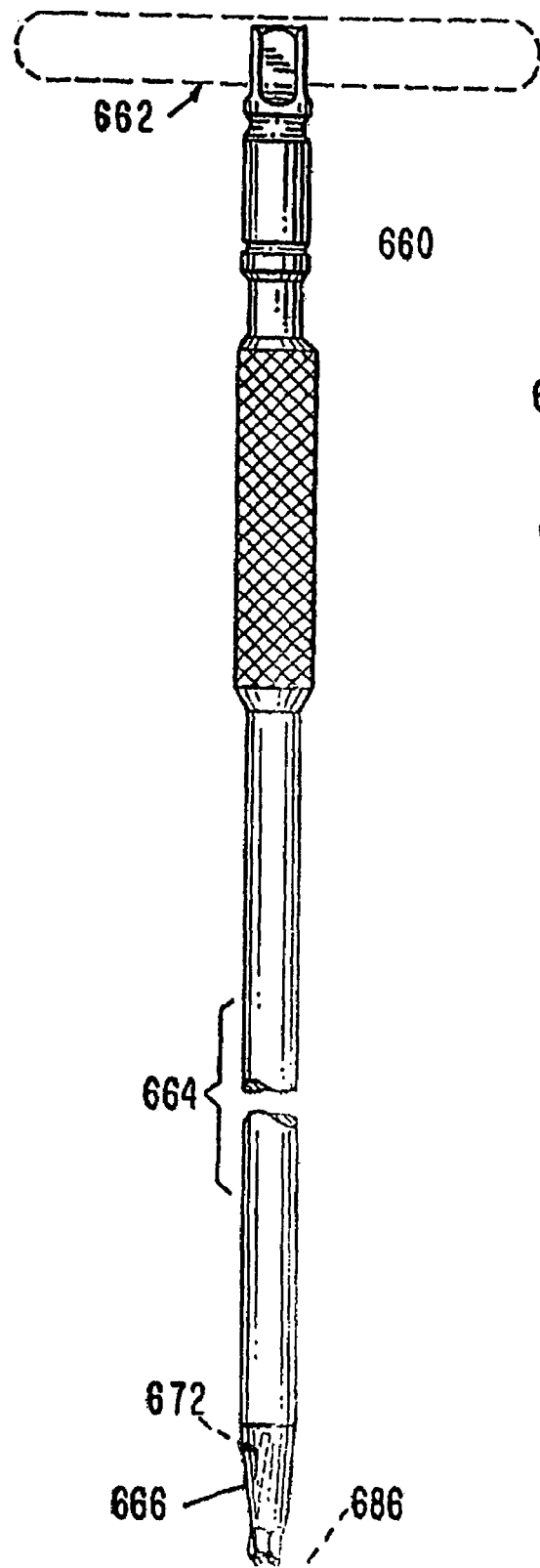
FIG. 28 is a perspective view of one embodiment of a surgical instrument.

According to one application, the fastener 600 is inserted into the access device 20 and guided to the prepared hole at the entry point 92 in the vertebrae. The fastener 600 preferably is simultaneously supported and advanced into the hole so that the fastener 600 is secured in the in the hole beneath the entry point 92. In the illustrated embodiment the fastener 600 is supported and attached to the bone by an endoscopic screwdriver apparatus 660, illustrated in FIGS. 28-29. The screwdriver 660 includes a proximal handle portion 662 (illustrated in dashed line), an elongated body portion 664, and a distal tool portion 666.

Figure 29:
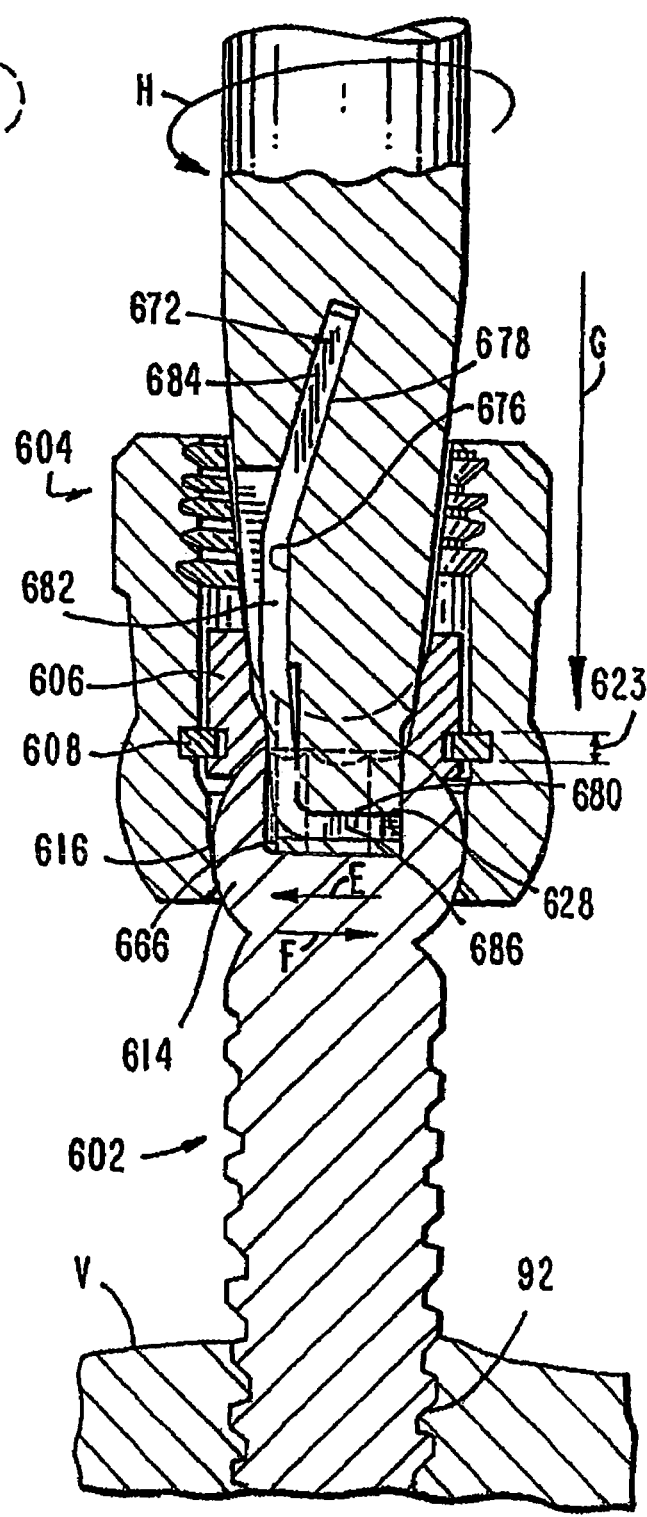
FIG. 29 is an enlarged sectional view of the fastener of FIGS. 26-27 coupled with the surgical instrument of FIG. 28, illustrating one stage of one application for treating the spine of a patient.

The distal tool portion 666, as illustrated in greater detail in FIG. 29 includes a substantially hexagonal outer periphery that is received in the substantially hexagonal recess 628 in the joint portion 614 of the screw member 602. A spring member at the distal tool portion 666 releasably engages the hexagonal recess 628 of the screw member 602 to support the fastener 600 during insertion and tightening. In the illustrated embodiment, a spring member 672 is configured to engage the side wall of the recess 628. More particularly, a channel or a groove is provided in the tip portion 666 for receiving the spring member 672. The channel or groove includes a medial longitudinal notch portion 676, a proximal, angled channel portion 678, and a distal substantially transverse channel portion 680. The spring member 672 is preferably manufactured from stainless steel and has a medial portion 682, proximal portion 684, and a transverse distal portion 686. The medial portion 682 is partially received in the longitudinal notch portion 676. The proximal portion 684 preferably is angled with respect to the medial portion 682 and is fixedly received in the angled channel portion 678. The transverse distal portion 686 preferably is slidably received in the transverse channel 680. The medial portion 682 of the spring member 672 is partially exposed from the distal tip portion 666 and normally is biased in a transverse outward direction with respect to the longitudinal axis (indicated by arrow E), in order to supply bearing force against the wall of the recess 628. Alternatively, the distal tip portion of the screwdriver may be magnetized in order to hold the screw portion 602. Similarly, the distal tip portion may include a ball bearing or similar member which is normally biased in a radially outward direction to engage the interior wall of the recess 628 to secure the fastener 600 to the screwdriver distal tip 666. Other means may be provided for temporarily but securely coupling the fastener 600 with the screwdriver distal tip 666.

The insertion of the fastener 600 into the prepared hole that extends into the vertebrae from the entry point 92 may be achieved by insertion of screwdriver 660 into access device 20 (indicated by arrow G). This procedure may be visualized by the use of the endoscope 500 in conjunction with fluoroscopy, or by way of any other suitable viewing element. The screw portion 602 is threadedly advanced by the endoscopic screwdriver 660 into the prepared hole that extends beneath the entry point 92 (indicated by arrow H). The endoscopic screwdriver 660 is subsequently separated from the fastener 600, by applying a force in the proximal direction, and thereby releasing the distal tip portion 666 from the hexagonal recess 628 (e.g., causing the transverse distal portion 686 of the spring member 672 to slide within the transverse recess 680 against the bias, indicated by arrow F), and removing the screwdriver 660 from the access device 20. An alternative method may use a guidewire, which is fixed in the hole beneath the entry point 92, and a cannulated screw which has an internal lumen and is guided over the guidewire into the hole beneath the entry point 92. Where a guidewire system is used, the screwdriver also would be cannulated so that the screwdriver would fit over the guidewire.

For a two-level fixation, it may be necessary to prepare several holes and attach several fasteners 600. Preferably, the access device 20 is sized to provide simultaneous access to all vertebrae in which the surgical procedure is being performed. In some cases, however, additional enlargement or repositioning of the distal portion of the access device 20 may be helpful in providing sufficient access to the outer vertebrae, e.g., the L4 and S1 vertebrae. In the illustrated embodiment, the expander apparatus 200 may be repeatedly inserted into the access device 20 and expanded in order to further open or to position the skirt portion 24. In one procedure, additional fasteners are inserted in the L4 and S1 vertebrae in a similar fashion as the fastener 600 inserted into the L5 vertebra as described above. (When discussed individually or collectively, a fastener and/or its individual components will be referred to by the reference number, e.g., fastener 600, housing 604, and all fasteners 600. However, when several fasteners and/or their components are discussed in relation to one another, an alphabetic subscript will be used, e.g., fastener 600*a* is moved towards fastener 600*b*.)

In one application, after the fasteners 600 are advanced into the vertebrae, the housing portions 604 of the fasteners 600 are substantially aligned such that their upright portions 630 and 631 face upward, and the notches 632 are substantially aligned to receive the elongated member 650 therein. The frictional mounting of the housing 604 to the screw member 602, described above, allows the housing 604 to be temporarily positioned until a subsequent tightening step is performed, described below.

Positioning of the housing portions 604 may be performed by the use of an elongated surgical instrument capable of contacting and moving the housing portion to the desired orientation. One such instrument for positioning the housings 604 is a grasper apparatus 700, illustrated in FIG. 30. The grasper apparatus 700 includes a proximal handle portion 702, an elongated body portion 704, and distal nose portion 706. The distal nose portion 706 includes a pair of grasping jaws 708*a* and 708*b*, which are pivotable about pin 710 by actuation of the proximal handle portion 702. The grasping jaws 708*a* and 708*b* are illustrated in the closed position in FIG. 30. Pivoting the movable handle 714 towards stationary handle 712 causes longitudinal movement of actuator 716, which in turn pivots the jaw 708*b* towards an open position (illustrated in dashed line). The biasing members 718 and 720 are provided to return the handles 712 and 714 to the open position and bias the jaws 708*a* and 708*b* to the closed position.

In one application, the elongated member 650 is inserted into the access device 20. In one application, the elongated member 650 is manufactured from a biocompatible material and is sufficiently strong to maintain the position of the vertebrae, or other body structures, coupled by the elongate member 650 with little or no relative motion therebetween. In one embodiment, the elongated members 650 are manufactured from Titanium 6/4 or titanium alloy. The elongated member 650 also may be manufactured from stainless steel or any other suitable material. The transverse shape, width (e.g., radii), and lengths of the elongated members 650 are selected by the physician to provide the best fit for the positioning of the screw heads. Such selection may be performed by placing the elongated member 650 on the skin of the patient overlying the location of the fasteners and viewed fluoroscopically. For example, a 70 mm preformed rod having a 3.5" bend radius may be selected for the spinal fixation.

In one application, the elongated member 650 is fixed to each of the fasteners 600, and more particularly, to the housings 604 of each fastener 600. The grasper apparatus 700, described above, is also particularly useful for inserting the elongated member 650 into the access device 20 and positioning it with respect to each housing 604. As illustrated in FIG. 30, the jaws 708*a* and 708*b* of the grasper apparatus 700 each has shaped (e.g., curved) contact portions 722*a* and 722*b* for contacting and holding the outer surface of the elongated member 650.

As illustrated in FIG. 31, the grasper apparatus 700 may be used to insert the elongated member 650 into the operative space 90 defined at least partially by the skirt portion 24 of the access device 20. In some embodiments, the cut-out portions 56 and 58 provided in the skirt portion 24 assist in the process of installing the elongated member 650 with respect to the housings 604. The cut-out portions 56 and 58 allow an end portion 652 of the elongated member 650 to extend beyond the operative space without raising or repositioning the skirt portion 24. The elongated member 650 is positioned within the recesses in each housing 604 defined by grooves 632 disposed between upright members 630 and 631. The elongated member 650 is positioned in an orientation substantially transverse to the longitudinal axis of each housing 604.

Figures 32, 33, 34:
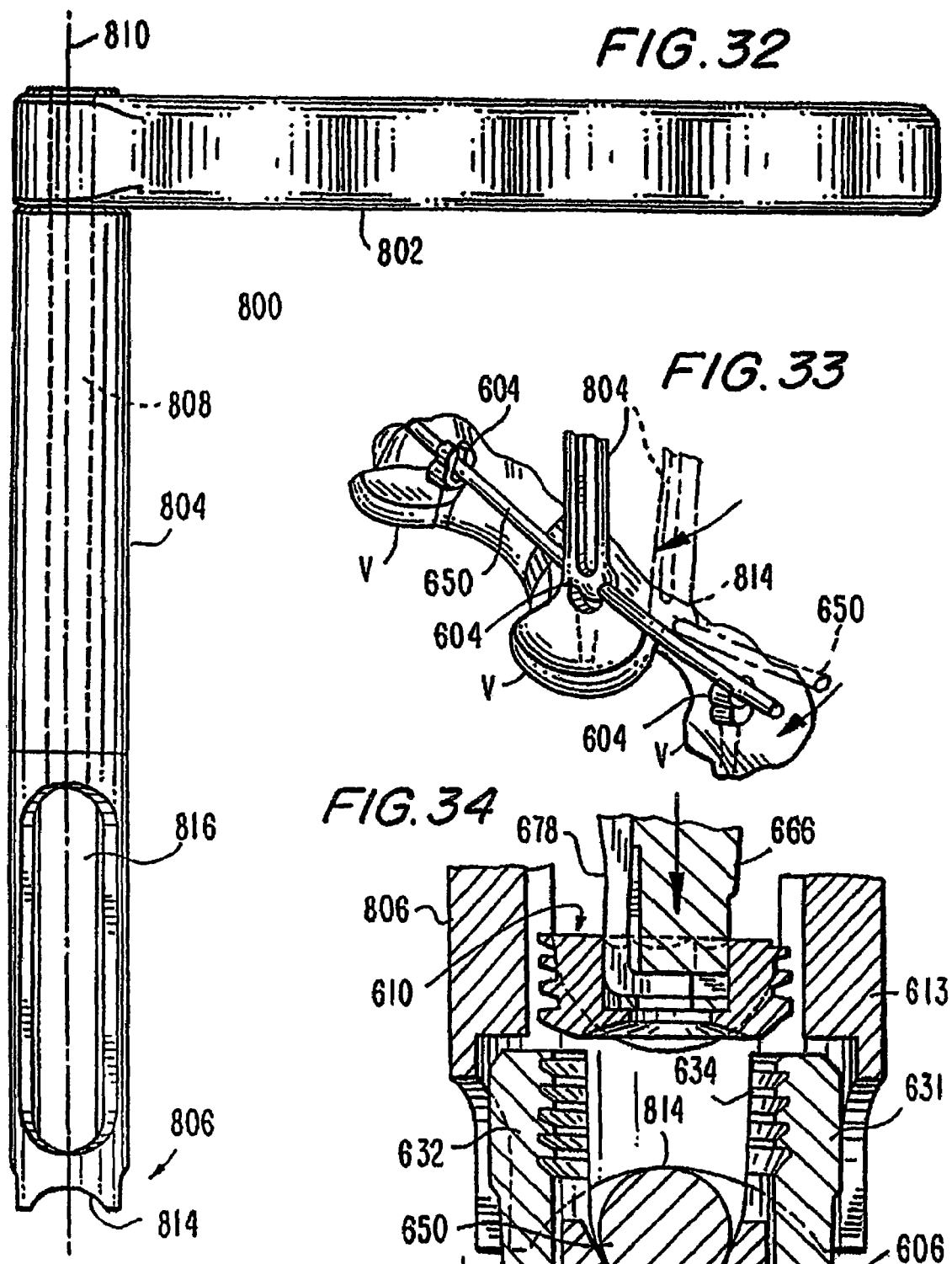
FIG. 32 is a side view of one embodiment of another surgical instrument.
FIG. 33 is a perspective view similar to FIG. 31 illustrating the apparatuses of FIGS. 26 and 32, in one stage of one application for treating the spine of a patient.
FIG. 34 is an enlarged sectional view of the apparatus of FIGS. 26 and 32, illustrating one stage of one application for treating the spine of a patient.

Further positioning of the elongated member 650 may be performed by guide apparatus 800, illustrated in FIG. 32. Guide apparatus 800 is useful in cooperation with an endoscopic screwdriver, such as endoscopic screwdriver 660 (illustrated in FIG. 28), in order to position the elongated member 650, and to introduce and tighten the cap screw 610, described above and illustrated in FIG. 27. Tightening of the cap screw 610 with respect to the housing 604 fixes the orientation of the housing 604 with respect to the screw portion 602 and fixes the position of the elongated member 650 with respect to the housings 604.

In the illustrated embodiment, the guide apparatus 800 has a proximal handle portion 802, an elongated body portion 804, and a distal tool portion 806. The elongated body portion 804 defines a central bore 808 (illustrated in dashed line) along its longitudinal axis 810. The central bore 808 is sized and configured to receive the endoscopic screwdriver 660 and cap screw 610 therethrough. In one embodiment, the diameter of the central bore 808 of the elongated body portion 804 is about 0.384-0.388 inches in diameter, and the external diameter of the endoscopic screwdriver 660 (FIG. 28) is about 0.25 inches. The proximal handle portion 802 extends transverse to the longitudinal axis 810, which allows the physician to adjust the guide apparatus 800 without interfering with the operation of the screwdriver 660.

The distal portion 806 of the apparatus includes several shaped cut out portions 814 which assist in positioning the elongated member 650. As illustrated in FIG. 33, the cut out portions 814 are sized and configured to engage the surface of elongated member 650 and move the elongated member 650 from an initial location (illustrated in dashed line) to a desired location. In the illustrated embodiment, the cut out portions 814 are semicircular, to match the round elongated member 650. However, other shaped cut out portions may be provided to match other shaped elongated members.

As illustrated in FIG. 34, the guide apparatus 800 is used in cooperation with the endoscopic screwdriver 660 to attach the cap screw 610. The distal end of the body portion 804 includes a pair of elongated openings 816. The openings 816 provide a window to enable the physician to endoscopically view the cap screw 610 retained at the distal tip 666 of the endoscopic screw driver 660. Fewer or more than two openings can be provided and the openings 816 need not be elongated.

The guide apparatus 800 and the endoscopic screwdriver 660 cooperate as follows in one application. The guide apparatus 800 is configured to be positioned in a surrounding configuration with the screwdriver 600. In the illustrated embodiment, the body portion 804 is configured for coaxial placement about the screwdriver 660 in order to distribute the contact force of the guide apparatus 800 on the elongated member 650. The distal portion 806 of the guide apparatus 800 may bear down on the elongated member 650 to seat the elongated member 650 in the notches 632 in the housing 604. The "distributed" force of the guide apparatus 800 may contact the elongated member 650 on at least one or more locations. In addition, the diameter of central bore 808 is selected to be marginally larger than the exterior diameter of cap screw 610, such that the cap screw 610 may freely slide down the central bore 808, while maintaining the orientation shown in FIG. 34. This configuration allows the physician to have effective control of the placement of the cap screw 610 into the housing 604. The cap screw 610 is releasably attached to the endoscopic screwdriver 660 by means of spring member 672 engaged to the interior wall of hexagonal recess 611 as it is inserted within the bore 808 of the body portion 804 of guide apparatus 800. The cap screw 610 is attached to the housing 604 by engaging the threads 615 of the cap screw 610 with the threads 634 of the housing.

Figure 35:
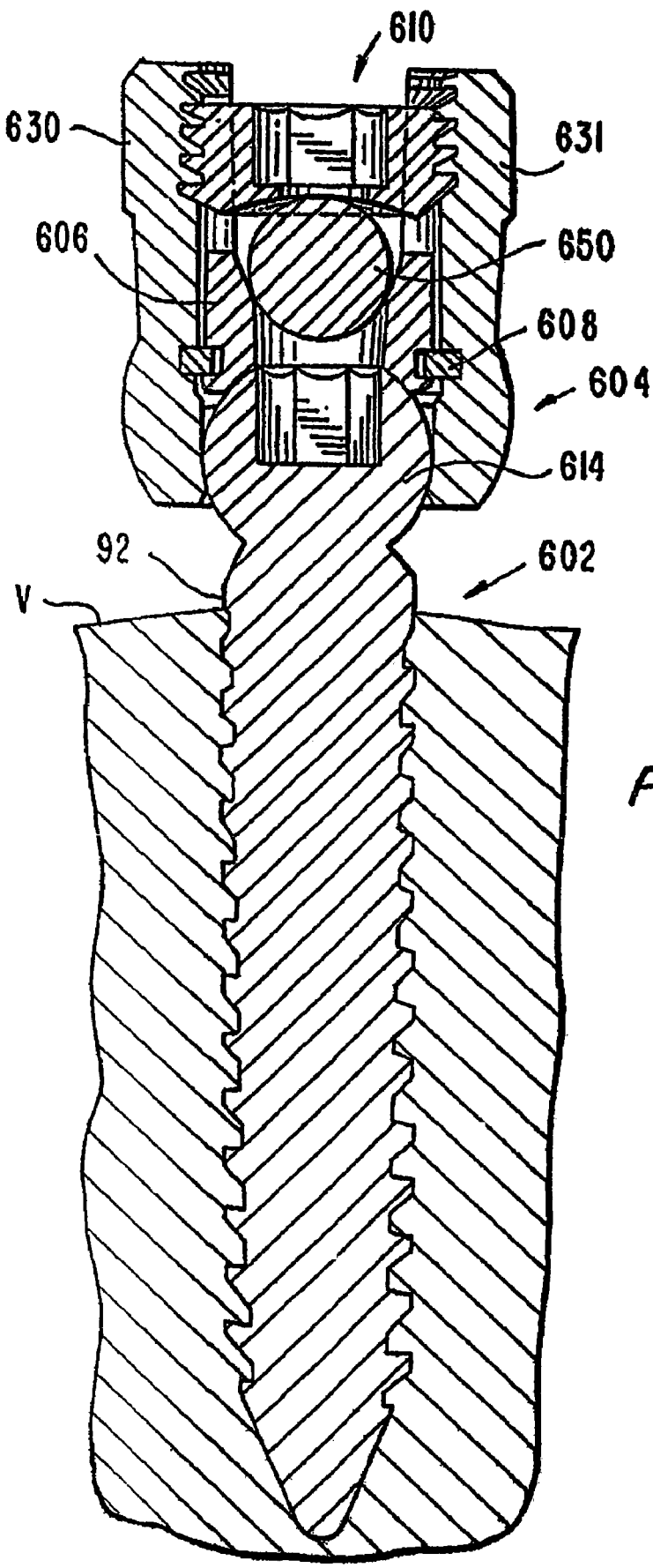
FIG. 35 is an enlarged sectional similar to FIG. 34, illustrating one stage of one application for treating the spine of a patient.

As illustrated in FIG. 35, tightening of the cap screw 610 fixes the assembly of the housing 604 with respect to the elongated member 650. In particular, the distal surface of the cap screw 610 provides a distal force against the elongated member 650, which in turn drives the spacer member 606 against the joint portion 614 of the screw portion 602, which is fixed with respect to the housing 604.

If locations of the vertebrae are considered acceptable by the physician, then the fixation procedure is substantially complete once the cap screws 610 have been attached to the respective housings 604, and tightened to provide a fixed structure as between the elongated member 650 and the various fasteners 600. However, if compression or distraction of the vertebrae with respect to one another is required additional apparatus would be used to shift the vertebrae prior to final tightening all of the cap screws 610.

In the illustrated embodiment, this step is performed with a surgical instrument, such as a compressor-distractor instrument 900, illustrated in FIG. 36, which is useful to relatively position bone structures in the cephcaudal direction and to fix their position with respect to one another. Thus, the compressor-distractor instrument 900 has the capability to engage two fasteners 600 and to space them apart while simultaneously tightening one of the fasteners to fix the spacing between the two vertebrae, or other bone structures. Moreover, the compressor-distractor instrument 900 may also be used to move two fasteners 600, and the vertebrae attached thereto into closer approximation and fix the spacing therebetween.

The distal tool portion 902 of one embodiment of the compressor-distractor instrument 900 is illustrated in FIG. 36. The distal tool portion 902 includes a driver portion 904 and a spacing member 906. The driver portion 904 has a distal end portion 908 with a plurality of wrenching flats configured to engage the recess 611 in the proximal face of the cap screw 610, and to apply torque to the cap screw. The driver portion 904 is rotatable about the longitudinal axis (indicated by arrow M) to rotate the cap screw 610 relative to the fastener 600. Accordingly, the driver portion 904 can be rotated to loosen the cap screw 610 on the fastener 600 and permit movement of the elongated member 650 connected with the vertebra relative to the fastener 600 connected with the vertebra. The cap screw 610 can also be rotated in order to tighten the cap screw 610 and clamp the elongated member 650 to the fastener 600.

The distal tool portion 902 may also include a spacing member, such as spacing member 906, which engages an adjacent fastener 600*b* while driver member 904 is engaged with the housing 604*a* to move the fastener 600*b* with respect to the fastener 600*a*. In one embodiment, spacing member 906 comprises a jaw portion that is pivotably mounted to move between a first position adjacent the driver portion and a second position spaced from the driver portion, as shown in FIG. 36. The distal tip 910 of the spacing member 906 is movable relative to the driver portion 904 in a direction extending transverse to the longitudinal axis. (Further details and features related to compressor-distractor apparatuses are described in U.S. application Ser. No. 10/178,875, filed Jun. 24, 2002, entitled "Surgical Instrument for Moving Vertebrae," published as U.S. Patent Application Publication No. 2003/0236529A1 on Dec. 25, 2003, which is incorporated by reference in its entirety herein. Additionally, further details related to instrumentation for moving a vertebra are described in U.S. Pat. No. 6,648,888, issued Nov. 18, 2003; PCT Application No. PCT/US02/28106, filed Sep. 5, 2002, titled SURGICAL INSTRUMENT FOR MOVING VERTEBRAE; PCT Application No. PCT/US03/27879, filed Sep. 5, 2003, titled SURGICAL INSTRUMENT FOR MOVING A VERTEBRAE; and PCT Application No. PCT/US03/04361, filed Feb. 13, 2003, titled APPARATUS FOR CONNECTING A LONGITUDINAL MEMBER TO A BONE PORTION, which are hereby incorporated by reference in their entireties herein.)

As illustrated in FIG. 36, the spacer member 906 can be opened with respect to the driver portion 904 to space the vertebrae farther apart (as indicated by arrow N). The distal portion 910 of the spacer member 906 engages the housing 604*b* of fastener 600*b* and moves fastener 600*b* further apart from fastener 600*a* to distract the vertebrae. Where the vertebrae are to be moved closer together, e.g. compressed, the spacer member 906 is closed with respect to the driver portion 904 (arrow P), as illustrated in FIG. 37. The distal portion 910 of the spacer member 906 engages the housing 604*b* of the fastener 600*b* and moves the fastener 600*b* towards the fastener 600*a*. When the spacing of the vertebrae is acceptable to the physician, the cap screw 610*a* is tightened by the driver member 904, thereby fixing the relationship of the housing 604*a* with respect to the elongated member 650, and thereby fixing the position of the vertebrae, or other bone structures, with respect to one another. In one application, once the elongated member 650 is fixed with respect to the fasteners 600, the fixation portion of the procedure is substantially complete.

2. Fusion Systems and Devices

Although fixation may provide sufficient stabilization, in some cases it is also desirable to provide additional stabilization. For example, where one or more discs has degraded to the point that it needs to be replaced, it may be desirable to position an implant, e.g., a fusion device, a prosthetic disc, a disc nucleus, etc., in the intervertebral space formerly occupied by the disc.

Figure 48:
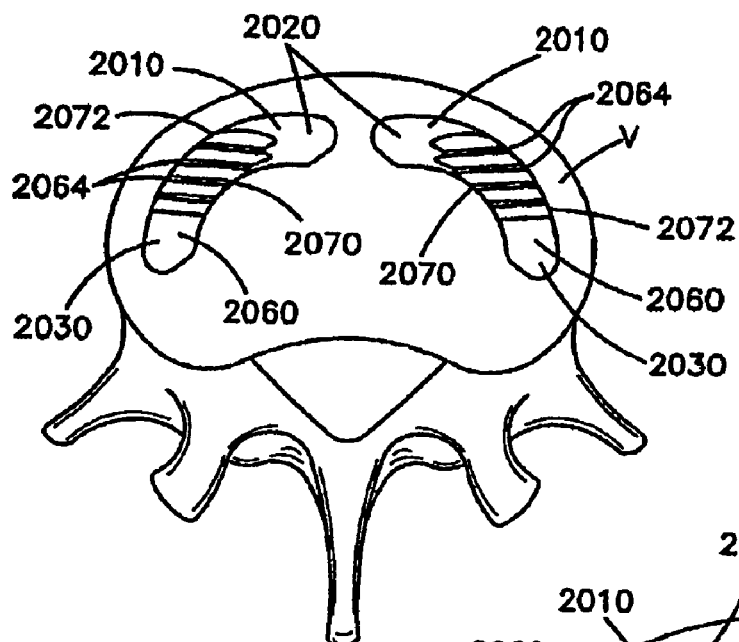
FIG. 48 is a view showing a pair of the spinal implants of FIG. 38 in first relative positions between adjacent vertebrae.
Figure 49:
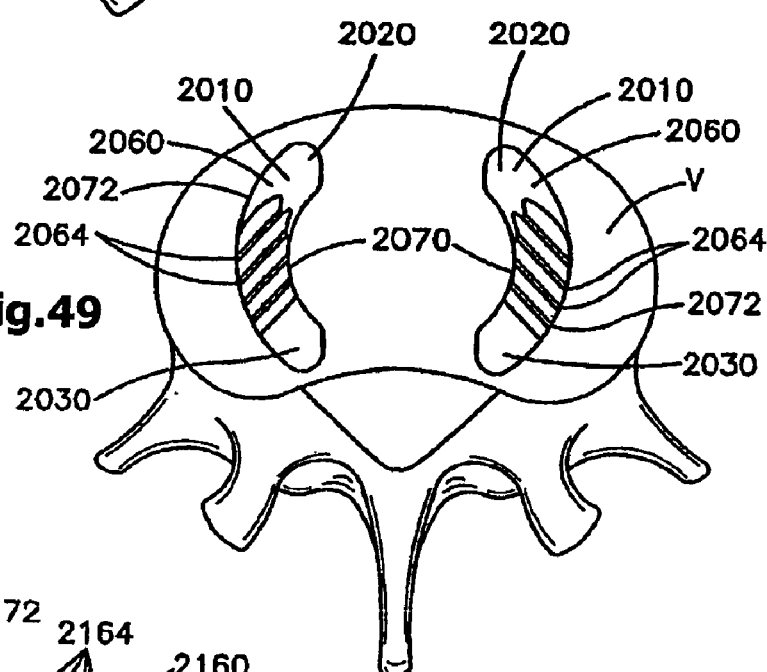
FIG. 49 is a view showing a pair of the spinal implants of FIG. 38 in second relative positions between adjacent vertebrae.

In one application, a fusion device is inserted between adjacent vertebrae V. Portions of the fusion procedure can be performed before, during, or after portions of the fixation procedure. FIGS. 38-42 illustrate one embodiment of a fusion device, referred to herein as a spinal implant 2010, that is inserted between adjacent vertebrae. The spinal implant 2010 preferably is placed between adjacent vertebrae to provide sufficient support to allow fusion of the adjacent vertebrae, as shown in FIGS. 48-49. The spinal implants 2010 are preferably made from an allograft material, though other materials could also be used, including autograft, xenograft, or some non-biologic biocompatible material, such as titanium or stainless steel. Also, where non-biologic materials are used, the implant 2010 may be configured as a cage or other suitable configuration.

The spinal implant 2010 (FIGS. 38-42) has a first end 2020 for insertion between adjacent vertebrae V. The first end 2020 has a tapered surface 2022 to facilitate insertion of the implant between adjacent vertebrae V. The surface 2022 defines an angle X of approximately 45° as shown in FIG. 41.

Figure 51:
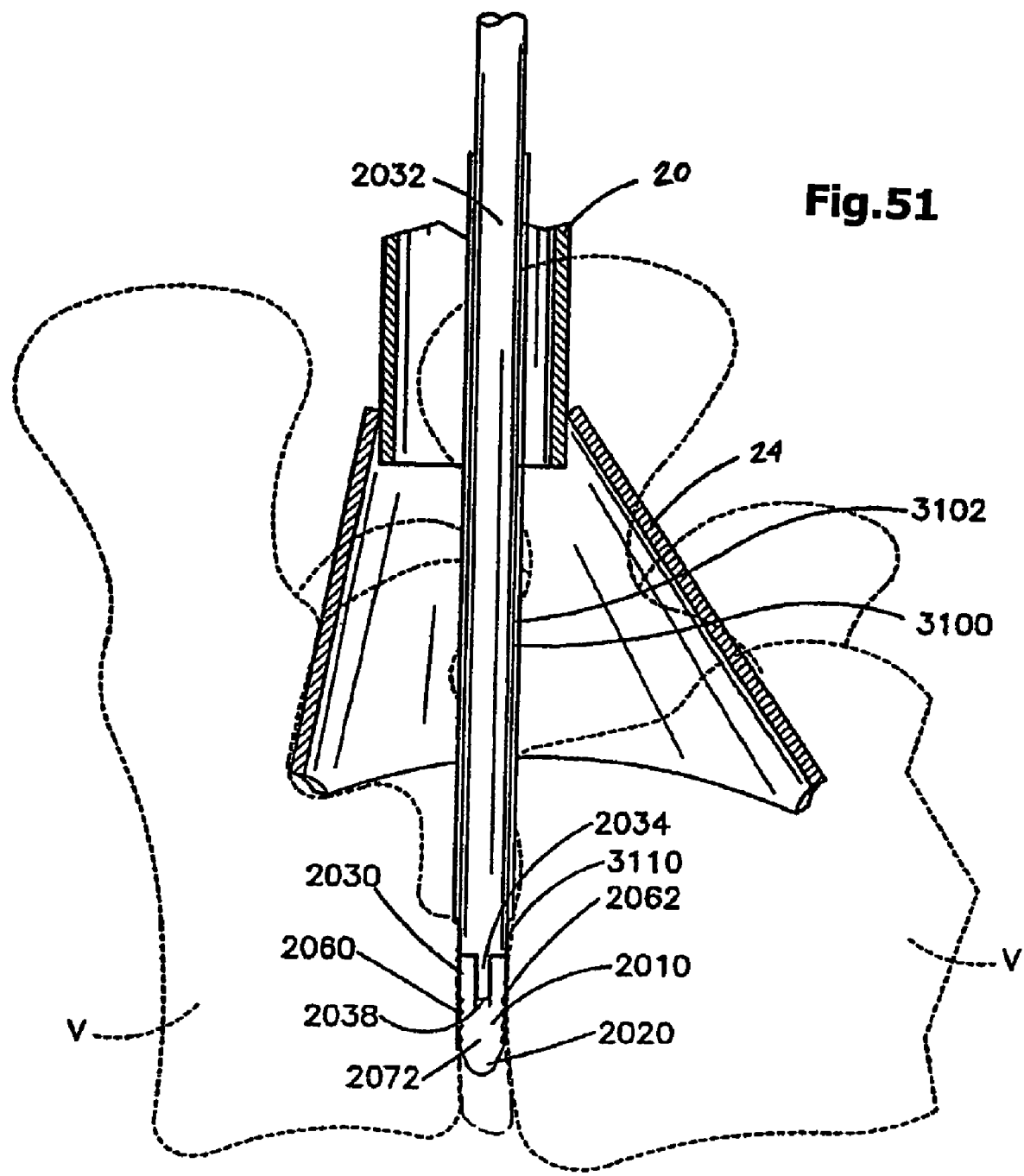
FIG. 51 is a view showing a spinal implant being inserted between the adjacent vertebrae according to one application.
Figure 54:
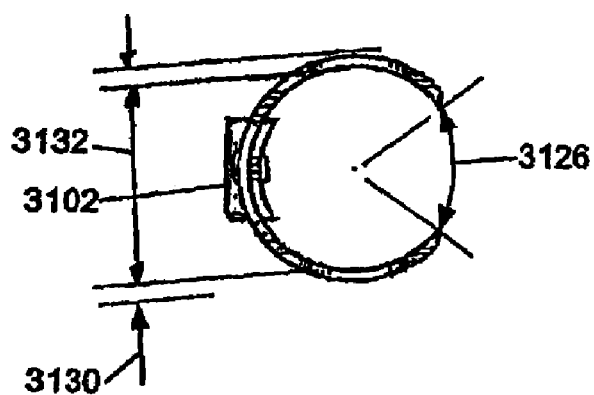
FIG. 54 is a top view of the apparatus of FIG. 52.
Figure 56:
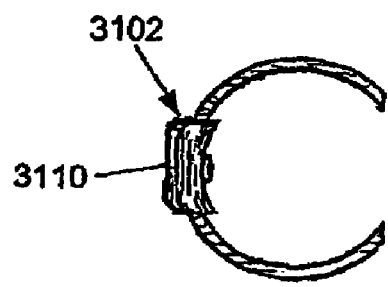
FIG. 56 is a bottom view of the apparatus of FIG. 52.
Figure 55:
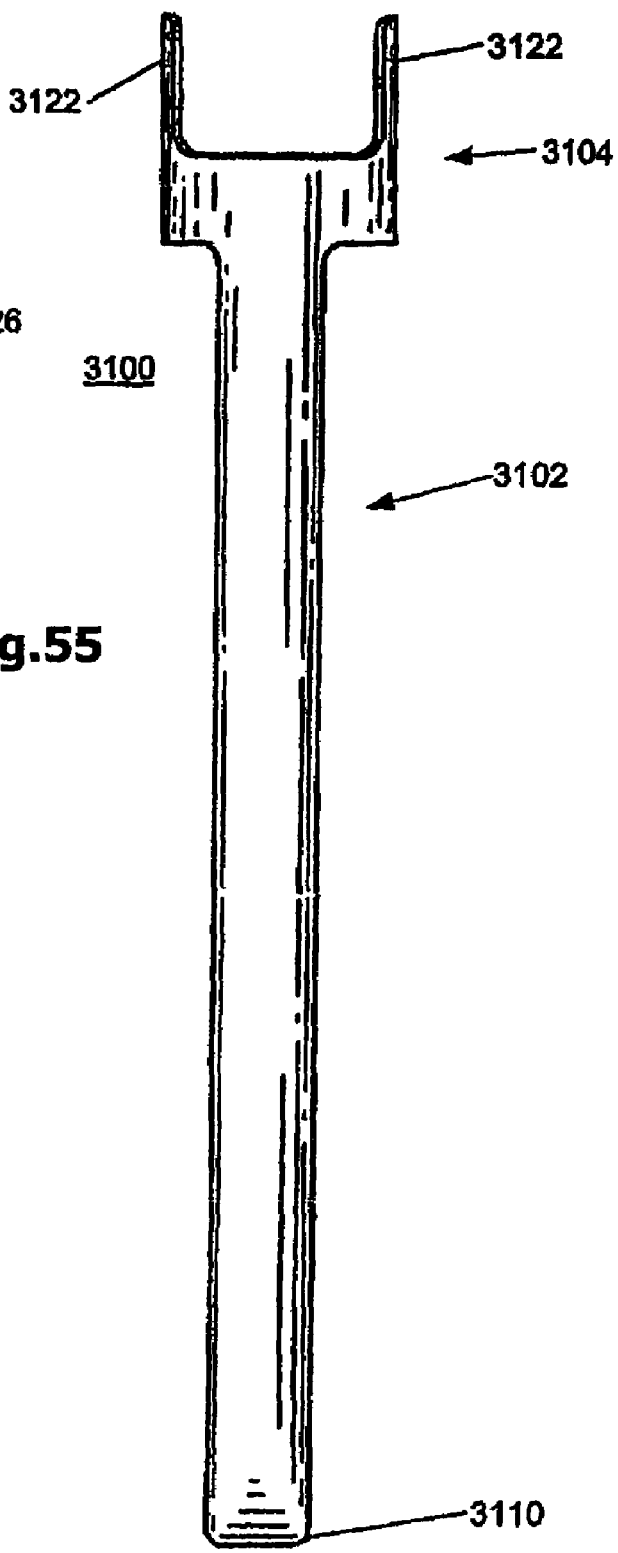
FIG. 55 is a back view of the apparatus of FIG. 52.

The spinal implant 2010 (FIGS. 38-39) has a second end 2030 that is engageable with a tool 2032 (FIG. 51) for inserting the implant between the adjacent vertebrae V. The tool 2032 has a pair of projections 2034, one of which is shown in FIG. 51, that extend into recesses 2036 and 2038 in the end 2030 of the implant 2010. The recesses 2036 and 2038 (FIGS. 38-39) extend from the second end 2030 toward the first end 2020. The recess 2036 (FIG. 41) is defined by an upper surface 2040 and a lower surface 2042 extending generally parallel to the upper surface 2040. The recess 2038 (FIG. 39) has a lower surface 2046 and an upper surface 2048. The upper surface 2048 extends generally parallel to the lower surface 2046.

The recesses 2036 and 2038 define a gripping portion 2052. The projections 2034 on the tool 2032 extend into the recesses 2036 and 2038 and grip the gripping portion 2052. The projections 2034 engage the upper and lower surfaces 2040 and 2042 of the recess 2036 and the upper and lower surfaces 2046 and 2048 of the recess 2038. Accordingly, the tool 2032 can grip the implant 2010 for inserting the implant between the adjacent vertebrae V.

As viewed in FIGS. 38-41, the implant 2010 has an upper surface 2060 for engaging the upper vertebra V. The implant 2010 has a lower surface 2062, as viewed in FIGS. 38-41, for engaging the lower vertebra V. The upper and lower surfaces 2060 and 2062 extend from the first end 2020 to the second end 2030 of the implant 2010 and parallel to the upper and lower surfaces 2040, 2042, 2046, and 2048 of the recesses 2036 and 2038. The upper surface 2060 has teeth 2064 for engaging the upper vertebra V. The lower surface 2062 has teeth 2066 for engaging the lower vertebra V. Although FIGS. 38-39 show four teeth 2064 and four teeth 2066, it is contemplated that any number of teeth could be used.

A first side surface 2070 and a second side surface 2072 extend between the upper and lower surfaces 2060 and 2062. The first side surface 2070 extends along a first arc from the first end 2022 of the implant 2010 to the second end 2030. The second side surface 2072 extends along a second arc from the first end 2022 to the second end 2030. The first and second side surfaces 2070 and 2072 are concentric and define portions of concentric circles. The teeth 2064 and 2066 extend parallel to each other and extend between the side surfaces 2070 and 2072 and along secant lines of the concentric circles defined by the side surfaces.

The implant 2010 preferably is formed by harvesting allograft material from a femur, as known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2010.

A pair of spinal implants 2010 may be placed bilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters can be used to sequentially distract the disc space until the desired distance between the vertebrae V is achieved. The fusion device or implant 2010 is placed between the vertebrae V using the tool 2032. The first end 2020 of the implant 2010 is inserted first between the vertebrae V. The implant 2010 is pushed between the vertebrae V until the end 2030 of the implant is between the vertebrae. A second spinal implant 2010 is inserted on the ipsilateral side using the same procedure.

A shield apparatus 3100 with an elongated portion 3102 may be used to facilitate insertion of the implants 2010 between the vertebrae V. A distal portion 3110 of the apparatus 3100 may be placed in an annulotomy. The implant 2010 is inserted with the side surface 2170 facing the elongated portion 3102 so that the apparatus 3100 can act as a "shoe horn" to facilitate or guide insertion of the implants 2010 between the vertebrae.

The implants 2010 may be inserted between the vertebrae V with the first ends 2020 located adjacent each other and the second ends 2030 spaced apart from each other, as shown in FIG. 48. The implants 2010 may also be inserted between the vertebrae V with the first ends 2020 of the implants 2010 spaced apart approximately the same distance that the second ends 2030 are spaced apart. It is contemplated that the implants 2010 may be inserted in any desired position between the vertebrae V. It is also contemplated that in some embodiments only one implant 2010 may be inserted between the vertebrae V. Furthermore, it is contemplated that the implants 2010 may be inserted between vertebrae using an open procedure.

Figure 50:
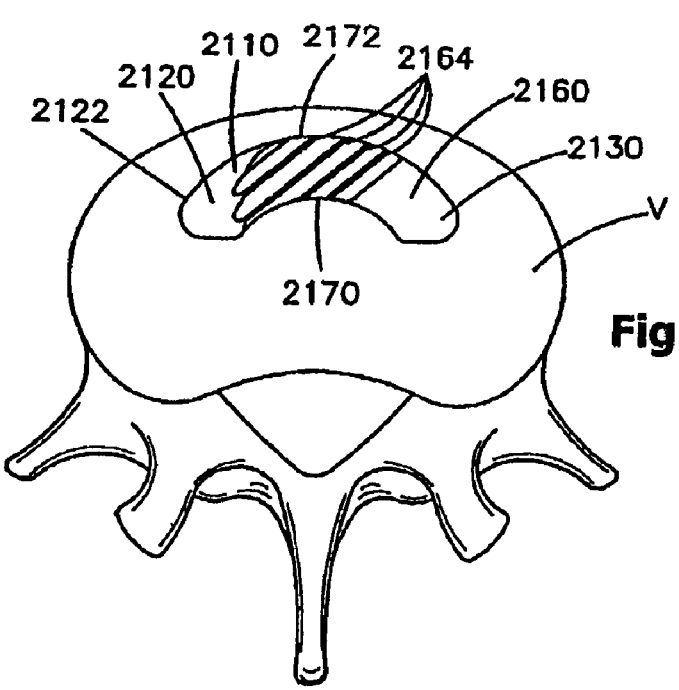
FIG. 50 is a view showing the spinal implant of FIG. 43 between adjacent vertebrae.

Another embodiment of a fusion device or spinal implant 2110 is illustrated in FIGS. 43-47. The spinal implant 2110 is substantially similar to the embodiment disclosed in FIGS. 38-42. The implant 2110 is placed between the adjacent vertebrae V to provide sufficient support to allow fusion of the adjacent vertebrae, as shown in FIG. 50. The spinal implant 2110 is preferably made from an allograft material, though the materials described above in connection with the spinal implant 2010 may also be used. Also, as with the implant 2010, the implant 2110 may be formed as a cage or other suitable configuration.

Figure 65:
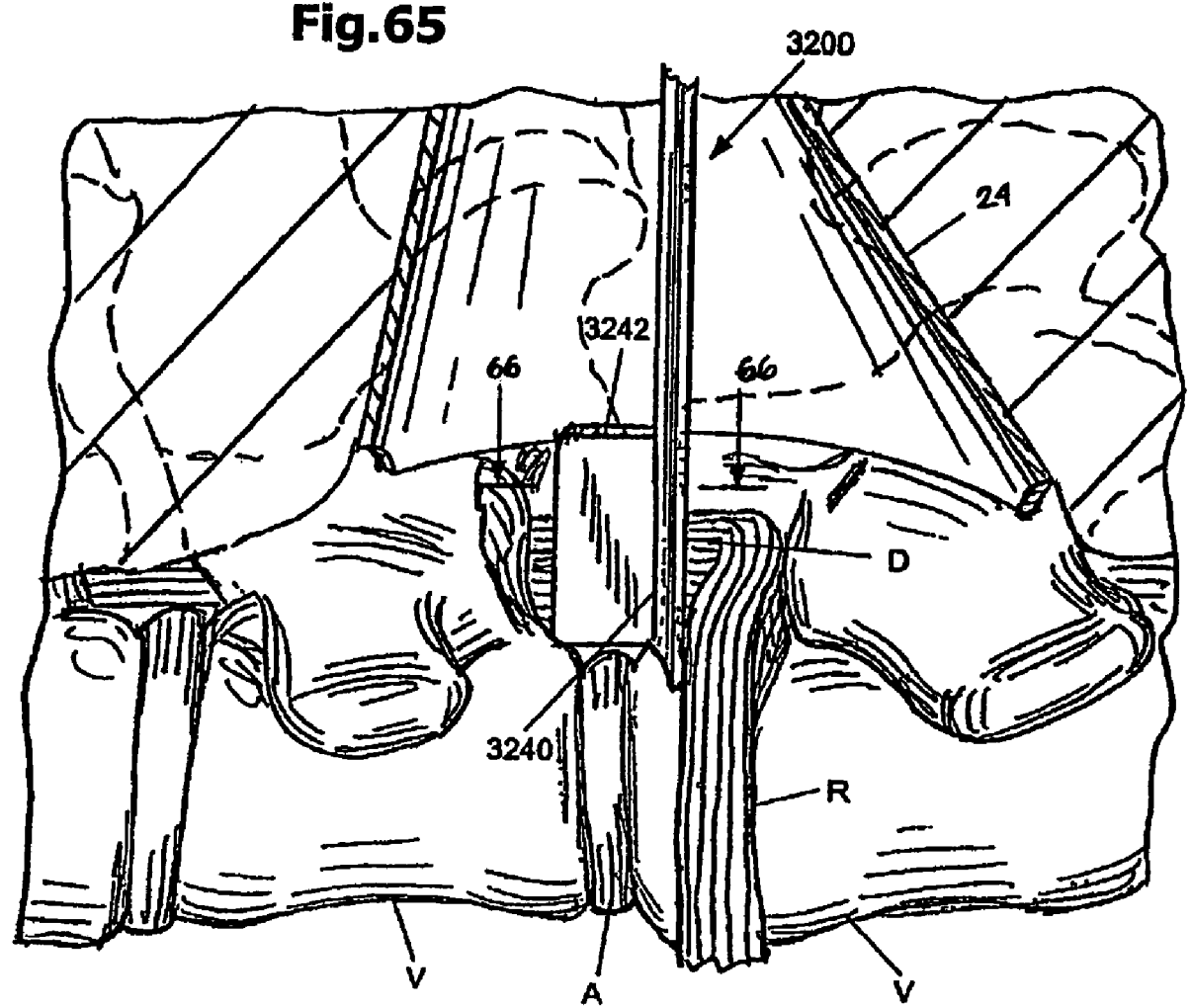
FIG. 65 is a sectional view, similar to FIG. 57, of the apparatus of FIG. 63, used in conjunction with additional structure in a patient.

The spinal implant 2110 (FIGS. 43-47) has a first end 2120 for insertion between the adjacent vertebrae V. The first end 2120 has a tapered surface 2122 to facilitate insertion of the implant between the adjacent vertebrae V. The surface 2122 defines an angle Y of approximately 45° as shown in FIG. 65.

The spinal implant 2110 (FIGS. 43-44) has a second end 2130 that is engageable with the projections 2034 on the tool 2032 for inserting the implant between the adjacent vertebrae V. The projections 2034 extend into recesses 2136 and 2138 in the end 2130 of the implant 2110. The recesses 2136 and 2138 extend from the second end 2130 toward the first end 2120. The recess 2136 (FIGS. 43 and 46) is defined by an upper surface 2140 and a lower surface 2142 extending generally parallel to the upper surface 2140. The recess 2138 (FIG. 44) has a lower surface 2146 and an upper surface 2148 extending generally parallel to the lower surface 2146.

The recesses 2136 and 2138 define a gripping portion 2152. The projections 2034 on the tool 2032 extend into the recesses 2136 and 2138 and grip the gripping portion 2152. The projections 2034 engage the upper and lower surfaces 2140 and 2142 of the recess 2136 and the upper and lower surfaces 2146 and 2148 of the recess 2138. Accordingly, the tool 2032 can grip the implant 2110 for inserting the implant between the adjacent vertebrae V.

As viewed in FIGS. 43-46, the implant 2110 has an upper surface 2160 for engaging the upper vertebra V. The implant 2110 has a lower surface 2162, as viewed in FIGS. 43-46, for engaging the lower vertebra V. The upper and lower surfaces 2160 and 2162 extend from the first end 2120 to the second end 2130 of the implant 2110 and parallel to the upper and lower surfaces 2140, 2142, 2146, and 2148 of the recesses 2136 and 2138. The upper surface 2160 has teeth 2164 for engaging the upper vertebra V. The lower surface 2162 has teeth 2166 for engaging the lower vertebra V. Although FIG. 44 shows four teeth 2164 and four teeth 2166, it is contemplated that any number of teeth could be used.

A first side surface 2170 and a second side surface 2172 extend between the upper and lower surfaces 2160 and 2162. The first side surface 2170 extends along a first arc from the first end 2122 of the implant 2110 to the second end 2130. The second side surface 2172 extends along a second arc from the first end 2120 to the second end 2130. The first and second side surfaces 2170 and 2172 are concentric and define portions of concentric circles. The teeth 2164 and 2166 extend parallel to each other and between the side surfaces 2170 and 2172 along secant lines of the concentric circles defined by the side surfaces.

The implant 2110 preferably is formed by harvesting allograft material from a femur, as is known in the art. The femur is axially cut to form cylindrical pieces of allograft material. The cylindrical pieces are then cut in half to form semi-cylindrical pieces of allograft material. The semi-cylindrical pieces of allograft material are machined into the spinal implants 2110.

A spinal implant 2110 is placed unilaterally between the adjacent vertebrae V. The access device 20 is positioned in the patient's body adjacent the vertebrae V. The skirt portion 24 of the access device 20 preferably is in a radially expanded condition to provide a working space adjacent the vertebrae V as described above. Disc material between the vertebrae V can be removed using instruments such as kerrisons, rongeurs, or curettes. A microdebrider may also be utilized to remove the disc material. An osteotome, curettes, and scrapers can be used to prepare end plates of the vertebrae V for fusion. Preferably, an annulus of the disc is left between the vertebrae V.

Distracters are used to sequentially distract the disc space until the desired distance between the vertebrae V is achieved. The implant 2110 is placed between the vertebrae V using the tool 2032. It is contemplated that the apparatus 3100 could be used also. The first end 2120 of the implant 2110 is inserted first between the vertebrae V. The implant 2110 is pushed between the vertebrae V until the end 2130 of the implant is between the vertebrae. It is contemplated that the implant 2110 may be inserted in any desired position between the vertebrae V. It is also contemplated that in some embodiments more than one implant 2110 may be inserted between the vertebrae.

The apparatus or shield 3100 for use in placing the fusion devices or spinal implants between the vertebrae is illustrated in FIGS. 52-56. The apparatus 3100 preferably includes an elongated body portion 3102, which protects the nerve root or dura, and a mounting portion 3104, which allows for the surgeon to releasably mount the apparatus 3100 to the access device 20. Consequently, the surgeon is able to perform the surgical procedures without requiring the surgeon or an assistant to continue to support the apparatus 3100 throughout the procedure, and without reducing the field of view.

The apparatus 3100 may be manufactured from a biocompatible material such as, for example, stainless steel. In the illustrated embodiment, apparatus 3100 is manufactured from stainless steel having a thickness of about 0.02 inches to about 0.036 inches. The elongated body portion 3102 has dimensions that correspond to the depth in the body in which the procedure is being performed, and to the size of the body structure that is to be shielded by elongated body portion 3102. In one embodiment, the elongated body portion 3102 has a width 3106 of about 0.346 inches and a length of about 5.06 inches (FIG. 53), although other dimensions would be appropriate for spinal surgical procedures performed at different locations, or for surgical procedures involving different body structures. The distal tip portion 3110 of the apparatus 3100 may have a slightly curved "bell mouth" configuration which allows for atraumatic contact with a body structure, such as a nerve. It is contemplated that the elongated body portion may have any desired shape.

The mounting portion 3104 preferably allows the apparatus 3100 to be secured to a support structure in any number of ways. In one embodiment, mounting portion 3104 may include a ring portion. With reference to FIGS. 52-56, ring portion 3120 has a substantially ring-shaped configuration with an opening 3124, which defines an angle 3126 of about 90 degrees of the total circumference of the ring portion 3120. As will be described in greater detail below, the angle 3126 is a nominal value, because the ring portion 3104 is resilient, which permits the opening 3124 to change size during the mounting process.

In the illustrated embodiment, the mounting portion 3104 has a substantially cylindrical configuration in order to be mounted within the interior lumen of the access device 20, as will be described below. The ring portion 3104 has an exterior dimension 3130 of about 0.79 inches, and an interior dimension 3132 of about 0.76 inches. It is understood that the dimensions of the ring portion 3104 can be different, such as, for example, where the access device 20 has a different interior dimension. Moreover, the cylindrical shape of the ring portion 3104 can change, such as, for example, where the apparatus 3100 is used with a support member having a differently shaped internal lumen.

Finger grip portions 3122 preferably extend from the mounting portion 3104 and allow the surgeon to apply an inwardly directed force (as indicated by arrows A) to the ring portion 3120. The resilient characteristics of the ring portion 3120 allow the material to deflect thereby reducing the exterior dimension 3130 and reducing the spacing 3124. Releasing the finger grip portions 3122 allows the ring portion to move towards its undeflected condition, thereby engaging the interior wall of the access device 20.

The elongated body portion 3102 and the mounting portion 3104 may be manufactured from a single component, such as a sheet of stainless steel, and the mounting portion 3104 may be subsequently formed into a substantially cylindrical shape. In another embodiment, the mounting portion 3104 may be manufactured as a separate component and coupled to the elongated body portion, by techniques such as, for example, welding and/or securement by fasteners, such as rivets.

The access device 20 serves as a stable mounting structure for apparatus 3100. In particular, mounting portion 3104 is releasably mounted to the interior wall of proximal wall portion 22 of access device 20. Elongated body portion 3102 extends distally into the operative site to protect the desired body structure, such as the nerve, as will be described below.

To install the apparatus 3100 within the interior passage of the proximal wall portion 22, the surgeon may apply an inwardly directed force on the ring portion 3120, thereby causing the ring portion to resiliently deform, as illustrated by dashed line and arrows B in FIG. 59. The surgeon subsequently inserts the apparatus 3100 into the interior lumen of the proximal wall portion 22 (as indicated by arrow C) to the position of ring portion 3104 illustrated in solid line in FIG. 58. When the surgeon releases the finger grip portions 3122, the ring portion 3120 resiliently moves towards its undeflected configuration, thereby engaging the interior lumen of the proximal wall portion 22. Advantages of some embodiments include that the mounting portion 3104 is easily removed and/or moved with respect to the access device 20 without disturbing the position of the access device 20 or any other instrumentation.

Figure 57:
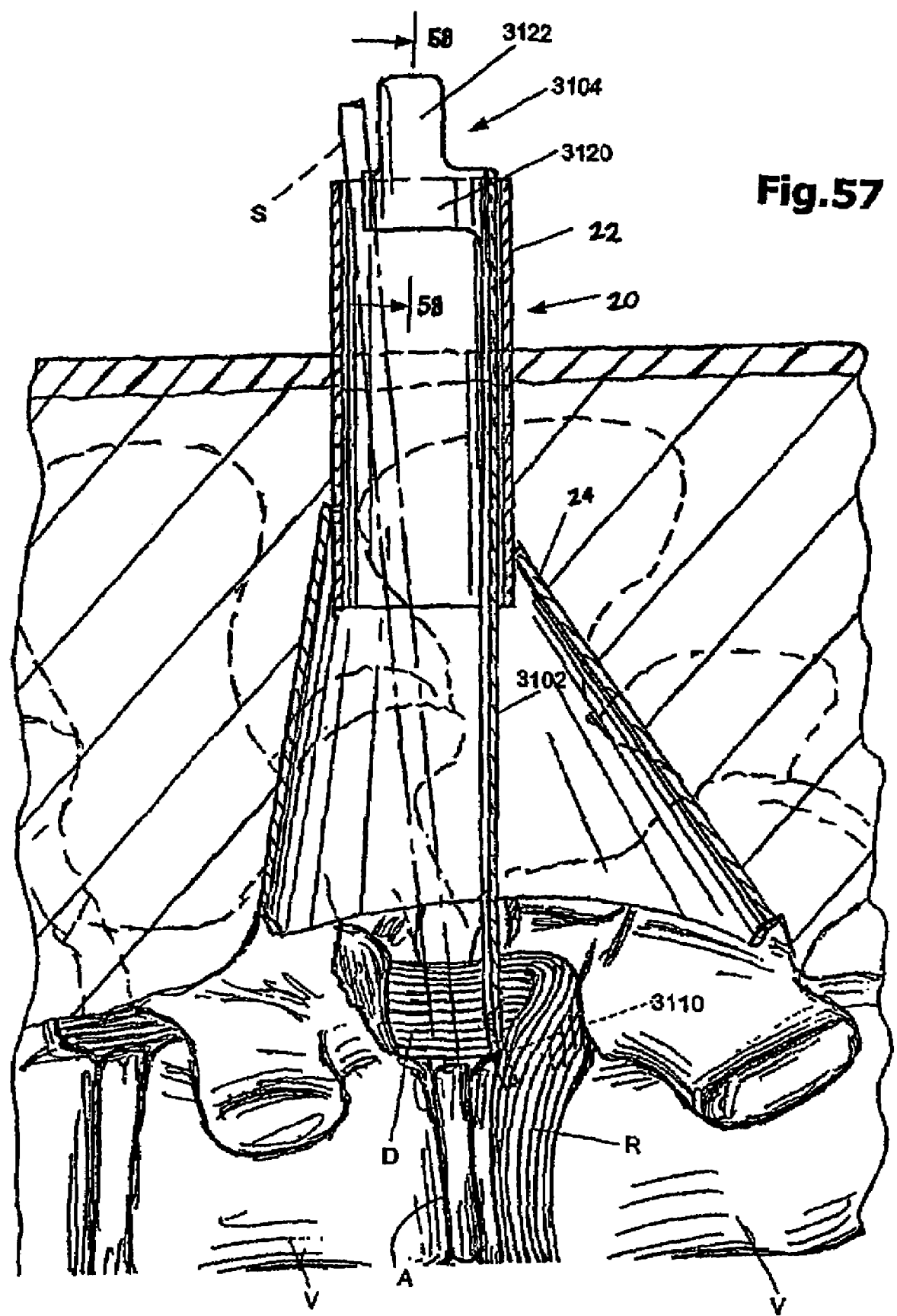
FIG. 57 is a sectional view of the apparatus of FIG. 52, used in conjunction with additional structure in a patient.

As illustrated in FIG. 57, the configuration of the mounting portion 3104 and the elongated body portion 3102 allow the elongated body portion to occupy a small space along the periphery of the proximal wall portion 3122. This allows the apparatus to, protect the desired body structure without blocking access for the insertion of other surgical instrumentation, and without blocking visibility by the surgeon during the procedure.

The mounting portion 3104 is one configuration for mounting the apparatus 3100 to the support structure. It is contemplated that the apparatus 3100 may be mounted within the access device 20 in any suitable manner.

When in position, the distal end portion 3110 covers the exiting nerve root R, while exposing the disc annulus A (See FIG. 57). As discussed above, the debridement and decortication of tissue covering the vertebrae, as well as a facetectomy and/or laminectomy if indicated, are preferably performed prior to the insertion of apparatus 3100 into the surgical space. Accordingly, in some embodiments, there is no need to displace or retract tissue, and apparatus 3100 merely covers the nerve root and does not substantially displace the nerve root or any other body tissue. It is understood that the term "cover" as used herein refers to apparatus 3100 being adjacent to the body structure, or in contact with the body structure without applying significant tension or displacement force to the body structure.

Additional surgical instrumentation S may be inserted into the access device to perform procedures on the surrounding tissue. For example, an annulotomy may be performed using a long handled knife and kerrisons. A discectomy may be completed by using curettes and rongeurs. Removal of osteophytes which may have accumulated between the vertebrae may be performed using osteotomes and chisels.

Figure 60:
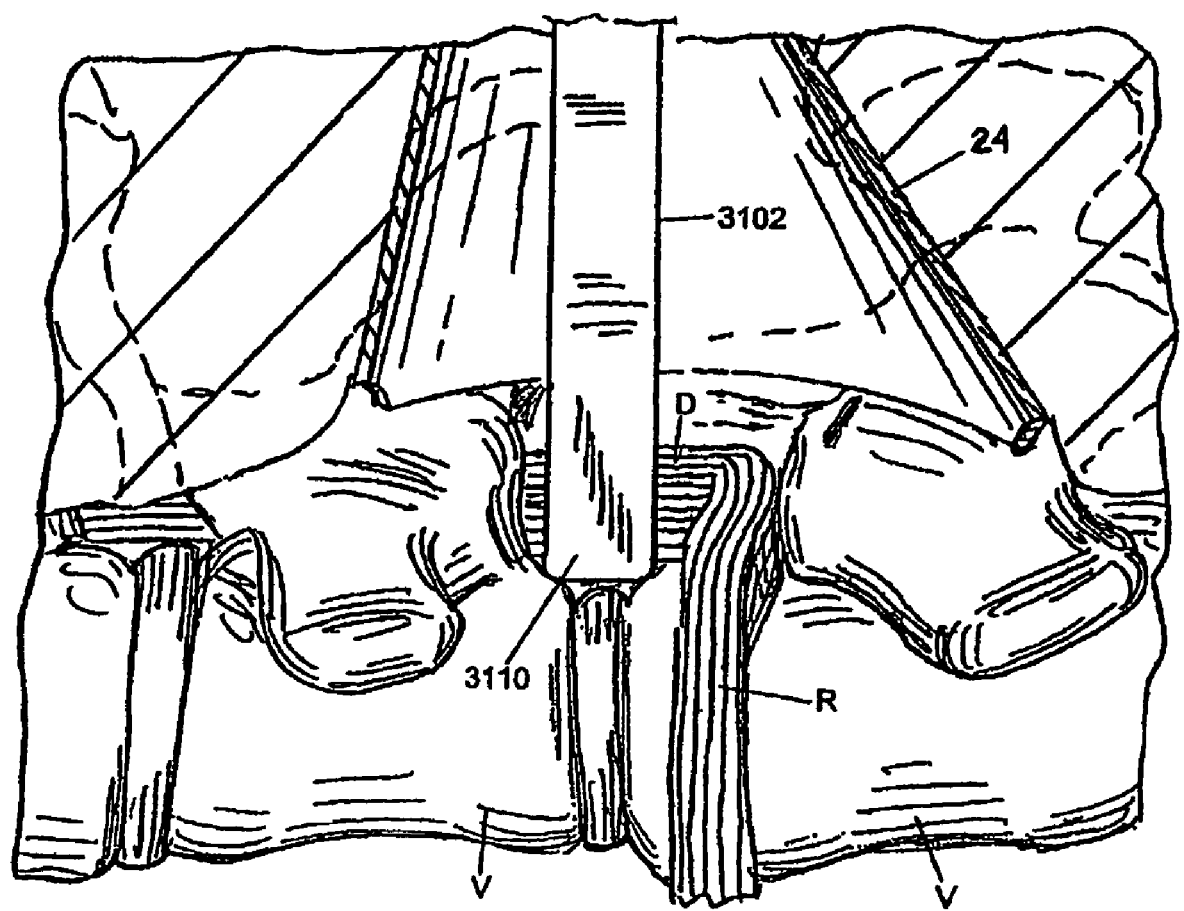
FIG. 60 is a sectional view, similar to FIG. 57, illustrating an alternative position of the apparatus of FIG. 52.

As illustrated in FIG. 60, the elongated body portion 3102 preferably is rotated to protect the spinal cord, or dura D, during the above procedures. The surgeon may change the position of the apparatus 3100 by approximating the finger grips 3122 to release the ring portion from engagement with the inner wall of the proximal wall portion 20, and then re-position the apparatus 3100 without disturbing the access device 20 (as shown in FIG. 58).

Figure 61:
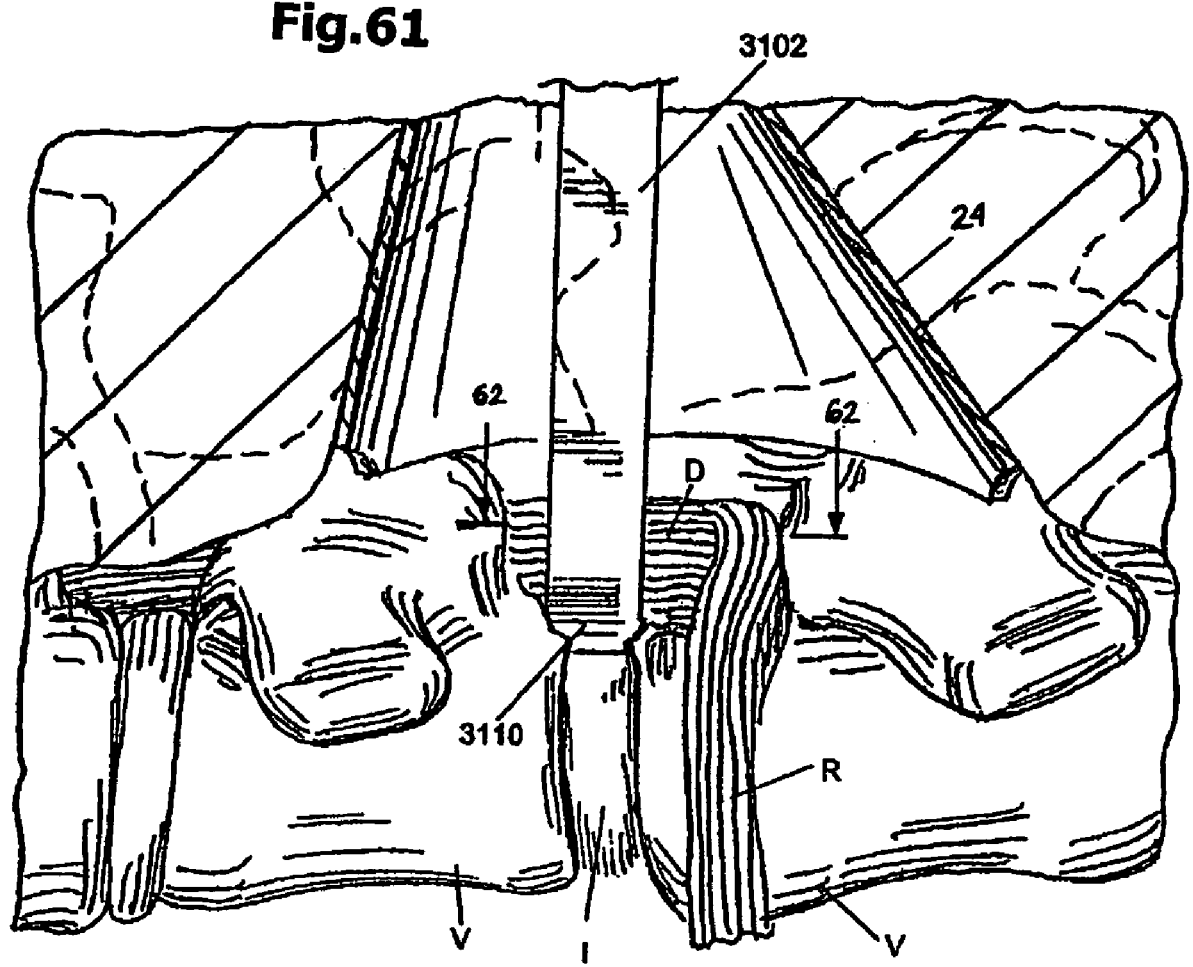
FIG. 61 is a sectional view, similar to FIG. 57, illustrating another alternative position of the apparatus of FIG. 52.
Figure 62:
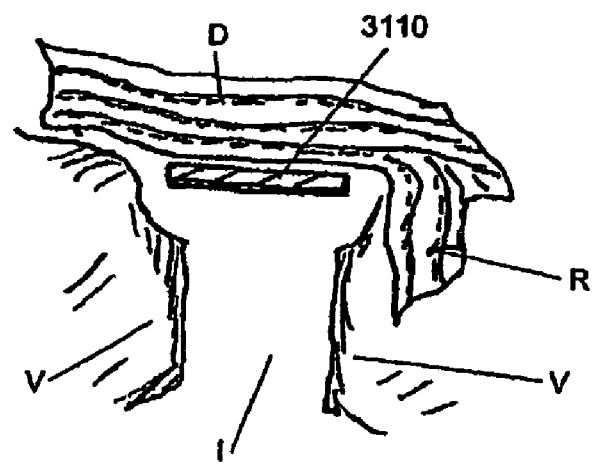
FIG. 62 is a transverse sectional view of the apparatus of FIG. 61, taken along lines 62-62 of FIG. 61.

During certain surgical procedures, it may be useful to introduce crushed bone fragments or the fusion devices 2010 or 2110 to promote bone fusion. As illustrated in FIGS. 61-62, apparatus 3100 is useful to direct the implants into the space I between adjacent vertebrae V. As shown in the figures, the distal portion 3110 of the elongated body portion 3102 is partially inserted into the space I. The distal end portion 3110, is positioned between adjacent vertebrae V, and creates a partially enclosed space for receiving the implants or other material therein.

Another embodiment of the apparatus or shield is illustrated in FIGS. 63-64, and designated apparatus 3200. Apparatus 3200 is substantially identical to apparatus 3100, described above, with the following differences noted herein. In particular, distal end portion 3210 includes a pair of surfaces 3240 and 3242. Surface 3240 is an extension of elongated shield portion 3202, and surface 3242 extends at an angle with respect to surface 3240. In one embodiment, surfaces 3240 and 3242 defined an angle of about 90 degrees between them. Alternatively another angle between surfaces 3240 and 3242 may be defined as indicated by the body structures to be protected.

Figure 66:
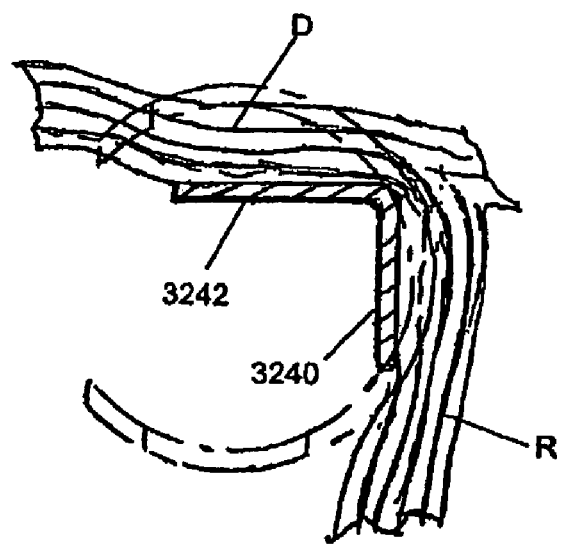
FIG. 66 is a transverse sectional view of the apparatus of FIG. 63, taken along lines 66-66 of FIG. 65.

Distal end portion 3210 allows the apparatus to provide simultaneous shielding of both the dura D and the nerve root R. In FIGS. 65-66, surface 3242 shields the dura D, and surface 3240 shields the nerve root R. It is understood that surfaces 3240 and 3242 may be interchanged with respect to which tissue they protect during the surgical procedure.

According to one technique, once the fusion and fixation portions of the procedure have been performed, the procedure is substantially complete. The surgical instrumentation, such as the endoscope 500 can be withdrawn from the surgical site. The access device 20 is also withdrawn from the site. The muscle and fascia typically close as the access device 20 is withdrawn through the dilated tissues in the reduced profile configuration. The fascia and skin incisions are closed in the typical manner, with sutures, etc. The procedure described above may be repeated for the other lateral side of the same vertebrae, if indicated.

II. Surgical Procedures that may be Performed with the Systems Described Herein As discussed above, the systems disclosed herein can be used to access a surgical location at or near the spine of a patient to enable procedures on the spine. These procedures can be applied to one or more vertebral levels, as discussed above. Additional procedures and combinations of procedures that may be performed using the systems described herein are discussed below. In various forms, these procedures involve an anterior lumbar interbody fusion, a minimally invasive lumbar interbody fusion, and other procedures particularly enabled by the access devices and systems described above.

A. Procedures Involving Anterior Lumbar Interbody Fusion

The access devices and systems described herein are amenable to a variety of procedures that may be combined with an anterior lumbar interbody fusion (referred to herein as an "ALIF").

In one embodiment of a first method, three adjacent vertebrae, such as the L4, the L5, and the S1 vertebrae of the spine, are treated by first performing an ALIF procedure. Such a procedure may be performed in a convention manner. The ALIF involves exposing a portion of the spine, in particular the vertebrae and discs located in the interbody spaces, i.e., the spaces between adjacent vertebrae. Any suitable technique for exposing the interbody spaces may be employed, e.g., an open, mini-open, or minimally invasive procedure. In one embodiment, the interbody spaces between the L4, L5, and S1 vertebrae are exposed to the surgeon. Once exposed, the surgeon may prepare the interbody space, if needed, in any suitable manner. For example, some or all of the disc may be removed from the interbody space and the height of the interbody space may be increased or decreased. The interbody space between the L4 and the L5 vertebrae may be exposed separately from the interbody space between the L5 and S1 vertebrae or they may be generally simultaneously exposed and prepared.

After the interbody space has been exposed and prepared, a suitable fusion procedure may be performed. For example, in one example fusion procedure, one or more fusion devices may be placed in the interbody space. Any suitable fusion device may be used, e.g., a fusion cage, a femoral ring, or another suitable implant. Various embodiments of implants and techniques and tools for the insertion of implants are described in U.S. application Ser. No. 10/280,489, filed Oct. 25, 2002, which has been published as Publication No. 2003/0073998 on Apr. 17, 2003, which is hereby incorporated by reference herein in its entirety. In one variation, one or more fusion cages may be placed in an interbody space, e.g., between the L4 and L5 vertebrae, between the L5 and S1 vertebrae, or between the L4 and L5 vertebrae and between the L5 and S1 vertebrae. In another variation, one or more femoral rings may be substituted for one or more of the fusion cages and placed between the L4 and L5 vertebrae and/or between the L5 and S1 vertebrae. In another variation, one or more fusion devices are combined with a bone growth substance, e.g., bone chips, to enhance bone growth in the interbody space(s).

After anterior placement of the fusion device, an access device is inserted into the patient to provide access to a spinal location, as described above. A variety of anatomical approaches may be used to provide access to a spinal location using the access device 20. The access device preferably is inserted generally posteriorly. As used herein the phrase "generally posteriorly" is used in its ordinary sense and is a broad term that refers to a variety of surgical approaches to the spine that may be provided from the posterior side, i.e., the back, of the patient, and includes, but is not limited to, posterior, postero-lateral, retroperitoneal, and transforaminal approaches. Any of the access devices described or incorporated herein, such as the access device 20, could be used.

The distal end of the access device may be placed at the desired surgical location, e.g., adjacent the spine of the patient with a central region of the access device over a first vertebrae. In one procedure, the distal end of the access device is inserted until it contacts at least a portion of at least one of the vertebrae being treated or at least a portion of the spine. In another procedure, the distal end of the access device is inserted until it contacts a portion of the spine and then is withdrawn a small amount to provide a selected gap between the spine and the access device. In other procedures, the access device may be inserted a selected amount, but not far enough to contact the vertebrae being treated, the portion of the vertebrae being treated, or the spine.

The access device may be configured, as described above, to provide increased access to the surgical location. The access device can have a first configuration for insertion to the surgical location over the first vertebra and a second configuration wherein increased access is provided to the adjacent vertebrae. The first configuration may provide a first cross-sectional area at a distal portion thereof. The second configuration may provide a second cross-sectional area at the distal portion thereof. The second cross-sectional area preferably is enlarged compared to the first cross-sectional area. In some embodiments, the access device may be expanded from the first configuration to the second configuration to provide access to the adjacent vertebrae above and below the first vertebra.

When it is desired to treat the L4, L5, and S1 vertebrae, the access device may be inserted over the L5 vertebrae and then expanded to provide increased access to the L4 and S1 vertebrae. In one embodiment, the access device can be expanded to an oblong shaped configuration wherein the access device provides a first dimension of about 63 mm, and a second dimension perpendicular to the first dimension of about 24 mm. In another embodiment, the access device can be expanded to provide a first dimension of about 63 mm, and a second dimension perpendicular to the first dimension of about 27 mm. These dimensions provide a surgical space that is large enough to provide access to at least three adjacent vertebrae without exposing excessive amounts of adjacent tissue that is not required to be exposed for the procedures being performed. Other dimensions and configurations are possible that would provide the needed access for procedures involving three adjacent vertebrae.

When the access device is in the second configuration, fixation of the three vertebrae may be performed. As discussed above, fixation is a procedure that involves providing a generally rigid connection between at least two vertebrae. Any of the fixation procedures discussed above could be used in this method, as could other fixation procedures. One fixation procedure that could be used is discussed above in connection with FIG. 36 wherein the fasteners 600a, 600b, and 600c are advanced through the access device 20 to three adjacent vertebrae and are attached to the vertebrae. The three fasteners 600a, 600b, and 600c are interconnected by the elongated member 650. The three fasteners 600a, 600b, and 600c and the elongate member 650 comprise a first fixation assembly. A second fixation assembly may be applied to the patient on the opposite side of the spine, i.e., about the same location on the opposite side of the medial line of the spine. Other fixation procedures could be applied, e.g., including two fasteners that coupled to the L4 and the S1 vertebrae and an elongate member interconnecting these vertebrae.

One variation of the first method provides one level of fixation on the anterior side of the patient, e.g., when the fusion device is placed in the interbody space. For example, fixation of the L5 and S1 vertebrae could be provided on the anterior side of the spine, in addition to the other procedures set forth above (e.g., a two level postero-lateral fixation). Also, fixation of the L4 and L5 vertebrae could be provided on the anterior side of the spine, in addition to the other procedures set forth above (e.g., a two level postero-lateral fixation).

In a second method, substantially the same steps as set forth above in connection with the first method would be performed. In addition, after the access device is inserted, a decompression procedure is performed through the access device. A decompression procedure is one where unwanted bone is removed from one or more vertebrae. Unwanted bone can include stenotic bone growth, which can cause impingement on the existing nerve roots or spinal cord. Decompression procedures that may be performed include laminectomy, which is the removal of a portion of a lamina(e), and facetectomy, which is the removal of a portion of one or more facets. In one variation of this method, decompression includes both a facetectomy and a laminectomy. Any suitable tool may be used to perform decompression. One tool that is particularly useful is a kerrison.

In a third method, substantially the same steps as set forth above in connection with the first method would be performed. That is, an ALIF procedure is performed in combination with a fixation procedure. In addition, a fusion procedure may be performed through the access device which may have been placed generally posteriorly, e.g., postero-laterally, tranforaminally or posteriorly, whereby bone growth is promoted between the vertebrae and the fixation assembly, including at least one of the fasteners 600a, 600b, 600c and/or the elongate element 650. This procedure is also referred to herein as an "external fusion" procedure.

One example of an external fusion procedure that may be performed involves placement of a substance through the access device intended to encourage bone growth in and around the fixation assembly. Thus, fusion may be enhanced by placing a bone growth substance adjacent any of the fasteners 600a, 600b, 600c and/or the elongate member 650. The bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance can cause bone to bridge across from the vertebra(e) to one or more components of the fixation assembly.

In a fourth method, substantially the same steps as set forth above in connection with the second method would be performed. That is, an ALIF procedure is performed anteriorly, and a decompression procedure and a fixation procedure are performed through the access device which may be placed generally posteriorly, e.g., postero-laterally, tranforaminally, or posteriorly. In addition, bone growth substance is placed in and around a fixation assembly through the access device, as discussed above in connection with the third method. The bone growth substance encourages bone to bridge across from the vertebrae to the fixation assembly.

In a fifth method, an ALIF procedure is performed, as discussed above in connection with the second method. After one or more fusion devices is placed in the interbody space, access is provided by way of the access device, as discussed above, from any suitable anatomical approach, e.g., a generally posterior approach. Preferably, a postero-lateral approach is provided. After access has been provided, a bone growth substance, such as those discussed above in connection with the third method, is delivered through the access device. The bone growth substance is placed adjacent an interbody space, e.g., the space between the L4 and the L5 vertebrae and/or between the L5 and the S1 vertebrae. The bone growth substance encourages fusion of the adjacent vertebrae, e.g., L4 to L5 and/or L5 to S1, by stimulating or enhancing the growth of bone between adjacent vertebrae, as discussed above.

In a sixth method, substantially the same steps described in connection with the first method are performed, except that the fixation procedure is optional. In one variation of the sixth method, the fixation procedure is not performed. However, after the access device is inserted, a bone growth substance is placed in and around one or more interbody spaces through the access device. Where the sixth method involves a two level procedure, the bone growth substance can be placed adjacent the interbody space between the L4 and the L5 vertebra and/or between the L5 and the S1 vertebra. Thus, bone growth may occur in the interbody space and adjacent the interbody space between the vertebrae.

The foregoing discussion illustrates that an ALIF procedure can be combined with a variety of procedures that can be performed through an access device disclosed herein. In addition, though not expressly set forth herein, any combination of the procedures discussed above, and any other suitable known procedure, may also be combined and performed through the access devices described herein, as should be understood by one skilled in the art.

B. Spine Procedures Providing Minimally Invasive Lumbar Interbody Fusion

Another category of procedures that may be performed with the access devices and systems described above involves a minimally invasive lumbar interbody fusion (referred to herein as a "MILIF"). MILIF procedures are particularly advantageous because they permit the surgeon to perform a wide variety of therapeutic procedures without requiring fusion by way of an anterior approach, as is required in an ALIF. This provides a first advantage of allowing the surgeon to perform all procedures from the same side of the patient and also possibly from the same approach. Also, the access devices and systems disclosed herein provide the further advantage of enabling two level procedures, and many other related procedures, to be performed by way of a single percutaneous access. These and other advantages are explained more fully below.

In a first MILIF method, a two level postero-lateral fixation of the spine involving three adjacent vertebrae, such as the L4, L5, and S1 vertebrae, is provided. Analogous one level procedures and two level procedures involving any other three vertebrae also may be provided. In addition, the access devices and systems described herein could be used or modified to accommodate other multi-level procedures, such as a three level procedure. The surgeon inserts an access device such as described herein to a surgical location near the spine. As discussed above, the access devices are capable of a wide variety of anatomical approaches. In this procedure, a postero-lateral approach is preferred. Once the access device is inserted to a location adjacent the spine, as discussed above, it may be configured, e.g., expanded, as discussed above, to a configuration wherein sufficient access is provided to the surgical location.

Any suitable fusion process may then be performed. For example, an implant may be advanced through the access device into the interbody space in order to maintain disc height and allow bone growth therein, e.g., as in a fusion procedure. In order to ease insertion of the implant, it may be beneficial to prepare the interbody space. Interbody space preparation may involve removal of tissue or adjusting the height of the interbody space through the access device, such as in a distraction procedure. Once the interbody space is prepared, a suitable implant may be advanced through the access device into the interbody space, taking care to protect surrounding tissues. Various embodiments of implants and techniques and tools for their insertion are described in U.S. application. Ser. No. 10/280,489, incorporated by reference hereinabove. In general, the implant preferably is an allograft strut that is configured to maintain disc height and allow bone growth in the interbody space.

In addition to providing a suitable fusion, the first method provides fixation of the vertebrae. The fixation procedure may take any suitable form, e.g., any of the fixation procedures similar to those disclosed above. In particular, when the access device is in the expanded or enlarged configuration, fixation of the three adjacent vertebrae may be performed. One fixation procedure that could be used is discussed above in connection with FIG. 36 wherein the fasteners 600*a*, 600*b*, and 600*c* are advanced through the access device 20 to three adjacent vertebrae and are attached to the vertebrae. The three fasteners 600*a*, 600*b*, and 600*c* are interconnected by way of the elongated member 650. As discussed above, a second fixation assembly may be applied to the patient on the opposite side of the spine, e.g., about the same location on the opposite side of the medial line of the spine.

In a second MILIF method, substantially the same procedures set forth above in connection with the first MILIF method are performed. In addition, a suitable decompression procedure may be performed, as needed. As discussed above, decompression involves removal of unwanted bone by way of a suitable decompression technique that may be performed through the access device. In one embodiment, decompression is performed through the access device after the access device has been expanded. As discussed above, suitable decompression techniques include a laminectomy, a facetectomy, or any other similar procedure. Decompression for the L4, the L5, and/or the S1 vertebrae may be needed and can be performed through the access devices described herein without requiring the access device to be moved from one position to another.

In a third MILIF method, substantially the same procedures set forth above in connection with the first MILIF method are performed. In addition, a further fusion procedure, e.g., a fusion procedure external to the interbody space, is provided. The external fusion procedure is performed adjacent to the interbody space wherein bone growth may be promoted in the proximity of the fixation assembly, e.g., above the postero-lateral boney elements of the spine, such as the facet joints and the transverse processes. In one embodiment, when the fixation assembly comprising the fasteners 600a, 600b, 600c and/or the elongate element 650 has been applied to three adjacent vertebrae, a substance is applied through the access device to one or more components of the fixation assembly to maintain or enhance the formation and/or growth of bone in the proximity of the fixation assembly. For example, a bone growth substance may be placed adjacent any of the fasteners 600a, 600b, 600c and/or the elongate member 650. Bone growth substance may take any suitable form, e.g., small bone chips taken from the patient (e.g., autograft), from another donor source (e.g., allograft or xenograft), and orthobiologics.

After the bone growth substance is applied to the fixation assembly, the access device is removed. Absent the retracting force provided by the access device, the patient's tissue generally collapses onto the bone growth substance. The tissue will thereby maintain the position of the bone growth substance adjacent to the fixation assembly. The presence of the bone growth substance advantageously causes bone to grow between the vertebrae and the fixation assembly to form a bridge therebetween.

A fourth MILIF method involves substantially the same procedures performed in connection with the third MILIF method. In particular, one or more implants are positioned in the interbody spaces through an access device, a fixation procedure is performed through the access device, and a further fusion procedure is performed wherein bone growth substance is positioned adjacent the interbody space through the access device. In addition, a decompression procedure is performed through the access device that may include a facetectomy and/or a laminectomy.

A fifth MILIF method involves substantially the same procedures performed in connection with the first MILIF method, except that the fixation is optional. In one embodiment, the fixation is not performed. In addition, a further fusion procedure is performed through the access device wherein bone growth substance is positioned adjacent the interbody space, as discussed above.

A sixth MILIF method is substantially the same as the fifth MILIF method, except that a further fusion procedure is performed through the access device. In particular, an implant is positioned in the interbody space through an access device, a decompression procedure is performed through the access device, and a further fusion procedure is performed whereby bone growth substance is placed adjacent the interbody space through the access device. As discussed above, the decompression procedure may include a facetectomy, a laminectomy, and any other suitable procedure. As with any of the methods described herein, the procedures that make up the sixth MILIF method may be performed in any suitable order. Preferably the decompression procedure is performed before the external fusion procedure.

The foregoing discussion illustrates that a MILIF procedure can include a variety of procedures that can be performed through an access device described herein. In addition, though not expressly set forth herein, any combination of the procedures discussed above, and any other suitable known procedures, may also be combined, as should be understood by one skilled in the art.

C. Other Multi-level Procedures

While the foregoing procedures have involved interbody fusion, the access devices and systems described herein can be employed in a variety of single level and multi-level procedures (e.g., more than two levels) that do not involve an interbody fusion. For example, a discectomy can be performed through the access devices described herein without implanting an interbody fusion device thereafter, e.g., to remove a herneation. In another embodiment, a discectomy can be performed in more than one interbody space without inserting an interbody fusion device into each interbody space, e.g., to remove multiple hemeations. In another embodiment, a single or multi-level decompression procedure can be performed to remove unwanted bone growth.

It will be understood that the foregoing is only illustrative of the principles of the invention, and that various modifications, alterations, and combinations can be made by those skilled in the art without departing from the scope and spirit of the invention. Some additional features and embodiments are described below.

III. Additional Embodiments of Systems and Methods for Performing Surgical Procedures through an Access Device with an Expandable Proximal Portion Additional advantages can be provided by the embodiments described below. In particular, various embodiments described hereinbelow include access devices that include expandable proximal portions, e.g., those that are particularly well adapted for multistage expansion. In some embodiments, an access device is provided with an expandable proximal portion that is configured to expand to increase the size of a passage defined by the access device. The apparatuses described herein enable a surgeon to perform a wide variety of surgical methods, including those described herein.

A. Assemblies for Providing Access to a Surgical Location

Figure 67:
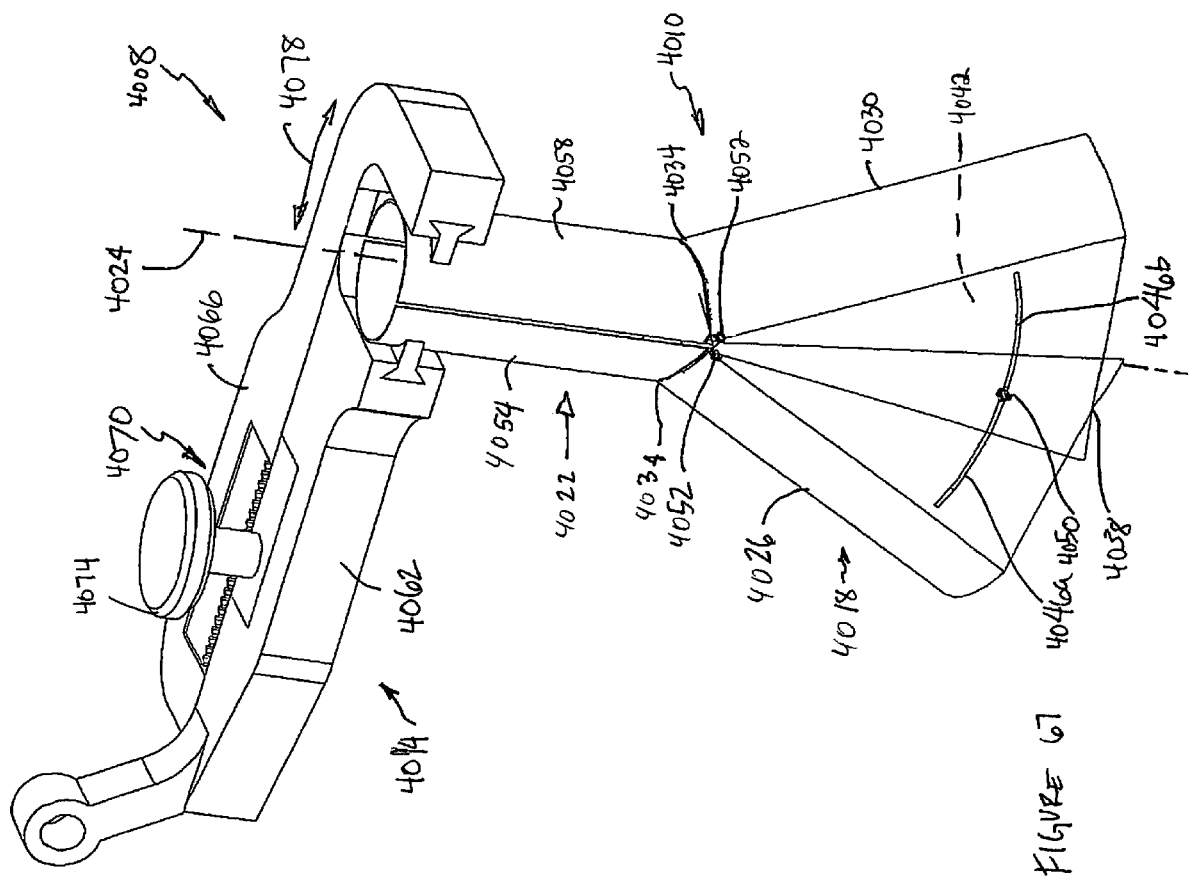
FIG. 67 is a perspective view of one embodiment of an access device and a mount for supporting the access device, wherein the mount is in a first position.
Figure 68:
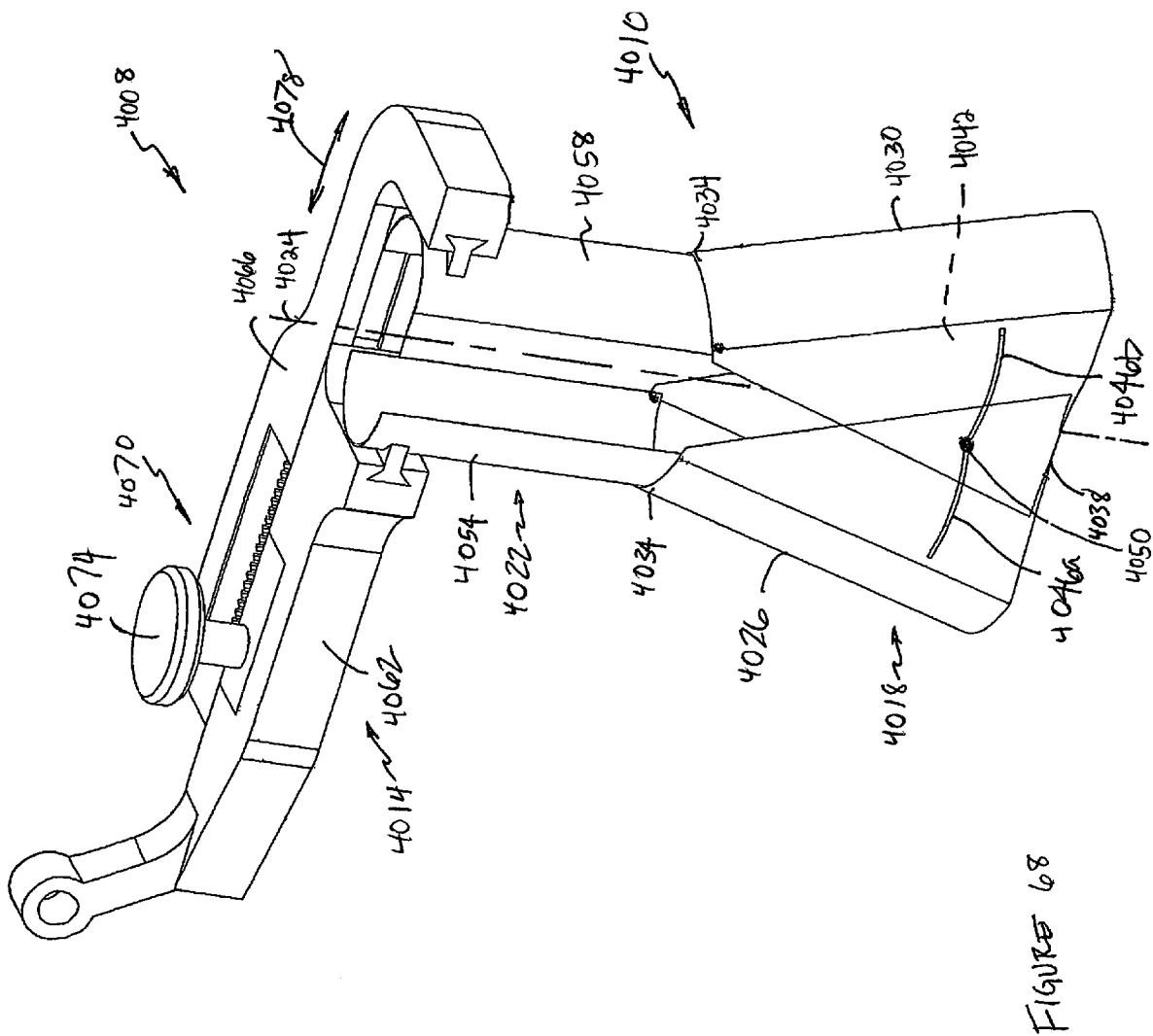
FIG. 68 is similar to FIG. 67, but shows the mount in a second position.

FIGS. 67-68 show an access assembly 4008 that includes an access device or retractor 4010 coupled with a mount fixture 4014. In the illustrated embodiment, the access device 4010 is an elongate body having a distal portion 4018 and a proximal portion 4022 defining a passage therethrough. The distal and proximal portions 4018, 4022 preferably are made from a rigid, radiolucent material, which is visible under fluoroscopy. The distal and proximal portions 4018, 4022 preferably have sufficient strength to retract tissue. Examples of materials that may be used and other details which can be incorporated into the access device 4010 are described hereinabove and can be found in the patents and applications incorporated by reference herein. The distal portion 4018 extends along a longitudinal axis 4024 and comprises a first overlapping section 4026 and a second overlapping section 4030. The first overlapping section 4026 extends between a proximal end 4034 and a distal end 4038 of the distal portion 4018. The second overlapping section 4030 extends between the proximal end 4034 and the distal end 4038 of the distal portion 4018. The overlapping sections 4026, 4030 overlap each other to create an enclosed space 4042 therebetween.

The first and second overlapping sections 4026, 4030 are coupled in a manner that permits expansion of the distal portion 4018 at the distal end 4038. In one embodiment, corresponding arcuate slots 4046a, 4046b are formed in the first overlapping section 4026 and the second overlapping section 4030, respectively. In one embodiment, a sliding rivet 4050 extends through the corresponding slots 4046a, 4046b thereby coupling the slots. The slots 4046a, 4046b and the rivet 4050 enable the distal portion 4018 to be expanded by allowing the rivet 4050 to slide along the slots while the overlapping sections 4026 and 4030 move away from each other. In another embodiment, a pair of slots and a rivet are each provided on opposite sides of the distal portion 4018, such that two rivets in corresponding slots are provided adjacent each edge of the overlapping sections. In some embodiments, the distal portion 4018 is arranged to expand from a circular cross-section configuration to a non-circular cross-section configuration.

Figure 75A:
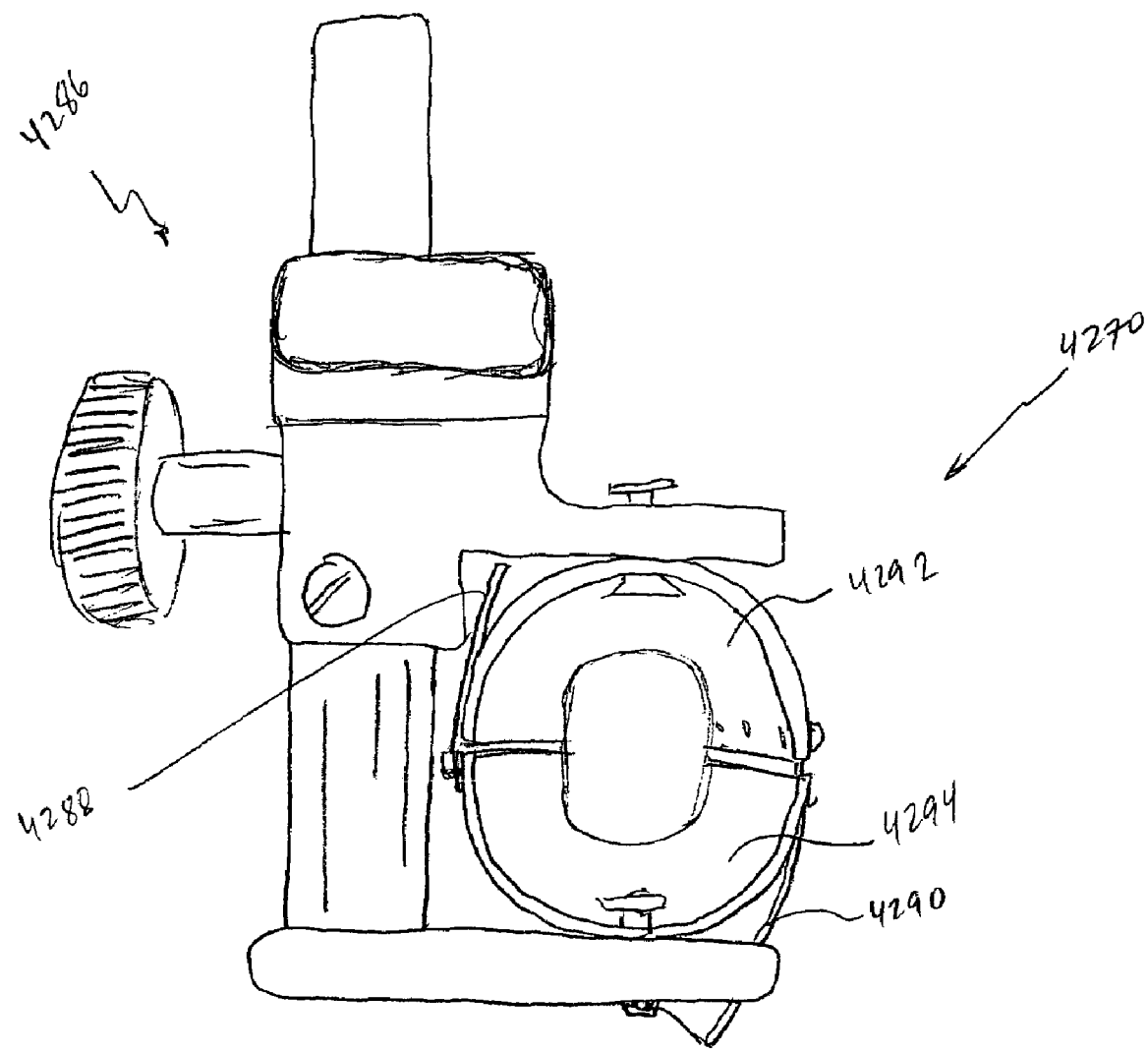
FIG. 75A is a top view of another embodiment of an access device similar to that of FIG. 69, with the proximal portion shown in a reduced configuration and coupled with a mount for supporting the access device.
Figure 75C:
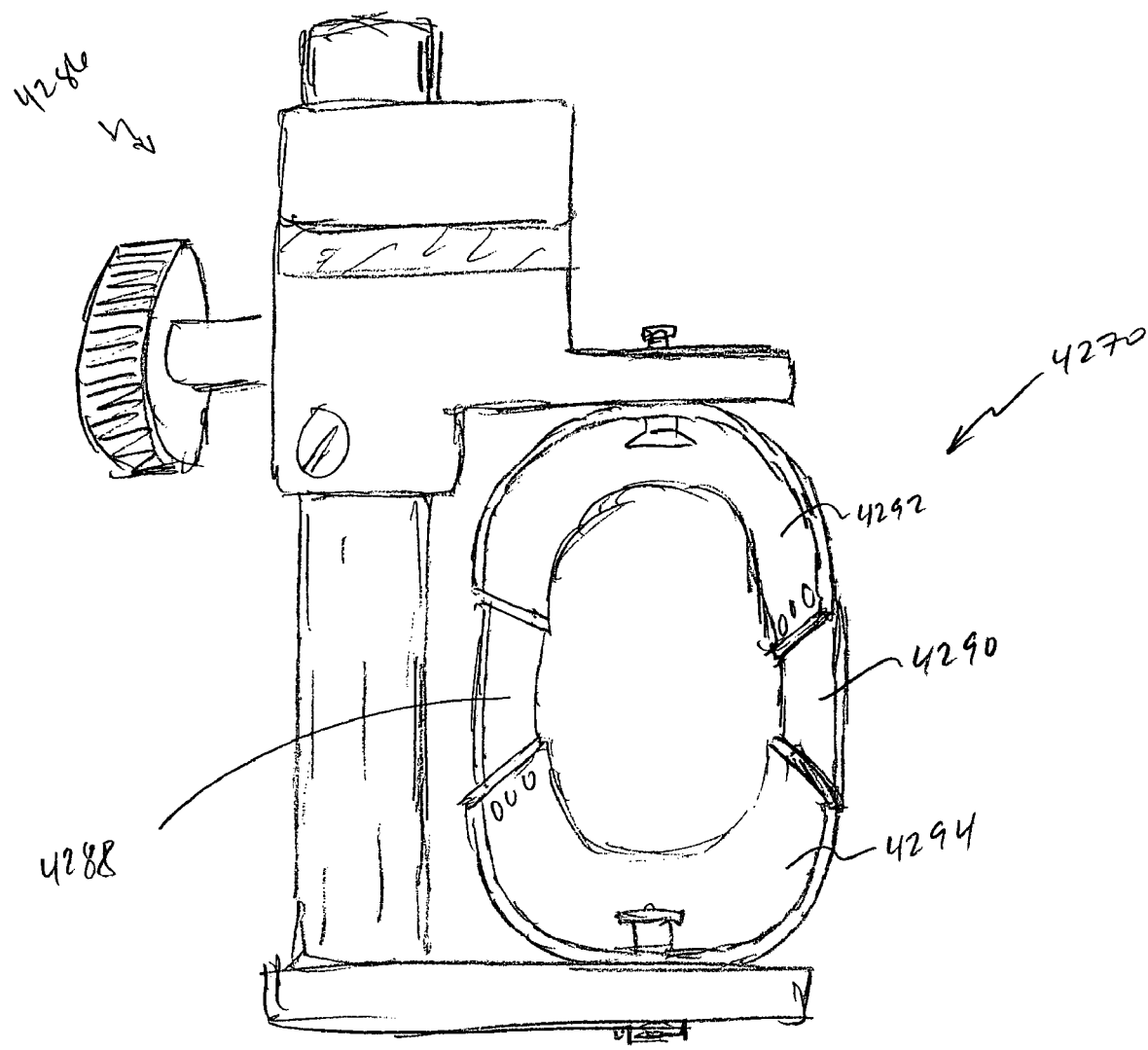
FIG. 75C is a top view of the access device of FIG. 75A, with the proximal portion shown in an enlarged configuration.

In another embodiment an access assembly includes an access device 4270, shown in FIGS. 75A-75G, wherein a rivet 4272 need only engage one slot 4274. The rivet 4272 slides only along a slot 4274 in one of the overlapping sections 4276. However, as best shown in FIG. 75E, rivets 4272, 4278 can be provided on opposite sides of the distal portion 4280, such that each overlapping portion 4276, 4282 contains one arcuate slot 4274, 4284 for engaging one corresponding rivet 4272, 4278. Further details regarding other expansion mechanisms are described above and can be found in U.S. Pat. Nos. 6,187,000 and 6,524,320, and other patents and applications, incorporated by reference herein.

With continued reference to FIGS. 67-68, the distal portion 4018 advantageously is also expandable at the proximal end 4034. In one embodiment, the proximal end 4034 of the distal portion 4018 is coupled with the mount fixture 4014, described further below, to enable the proximal end 4034 to translate in a direction perpendicular to the longitudinal axis 4024. In the illustrated embodiment, pivotal connections 4052 are provided near the proximal end 4034 of the distal portion 4018, to couple the proximal end 4034 of the distal portion 4018 to proximal portion 4022 which is coupled to mount fixture 4014. In this embodiment, the distal end of the proximal portion 4022 is coupled with the distal portion 4018 via the pivotal connections 4052 and is coupled with the mount fixture 4014 in a manner discussed in more detail below. One example of a pivotal connection comprises a pivoting rivet that extends through a hole formed in the distal portion 4018 near the proximal end 4034.

The proximal portion 4022 comprises a first elongate body 4054 and a second elongate body 4058. In the illustrated embodiment, the first and second elongate bodies 4054, 4058 comprise half-tubes. Thus, when the first elongate body 4054 is positioned close to the second elongate body 4058, the proximal portion comprises a substantially enclosed structure, e.g., a substantially enclosed tube having a generally circular inner diameter (see FIG. 67). However, one skilled in the art will appreciate that a wide variety of shapes could be used. In some applications, the first and second elongate bodies 4054, 4058 could be formed in a shape other than half-tube, e.g., with a non-constant radius. In one application, the elongate bodies 4054, 4058 have cross-sections with non-constant radii and when joined define an oblong or an oval cross-section. In other embodiments, the elongate bodies 4054, 4058 do not have curved cross-sectional profiles. In some embodiments, the proximal portion 4022 does not provide a continuous side surface.

The mount fixture 4014 comprises a fixed arm 4062 that can be attached to a flex arm (not shown) and an articulating arm 4066. The flex arm is a generally fixed structure that can take any of a number of suitable forms as discussed above and in the patents and applications incorporated by reference herein, or other suitable forms which will be recognized by one skilled in the art. In one embodiment, the mount fixture 4014 includes a rack and pinion mechanism 4070 that includes a knob 4074 and that couples the fixed arm 4062 and the articulating arm 4066. The rack and pinion mechanism 4070 is capable of converting the rotational motion of the knob 4074 into translational motion of the articulating arm 4066. An arrow 4078 shown in FIG. 67 illustrates the translational motion of articulating arm 4066. Any other mechanism or device that provides translation of the arms 4062, 4066 with respect to each other, e.g., a sliding bearing surface, may be used in place of a rack and pinion arrangement.

Figure 78:
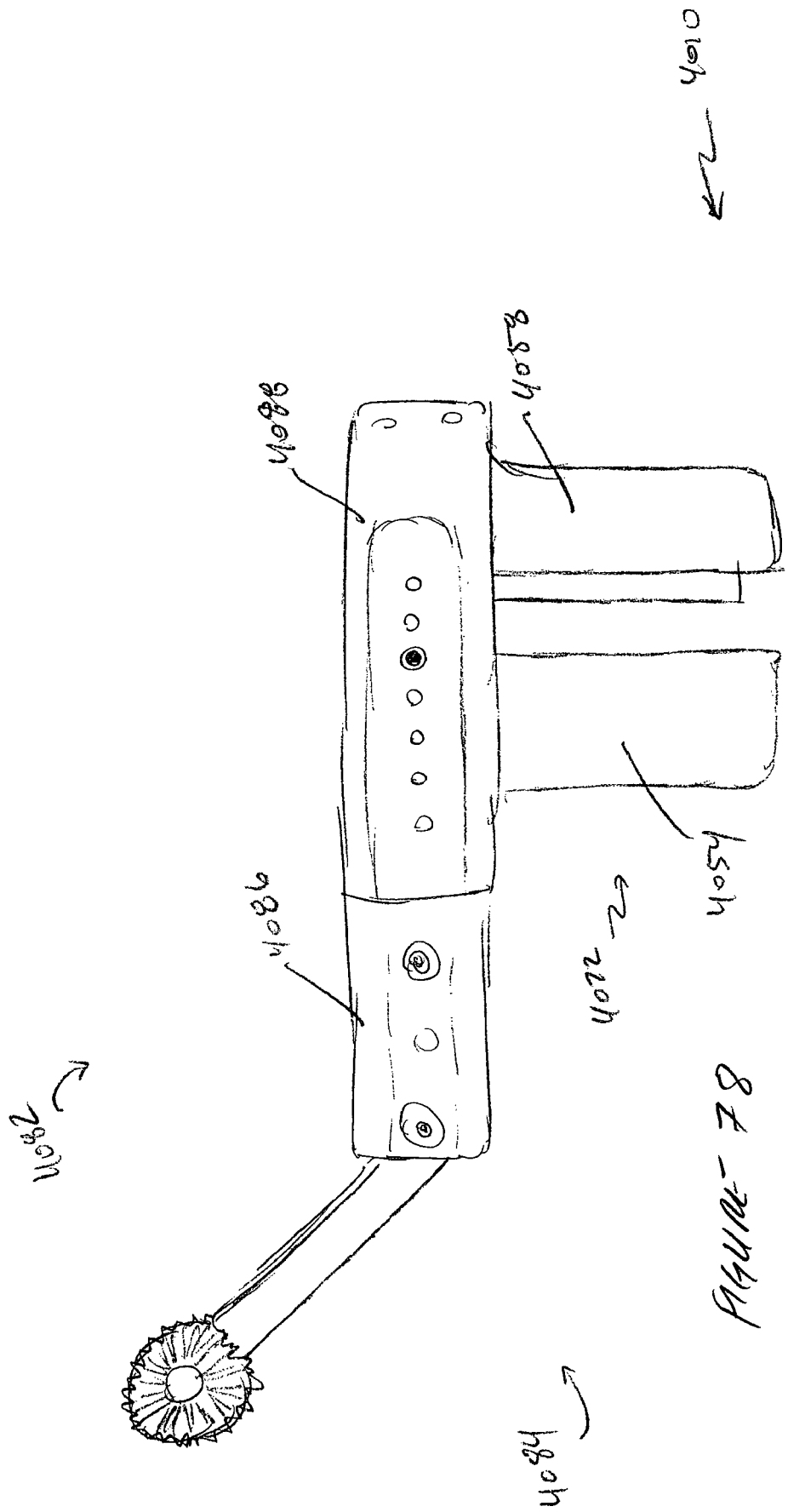
FIG. 78 is a font view of the access assembly of FIG. 76, shown in a partially-expanded configuration.
Figure 79:
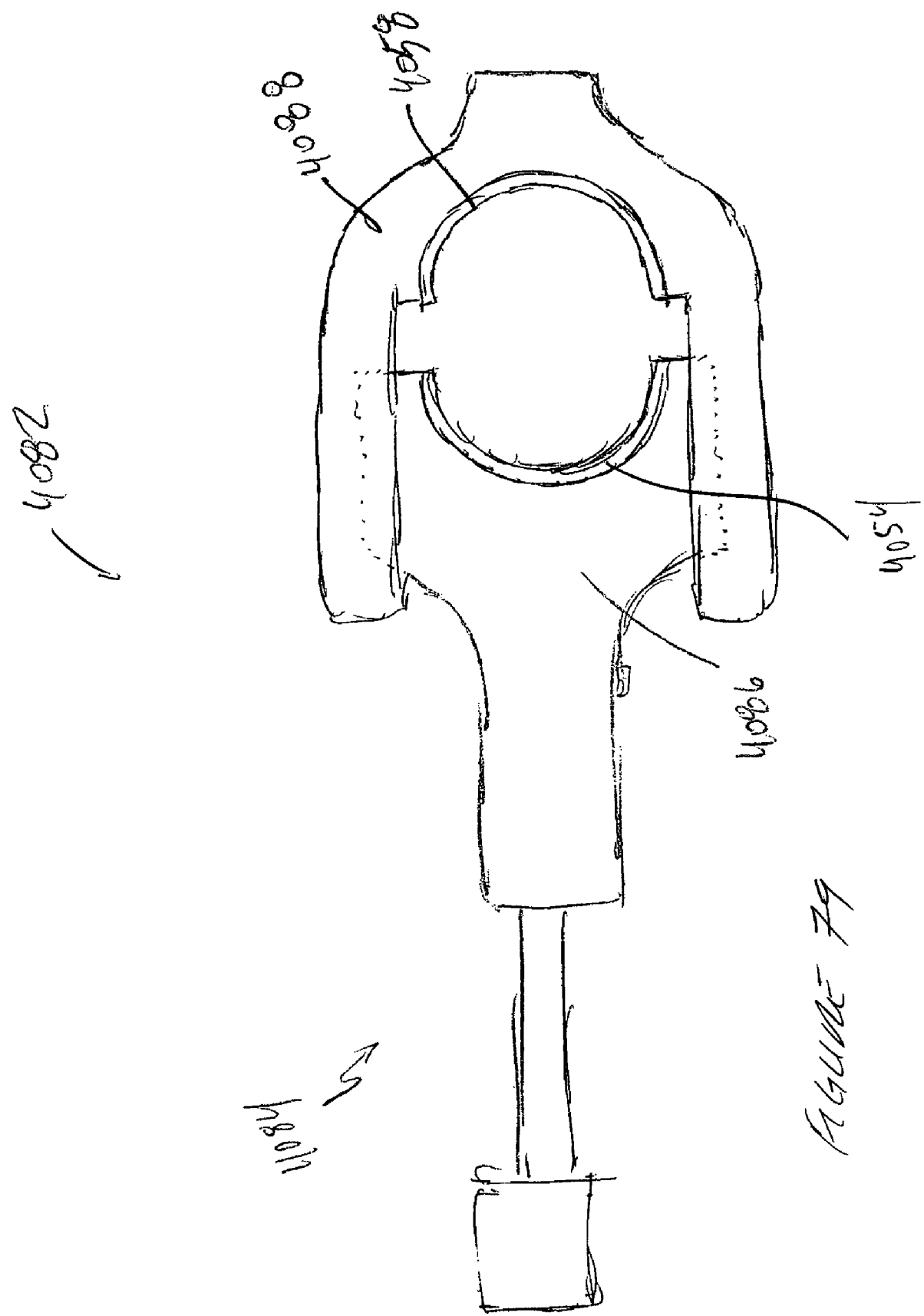
FIG. 79 is a top view of the access assembly of FIG. 76, shown in the partially-expanded configuration.
Figure 80:
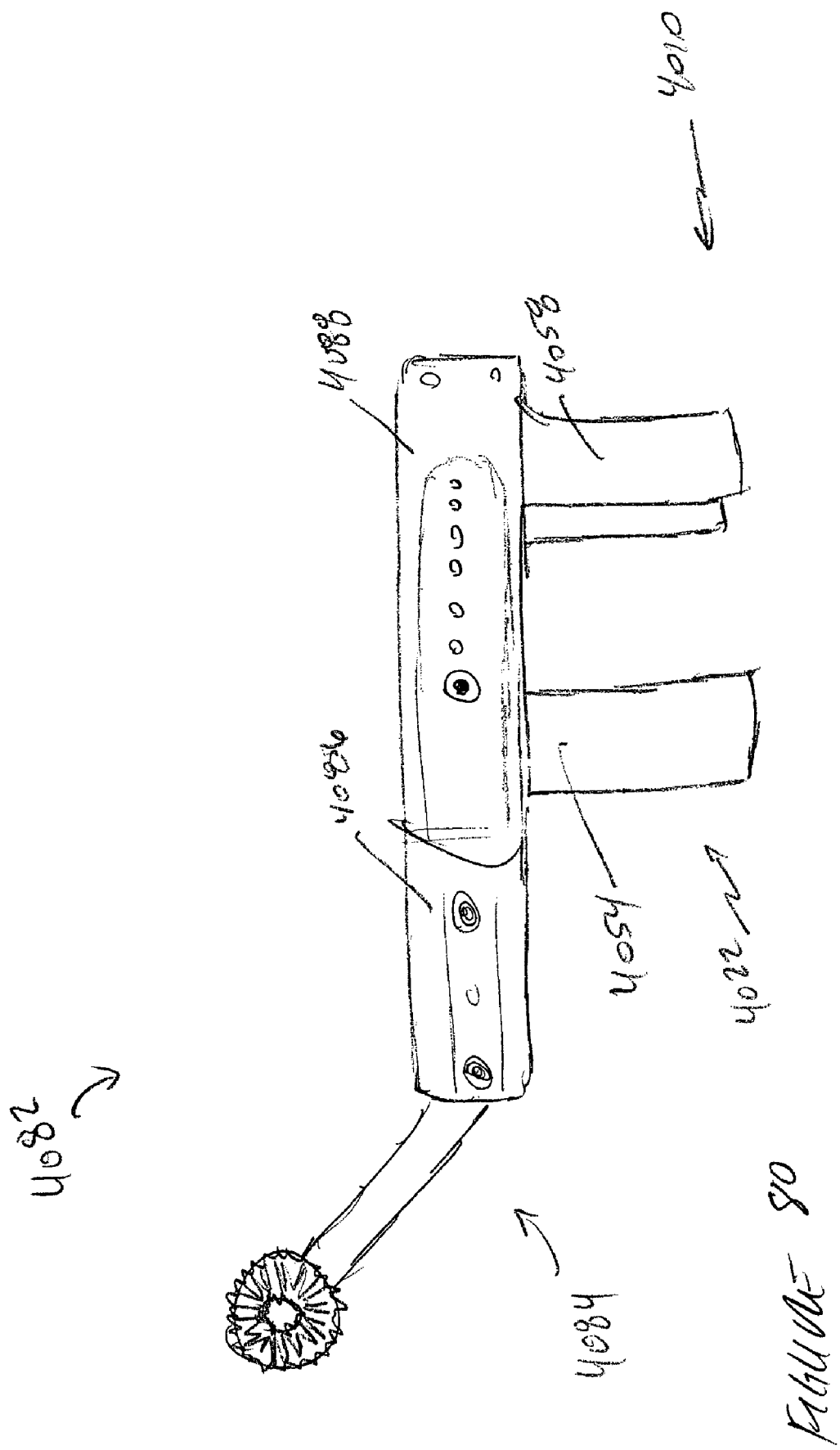
FIG. 80 is a font view of the access assembly of FIG. 76, shown in a fully-expanded configuration.
Figure 81:
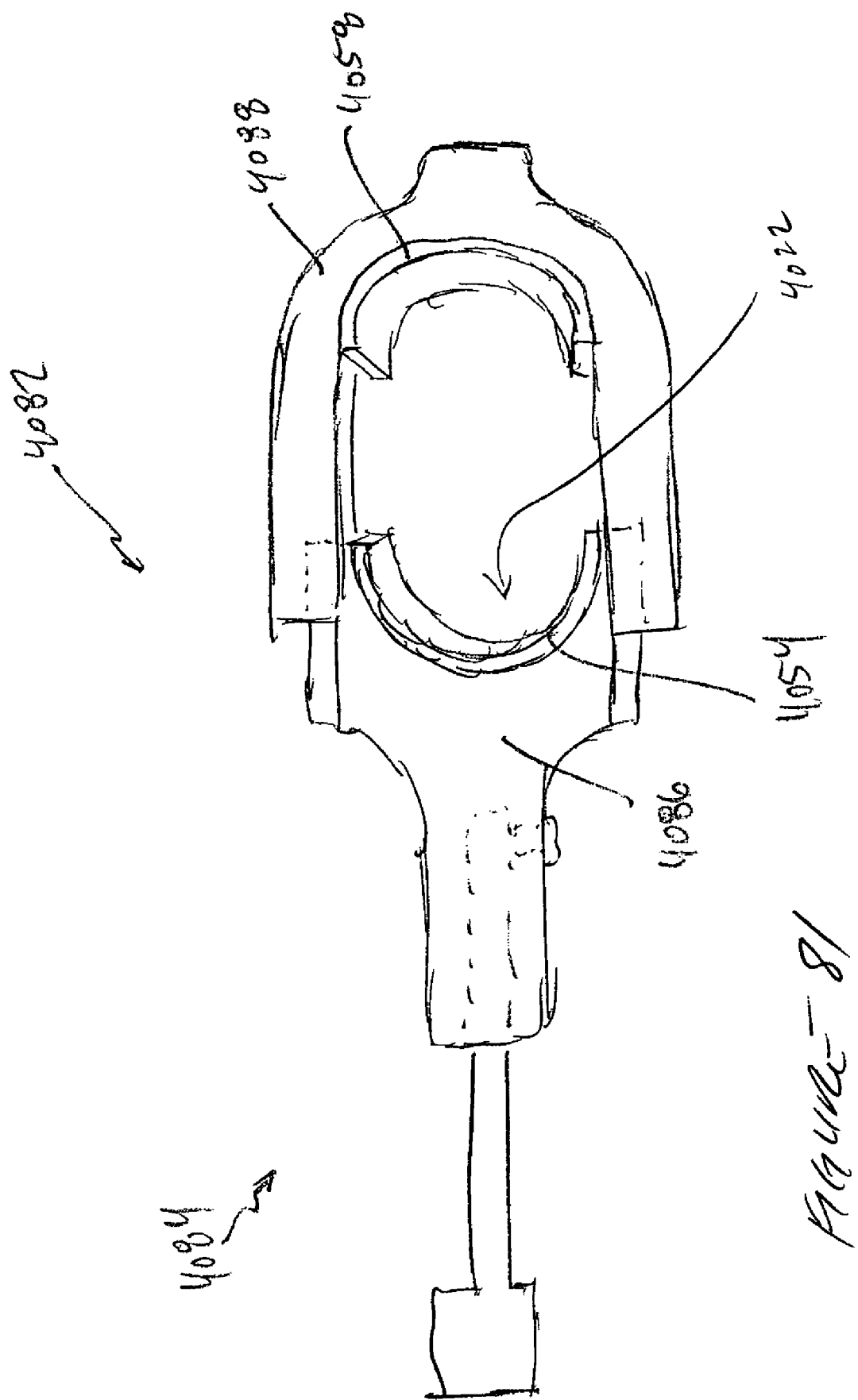
FIG. 81 is a top view of the access assembly of FIG. 76, shown in the fully-expanded configuration.
Figure 82:
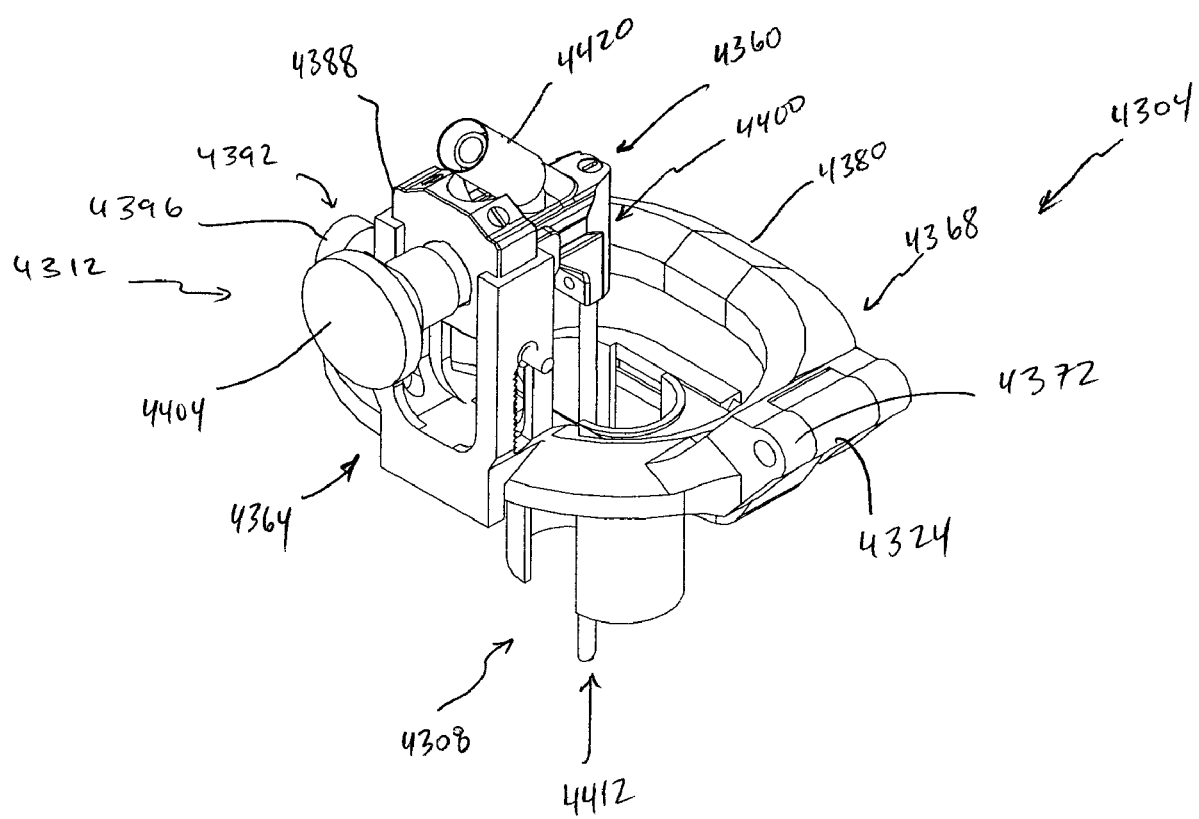
FIG. 82 is a front-side perspective view of one embodiment of a surgical assembly.
Figure 83:
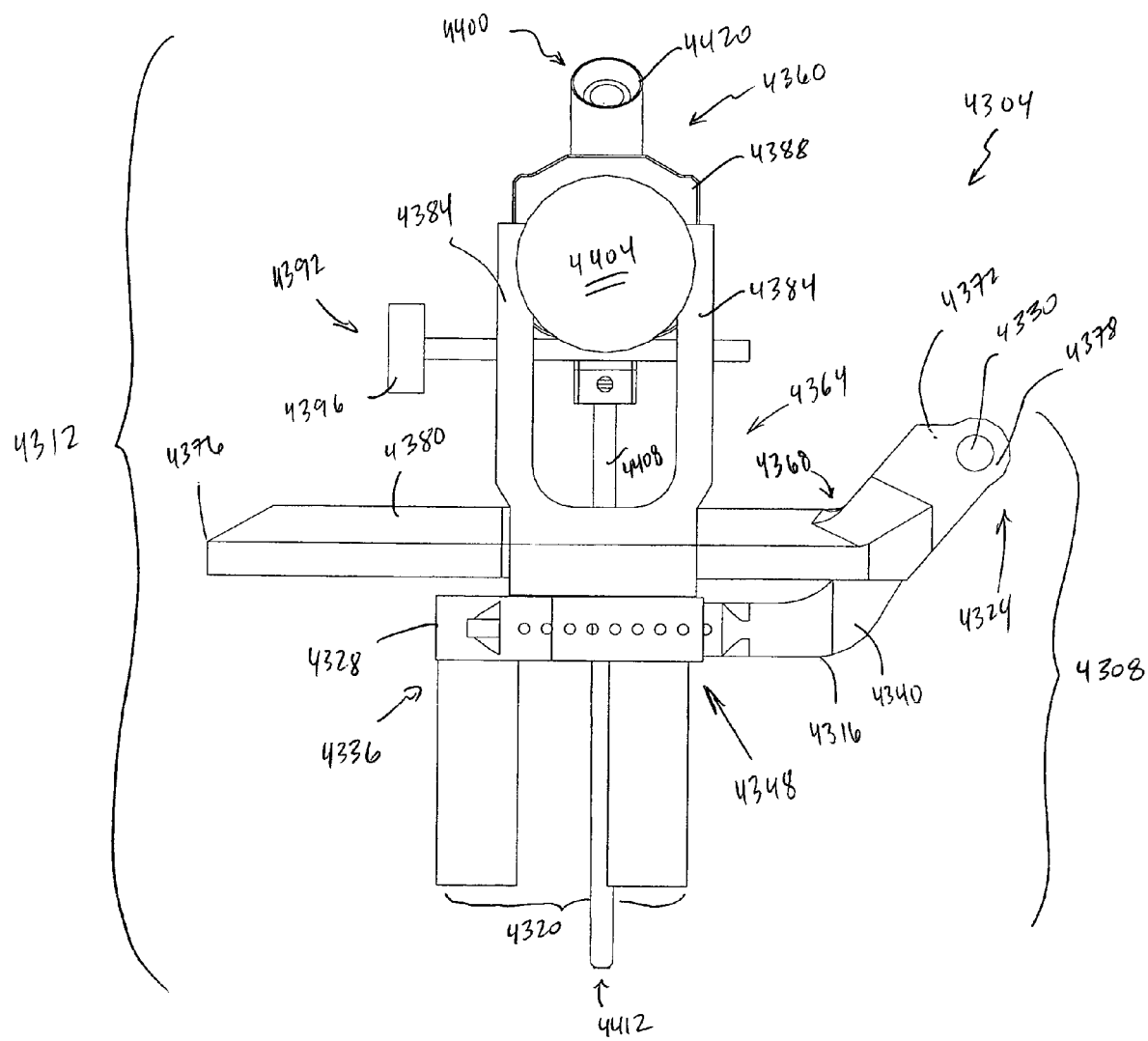
FIG. 83 is a front elevation view of the surgical assembly of FIG. 82.
Figure 84:
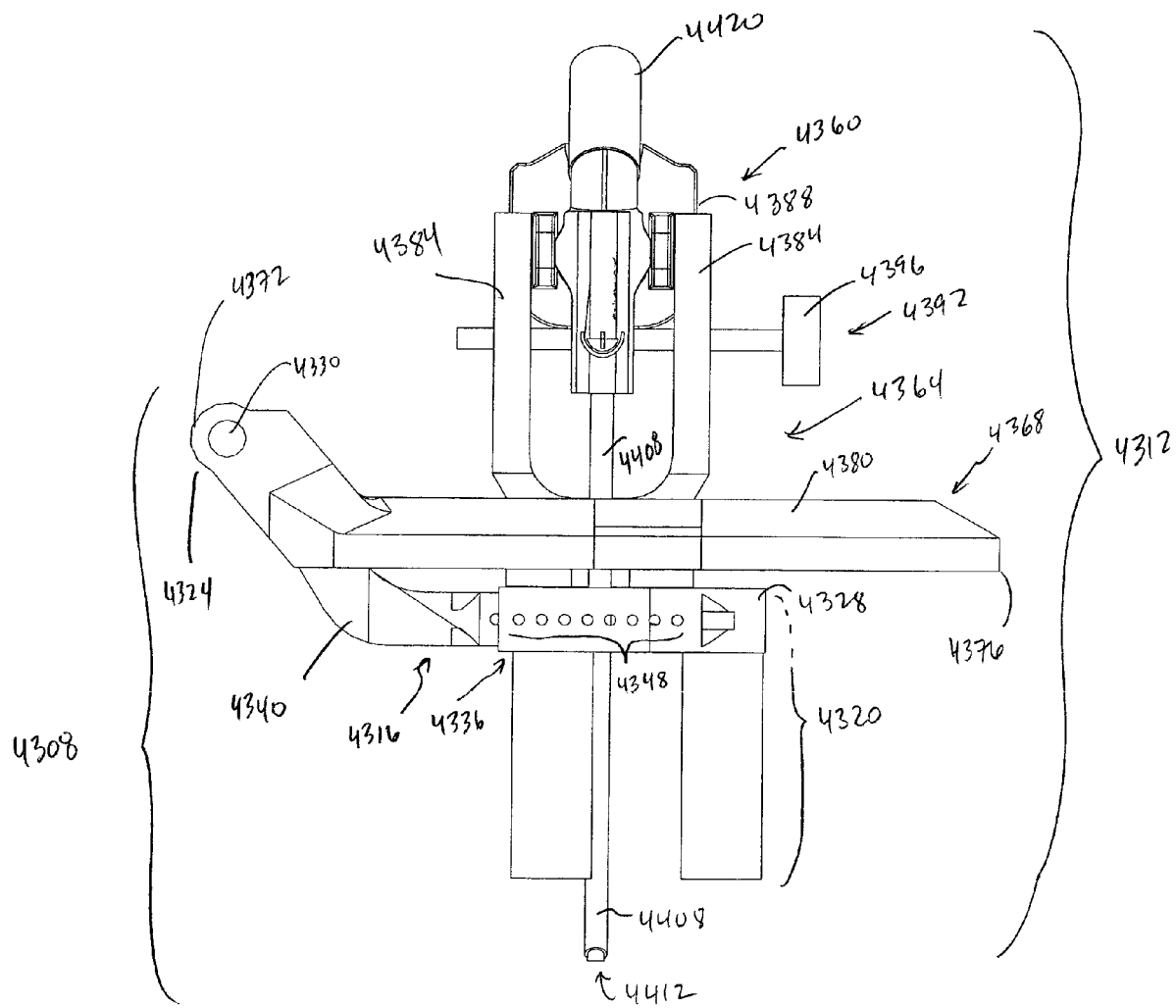
FIG. 84 is a rear elevation view of the surgical assembly of FIG. 82.
Figure 85:
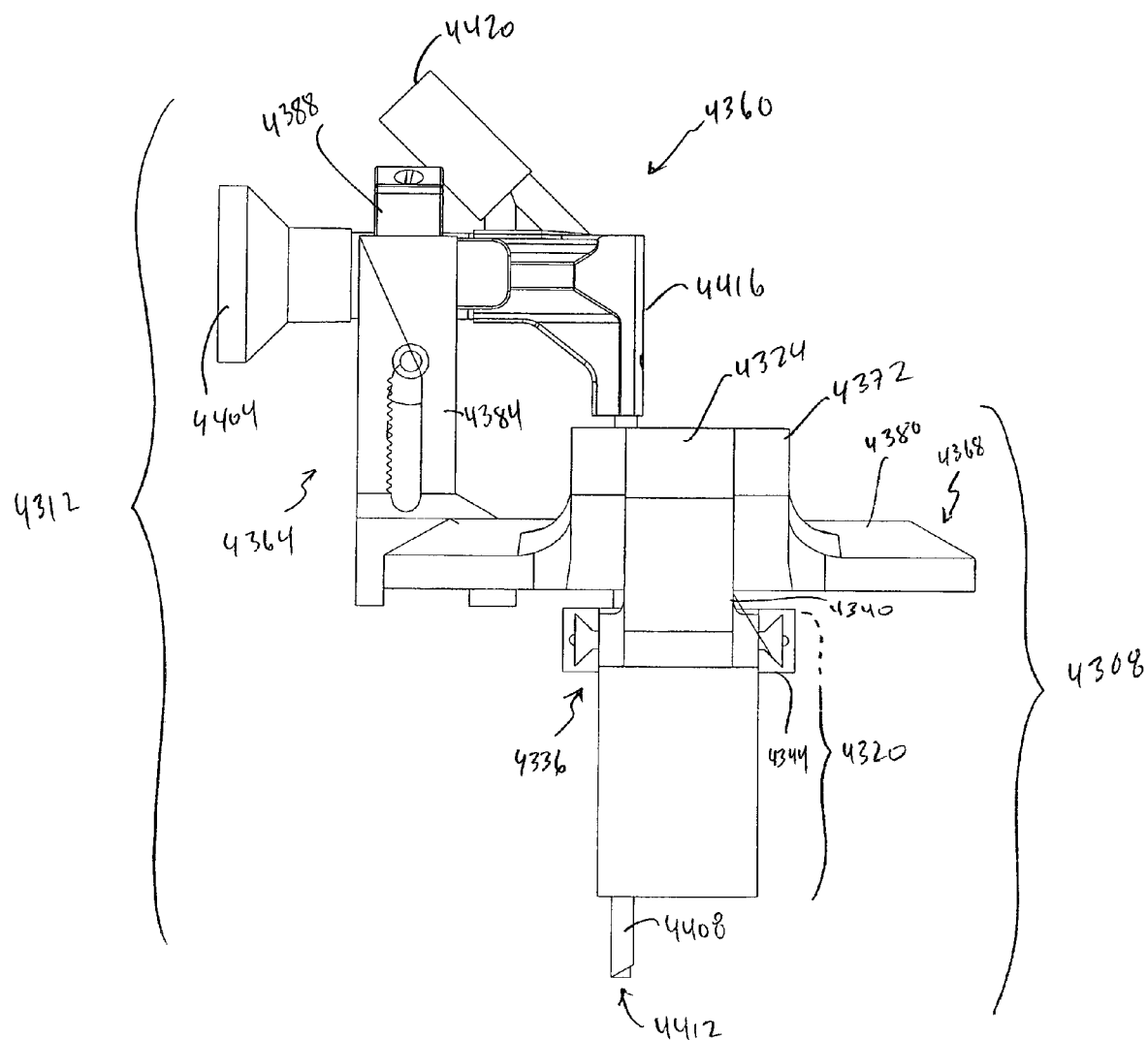
FIG. 85 is a side elevation view of the surgical assembly of FIG. 82.
Figure 86:
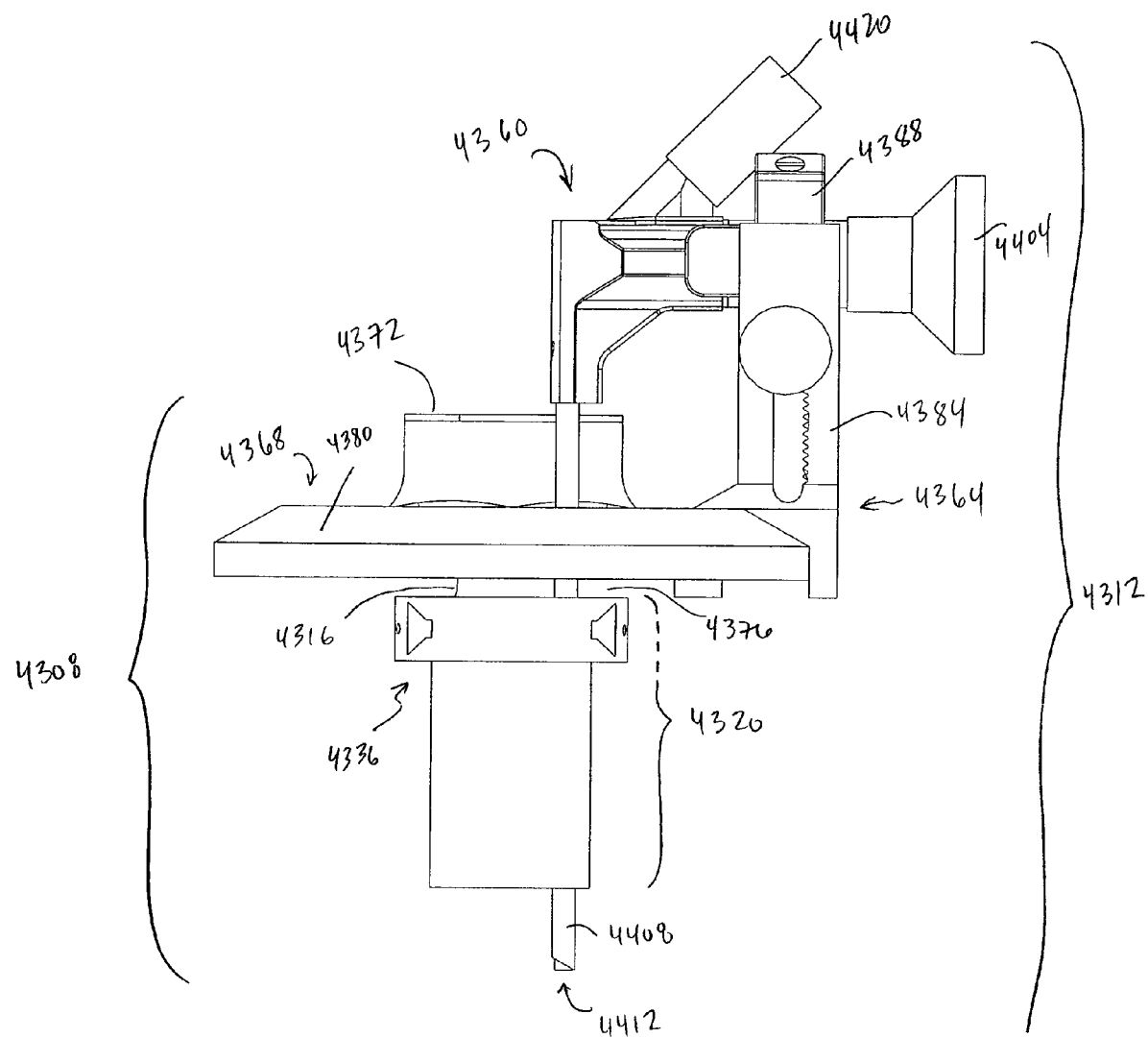
FIG. 86 is another side elevation view of the surgical assembly of FIG. 82.
Figure 87:
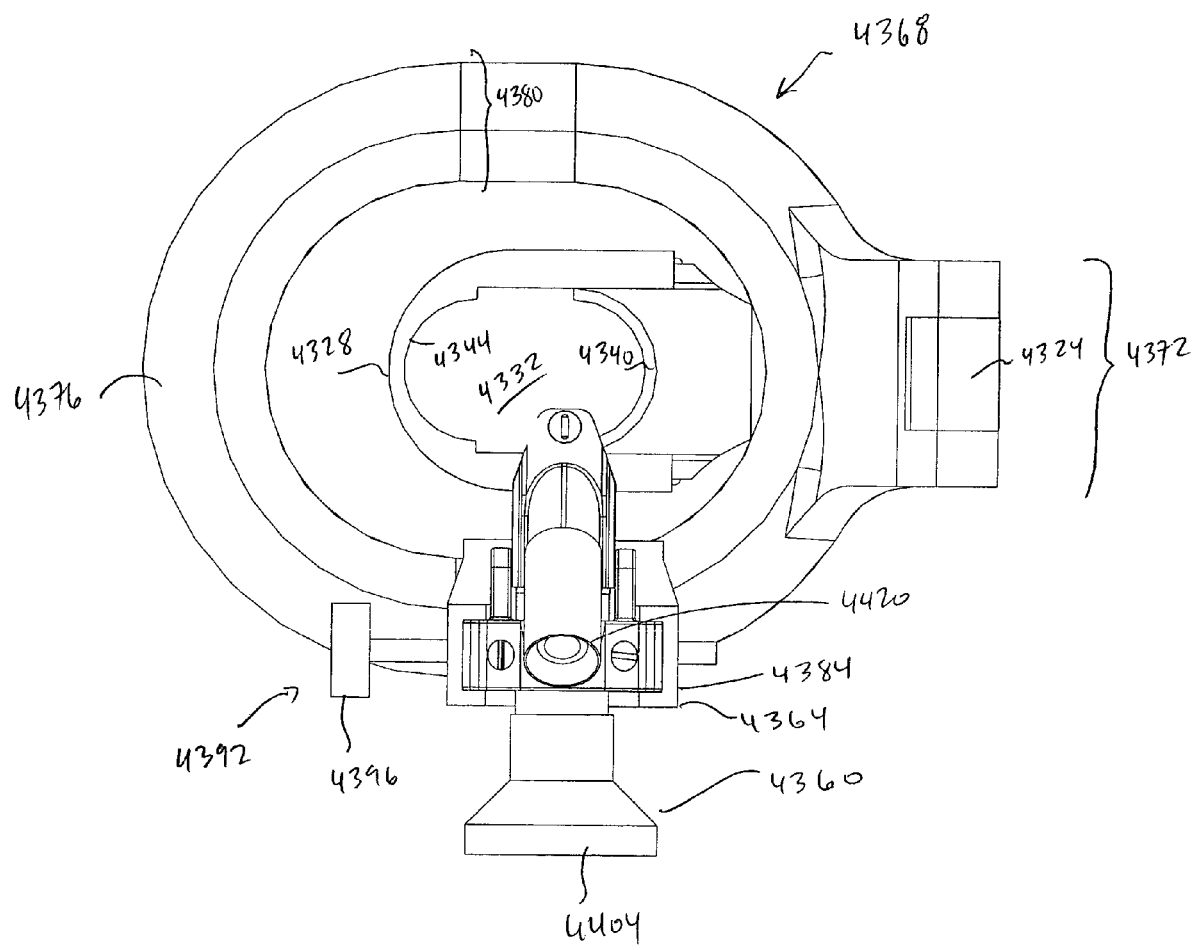
FIG. 87 is a top view of the surgical assembly of FIG. 82.
Figure 88:
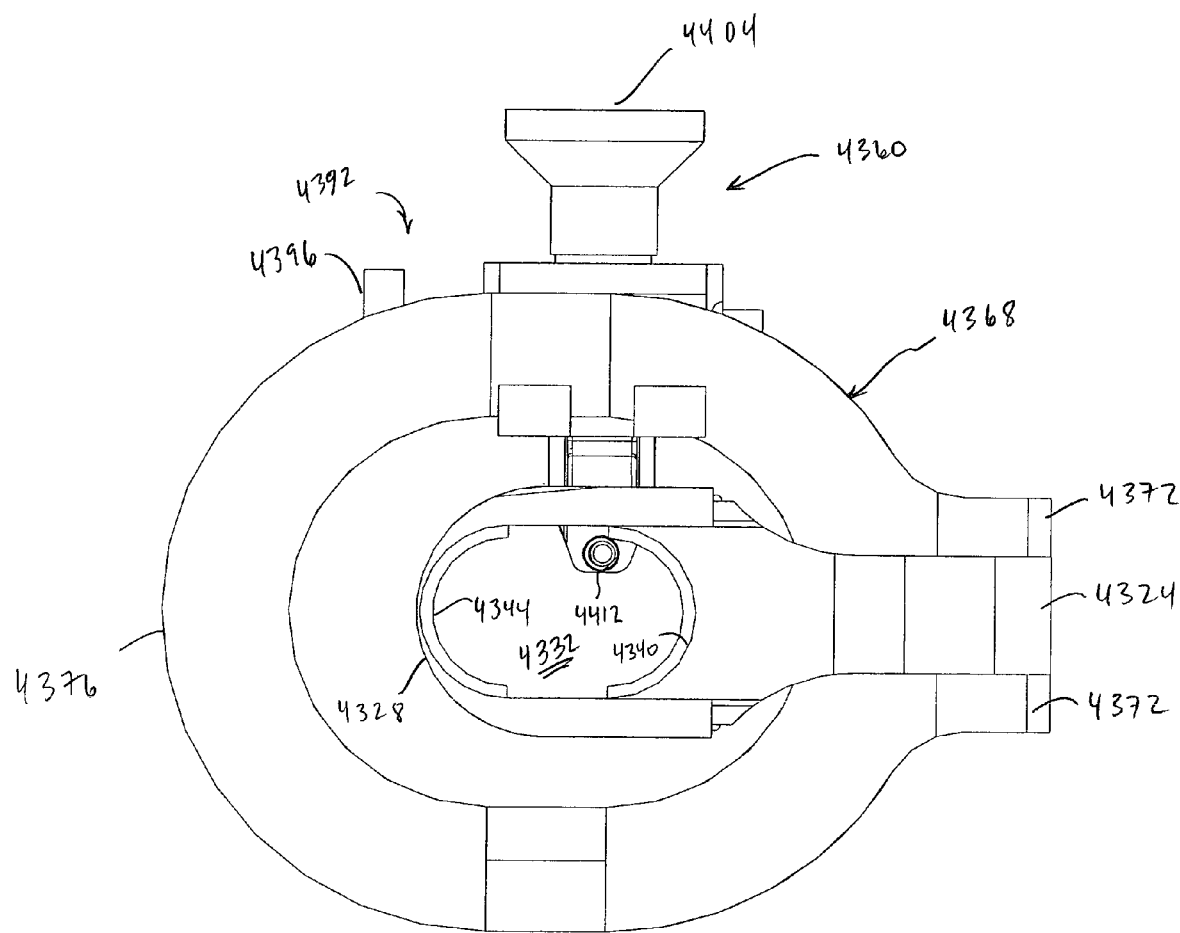
FIG. 88 is a bottom view of the surgical assembly of FIG. 82.
Figure 89:
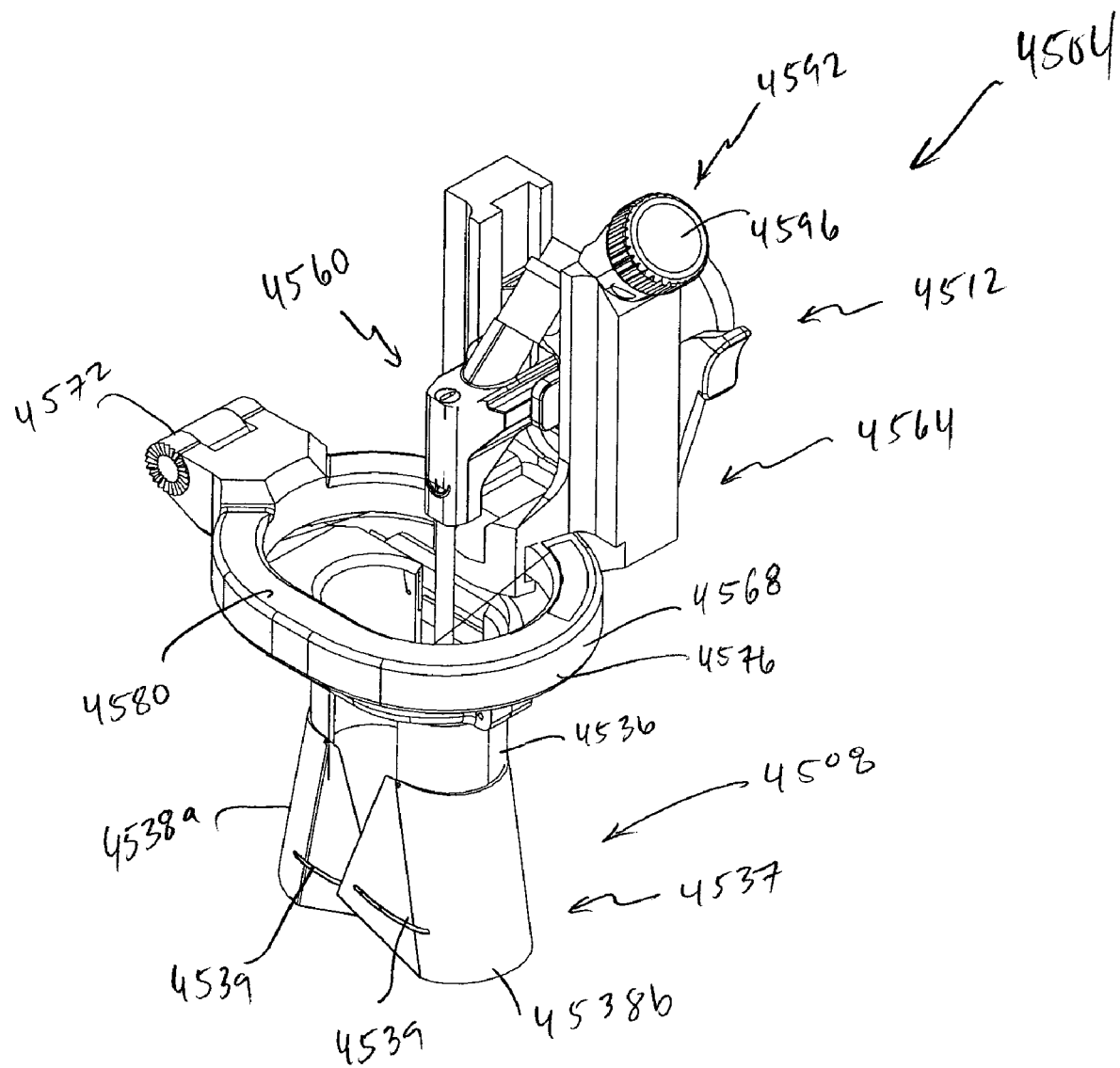
FIG. 89 is a rear-side perspective view of one embodiment of a surgical assembly.
Figure 90:
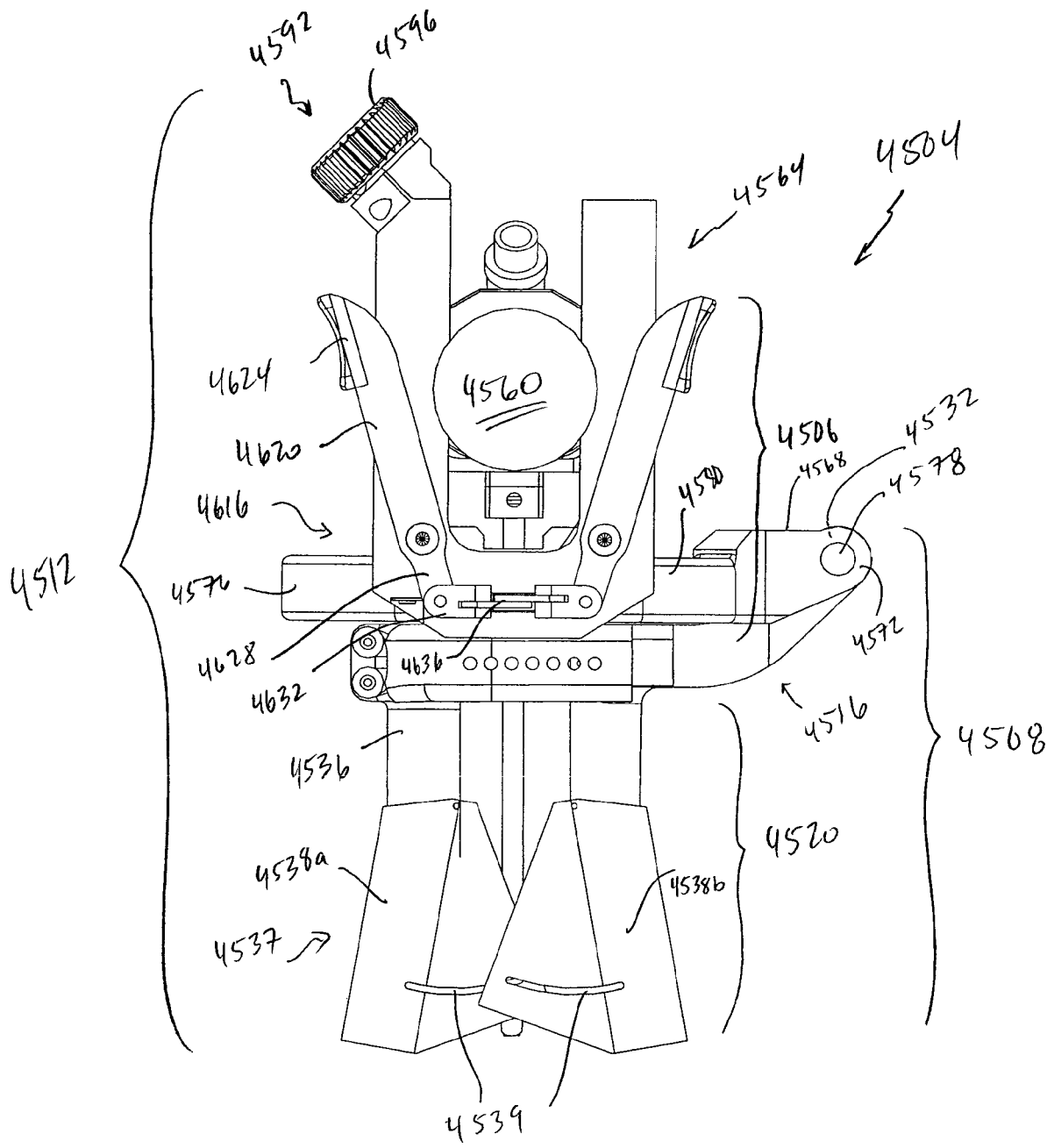
FIG. 90 is a front elevation view of the surgical assembly of FIG. 89.
Figure 91:
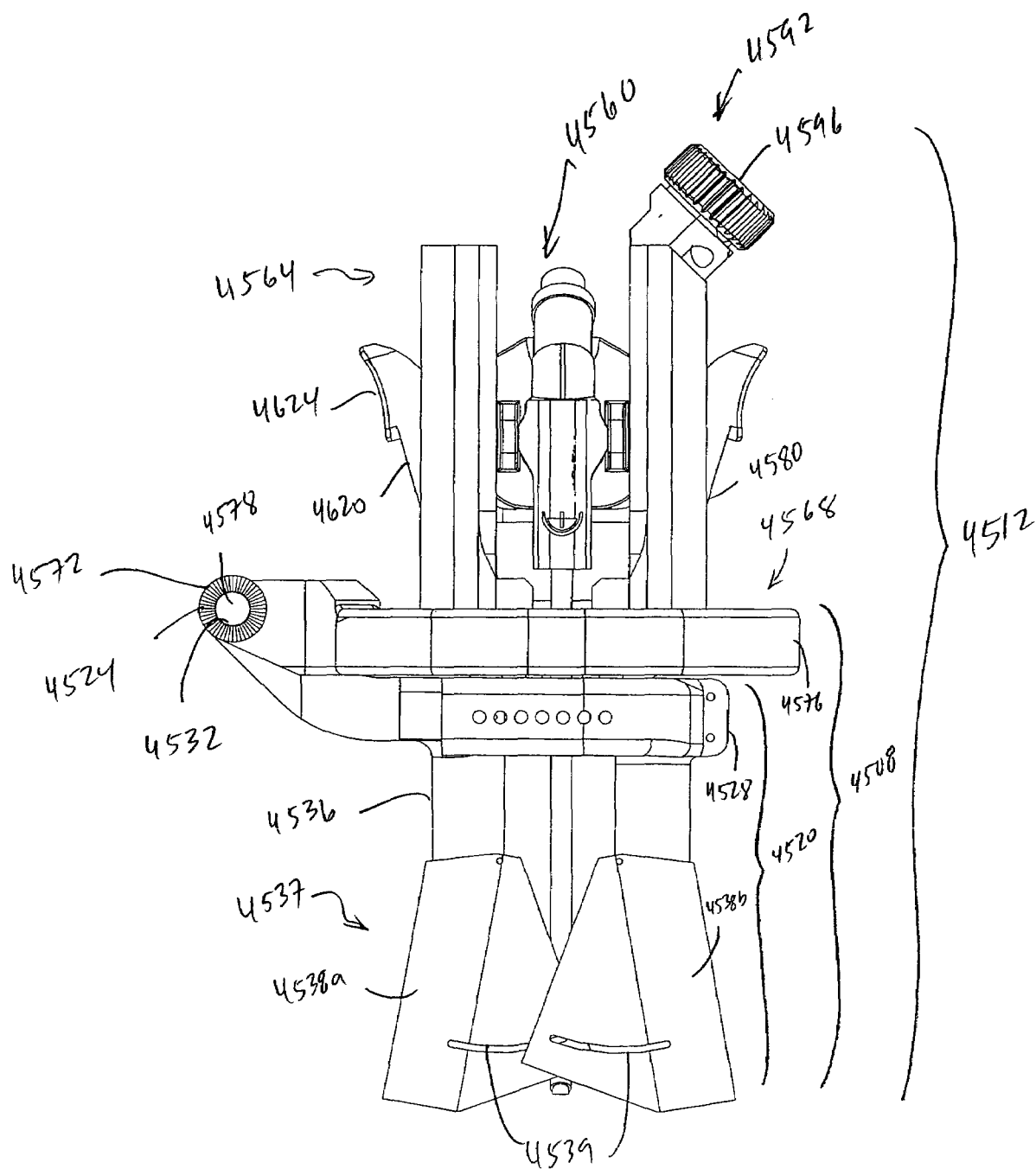
FIG. 91 is a rear elevation view of the surgical assembly of FIG. 89.
Figure 92:
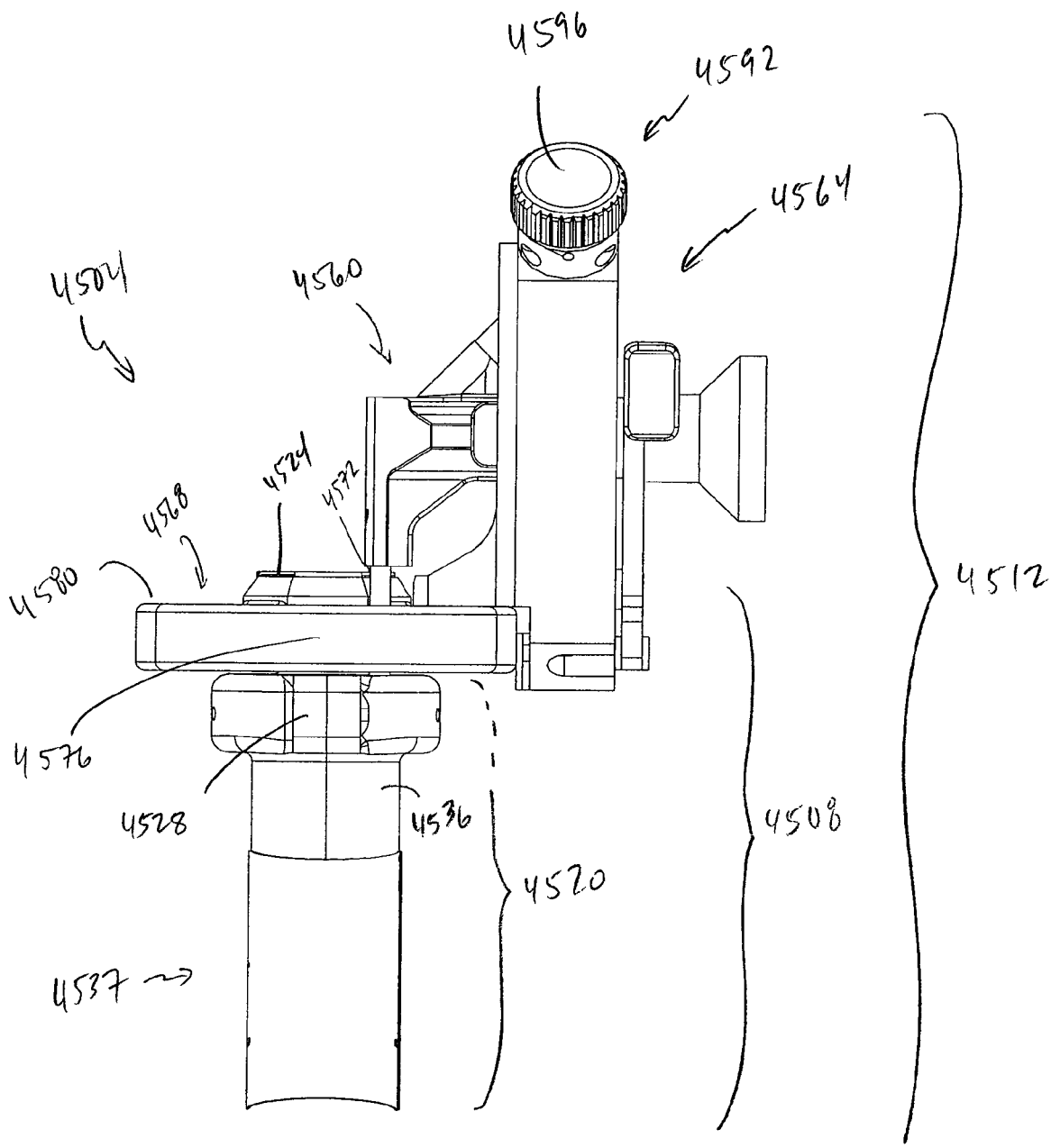
FIG. 92 is a side elevation view of the surgical assembly of FIG. 89.
Figure 93:
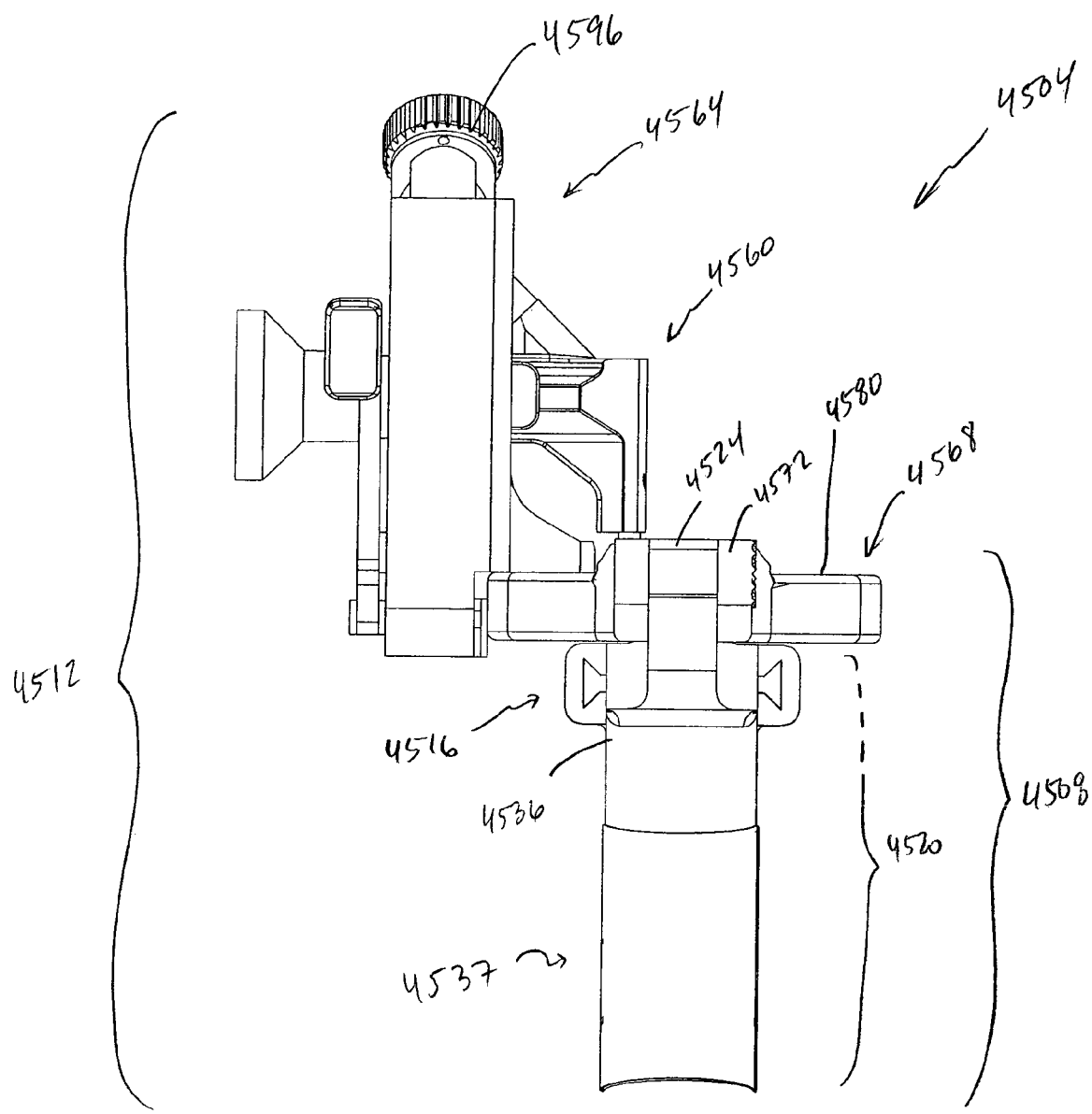
FIG. 93 is another side elevation view of the surgical assembly of FIG. 89.
Figure 94:
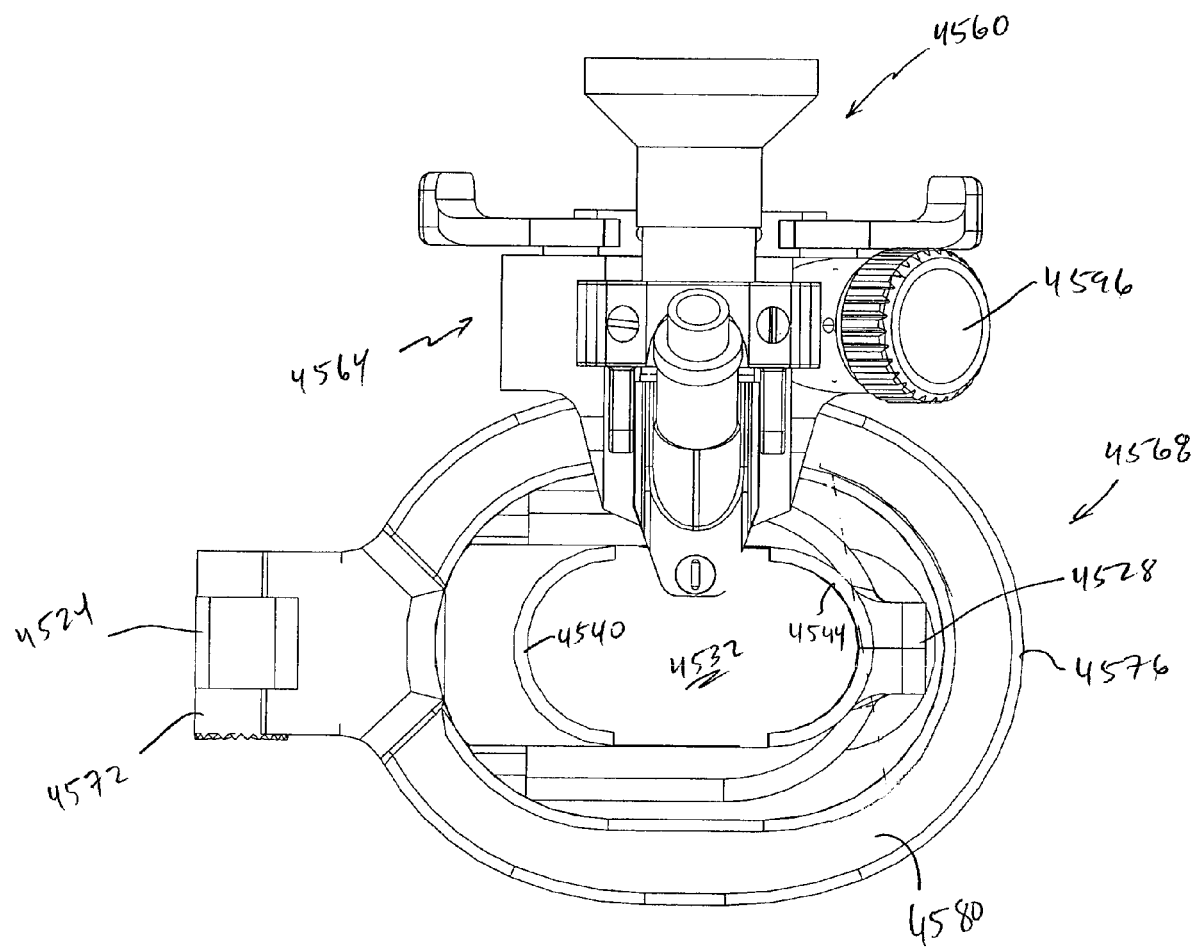
FIG. 94 is a top view of the surgical assembly of FIG. 89.

As discussed above, the proximal portion 4022 comprises first and second elongate bodies 4054, 4058. The first elongate body 4054 is coupled with the fixed arm 4062 and the second elongate body 4058 is coupled with the articulating arm 4066. Thus, rotation of the knob 4074, which provides the translational motion of the articulating arm 4066 with respect to the fixed arm 4062 also provides translational motion of the second elongate body 4058 of the proximal portion 4022 with respect to the first elongate body 4054 of the proximal portion 4022. Therefore, the arrow 4078 also illustrates the translational motion of the second elongate body 4058 of the proximal portion 4022 with respect to the first elongate body 4054 of the proximal portion 4022. Illustrations of another mount embodiment 4286 are shown in FIGS. 75A-75G and are discussed above FIGS. 76-81 show another variation of an access assembly 4082 that includes the access device 4010 and a mount fixture 4084. The mount fixture 4084 includes a fixed arm 4086 that may be coupled with the first elongate body 4054 and an articulating arm 4088 that may be coupled with the second elongate body 4058. The fixed arm 4086 preferably is coupled with a support, such as a flex arm (not shown), and is slidably coupled with the articulating arm 4088. In one embodiment, the slidable coupling of the fixed and articulating arms 4086, 4088 is provided by a flange-in-slot arrangement, e.g., a dovetail arrangement. In one form, the flange-in-slot arrangement is provided by forming a U-shaped channel or slot on opposite inwardly facing sides of the articulating arm 4088 and by forming an outwardly extending flange on one or both sides of the fixed arm 4086. The U-shaped channels or slots are configured to receive the outwardly extending flanges in a secure manner that permits the U-shaped channels or slots to slide on the flanges By sliding the slots on the flanges, the proximal portion 4022 of the access device 4010 may be articulated from a contracted configuration, where the first and second elongate bodies 4054, 4058 are moved close together, as illustrated in FIGS. 76-81, to a partially-expanded configuration, where the first and second elongate bodies 4054, 4058 are moved apart, as illustrated in FIGS. 78-79. By sliding the slots on the flanges, the proximal portion 4022 of the access device 4010 may be further articulated to a fully-expanded configuration, where the first and second elongate bodies 4054, 4058 are moved fully apart, as illustrated in FIGS. 80-81. As discussed above in connection with the access assembly 4008, the access device 4010 also has a distal portion, similar to the distal portion 4018, that is enlargeable.

The access assembly 4082 can be configured to be positionable in more than three configurations. For example, a detent arrangement is provided in one embodiment wherein many discrete positions, e.g., more than three, seven, or more than seven discrete positions, may be provided. In another embodiment, the access assembly 4082 can be configured to be positionable throughout a continuous range of positions. Other slidable couplings of the fixed and articulating arms 4086, 4088 may also be provided, e.g., providing a single slot and flange arrangement, providing slots on the fixed arm 4086 and flanges on the articulating arm 4088, etc.

With reference to FIGS. 67-68, the access device 4010 is configured for multi-stage expansion. In one embodiment, two-stage expansion is provided. In particular, the distal portion 4018 can be expanded at the distal end 4038, e.g., using the slot and sliding rivet arrangement as discussed above and an expander tool as discussed further below. The distal portion 4018 can be expanded at the proximal end 4034 using the rack and pinion mechanism 4070 of the mount fixture 4014. The distal portion 4018 thus may be positioned in a first position, illustrated in FIG. 67, wherein the proximal end 4034 of the distal portion 4018 has the smallest profile and the distal end 4038 of the distal portion 4018 has the largest profile. The distal portion 4018 may also be positioned in a second position, illustrated in FIG. 68, wherein the proximal end 4034 and the distal end 4038 of the distal portion 4018 both have enlarged profiles. The distal portion 4018 also may be positioned in a third position, wherein the proximal end 4034 and the distal end 4038 of the distal portion 4018 both have contracted profiles. The contracted profile is a low-profile configuration that may be used for inserting the access device 4008 into the patient. Further details for maintaining the contracted profile of the device are described below.

As disclosed above, and in the patents and patent applications incorporated by reference below, the distal portion 4018, the proximal portion 4022, or both the distal and proximal portions 4018, 4022 may be arranged to have a variety of selectable positions between the third position and the second position. In some embodiments, the distal portion 4018, the proximal portion 4022, or both the distal and proximal portions 4018, 4022 may be arranged to be positionable in a large number of intermediate positions between the second position and the third position. Moreover, the pivoting connection between the proximal portion 4022 and distal portion 4018 allows the operator to vary the angle of the proximal portion relative to the distal portion, which improves the ability to access and visualize a working location.

FIGS. 69-71 illustrate another embodiment of an access assembly 4108 having an access device 4110 coupled with the mount fixture 4014. The access device 4110 has a proximal portion 4114 that is configured to prevent tissue encroachment into the space defined therein. In one embodiment, a first overlapping shroud 4118 is coupled with a longitudinal edge 4122 of the first elongate body 4054 and a second overlapping shroud 4126 is coupled with a longitudinal edge 4130 of the second elongate body 4058. The shrouds 4118, 4126 can be coupled with the first and second elongate bodies 4054, 4058 in any suitable manner. For example, as shown, three fasteners could be provided along the longitudinal edge 4122 of the first elongate body 4054 to couple the first elongate shroud 4118 with the first elongate body 4054. Of course, the shrouds 4118, 4126 may be coupled with the elongate bodies 4054, 4058 in a similar manner.

FIG. 70 illustrates one manner of arranging the shrouds 4118, 4126 that is particularly advantageous for insertion into the body. In particular, the shrouds 4118, 4126 can be arranged to wrap around at least a part of the proximal portion 4114. For example, in one embodiment, each of the shrouds 4118, 4126 are made of a flexible material that have a predetermined shape configured to wrap around the elongate bodies 4054, 4058 to which they are not coupled. This configuration, referred to herein as the "wrapped configuration," provides the smallest profiles of the proximal portion 4114, which is beneficial for inserting the access device 4110 into the patient. Although it is preferable for the shroud to be capable of wrapping around the elongated bodies, FIGS. 75A-75G illustrate an alternative embodiment in which the shrouds 4288, 4290 do not wrap around the elongate bodies 4292, 4294.

FIG. 71 shows the arrangement of the shrouds 4118, 4126 when the mount fixture 414 moves the access device 4110 to the position shown in FIG. 69. In particular, the shrouds 4118, 4126 are straightened out, or un-wrapped, and extend from the longitudinal edges 4122, 4130 respectively. In this position, the first and second elongate bodies 4054, 4058 and the first and second shrouds 4118, 4126 defines a proximal access space 4134 that is maintained generally free of the surrounding tissue.

Figure 72:
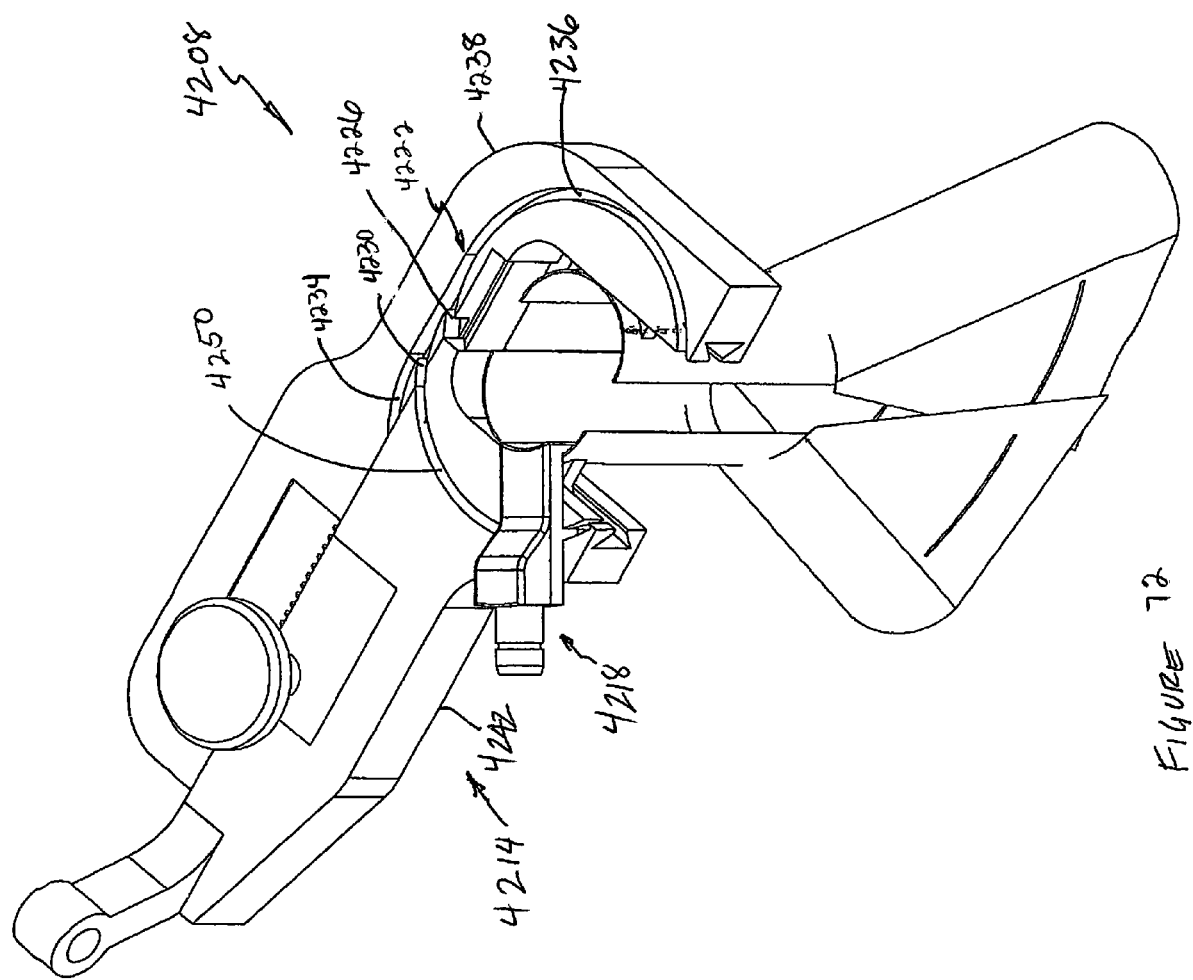
FIG. 72 is a perspective view of an assembly of an access device and a mount, the mount having a multi-leaved track.

FIG. 72 shows one embodiment of an access assembly 4208 that includes the access device 4010 and a mount 4214. The mount 4214 can be used with any suitable access device, e.g., the access device 4110. The mount 4214 is similar to the mount fixture 4014, except as set forth below. The mount 4214 includes a light guide 4218 and a multi-leaved track 4222. The light guide 4218 provides a channel through which light and/or optics can be introduced into the access device 4010 and ultimately to the surgical location, in particular at or near a spinal location. Although the embodiments herein are described with a light guide 4218, it will be appreciated that the access device 4010 or 4110 and mount 4214 can be used with a variety of different visualization systems, including endoscopes, microscopes and loupes. The multi-leaved track 4222 includes more than one track about which the light guide 4218 moves. In the embodiment illustrated in FIGS. 72-74B, the multi-leaved track 4222 includes a first track 4226, a second track 4230, a third track 4234, and a track extension 4236.

The mount 4214 is provided with an articulating arm 4238 and a fixed arm 4242. The articulating arm 4238 is moved via a rack and pinion mechanism 4246. As can be seen, each of the tracks 4226, 4230, 4234 are provided on the articulating arm 4238. The fixed arm 4242 has an arcuate track portion 4250 that can be aligned with any of the tracks 4226, 4230, 4234 to provide extended range of motion for the light guide 4218 in relation to the fixed arm 4242. Similarly, the track extension 4236 provides an extended range of motion for the light guide 4218 in relation to the articulating arm 4238. In the illustrated embodiment, the tracks 4226, 4230, 4234, when aligned with the arcuate track portion 4250 and the track extension 4236, extend through an arc of about 300 degrees. Of course, tracks having greater or lesser extent can also be provided.

In FIG. 72, the articulating arm 4238 has been moved to a position where the arcuate track portion 4250 on the fixed arm 4242 is aligned with the second track 4230. In this position, the proximal end 4034 of the distal portion 4018 of the access device 4010 is partially opened. The arcuate track portion 4250 and the second track 4230 form an extended track about which the light guide 4218 can be moved when the fixed arm 4242 and the articulating arm 4238 are in the position shown in FIG. 72.

Figure 73A:
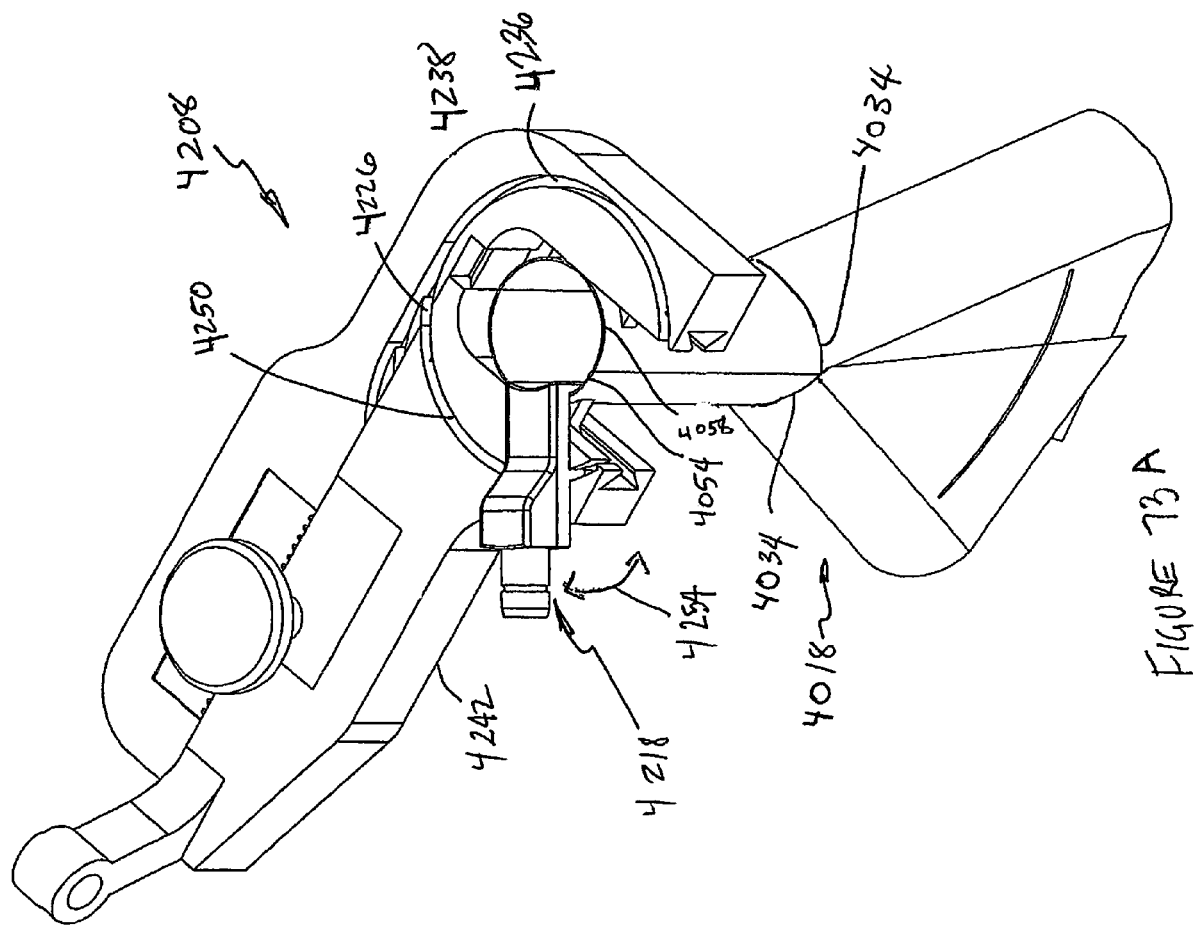
FIGS. 73A-73B illustrate the operation of the multi-leaved track of FIG. 72 when the access device is in the first position.

FIG. 73A is similar to FIG. 72, except that the articulating arm 4238 is in a different position with respect to the fixed arm 4242. In particular, the articulating arm 4238 is located in the most-retracted position, i.e., the position where the portion of the articulating arm 4238 with which the second elongate body 4058 is coupled and the portion of the fixed arm 4242 with which the first elongate body 4054 is coupled are close to each other. In this position, the proximal end 4034 of the distal section 4018 of the access device 4010 is in the closed position. When the mount 4214 is in this position, the arcuate track portion 4250 and the first track 4226 adjoin each other and form a continuing track in which the light guide 4218 can be moved. An arrow 4254 illustrates that the light guide 4218 can be moved about the arcuate track portion 4250 on the fixed arm 4242 and can be further moved through the first track 4226 on the articulating arm 4238.

Figure 73B:
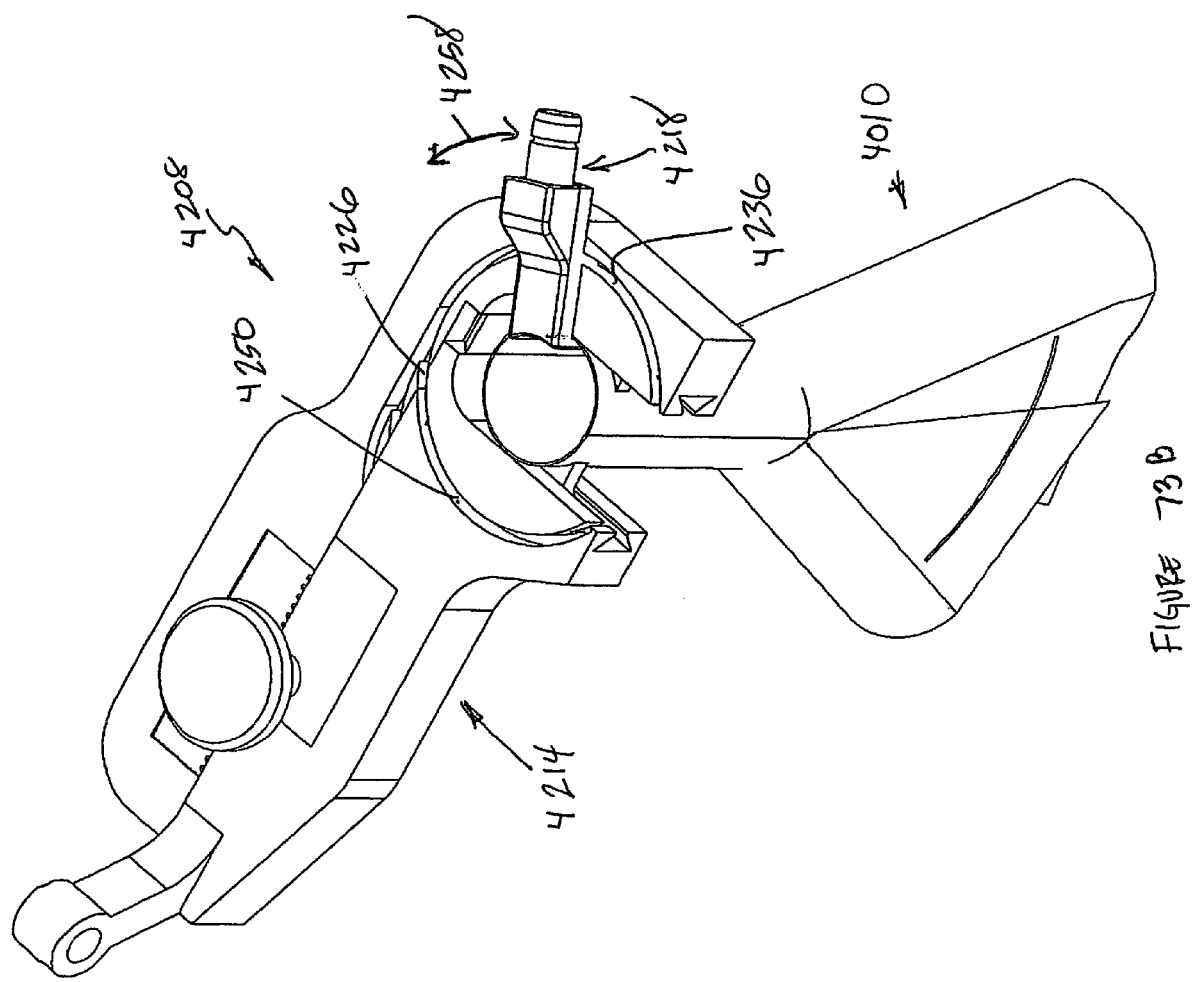

The range of motion of the light guide 4218 about the tracks of the mount 4214 is further illustrated in FIG. 73B. The light guide 4218 is shown moved through about one-half of the range of motion, from the arcuate track portion 4250, through the first track 4226, and along the extended track 4236 to a position that is approximately diametrically opposed to that shown in FIG. 73A. An arrow 4258 shows that the light guide 4218 may be further moved in either direction for desired lighting down the access device 4010 to a surgical location when the access assembly 4208 is in the position shown in FIG. 73B.

FIG. 74A is similar to FIG. 72, except that the articulating arm 4238 is in a different position with respect to the fixed arm 4242. In particular, the articulating arm 4238 is located in the most-extended position, i.e., the position where the portion of the articulating arm 4238 with which the second elongate body 4058 is coupled and the portion of the fixed arm 4242 with which the first elongate body 4054 is coupled are farthest from each other. In this position, the proximal end 4034 of the distal section 4018 of the access device 4010 is in the open position. When the mount 4214 is in this position, the arcuate track portion 4250 and the third track 4234 adjoin each other and form a continuing track in which the light guide 4218 can be moved.

Figure 74B:
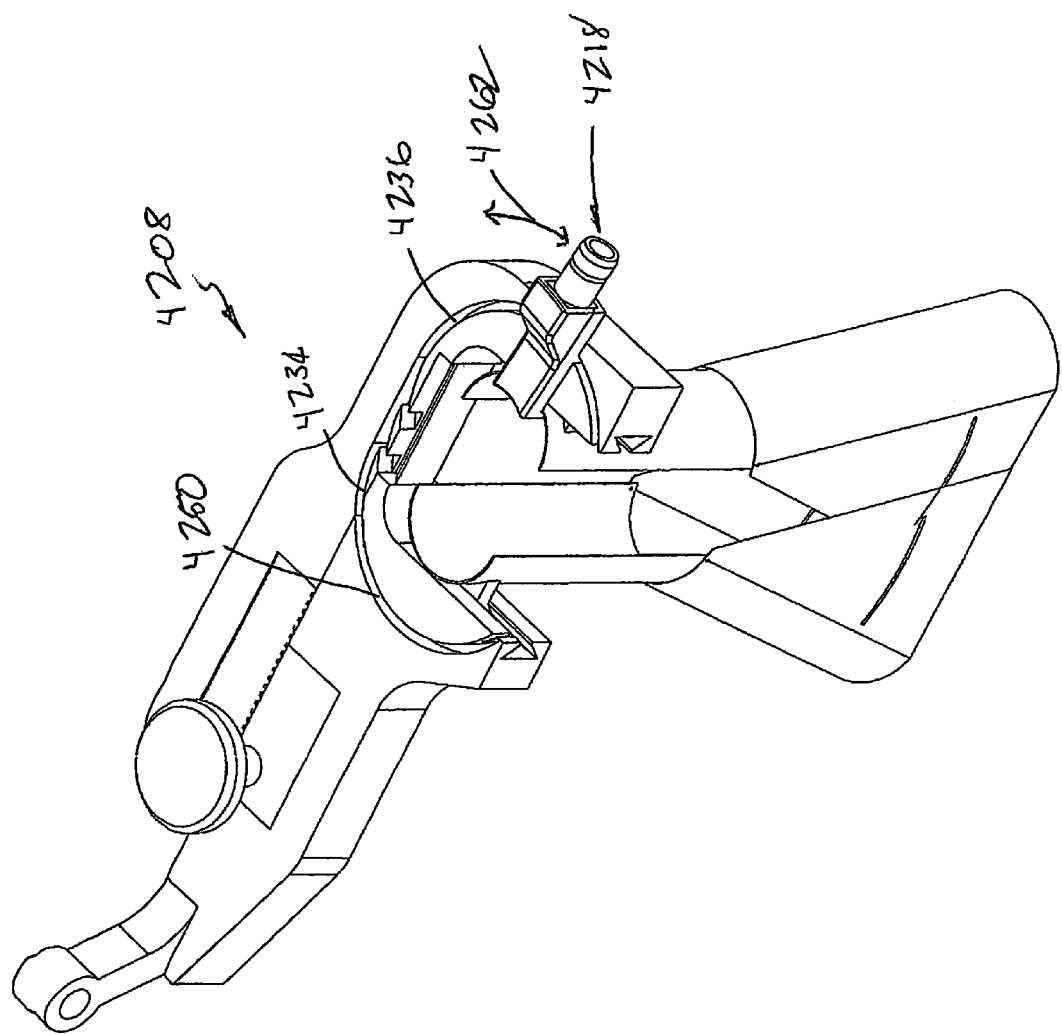

The range of motion of the light guide 4218 about the tracks of the mount 4214 is further illustrated in FIG. 74B. The light guide 4218 is shown moved through more than one-half of the range of motion, from the arcuate track portion 4250, through the third track 4234, and along the extended track 4236. An arrow 4262 shows that the light guide 4218 may be further moved in either direction for desired lighting down the access device 4010 to a surgical location when the access assembly 4208 is in the position shown in FIG. 74B. The track arrangements discussed above in connection with the access assembly 4208 can also be combined with the other access assemblies and variations thereof described herein, e.g., those described in connection with FIGS. 76-82.

In operation, any of the devices described herein can be used to provide access to a surgical location, and more preferably, are sized and configured to provide access to a spinal location. For example, these devices can be used in a posterolateral spinal procedure, and can be used for fixation of vertabrae, e.g., pedicle screw and transfacet screw fixation, interbody fusion, laminectomy, decompression, discectomy, any of a variety of motion preserving procedures, e.g., dynamic stabilization, partial or total disc replacement, nucleus replacement, or other procedures. Further details and features pertaining to access devices, systems, and methods are described in U.S. Patent Application No. 60/558,296, filed Mar. 31, 2004, Application No. 60/514,559, filed Oct. 24, 2003, application Ser. No. 10/678,744, filed Oct. 2, 2003, application Ser. No. 10/693,815, filed Oct. 24, 2003, application Ser. No. 10/693,250, filed Oct. 24, 2003, application Ser. No. 10/693,663, filed Oct. 24, 2003, and in U.S. Patent Application titled "Methods and Apparatuses for Minimally Invasive Replacement of Intervertebral Discs", Attorney Docket No. ENDIUS.030A, filed May 10, 2004, which are hereby incorporated by reference in their entireties herein.

As described above, the device 4010 is preferably inserted into a patient in a reduced configuration wherein the proximal portion 4022 of the device has its smallest configuration (e.g., when half-tubes are used, a circular cross-section), and the overlapping sections 4026, 4030 of the distal portion 4018 of the device are wrapped over each other to provide substantially the same cross-sectional size as the proximal portion. This is the third position as described above. A plastic tubing or sleeve such as described in U.S. Pat. No. 6,187,000 can be used to hold the distal portion of the device in a contracted configuration. Once inserted into the patient at a desired location, the sleeve can be removed, such as with a draw string extending outside of the patient and pulled by the operator. The overlapping sections 4026, 4030 of the distal portion 4018 may be naturally biased to a partially expanded configuration, with the overlapping sections moving relative to each other along the arcuate slots 4046a and 4046b through use of rivet 4050. An expander tool, such as described in U.S. Pat. No. 6,187,000 and U.S. Publication No. 2001/0049498 A1, can be inserted into the distal portion 4018 to fully expand the distal portion. During the expansion of the distal portion 4018, the outer surface of the device 4010 desirably retracts tissue to increase access to the surgical location.

With the distal portion 4018 expanded, the proximal portion 4022 can also be expanded, e.g., through operation of the rack and pinion mechanism 4070. Because of the pivotal connection between the proximal and distal portions, expansion of the proximal portion 4022 advantageously does not impact the cross-sectional area at the distal end 4038 of the distal portion 4018, but increases the size of the passage at the proximal end 4034 of the distal portion 4018.

In one embodiment, when the proximal portion 4022 of the device 4010 is in its reduced configuration and the overlapping sections 4026, 4030 of the distal portion 4018 are fully collapsed, the inner diameter of the passage from the proximal portion to the distal portion is about 10 to 30 mm. The proximal portion 4022 of the device 4010 may enlarge to a major axis of about twice or more the original inner diameter, and in one embodiment, may enlarge to a major axis of about 30 to 60 mm. More preferably, when the inner diameter of the passage of the reduced proximal portion is 16, 21 or 24 mm, the inner diameter of the proximal portion is expandable to a major axis of 21, 27 or 35 mm, respectively. It will be appreciated that a stop mechanism can be provided with the rack and pinion mechanism 4070 to prevent over-expansion of the proximal portion. Advantageously, the expanded dimension of the proximal portion is sized to allow easier insertion of devices such as plates or rods used in fixation, permitting such devices to be delivered in a horizontal orientation through the passage. Thus, in one embodiment, the proximal portion 4022 is enlargeable to a dimension sufficient to receive implant devices or components, e.g., a fixation rod or plate while the rod or plate is horizontally oriented, a spinial implant, such as an artificial disc, etc.

When the distal end 4038 of the distal portion is fully expanded, the inner diameter of the passage at the distal end 4038 may be about 15 to 80 mm, more preferably about 25 to 65 mm. In one preferred embodiment, the distal end 4038 of the distal portion is expandable from a straight tube to about 120 mm in the cephalad/caudal direction, and about 40 to 50 mm in the medial/lateral direction.

The device 4010 in one embodiment has an overall length of about 40 to 150 mm, and more preferably may have an overall length of about 40 to 60 mm for cervical procedures, about 60 to 80 mm for thoracic procedures, and about 80 to 150 mm for lumbar procedures. In one embodiment, the proximal and distal portions of the device may be about equal in length. It will be appreciated, however, that the distal portion of the device may be longer or shorter in order to provide access to desired locations within the body.

B. Surgical Assemblies that may Include an Access Device and a Viewing Element Support Member FIGS. 82-95 illustrate various embodiments of surgical assemblies that can be used to provide access to a surgical location. The embodiments of FIGS. 82-88 illustrate various embodiments of a surgical assembly having an expandable access device assembly. FIGS. 89-95 illustrate various embodiments of a surgical assembly that also have expandable access devices and that have a release mechanism that enables a viewing element to be positioned and to be quickly connected to and disconnected from the surgical assembly.

1. Surgical Assembly Including an Expandable Access Device Assembly

FIGS. 82-88 show one embodiment of a surgical assembly 4304 that includes an access assembly 4308 and a viewing assembly 4312. The access assembly 4308 is similar to those hereinbefore described and is used to provide access to a surgical location through an access device whereby surgical procedures, e.g., spinal procedures, may be performed. The viewing assembly 4312 provides a base upon which to mount any viewing or lighting element useful in such procedures and provides access to the proximal end of the access assembly 4308 so that surgical tools and implements may be delivered therethrough. As discussed more fully below, the access assembly 4308 preferably is mountable to a support structure, such as a flex arm, at a location off-set from the proximal end of the access device, e.g., at a elevation above the access device. Similarly, the viewing assembly 4312 preferably is mounted to a support structure, such as a flex arm, at a location off-set from the proximal end of the access device, e.g., at an elevation above the access device.

The access assembly 4308 preferably includes a mount fixture 4316 and an access device 4320. The mount fixture 4316 preferably extends from a first end 4324 to a second end 4328. The first end 4324 includes an aperture 4330 whereby the access assembly 4308 can be mounted to a support structure, e.g., a flex arm, which advantageously can support the surgical assembly 4304 in a convenient manner. The second end 4328 of the mount fixture 4316 includes an aperture 4332 wherein a proximal portion 4336 of the access device 4320 may be received. In one embodiment, the aperture 4332 is configured with a structure that clamps onto the proximal portion 4336 of the access device 4320, e.g., the at the proximal end thereof, so that movement of the access device 4320 may be coupled with movement of the mount fixture 4316.

A variation of the access device 4320 includes a distal portion that preferably is expandable. In one embodiment, the expandable distal portion expands from a first configuration to a second configuration, wherein the first configuration is adapted for minimally invasive advancement of the distal portion to a surgical location and the second configuration is adapted to provide sufficient access to the surgical location to enable a variety of procedure at the surgical location. In one embodiment, the expandable distal portion is similar to the distal portion 4018. In other embodiments, any of the other expandable distal portions disclosed or incorporated by reference herein may be coupled with the proximal potion 4336 of the access device 4320.

In one embodiment, the aperture 4332 is formed between a fixed portion 4340 and an articulating portion 4344 of the mount fixture 4316. In one embodiment, the articulating portion 4344 includes a slot that receives a laterally extending tab of the fixed portion 4340 whereby linear motion of the articulating portion 4344 is provided. This arrangement is similar to that described above in connection with FIGS. 76-81. In one embodiment, a ratchet device 4348 is provided. For example, a series of detent arrangements could be provided to enable the fixed portion 4340 and the articulating portion 4344 to be positioned at selected locations with respect to each other, as desired. The movement of the fixed portion 4340 and the articulating portion 4344 enable the expansion of the proximal portion 4336 of the access device 4320, as discussed above.

The viewing assembly 4312 includes a viewing element 4360, a viewing element support 4364, and a viewing element support base 4368. The viewing element support base 4368 extends from a first end 4372 to a second end 4376. In one embodiment, the first end 4372 includes an aperture 4378 whereby the viewing assembly 4312 can be mounted to a support structure, e.g., a flex arm (not shown). In the illustrated embodiment, the apertures 4330, 4378 are aligned so that a portion of the support structure to which the surgical assembly 4304 is connected may extends therethrough. In another embodiment, the apertures 4330, 4378 could be aligned with separate supports, e.g., separate flex arms. In such an arrangement, the mount fixture 4316 and the viewing element support base 4368 are separately mounted and separately supported.

The second end 4376 of the viewing assembly 4312 provides a location to support the viewing element 4360. Preferably, the second end 4376 includes a rail 4380 upon which the viewing element support 4364 may be mounted. For example, the lower end of the viewing element support 4364 may be formed to receive a portion of the rail 4380 whereby the viewing element support 4364 is coupled thereto. Preferably, the viewing element support 4364 is coupled to the rail 4380 in a secure manner which permits the viewing element support 4364 to be moved as desired about the rail 4380 to any selected position.

Some variations of the rail 4380 that may be employed include providing the rail 4380 with different perimeter shapes, e.g., circular, oval, elliptical, straight sided, or any combination thereof. In some embodiments, it may be advantageous to provide the rail 4380 with a perimeter shape that corresponds to either the contracted configuration, to a partially expanded configuration, or to the fully expanded configuration of the access device 4320, as discussed above. In another embodiment, the shape of the rail 4380 is adjustable in a manner similar to the adjustment of the access device 4320 and thus may have a first shape or configuration that corresponds to the contracted configuration of the access device 4320, a second shape or configuration that corresponds to the expanded configuration of the access device 4320, and any number of configurations intermediate the first and second configurations.

As discussed above, in some embodiments, the access assembly 4308 and the viewing assembly 4312 are separately mounted to a support structure, e.g., a flex arm, or are separately mounted to separate support structures, e.g., to separate flex arms. When separately mounted, the rail 4380 of a first configuration (e.g., a generally round perimeter) may be more easily removed and replaced with a rail of a second configuration (e.g., a generally oblong, oval, or other suitably shaped perimeter). The surgical assembly 4304 is thereby made more flexible by enabling a wide variety of advantageous combinations, some of which may be selected by the surgeon for a particular patient's needs.

As discussed above, the rail 4380 provides a base, e.g., a track, upon which the viewing element support 4364 may be mounted and positioned. The viewing element support 4364 may take any suitable form. For example, it may be advantageous to provide a pair of vertically extending members 4384 which position a cradle 4388 at an elevation above the rail 4380. The cradle 4388 is configured to receive and support a portion of the viewing element 4360. The viewing element support 4364 preferably includes an adjustment mechanism 4392 that provides adjustability in at least one direction. In the illustrated embodiment, the adjustment mechanism 4392 is actuated by a knob 4396 which raises or lowers the elevation of the viewing element 4360 with respect to the rail 4380.

In addition, a cap member may be provided to be placed over the viewing element 4360. The cradle 4388 and the cap member surround a portion of the viewing element 4360 and prevent it from being inadvertently dislodged from the surgical assembly 4304. The viewing element 4360 may be further secured in any suitable manner, e.g., by providing one or more fasteners, such as ball plungers which extend through the cap and into the cradle 4388.

The viewing element 4360 may be any of a number of components which facilitate the viewing of a surgical site. For example, the viewing element 4360 may be an endoscope 4400. The endoscope includes a lens barrel 4404, a scope barrel 4408, and a scope lens 4412. The scope lens 4412 is positioned at the lower-most end of the scope barrel 4408 so that the scope lens 4412 may be positioned as near to the surgical site as is feasible. The lens barrel 4404, the scope barrel 4408, and the scope lens 4412 are optically coupled so that image captured at the scope lens 4412 may be viewed at the proximal end of the lens barrel 4404. In one embodiment of the endoscope 4400, a first housing 4416 is provided to coupled the lens barrel 4404 with the scope barrel 4408.

A portion of the lens barrel 4404 may extend through an aperture defined by the cradle 4388 and the cap, whereby the endoscope 4400 is firmly and in some cases temporarily mounted to the surgical assembly 4304. A light input socket 4420 may be provided wherein any suitable lighting element, e.g., a light source, such as a fiber optic cable, may be inserted.

As discussed above, the surgical assembly 4304 advantageously can be arranged to be supported other than at any portion of the access device 4320, including the proximal portion 4336. In some embodiments, the surgical assembly 4304 is mounted to a flex arm at a lateral position with respect to the access device 4320. In other embodiment, the surgical assembly 4304 is mounted at an elevation different from that of the proximal end 4336 of the access device 4320. In the illustrated embodiment, the surgical assembly 4304 is mounted at an elevation between the proximal end 4336 of the access device 4320 and the proximal end of the viewing element 4360. This is accomplished by positioning the apertures 4330, 4378 whereby mounting is provided at an elevation above the rail 4380. By so positioning the apertures 4330, 4378 one or both of the access assembly 4308 and the viewing assembly 4312 may be easily removed from the support for the surgical assembly 4304, components thereof interchanged, and thereafter reattached to the surgical assembly support for flexible deployment by the surgeon.

2. Surgical Assemblies Including Viewing Element Assemblies Adapted for Quick Adjustment of a Viewing Element FIGS. 89-95 show one embodiment of a surgical assembly 4504 that is similar to the surgical assembly 4304. The surgical assembly 4504 also includes a coupling mechanism 4506 that enables quick and easy adjustment of a viewing element, e.g., about a support for the viewing element. In one embodiment, the coupling mechanism also enables the viewing element to be removed in a simple manner from the support for the viewing element.

The surgical assembly 4504 includes an access assembly 4508 and a viewing assembly 4512. The access assembly 4508 is similar to those hereinbefore described and is used to provide access to a surgical location through an access device whereby surgical procedures, e.g., spinal procedures, may be performed. The access assembly 4508 preferably is mountable to a support structure, such as a flex arm, at a location off-set from the proximal end of an access device thereof, e.g., at a elevation above the access device. Similarly, the viewing assembly 4512 preferably is mounted to a support structure, such as a flex arm, at a location off-set from the proximal end of the access device, e.g., at an elevation above the access device. The viewing assembly 4512 is similar to the viewing assembly, except as set forth below.

The access assembly 4508 preferably includes a mount fixture 4516 and an access device 4520. The mount fixture 4516 preferably extends from a first end 4524 to a second end 4528. The first end 4524 includes an aperture 4530 whereby the access assembly 4508 can be mounted to a support structure, e.g., a flex arm, which advantageously can support the surgical assembly 4504 in a convenient manner. The second end 4528 of the mount fixture 4516 includes an aperture 4532 wherein a proximal portion 4536 of the access device 4520 may be received. In one embodiment, the aperture 4532 is configured with a structure which clamps onto the proximal portion 4536, e.g., the proximal end, of the access device 4520 so that movement of the access device 4520 may be coupled with movement of the mount fixture 4516.

The access device 4520 also includes a distal portion 4537 that is coupled with the proximal portion 4536. The distal portion 4537 preferably is able to be actuated from a first configuration to a second configuration, wherein the first configuration is adapted for minimally invasive advancement of at least the distal portion 4537 of the access device 4520 to a surgical location. The second configuration is adapted to provide sufficient access to the surgical location to enable a variety of procedure at the surgical location. In one embodiment, the distal portion is expandable, e.g., in a manner similar to the expansion of the distal portion 4018.

The distal portion 4537 preferably is pivotally coupled with the proximal portion 4536 near a distal end of the proximal portion 4536. In one embodiment, the distal portion 4537 includes a first side portion 4538a and a second side portion 4538b. Preferably each of the first and second side portions 4538a, 4538b are movable with respect to each other such that the distal portion 4537 of the access device 4520 is expandable and contractable. In one embodiment, each of the first and the second portions 4538a, 4538b include an arcuate slot 4539 on each side of the distal portion 4537 that permits the expansion of the distal portion 4537 of the access device 4520. The first and second portion 4538a, 4538b permit the expansion of the access device 4520 in any suitable manner, e.g., by way of an expander tool.

As discussed above in connection with the aperture 4332, the aperture 4532 is formed between a fixed portion 4540 and an articulating portion 4544 of the mount fixture 4516. Further details of the illustrated embodiment of the mount fixture 4516 may be found above discussed in connection with the mount fixture 4316 and in connection with FIGS. 76-81 or in connection with any of the forgoing access assemblies.

The viewing assembly 4512 includes a viewing element 4560, a viewing element support 4564, and a viewing element support base 4568. The viewing element support base 4568 extends from a first end 4572 to a second end 4576. In one embodiment, the first end 4572 includes an aperture 4578 whereby the viewing assembly 4512 can be mounted to a support structure, e.g., a flex arm (not shown). In the illustrated embodiment, the apertures 4530, 4578 are aligned so that a portion of the support structure to which the surgical assembly 4504 is connected may extends therethrough. The viewing element support base 4568 preferably includes a rail 4580, as discussed above, which provides a track about which the viewing element support 4564 may be moved, as discussed below.

The viewing element support 4564 preferably includes an adjustment mechanism 4592 with at least one dimension of adjustability. In the illustrated embodiment, the adjustment mechanism 4592 is actuated by a knob 4596 which raises or lowers the elevation of the viewing element 4560. In the surgical assembly 4504, the knob 4596 is advantageously located at a convenient location, e.g., at an elevation above the coupling mechanism 4506. At this position, the knob 4596 of the adjustment mechanism 4592 will not obstruct the operation of the coupling mechanism 4506, discussed below.

Figure 95:
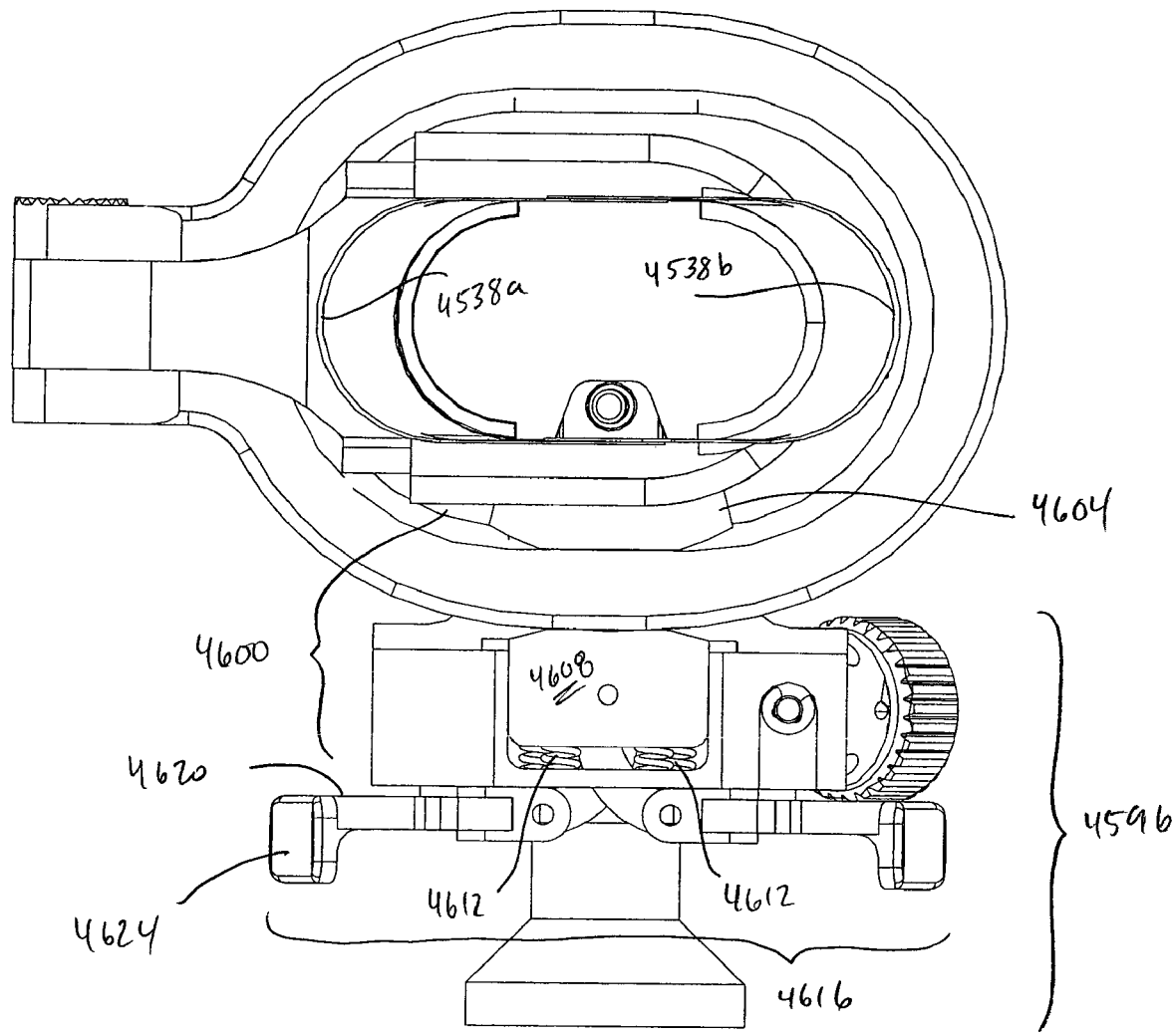
FIG. 95 is a bottom view of the surgical assembly of FIG. 89.

In one embodiment, the coupling mechanism 4506 includes a linkage that actuates a clamp 4600 (See FIG. 95). The clamp 4600 is coupled with the viewing element support 4564 and is configured to engage a support structure, e.g., to engage a portion of the rail 4580 of the viewing element support base 4568, to securely fasten the viewing element support 4564 thereto. In one embodiment the clamp 4600 includes a hook member 4604 that extends around a portion of the rail 4580. The hook member 4604 may form a portion of the viewing element support 4564. A lower portion of the hook member 4604 may extend around an inner portion of the rail 4580. The clamp 4600 preferably also includes a translatable jaw member 4608. In one embodiment, the jaw member 4608 is configured to be translated from a first position, which corresponds to the released position of the clamp 4600, to a second position, which corresponds to the engaged position of the clamp 4600. When in the first, or released position, the jaw member 4608 is separated from the hook member 4604 by a distance greater than the width of the rail 4580. When in the second, or engaged position, the jaw member 4608 is separated from the hook member 4604 by a distance that is somewhat less than the width of the rail 4580. In one embodiment, the jaw member 4608 is biased toward the second position, e.g., a force is applied against the jaw member 4608 so that the rail 4580 is firmly gripped by the clamp 4600. The clamp 4600 may be biased in any suitable fashion, e.g., by one or more springs 4612. In another embodiment, the jaw member 4608 comprises a spring block which is biased in a similar manner to a closed position to engage a portion of the viewing element support base 4568.

The clamp 4600 may be actuated in any suitable fashion. For example, in one embodiment, two mirror image linkages 4616 are provided to actuate the clamp 4600. The linkages 4616 include an elongate arm 4620 that is pivotally mounted to the viewing element support 4564. The elongate arm 4620 extends between a proximal end 4624 and a distal end 4628. The proximal end 4624 preferably is formed to be engaged by a finger of the surgeon, e.g., with a concave surface. The distal end 4628 of the elongate arm 4620 preferably is configured to engage a first end of a knuckle member 4632. The knuckle member 4632 is caused to move by the pivotal motion of the elongate member 4620. The knuckle member 4632 has a second end which is configured to engage a link member 4636. The link member 4636 extends between the knuckle member 4632 and a portion of the clamp 4600.

In one embodiment, the link member 4636 extends between the knuckle member 4632 and the clamp 4600 such that movement of the link member 4636 actuates the springs 4612, e.g., causes the springs to relax such that the jaw member 4608 is permitted to translate away from the hook member 4604. As the jaw member 4608 translates away from the hook member 4604, the viewing element support 4564, e.g., the rail 4580, is released from the clamp 4600. Of course, two non-symmetrical linkages or a single linkage could be provided in other embodiments.

C. Methods that may be Performed through Access Devices with Expandable Proximal Portions The surgical assembly 4304, as illustrated or as modified to include any structures described or incorporated herein by reference or the access device 4010 (and the other access devices described or incorporated herein by reference) and the surgical assembly 4504 as similarly or otherwise modified have a wide variety of applications wherein access is provided for one or more surgical instruments to perform surgical procedures. The surgical procedures that can be performed can include any of those discussed hereinabove. For example, in one application, a space similar to the space 4042 provides access that can be used to perform a two level posterolateral fixation of the spine involving the L4, L5 and S1 vertebrae. The access devices can be used to deliver a wide variety of fixation elements, including rigid, semi-rigid, or dynamic fixation elements. The access devices are not limited to the posterolateral approach nor to the L4, L5 and S1 vertebrae. The access devices may be applied in other anatomical approaches and with other vertebrae within the cervical, thoracic and lumbar spine. The access devices can be applied in procedures involving one or more vertebral levels and in anterior and lateral procedures. Further procedures in which the access devices described herein can be applied include procedures involving orthobiologics, bone morphogenetic proteins, and blood concentrators. The access devices can also be used with procedures involving prosthetics, such as disc nucleus replacement, facet joint replacement, or total disc replacement.

The access devices described herein also can be used in connection with interbody fusion, and fusion of the facets and transverse processes. Some of the fusion procedures that can be performed via the access devices described herein employ allograft struts, bone filling material (e.g., autograft, allograft or synthetic bone filling material), and cages and/or spacers. The cages and the spacers can be made of metal, a polymeric material, a composite material, or any other suitable material. The struts, cages, and spacers are used in the interbody space while the bone filling material can be used both interbody and posterolaterally. Any of the foregoing or other fusion procedures can be used in combination with the orthobiologics and can be performed via the access devices described herein.

Moreover, it is believed that the access devices described herein are generally applicable where any anatomical structure must be accessed beneath the skin and muscle tissue of the patient, and where it is desirable to provide sufficient space and visibility in order to manipulate surgical instrumentation and treat the underlying anatomical structure. For example, the access devices described herein are particularly useful for minimally invasive procedures, e.g. arthroscopic or endoscopic procedures, in which the expandable distal portion of any of the access devices prevents the instrument from dislodging or popping out of the operative site. The access provided by the access devices described herein enables other minimally invasive surgical procedures, some of which are disclosed in the patents and applications incorporated by reference herein.

The various devices, methods, procedures, and techniques described above provide a number of ways to carry out the invention. Of course, it is to be understood that not necessarily all objectives or advantages described may be achieved in accordance with any particular embodiment described herein. Also, although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A retractor comprising:
   a proximal portion comprising a first side portion having a first longitudinal edge and a second side portion having a second longitudinal edge, the first and second longitudinal edges each having a length such that when inserted within the patient, at least part of each longitudinal edge extends outside the patient while at least part of each longitudinal edge extends inside the patient, the first and second side portions being movable relative to each other from a first configuration in which the first and second longitudinal edges are positioned in close proximity to each other to a second configuration in which the first and second longitudinal edges are spaced apart by a selected distance, wherein when in the second configuration, a cross-sectional area of said proximal portion is constant along the length of the first and second longitudinal edges; and
   a distal portion coupled with the proximal portion, the distal portion having an outer surface and an inner surface partially defining a path, said distal portion capable of having an expanded configuration when inserted within the patient wherein the cross-sectional area of said path at a first location is greater than the cross-sectional area of said path at a second location, wherein the first location is distal to the second location; wherein the retractor is configured such tat the distal portion is moveable into the expanded configuration while the proximal portion remains in the first configuration.

2. The retractor of claim 1, wherein the distal portion further comprises a first overlapping section and a second overlapping section, the first and second overlapping portions extending between the proximal portion and a distal end of the distal portion.

3. The retractor of claim 2, wherein the first and second overlapping sections overlap each other to create an enclosed space therebetween.

4. The retractor of claim 2, wherein the first and second overlapping sections are coupled.

5. The retractor of claim 4, wherein a guide pin attached to one of the first and second overlapping sections extends into the other of the first and second overlapping sections.

6. The retractor of claim 2, wherein the distal portion is configured such that the first overlapping section and the second overlapping section are capable of moving in a generally planar manner.

7. The retractor of claim 1, wherein the distal portion has a first configuration for insertion into the patient and is moveable to the expanded configuration after insertion, the first configuration having a generally circular cross-section and the expanded configuration having an oblong configuration.

8. The retractor of claim 1, wherein the proximal portion defines an inside surface at least partially defining the path and at least a portion of the proximal portion comprises a circular transverse cross-section within the inside surface.

9. The retractor of claim 1, wherein the proximal portion defines an inside surface at least partially defining the path and at least a portion of the proximal portion comprises an oblong transverse cross-section within the inside surface.

10. The retractor of claim 9, wherein the proximal portion defines an inside surface at least partially defining the path and at least a portion of the proximal portion comprises an oval transverse cross-section within the inside surface.

11. The retractor of claim 1 further comprising:
    a fixture having a first mount portion and a second mount portion engaging said first mount portion, said first mount portion being coupled with said first side portion and said second mount portion being coupled with said second side portion, said second mount portion moveable laterally relative to the first mount portion.

12. The method of claim 11, wherein the retractor is inserted laterally to a spinal location.

13. The retractor of claim 11, wherein said first mount portion is configured to be coupled with a support arm and to be stationary with respect thereto and said second mount portion is configured to be articulated with respect to said first mount portion.

14. The retractor of claim 13, wherein said first mount portion comprises a slot and said second mount portion comprises a flange configured to extend into and to be slidable within said slot.

15. A retractor comprising:
    a first elongate body having a first proximal portion having a length such that when the retractor is inserted into a patient to a surgical location, at least part of the first proximal portion extends outside the patient while at least art of the first proximal portion extends inside the patient, and a first distal portion, the first elongate body partially defining a path through which surgical instruments can be inserted to the surgical location adjacent the spine; and
    a second elongate body having a second proximal portion having a length such that when the retractor is inserted into the patient to the surgical location, at least part of the second proximal portion extends outside the patient while at least part of the second proximal portion extends inside the patient, and a second distal portion, the second elongate body partially defining the path,
    wherein the first elongate body is configured to be adjacent the second elongate body in a low-profile configuration for insertion into the patient, a portion of the path having a generally circular cross-section in the low-profile configuration, wherein the first elongate body and the second elongate body are separated by a gap in an expanded configuration, the gap in the expanded configuration having a substantially constant cross-section along the length of the first and second proximal portions and a generally oblong cross-section that increases along the length of the first and second distal portions, the first distal portion and the second distal portion are configured such that when inserted within a patient and positioned in the expanded configuration, the cross-sectional area of the path at a first location is greater than the cross-sectional area of the path at a second location, wherein the first location is distal to the second location.

16. A method of minimally invasive spine surgery comprising:
    making an incision;
    positioning an access device in the incision, the access device having a length selected to span from the incision to a surgical site proximate a vertebra, the access device having a proximal portion and a distal portion, wherein an inner surface of the proximal portion and an inner surface of the distal portion together form a continuous pathway from the incision to proximate the vertebra;

performing a first expansion by expanding the distal portion of the access device such that a cross-sectional area of the distal portion at a first location is greater than a cross-sectional area of the distal portion at a second location, wherein the first location is distal to the second location, wherein the step of expanding the distal portion is performed without substantially actuating the proximal portion; and performing a second expansion by expanding the access device along the length of the access device by separating a first elongate body of the access device from a second elongate body of the access device along the length of the access device, the expanded access device providing a continuous pathway from the incision to proximate the vertebra, wherein a cross-sectional area of said proximal portion is constant along a length of the proximal portion in the expanded access device, wherein the step of performing the first expansion and the step of performing the second expansion are performed independently.

17. A method for accessing a surgical location within a patient, comprising:

providing a retractor for insertion into the patient, wherein the retractor has a proximal portion and a distal portion, the proximal portion has a first longitudinal edge on a first side portion and a second longitudinal edge on a second side portion, the distal portion is coupled with the proximal portion, wherein the proximal and distal portions each have outer surface and an inner surface partially defining a path extending from a proximal end of the retractor to a distal end of the retractor;

inserting the retractor into the patient to the surgical location, wherein the first and second longitudinal edges of the proximal portion are positioned in close proximity to each other as the retractor is inserted into the patient, the first and second longitudinal edges each having a length such that the step of inserting the retractor into the patient to the surgical location results in at least part of each longitudinal edge extending outside the patient while at least part of each longitudinal edge extends inside the patient;

expanding the distal portion of the retractor such that the cross-sectional area of the path at a first location is greater than the cross-sectional area of said path at a second location, wherein the first location is distal to the second location, wherein the first and second longitudinal edges of the proximal portion remain in close proximity to each other while the distal portion is expanded; and expanding the proximal and distal portions of the retractor such that the first and second longitudinal edges are spaced apart by a selected distance, wherein when in the spaced-apart configuration, a cross-sectional area of the proximal portion is constant along the length of the first and second longitudinal edges.

18. The method of claim 17, wherein the retractor is inserted laterally to a spinal location.

19. The method of claim 17, wherein the retractor is inserted posterolaterally to a spinal location.

20. The method of claim 17, wherein the retractor is inserted anteriorly to a spinal location.

* * * * *

UNITED STATES PATENT AND TRADEMARK OFFICE
CERTIFICATE OF CORRECTION

PATENT NO.       : 7,645,232 B2
APPLICATION NO.  : 10/845389
DATED            : January 12, 2010
INVENTOR(S)      : Alan E. Shluzas It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1071 days.

Signed and Sealed this

Sixteenth Day of November, 2010

David J. Kappos
*Director of the United States Patent and Trademark Office*